US012616706B2

(12) United States Patent
Manfredi et al.

(10) Patent No.: US 12,616,706 B2
(45) Date of Patent: May 5, 2026

(54) COMPOSITIONS AND METHODS OF USE COMPRISING SUBSTANCES WITH NEURAL PLASTICITY ACTIONS ADMINISTERED AT NON-PSYCHEDELIC/PSYCHOTOMIMETIC DOSAGES AND FORMULATIONS

(71) Applicant: Arbormentis LLC, Miami Beach, FL (US)

(72) Inventors: Paolo L. Manfredi, Miami Beach, FL (US); Charles E. Inturrisi, New York, NY (US); Sara De Martin, Vigonza (IT); Andrea Mattarei, Perarolo di Vigonza (IT); Maurizio Rolando, Genoa (IT); Giovanni Giordano, Genoa (IT); Claudia Lodovichi, Padua (IT); Paola Brun, Padua (IT); Marco Pappagallo, New York, NY (US); Franco Folli, Milan (IT); Andrea Alimonti, Bellinzona (CH); Jacopo Sgrignani, Almenno San Salvatore (IT); Andrea Cavalli, Zurich (CH)

(73) Assignee: Arbormentis LLC, Miami Beach, FL (US)

( * ) Notice: Subject to any disclaimer, the term of this patent is extended or adjusted under 35 U.S.C. 154(b) by 1171 days.

(21) Appl. No.: 17/435,571

(22) PCT Filed: Mar. 6, 2020

(86) PCT No.: PCT/US2020/021400

§ 371 (c)(1),
(2) Date: Sep. 1, 2021

(87) PCT Pub. No.: WO2020/181194

PCT Pub. Date: Sep. 10, 2020

(65) Prior Publication Data

US 2022/0143051 A1 May 12, 2022

Related U.S. Application Data

(60) Provisional application No. 62/844,151, filed on May 7, 2019, provisional application No. 62/814,929, filed on Mar. 7, 2019.

(51) Int. Cl.

| | |
|---|---|
| ***C07D 209/16*** | (2006.01) |
| ***A61K 31/13*** | (2006.01) |
| ***A61K 31/135*** | (2006.01) |
| ***A61K 31/137*** | (2006.01) |
| ***A61K 31/4045*** | (2006.01) |
| ***A61K 31/485*** | (2006.01) |
| ***A61K 31/55*** | (2006.01) |
| ***A61K 31/675*** | (2006.01) |
| ***A61K 33/00*** | (2006.01) |
| ***A61K 33/06*** | (2006.01) |
| ***A61K 33/30*** | (2006.01) |
| ***A61P 1/16*** | (2006.01) |
| ***A61P 3/10*** | (2006.01) |
| ***A61P 25/28*** | (2006.01) |
| ***A61P 27/10*** | (2006.01) |
| ***C07C 217/60*** | (2006.01) |

(Continued)

(52) U.S. Cl.
CPC ............ *A61K 31/675* (2013.01); *A61K 31/13* (2013.01); *A61K 31/135* (2013.01); *A61K 31/137* (2013.01); *A61K 31/4045* (2013.01); *A61K 31/485* (2013.01); *A61K 31/55* (2013.01); *A61K 33/00* (2013.01); *A61K 33/06* (2013.01); *A61K 33/30* (2013.01); *A61P 1/16* (2018.01); *A61P 3/10* (2018.01); *A61P 25/28* (2018.01); *A61P 27/10* (2018.01); *C07C 217/60* (2013.01); *C07D 209/16* (2013.01); *C07D 471/06* (2013.01); *C07D 471/22* (2013.01); *C07F 9/5728* (2013.01)

(58) Field of Classification Search
CPC .................................................... C07D 209/16
See application file for complete search history.

(56) References Cited

U.S. PATENT DOCUMENTS

| | | | |
|---|---|---|---|
| 4,491,664 | A | 1/1985 | Oppolzer |
| 5,593,876 | A | 1/1997 | Stamler et al. |

(Continued)

FOREIGN PATENT DOCUMENTS

| | | | |
|---|---|---|---|
| CH | 463525 | A | 10/1968 |
| CN | 108314641 | A | 7/2018 |

(Continued)

OTHER PUBLICATIONS

Alzheimer's disease [online] retrieved from the internet on Mar. 25, 2022 URLhttps:/Avww.mayoclinic.org/diseases-conditions/alzheimers-disease/symptoms-causes/syc-.*
Chen, et al. Amyloid beta:structure, biology and structure-based therapeutic development. ActaPharmacologicaSinica 2017:1205-1235.*
Substituted tryptamine [online] retrieved from the internet on Nov. 14, 2024. URL https://en.wikipedia.org/wiki/Substituted_tryptamine.*
Leonard JB, Anderson B, Klein-Schwartz W. Does getting high hurt? Characterization of cases of LSD and psilocybin-containing mushroom exposures to national poison centers between 2000 and 2016. J Psychopharmacol. Dec. 2018;32(12):1286-1294.

(Continued)

*Primary Examiner* — Shawquia Jackson
(74) *Attorney, Agent, or Firm* — Wood Herron & Evans LLP

(57) ABSTRACT

Compositions and methods of use comprising serotonin (5-HT) receptor agonists and NMDAR modulating substances, including especially certain substances classified as 5-HT2A agonists presently disclosed to exert NMDAR modulating effects, administered as modulators of neural plasticity, at non-psychedelic/psychotomimetic dosages, posology and formulations, for treatment of diseases and conditions and for improving functions (neuroplastogens).

53 Claims, 58 Drawing Sheets

(51) Int. Cl.

| | |
|---|---|
| ***C07D 471/06*** | (2006.01) |
| ***C07D 471/22*** | (2006.01) |
| ***C07F 9/572*** | (2006.01) |

(56) References Cited

U.S. PATENT DOCUMENTS

| | | | |
|---|---|---|---|
| 5,958,919 | A | 9/1999 | Olney et al. |
| 6,995,159 | B2 | 2/2006 | Chiang et al. |
| 8,637,648 | B1 | 1/2014 | Mash et al. |
| 9,468,611 | B2 | 10/2016 | Manfredi et al. |
| 9,783,535 | B2 | 10/2017 | Mash et al. |
| 2006/0223998 | A1 | 10/2006 | Zhang et al. |
| 2007/0049758 | A1 | 3/2007 | Dillon et al. |
| 2010/0016280 | A1 | 1/2010 | Nichols et al. |
| 2012/0108510 | A1 † | 5/2012 | YoungÂ |
| 2018/0021326 | A1 † | 1/2018 | Stamets |
| 2020/0330405 | A1 † | 10/2020 | Foster |

FOREIGN PATENT DOCUMENTS

| | | | |
|---|---|---|---|
| DE | 3436386 | A1 | 4/1986 |
| EP | 2682119 | A1 | 1/2014 |
| JP | H02138161 | A | 5/1990 |
| WO | 2004000205 | A2 | 12/2003 |
| WO | 2006079999 | † | 8/2006 |
| WO | 2009102805 | A1 | 8/2009 |
| WO | 2010033392 | A2 | 3/2010 |
| WO | 2010081036 | A2 | 7/2010 |
| WO | 2014117089 | A1 | 7/2014 |
| WO | 2018144551 | A2 | 8/2018 |
| WO | 2018148605 | † | 8/2018 |
| WO | 2018195455 | † | 10/2018 |
| WO | 2018204359 | A1 | 11/2018 |
| WO | 2018206757 | A1 | 11/2018 |
| WO | 2019109124 | † | 6/2019 |
| WO | 2020157569 | † | 1/2020 |
| WO | 2020097320 | † | 5/2020 |
| WO | 2020157569 | A1 | 8/2020 |
| WO | 2020212948 | A1 | 10/2020 |
| WO | 2021168082 | A1 | 8/2021 |

OTHER PUBLICATIONS

Lepousez G, Nissant A, Lledo PM Adult neurogenesis and the future of the rejuvenating brain circuits. Neuron 2015;86:387-401.

Leslie RA, Moorman JM, Grahame-Smith DG. Lithium enhances 5-HT2A receptor-mediated c-fos expression in rat cerebral cortex. Neuroreport. Dec. 13, 1993;5(3):241-4.

Li N, Lee B, Liu RJ, et al. mTOR-dependent synapse formation underlies the rapid antidepressant effects of NMDA antagonists. Science. 2010;329(5994):959-964. doi:10.1126/science.1190287.

Liu ZY, Zhong QW, Tian CN, Ma HM, Yu JJ, Hu S. NMDA receptor-driven calcium influx promotes ischemic human cardiomyocyte apoptosis through a p38 MAPK-mediated mechanism. J Cell Biochem. 2019;120(4):4872-4882.

Lledo PM, Alonso M, Grubb MS Adult neurogenesis and functional plasticity in neuronal circuits. Nature reviews Neuroscience 2006; 7:179-193.

Lledo PM, Saghatelyan A. Integrating new neurons into the adult olfactory bulb: joining the network, life-death decisions, and the effects of sensory experience. Trends in Neurosciences 2005; 28:248-254.

Lozano I, Van der Werf R, Bietiger W, Seyfritz E, Peronet C, Pinget M, Jeandidier N, Maillard E, Marchioni E, Sigrist S, Dal S. High-fructose and high-fat diet-induced disorders in rats: Impact on diabetes risk, hepatic and vascular complications. Nutrition & Metabolism 2016, 13:15.

Ly C, Greb AC, Cameron LP, et al. Psychedelics Promote Structural and Functional Neural Plasticity. Cell Rep. 2018;23(11):3170-3182.

Madsen M.K; Burmester, D; Stenbæk, D.S. Psilocybin occupancy of brain serotonin 2A receptors correlates with psilocin levels and subjective experience: a (11C) Cimbi-36 PET study in humans. European Neuropsychopharmacology, 2019, vol. 29.

Moore JX, Chaudhary N, Akinyemiju T. Metabolic Syndrome Prevalence by Race/Ethnicity and Sex in the United States, National Health and Nutrition Examination Survey, 1988-2012. Prev Chronic Dis 2017;14:160287.

Musso G, Cassader M, Gambino R. Non-alcoholic steatohepatitis: Emerging molecular targets and therapeutic strategies. Nature Review Drug Discovery 2016, 15: 249-274.

Nair AB, Jacob S. A simple practice guide for dose conversion between animals and human. J Basic Clin Pharm. 2016;7(2):27-31.

Nakamura, T. et al. Protein S-Nitrosylation as a Therapeutic Target for Neurodegenerative Diseases. Trends in Pharmacological Sciences, Jan. 2016, vol. 37, No. 1, 73-84.

Nazareth Veloso AW, Filgueiras GB, Lorenzo P, and Estanislau C., Modulation of Grooming Behavior in Rats by Different Test Situations, Psychology & Neuroscience 2016, vol. 9, No. 1, 91-104.

Nichols DE et al., 2016 Psychedelics as medicines; an emerging new paradigm, Clinical Pharmacology & Therapeutics, vol. 101, No. 2.

Ogrodnik M, Zhu Y, Langhi LGP, Tchkonia T, Kruger P, Fielder E, Victorelli S, Ruswhandi RA, Giorgadze N, Pirtskhalava T, Podgorni O, Enikolopov G, Johnson KO, Xu M, Inman C, Palmer AK, Schafer M, Weigl M, Ikeno Y, Burns TC, Passos JF, von Zglinicki T, Kirkland JL, Jurk D Obesity-Induced Cellular Senescence Drives Anxiety and Impairs Neurogenesis. Cell Metabolism 2019, 29:1061-1077.

Onogi H, Ishigaki S, Nakagawasai O, et al. Influence of memantine on brain monoaminergic neurotransmission parameters in mice: neurochemical and behavioral study. Biol Pharm Bull. 2009;32(5):850-855.

Polito V, Stevenson RJ (2019) A systematic study of microdosing psychedelics. PLOS One 14(2): e0211023.

Rambousek L, Palenicek T, Vales K, Stuchlik A. The effect of psilocin on memory acquisition, retrieval, and consolidation in the rat. Front Behav Neurosci. 2014;8:180.

Rautio et al. (2018) Nature Reviews Drug Discovery vol. 17, pp. 559-587.

Redolfi N, Galla L, Maset A, Murru L, Savoia E, Zamparo I, Gritti A, Billuart P, Passafaro M, Lodovichi C. Oligophrenin-1 regulates number morphology and synaptic properties of adult-born inhibitory interneurons in the olfactory bulb. Human Molecular Genetics 2016; 25:5198-5211.

Rickli, A. et al., Opioid-induced inhibition of the human 5-HT and noradrenaline transporters in vitro: link to clinical reports of serotonin syndrome, British Journal of Pharmacology (2018) 175:532-543.

Rochefort C, Gheusi G, Vincent JD, Lledo PM. Enriched odor exposure increases the number of newborn neurons in the adult olfactory bulb and improves odor memory. The Journal of neuroscience: the official journal of the Society for Neuroscience 2002; 22:2679-2689.

Rosanoff, A. Magnesium and hypertension. Clin Calcium. Feb. 2005; 15(2):255-60.

Sala, G. Antioxidants Partially Restore Glutamate Transport Defect in Leber Hereditary Optic Neuropathy Cybrids. Journal of Neuroscience Research 2008, 86:3331-3337.

Schmidt KG et al., Neurodegenerative diseases of the retina and potential for protection and recovery. Curr Neuropharmacol. Jun. 2008;6(2):164-78.

Sellers EM, Romach MK, Leiderman DB. Studies with psychedelic drugs in human volunteers. Neuropharmacology. Nov. 2018;142:116-134.

Sengupta P. The Laboratory Rat: Relating Its Age With Human's. Int J Prev Med. 2013;4(6):624-630.

Studerus E, Gamma A, Kometer M, Vollenweider FX. Prediction of Psilocybin Response in Healthy Volunteers. PLoS One. 2012;7(2) e30800.

Studerus E, Kometer M, Hasler F, Vollenweider FX. Acute, subacute and long-term subjective effects of psilocybin in healthy humans: a pooled analysis of experimental studies. J Psychopharmacol. Nov. 2011;25(11):1434-52.

(56) References Cited

OTHER PUBLICATIONS

Varma R et al. Visual Impairment and Blindness in Adults in the United States: Demographic and Geographic Variations From 2015 to 2050. JAMA Ophthalmol. Jul. 1, 2016;134(7):802-9.
Vitolo OV, Manfredi PL, Inturrisi CE, DiGuglielmo G, Hanania T, Bernstein G, DeMartin S, Fogaca M, Duman R, Traversa S. Development of the N-Methyl-D-Aspartate Receptor (NMDAR) Antagonist d-Methadone (REL 1017) for the Treatment of Depression and Other CNS Disorders. American Society of Clinical Psychopharmacology annual meeting, May 2019.
Wolfensberger, TJ. Macular Edema—Rationale for Therapy. Dev Ophthalmol. 2017; 58:74-86.
Xu T, Pandey SC. Cellular localization of serotonin2A (5-HT2A) receptors in the rat brain. Brain Res Bull. Apr. 2000;51(6):499-505.
Zhong P, Yuen EY, Zhen Yan. Modulation of Neuronal Excitability by Serotonin-NMDA Interactions in Prefrontal Cortex. Mol Cell Neurosci. Jun. 2008; 38(2):290-299.
Arvanov et.al. LSD and DOB: interaction with 5-HTa receptors to inhibit NMDA receptor mediated transmission in the rat prefrontal cortex in European Journal of Neuroscience, 2001, vol. 11(9), pp. 1-7. abstract.
Brown, et.al. Pharmacokinetics of Escalating Doses of Oral Psilocybin in Healthy Adults in Clin Pharmacokinet., 2017, vol. 56, pp. 1543-1554. abstract; p. 1544, col. 1, para 1; p. 1551, Table 4.
Catlow et.al. Effects of psilocybin on hippocampal neurogenesis and extinction of trace fear conditioning in Exp. Brain Res. 2013, vol. 228, pp. 481-491. abstract ; p. 487, col. 2, para 3; p. 489, col. 1, para 1.
Farber et.al. Serotonergic Agents that Activate 5HT2A Receptors Prevent NMDA Antagonist Neurotoxicity in Neuropsychopharmacology, 1998, vol. 18(1), pp. 57-62. Abstract.
International Search Report and Written Opinion in International Patent Application No. PCT/US2020/021400, dated Jul. 8, 2020, 13 pgs.
Ahmed, Hazem et al: "N-Methyl-D-Aspartate (NMDA) receptor modulators: a patent review (2015-present)", Expert Opinion on Therapeutic Patents, vol. 30, No. 10, Oct. 2, 2020 (Oct. 2, 2020), pp. 743-767.
Baird, David B. et al: "Intramolecular Amination of p-Benzoquinones : Formation of 1,2,3,5-Tetrahydrobenzo[1,2-b:4,5-b']dipyrroles and 1,2,3,4-Tetrahydropyrido-[2,3-g]quinolines", J.C.S. Perkin I, Jan. 1, 1973 (Jan. 1, 1973), pp. 832-839.
Baltzly, Richard et al: "Synthetic Analogs of Oxytocic Drugs. I. Phenethyl [beta]-Alanine Derivatives", Journal of the American Chemical Society, vol. 71, No. 4, Apr. 1, 1949 (Apr. 1, 1949), pp. 1162-1164.
Blaazer, Antoni R et al: "Structure-Activity Relationships of Phenylalkylamines as Agonist Ligands for 5-HT2A Receptors", Chemmedchem Communications, Wiley-VCH, DE, vol. 3, No. 9, Jul. 30, 2008 (Jul. 30, 2008), pp. 1299-1309.
Bryson, Alexander et al: "5-HT2A Agonists: A Novel Therapy for Functional Neurological Disorders?", International Journal of Neuropsychopharmacology, vol. 20, No. 5, Feb. 8, 2017 (Feb. 8, 2017), pp. 422-427.
Cameron, Lindsay P. et al: "Chronic, Intermittent Microdoses of the Psychedelic, N,N-Dimethyltryptamine (DMT) Produce Positive Effects on Mood and Anxiety in Rodents", ACS Chemical Neuroscience, vol. 10, No. 7, Mar. 4, 2019 (Mar. 4, 2019), pp. 3261-3270.
Caspar. Achim T. et al: "Metabolic fate and detectability of the new psychoactive substances 2-(4-bromo-2,5-dimethoxypheny1)-N-[(2-methoxyphenyl)methyl]ethanamine (25B-NBOMe) and 2-(4-chloro-2,5-dimethoxyphenyl)-N-[(2-methoxyphenyl)methyl]ethanamine (25C-NBOMe) in human and rat urine by GC-MS, LC-MSn, and LC-HR-MS/MS approaches", Journal of Pharmaceutical and Biomedical Analysis, Elsevier B.V, Amsterdam, NL, vol. 134, Nov. 27, 2016 (Nov. 27, 2016), pp. 158-169.
Catlow, Briony J. et al: "Effects of psilocybin on hippocampal neurogenesis and extinction of trace fear conditioning", Experimental Brain Research, vol. 228, No. 4, Jun. 2, 2013 (Jun. 2, 2013), pp. 481-491.
Eshleman, Amy J. et al: "Neurochemical pharmacology of psychoactive substituted N-benzylphenethylamines: High potency agonists at 5-HT2A receptors", Biochemical Pharmacology, vol. 158, Dec. 1, 2018 (Dec. 1, 2018), pp. 27-34.
European Search Report in European Patent Application No. 23162422.2, dated Jun. 26, 2023, 31 pgs.
European Search Report in European Patent Application No. 23162424.8, dated Jun. 23, 2023, 17 pgs.
European Search Report in European Patent Application No. 23162430.5, dated Jun. 26, 2023, 15 pgs.
European Search Report in European Patent Application No. 23162442.0, dated Jul. 20, 2023, 18 pgs.
Glennon, Richard A et al: "5-HT1 and 5-HT2 binding characteristics of 1-(2,5-dimethoxy-4-bromopheny1)-2-aminopropane analogues", Journal of Medicinal Chemistry, vol. 29, No. 2, Feb. 1, 1986 (Feb. 1, 1986), pp. 194-199.
Glennon, Richard A. et al: "Beta-Oxygenated Analogues of the 5-HT2A Serotonin Receptor Agonist 1-(4-Bromo-2,5-dimethoxyphenyl)-2-aminopropane", Journal of Medicinal Chemistry, American Chemical Society, US, vol. 47, No. 24, Nov. 18, 2004 (Nov. 18, 2004), pp. 6034-6041.
Glennon, Richard A. et al: "Binding of phenylalkylamine derivatives at 5-HT1C and 5-HT2 serotonin receptors: evidence for a lack of selectivity", Journal of Medicinal Chemistry, vol. 35, No. 4, Feb. 1, 1992 (Feb. 1, 1992), pp. 734-740.
Glennon, Richard A. et al: "Influence of Amine Substituents on 5-HT2A Versus 5-HT2C Binding of Phenylalkyl- and Indolylalkylamines", Journal of Medicinal Chemistry, American Chemical Society, US, vol. 37, No. 13, Jan. 1, 1994 (Jan. 1, 1994), pp. 1929-1935.
Glennon, Richard A. et al: "N-Methyl derivatives of the 5-HT2 agonist 1-(4-bromo-2,5-dimethoxypheny1)-2-aminopropane", Journal of Medicinal Chemistry, vol. 30, No. 5, May 1, 1987 (May 1, 1987), pp. 930-932.
Hamilton, Stephen Bancroft et al: "Electrophilic substitution in highly substituted diphenyl ethers", The Journal of Organic Chemistry, vol. 35, No. 10, Oct. 1, 1970 (Oct. 1, 1970), pp. 3342-3348.
Hisashi, Ishii et al: "Studies on lysergic acid diethylamide and related compounds. IX. Microbial transformation of amides related to lysergic acid diethylamide by Streptomyces roseochromogenes.", Chemical and Pharmaceutical Bulletin, vol. 27, No. 12, Jan. 1, 1979 (Jan. 1, 1979), pp. 3029-3038.
Kaga, Atsushi et al: "Nucleophilic Amination of Methoxy Arenes Promoted by a Sodium Hydride/Iodide Composite", Angewandte Chemie International Edition, Verlag Chemie, Hoboken, USA, vol. 56, No. 39, Aug. 16, 2017 (Aug. 16, 2017), pp. 11807-11811.
Kucklander, Uwe et al: "Synthese and Oxidation von 3-(2,5-Dihydroxyphenyl)-propylamin-Derivaten" Archiv Der Pharmazie, vol. 322, No. 4, Jan. 1, 1989 (Jan. 1, 1989), pp. 213-221.
Luo, Wei et al: "Biomolecular modification of carbon nanotubes for studies of cell adhesion and migration; Biomolecular modification of carbon nanotubes for studies of cell adhesion and migration", Nanotechnology, Institute of Physics Publishing, Bristol, GB, vol. 22, No. 49, Nov. 21, 2011 (Nov. 21, 2011), 494019 ( 8 pgs.).
Ly, Calvin et al: "Psychedelics Promote Structural and Functional Neural Plasticity", Cell Reports, vol. 23, No. 11, Jun. 1, 2018 (Jun. 1, 2018), pp. 3170-3182.
Madsen, Martin K et al: "Psychedelic effects of psilocybin correlate with serotonin 2A receptor occupancy and plasma psilocin levels", Neuropsychopharmacology, Springer International Publishing, Cham, vol. 44, No. 7, Jan. 26, 2019 (Jan. 26, 2019), pp. 1328-1334.
May, Jesse A. et al: "A Novel and Selective 5-HT2 Receptor Agonist with Ocular Hypotensive Activity: (S)-(+)-1-(2-Aminopropy1)-8,9-dihydropyrano[3,2-e ]indole", Journal of Medicinal Chemistry, vol. 46, No. 19, Sep. 1, 2003 (Sep. 1, 2003), pp. 4188-4195.
Monte, Aaron P. et al: "Stereoselective LSD-like Activity in a Series of d-Lysergic Acid Amides of (R)- and (S)-2-Aminoalkanes", Journal of Medicinal Chemistry, vol. 38, No. 6, Mar. 1, 1995 (Mar. 1, 1995), pp. 958-966.
Nason, Deane M. et al: "Substituted 6-phenyl-pyridin-2-ylamines: selective and potent inhibitors of neuronal nitric oxide synthase", Bioorganic & Medicinal Chemistry Letters, vol. 14, No. 17, Sep. 1, 2004 (Sep. 1, 2004), pp. 4511-4514.

(56) References Cited

OTHER PUBLICATIONS

Nichols, David E.: "Psychedelics", Pharmacological Reviews, vol. 68, No. 2, Feb. 3, 2016 (Feb. 3, 2016), pp. 264-355.
Prochazkova, Luisa et al: "Exploring the effect of microdosing psychedelics on creativity in an open-label natural setting", Psychopharmacology, Springer Verlag, Berlin, DE, vol. 235, No. 12, Oct. 25, 2018 (Oct. 25, 2018), pp. 3401-3413.
Richard T Layer et al: "Structurally modified ibogaine analogs exhibit differing affinities for NMDA receptors", European Journal of Pharmacology, vol. 309, No. 2, Jan. 1, 1996 (Jan. 1, 1996), pp. 159-165.
Sargent, Thornton et al: "Radiohalogen-labeled imaging agents. 3. Compounds for measurement of brain blood flow by emission tomography", Journal of Medicinal Chemistry, vol. 27, No. 8, Aug. 1, 1984 (Aug. 1, 1984) pp. 1071-1077.
Stoll, A et al: "Amide der stereoisomeren Lysergs&uren and Dihydrolysergs&uren. 38. Mitteilung fiber Mutterkornalkaloide", Helvetica Chimica Acta, Verlag Helvetica Chimica Acta, Hoboken, USA, vol. 38, No. 3, Jan. 1, 1955 (Jan. 1, 1955), pp. 421-433.
Troxler, F. et al: "Substitutionen am Ringsystem der Lysergsaure. III. Halogenierung. 45. Mitteilung uber Mutterkornalkaloide", Helvetica Chimica Acta, vol. 40, No. 7, Jan. 1, 1957 (Jan. 1, 1957), pp. 2160-2170.
Blair, J B et al: "Effect of Ring Fluorination on the Pharmacology of Hallucinogenic Tryptamines", Journal of Medicinal Chemistry, American Chemical Society, US, vol. 43, Jan. 1, 1992 (Jan. 1, 1992), pp. 2061-2064.
Blough, Bruce E et al: "Alpha-ethyltryptamines as dual dopamine-serotonin releasers", Bioorganic & Medicinal Chemistry Letters, Elsevier, Amsterdam NL, vol. 24, No. 19, Jul. 29, 2014 (Jul. 29, 2014), pp. 4754-4758.
Cozzi, Nicholas V et al: "Receptor binding profiles and quantitative structure-affinity relationships of some 5-substituted-N, N-diallyltryptamines", Bioorganic & Medicinal Chemistry Letters, Elsevier, Amsterdam NL, vol. 26, No. 3, Dec. 18, 2015 (Dec. 18, 2015), pp. 959-964.
European Supplementary Partial European Search Report in European Patent Application No. 20766059.8, dated Nov. 24, 2022, 25 pgs.
Lyon, R A et al: "Indolealkylamine analogs share 5-HT2 binding characteristics with phenylalkylamine hallucinogens", European Journal of Pharmacology, Elsevier Science, NL, vol. 145, No. 3, Jan. 19, 1988 (Jan. 19, 1988), pp. 291-297.
Nirogi, Ramakrishna V.S. et al: "Synthesis and structure-activity relationship of novel conformationally restricted analogues of serotonin as 5-HT6 receptor ligands", Journal of Enzyme Inhibition and Medicinal Chemistry, vol. 27, No. 3, Jul. 21, 2011 (Jul. 21, 2011), pp. 443-450.
Sherwood, Alexander M. et al: "Synthesis and Biological Evaluation of Tryptamines Found in Hallucinogenic Mushrooms: Norbaeocystin, Baeocystin, Norpsilocin, and Aeruginascin", Journal of Natural Products, vol. 83, No. 2, Feb. 28, 2020 (Feb. 28, 2020), pp. 461-467.
Alkhouri N, Lawitz E, Noureddin M. Looking Into the Crystal Ball: Predicting the Future Challenges of Fibrotic NASH Treatment. Hepatology Communications Mar. 2019: 605-613.
Anderson T, Petranker R, Rosenbaum D, Weissman CR, Dinh-Williams LA, Hui K, Hapke E, Farb NAS. Microdosing psychedelics: personality, mental health, and creativity differences in microdosers. Psychopharmacology (Berl). Jan. 20, 2019.
Arreola R.et al. Immunomodulatory effects mediated by serotonin J Immunol Res. 2015, 354957 (2015).
Azzolini et al., New natural amino acid-bearing prodrugs boost pterostilbene's oral pharmacokinetic and distribution profile, European Journal of Pharmaceutics and Biopharmaceutics, vol. 115, 2017, pp. 149-158 ISSN 0939-6411.
Baez MV, Cercato MC, Jerusalinsky DA. NMDA Receptor Subunits Change after Synaptic Plasticity Induction and Learning and Memory Acquisition. Neural Plast. 2018.
Baganz N.L.& Blakely, R.D. A dialogue between the immune system and brain, spoken in the language of serotonin. ACS Chem. Neurosci. 4, 48-63 (2013).
Barrett FS, Carbonaro TM, Hurwitz E, Johnson MW, Griffiths RR. Double-blind comparison of the two hallucinogens psilocybin and dextromethorphan: effects on cognition. Psychopharmacology (Berl). Oct. 2018;235(10):2915-2927.
Bayne T, Carter O. Dimensions of consciousness and the psychedelic state. Neurosci Conscious. 2018;2018(1).
Berger ML, Palangsuntikul R, Rebernik P, Wolschann P, Berner H. Tryptamines at NMDA, 5-HT1A, and 5-HT2A Receptors: A Comparative Binding and Modeling Study. Current Medicinal Chemistry, 2012, 19, 3044-3057.
Blair JB, Kurrasch-Orbaugh D, Marona-Lewicka D, Cumbay MG, Watts VJ, Barker EL, Nichols DE. Effect of ring fluorination on the pharmacology of hallucinogenic tryptamines. J Med Chem. Nov. 30, 2000;43(24):4701-10.
Blasco-Serra A, González-Soler EM, Cervera-Ferri A, Teruel-Marti V, Valverde-Navarro AA. A standardization of the Novelty-Suppressed Feeding Test protocol in rats. Neurosci Lett. Sep. 29, 2017;658:73-78. doi: 10.1016/j.neulet.2017.08.019. Epub Aug. 10, 2017. PMID: 28803957.
Brachman RA, McGowan JC, Perusini JN, et al. Ketamine as a Prophylactic Against Stress-Induced Depressive-like Behavior. Biol Psychiatry. 2016;79(9):776-786.
Brown RT, Nicholas CR, Cozzi NV, Gassman MC, Cooper KM, Muller D, Thomas CD, Hetzel SJ, Henriquez KM, Ribaudo AS, Hutson PR. Pharmacokinetics of Escalating Doses of Oral Psilocybin in Healthy Adults. Clin Pharmacokinet. Dec. 2017;56 (12):1543-1554.
Byrne CD, Targher, G. NAFLD: A multisystem disease. Journal of Hepatology 2015, 62: S47-S64.
Carhart-Harris RL, Roseman L, Bolstridge M, Demetriou L, Nienke J Pannekoek, Wall MB, Tanner M, Kaelen M, McGonigle J, Murphy K, Leech R, Curran HV, Nutt DJ. Psilocybin for treatment-resistant depression: fMRI-measured brain mechanisms Scientific Reports vol. 7, Article No. 13187 (2017).
Castanon N, Lasselin J, Capuron L. Neuropsychiatric Comorbidity in Obesity: Role of Inflammatory Processes. Frontiers in Endocrinology, May 2014: 74.
Ceglia I, Carli M, Baviera M, Renoldi G, Calcagno E. The 5-HT2A receptor antagonist M100,907 prevents extracellular glutamate rising in response to NMDA receptor blockade in the mPFC. Journal of Neurochemistry, 2004, 91, 189-199.
Celiker, H et al., Neuroprotective Effects of Memantine in the Retina of Glaucomatous Rats: An Electron Microscopic Study. J Ophthalmic Vis Res. Apr.-Jun. 2016; 11(2):174-82.
Chenu C, Serre CM, Raynal C, Burt-Pichat B and Delmas PD (1998) Glutamate receptors are expressed by bone cells and are involved in bone resorption. Bone 22:295-299.
Choi DW, Viseskul V., 1988. Opioids and non-opioid enantiomers selectively attenuate N-methyl-D-aspartate neurotoxicity on cortical neurons. Eur J Pharmacol 155, 27-35.
Codd et al., Serotonin and Norepinephrine activity of centrally acting analgesics: Structural determinants and role in antinociception. IPET 1995; 274 (3)1263-1269.
Davis M, Walters JK. Psilocybin: biphasic dose-response effects on the acoustic startle reflex in the rat. Pharmacol Biochem Behav. 1977;6(4):427-431.
De Martin S, Vitolo OV, Bernstein G, Alimonti A, Traversa S, Inturrisi CE, Manfredi PL. The NMDAR Antagonist Dextromethadone Increases Plasma BDNF levels in Healthy Volunteers Undergoing a 14-day In-Patient Phase 1 Study. ACNP annual meeting, Dec. 9-13, 2018; Hollywood, Florida.
Delyfer, MN et al., Evidence for glutamate-mediated excitotoxic mechanisms during photoreceptor degeneration in the rd1 mouse retina. Mol Vis. Sep. 1, 2005; 11:688-96.
Du Jardin K.G., Liebenberg N., Müller H.K. et al. Differential interaction with the serotonin system by S-ketamine, vortioxetine, and fluoxetine in a genetic rat model of depression. Psychopharmacology 2016; 233, 2813-2825.
Esfahani, MR et al., Memantine for axonal loss of optic neuritis. Graefes Arch Clin Exp Ophthalmol. Jun. 2012; 250(6):863-9.

(56) References Cited

OTHER PUBLICATIONS

Fadiman J, Korb S. Might Microdosing Psychedelics Be Safe and Beneficial? An Initial Exploration. J Psychoactive Drugs. Mar. 29, 2019:1-5.
Farber NB, M.D., Hanslick J, Kirby C, McWilliams L, Olney JW. Serotonergic agent that activate 5-HT2A receptors prevent NMDA antagonist neurotoxicity. Neuropsychopharmacology 1998—vol. 18, No. 1.
Flanagan TW, Nichols CD. Psychedelics as anti-inflammatory agents. Int Rev Psychiatry. Aug. 13, 2018:1-13.
Fogaça MV, Fukumoto K, Franklin T, et al. N-Methyl-D-aspartate receptor antagonist d-methadone produces rapid, mTORC1-dependent antidepressant effects. Neuropsychopharmacology. 2019;44(13):2230-2238.
González-Maeso J, Ang RL, Yuen T, et al. Identification of a serotonin/glutamate receptor complex implicated in psychosis. Nature. 2008;452(7183):93-97. doi:10.1038/nature06612.
Griffiths RR, Richards WA, Johnson MW, McCann UD, Jesse R. Mystical-type Experiences Occasioned by Psilocybin Mediate the Attribution of Personal Meaning and Spiritual Significance 14 Months Later. J Psychopharmacol. Aug. 2008;22(6):621-32.
Guzmán G, Hanlin RT, White C. Another new bluing species of Psilocybe from Georgia, U.S.A. Mycotaxon 2003; 86:179-183.
Halberstadt AL, Geyer MA. Multiple receptors contribute to the behavioral effects of indoleamine hallucinogens. Neuropharmacology. Sep. 2011;61(3):364-81.
Halpern, J. H., Hallucinogens: An Update, Current Psychiatry Reports (2003) 5:347-354.
Hasler F, Bourquin D, Brenneisen R, Bär T, Vollenweider FX. Determination of psilocin and 4-hydroxyindole-3-acetic acid in plasma by HPLC-ECD and pharmacokinetic profiles of oral and intravenous psilocybin in man. Pharm Acta Helv. 1997;72(3):175-184. doi: 10.1016/s0031-6865(97)00014-9.
Hasler F, Grimberg U, Benz MA, Huber T, Vollenweider FX. Acute psychological and physiological effects of psilocybin in healthy humans: a double-blind, placebo-controlled dose-effect study. Psychopharmacology (Berl). 2004;172(2):145-156. doi:10.1007/s00213-003-1640-6.
Honyiglo E Franchi A; Cartiser: Unpredictable Behavior Under the Influence of "Magic Mushrooms": A Case Report land Review of the Literature. Journal of Forensic Sciences, Dec. 2018.
Houston, M. The role of magnesium in hypertension and cardiovascular disease. J Clin Hypertens (Greenwich). Nov. 2011; 13(11):843-7.
Howell, N. Leber hereditary optic neuropathy: respiratory chain dysfunction and degeneration of the optic nerve. 1988 Vis Res 38:1495-1504.
Inturrisi, CE. NMDA receptors, nitric oxide and opioid tolerance. Regulatory Peptides, 1994, vol. 54, Issue 1.
Ito Y et al., Degenerative alterations in the visual pathway after NMDA-induced retinal damage in mice. Brain Res. May 30, 2008;1212:89-101.
Jacob III, P.; Shulgin, A.T. in NIDA Research Monograph 146 (Hallucinogens, an Update), 2000, Eds. Lin, G.C.; Glennon, R.A., pp. 74.
Johnson MW, Griffiths RR, Hendricks PS, Henningfield JE. The abuse potential of medical psilocybin according to the 8 factors of the Controlled Substances Act. Neuropharmacology. Nov. 2018;142:143-166.
Johnson MW, Richards W, Griffiths R. Human hallucinogen research: guidelines for safety. J Psychopharmacol. Aug. 2008;22(6):603-20.
Johnson MW, Sewell AR. Griffiths RR. Psilocybin dose-dependently causes delayed, transient headaches in healthy volunteers Drug and Alcohol Dependence, 2011, vol. 123, Issue 1, 132-40.
Kapur S, Seeman P. NMDA receptor antagonists ketamine and PCP have direct effects on the dopamine D2 and serotonin 5-HT2 receptors—implications for models of schizophrenia. Mol Psychiatry. 2002;7(8):837-44.
Kim H.K. et al., Mitochondrial dysfunction and lipid peroxidation in rat frontal cortex by chronic NMDA administration can be partially prevented by lithium treatment. J Psychiatr Res. May 2016;76:59-65.
Kvam TM, Stewart LH, Andreassen OA. Psychedelic drugs in the treatment of anxiety, depression and addiction. Tidsskr Nor Laegeforen. Nov. 12, 2018;138(18).
Lambert JE, Ramos-Roman MA, Browning JD, Parks EJ. Increased de novo lipogenesis is a distinct characteristic of individuals with nonalcoholic fatty liver disease. Gastroenterology 2014, 146: 726-735.
Pubchem, Psilocybine, Page Created Mar. 27, 2005, https://pubchem.ncbi.nlm.nih.gov/compound/10624.†
Pubchem, Baeocystin, Page Created Aug. 8, 2005, https://pubchem.ncbi.nlm.nih.gov/compound/Baeocystin.†
Pubchem, Psilocin, Page Created Mar. 25, 2005, https://pubchem.ncbi.nlm.nih.gov/compound/Psilocin.†
Pubchem, Norpsilocin, Page Created 9Â Feb. 2007, https://pubchem.ncbi.nlm.nih.gov/compound/14107683.†
Pubchem, Norbaeocystin, Page Created Oct. 25, 2006, https://pubchem.ncbi.nlm.nih.gov/compound/Norbaeocystin.†
Pubchem, Ibogaine, Page CreatedÂ Aug. 8, 2005Â,Âhttps://pubchem.ncbi.nlm.nih.gov/compound/Ibogaine.†
Pubchem, N,N-Dimethyltryptamine, Page Created Mar. 26, 2005, https://pubchem.ncbi.nlm.nih.gov/compound/N_N-Dimethyltryptamine.†
Pubchem, Lysergide, Page Created 8Â Jun. 2005, https://pubchem.ncbi.nlm.nih.gov/compound/Lysergide.†
Johnstad, Powerful substances in tiny amounts: An interview study of psychedelic microdosing, vol. 35(1):39-51, Nordic Studies on Alcohol and Drugs. Published Feb. 15, 2018.†
Aronson, Mansons Tropical Infectious Diseases (Twenty-Third Edition). ISBN: 9780702051012. Published 2014.†
Polito, A systematic study of microdosing psychedelics, vol. 14(2):1-26, PLOS One. Published Feb. 6, 2019.†
Olgun, Deuteronation and Aging, vol. 1100(1):400-403, Annals of the New York Academy of Sciences. Published Apr. 18, 2007.†
Auffret,Â The Many Faces of Apomorphine: Lessons from the Past and Challenges for the Future, vol. 18:91-107, Drugs in Rand D.Published May 8, 2018.†
Pubchem, 2,5-Dimethoxy-N,N-dimethyl-4-iodoamphetamine, Page Created Aug. 8, 2005Â,2005, https://pubchem.ncbi.nlm.nih.gov/compound/2_5-Dimethoxy-N_N-dimethyl-4-iodoamphetamine.†
Madsen. Psychedelic effects of psilocybin correlate with serotonin 2A receptor occupancy and plasma psilocin levels. vol. 44(7):1336, Neuropsychopharmacology. Published Jan. 26, 2019.†
Gregorio. d-Lysergic acid diethylamide, psilocybin, and other classic hallucinogens: Mechanism of action and potential therapeutic applications in mood disorders. vol. 242:69-96.Â Progress in Brain Research. Published Aug. 31, 2018.†
Farber, Serotonergic Agents That Activate 5HT2A Receptors Prevent NMDA Antagonist Neurotoxicity. vol. 18:57-62,Â Neuropsychopharmacology. Published Jan. 1, 1998.†

* cited by examiner
† cited by third party

NMDAR1

NMDAR2A

NMDAR2B

5HT2C

5HT2A

NMDAR

KERATOCYTE

5HT2C

5HT2A

No UVB

No UVB

UVB without treatment

UVB without treatment

UVB without treatment

UVB without treatment

D-Methadone 10 nM (0.01µM)

D-Methadone 10 nM (0.01µM)

D-Methadone 10 nM (0.01μM)

D-Methadone 10 nM (0.01μM)

D-Methadone 500 nM

D-Methadone 500 nM

D-Methadone 10 nM + Psilocin 5 nM

D-Methadone 10 nM + Psilocin 5 nM

D-Methadone 10 nM + Psilocin 5 nM

D-Methadone 10 nM + Psilocin 5 nM

D-Methadone 500 nM + Psilocin 5 nM

D-Methadone 500 nM + Psilocin 5 nM

D-Methadone 500 nM + Psilocin 5 nM

D-Methadone 500 nM + Psilocin 5 nM

Psilocin 5 nM

Psilocin 5 nM

Psilocin 5 nM

Psilocin 5 nM

Psilocin 10 nM + D-Methadone 10 nM

Psilocin 10 nM + D-Methadone 10 nM

Psilocin 10 nM + D-Methadone 10 nM

Psilocin 10 nM + D-Methadone 10 nM

COMPOSITIONS AND METHODS OF USE COMPRISING SUBSTANCES WITH NEURAL PLASTICITY ACTIONS ADMINISTERED AT NON-PSYCHEDELIC/PSYCHOTOMIMETIC DOSAGES AND FORMULATIONS

CROSS-REFERENCE TO RELATED APPLICATIONS

This application claims priority to and the benefit of the filing date of U.S. Patent Application No. 62/814,929, filed on Mar. 7, 2019, and U.S. Patent Application No. 62/844,151, filed on May 7, 2019, the disclosures of which are incorporated by reference herein in their entireties.

FIELD OF THE INVENTION

Various aspects of the present invention relate to compositions and methods including substances providing neural plasticity, and the administration of those substances at non-psychedelic and/or psychotomimetic dosages.

BACKGROUND OF THE INVENTION

The sections below are intended to introduce the reader to various aspects of art that may be related to various aspects of the present invention, which are described and/or claimed below. This discussion is believed to be helpful in providing the reader with background information to facilitate a better understanding of various aspects of the present invention. Accordingly, it should be understood that these statements are to be read in this light, and not as admissions of prior art.

Both the medical establishment and conventional wisdom define psychedelic substances, (including those in in the triptan family, and including substances classified as 5-HT2A agonists), by their ability to determine certain alterations in consciousness, emotion, and cognition, including positive and negative psychotomimetic symptoms (e.g., psychedelic effects, psychedelic experience, psychotomimetic effects). These psychedelic/psychotomimetic effects are known to laymen and doctors for their potential recreational misuse and to researchers in the psychiatric field for their potential therapeutic uses in psychiatry and research applications for the study of brain function. In the case of substances in the triptan family, these psychedelic/psychotomimetic effects are thought to be primarily induced by agonist actions at the 5-HT 2A receptor in the 5-HT receptor family.

Psychedelic substances are presently under investigation for the treatment of several psychiatric diseases and symptoms, including depression, PTSD, OCD, addiction, end-stage-cancer-associated anxiety. From the available scientific literature and other disclosures (including patents and patent applications), and from clinical studies currently underway, the psychedelic experience, which includes positive and negative psychotomimetic effects induced by a serotonin agonist substance, is an integral part of the intended treatment, the research applicability, and even the recreational misuses of these substances. In particular for therapeutic purposes, serotonin agonist psychedelic drugs are administered in a particular "setting" and preceded and followed by counseling and or psychotherapy and the whole session is supervised and closely monitored (Johnson M, Richards W, Griffiths R. Human hallucinogen research: guidelines for safety. J Psychopharmacol. 2008 August; 22(6):603-20). According to researchers and therapists, to achieve therapeutic efficacy for certain psychiatric disorders, the administration of the serotonin agonist at a dose that produces psychedelic and or psychotomimetic symptoms should be paired with ancillary therapies, which include a particular physical setting, in addition to pre, during and post drug administration counseling and/or psychotherapy (talk therapy). The psychedelic experience (which includes alterations in consciousness, emotion, and cognition, and positive and negative psychotomimetic symptoms) is thus viewed by researchers and scientists, to this day, as integral part of the potential therapeutic efficacy of psychedelic drugs.

The psychedelic drug is generally administered once in a single session (single dose of a psychedelic substance) with acute psychedelic/psychotomimetic effects lasting approximately four to six hours. In addition to the acute effects, psychological beneficial effects lasting months after a single session have been described and contribute to the current understanding of the potential beneficial effects of treatment with 5-HT agonist drugs [Griffiths R R, Richards W A, Johnson M W, McCann U D, Jesse R. Mystical-type Experiences Occasioned by Psilocybin Mediate the Attribution of Personal Meaning and Spiritual Significance 14 Months Later. J Psychopharmacol. 2008 August; 22(6):621-32); Carhart-Harris R L, Roseman L, Bolstridge M, Demetriou L, Nienke J Pannekoek, Wall M B, Tanner M, Kaelen M, McGonigle J, Murphy K, Leech R, Curran H V, Nutt D J. Psilocybin for treatment-resistant depression: fMRI-measured brain mechanisms Scientific Reports volume 7, Article number: 13187 (2017)].

The mechanisms underlying the potential effectiveness of 5-HT2A agonists administered in large "psychedelic/psychotomimetic" dosages (single sessions) for depression has been recently linked to BDNF and mToR pathways and has been potentially related to neural plasticity (Ly C, Greb A C, Cameron L P, et al. Psychedelics Promote Structural and Functional Neural Plasticity. Cell Rep. 2018; 23(11):3170-3182.).

Select NMDAR antagonists (open channel blockers) have been found to be effective for neurological and psychiatric diseases (for example, memantine, amantadine, and a dextromethorphan-quinidine combination are respectively FDA approved for Alzheimer's dementia, Parkinson disease and emotional lability secondary to pseudobulbar palsy; and esketamine is FDA approved for treatment resistant depression). In addition, another NMDAR antagonist, dextromethadone, is under investigation for psychiatric disorders and for a multiplicity of neurological diseases, syndromes and signs and symptoms (henceforth defined as "neuropsychiatric disorders") and ophthalmological, and metabolic disorders and disorders associated with aging (U.S. Pat. No. 9,468,611 and International Patent Application No. PCT/US2018/016159). Dextromethorphan in combination with bupropion is under investigation for depression and for agitation in dementia (Axsome Therapeutics).

Additionally, there is mounting evidence for actions of NMDAR antagonists, in particular ketamine and dextromethadone, in modulating neural plasticity (Li N, Lee B, Liu R J, et al. mTOR-dependent synapse formation underlies the rapid antidepressant effects of NMDA antagonists. Science. 2010; 329(5994):959-964. doi:10.1126/science.1190287; Vitolo O V, Manfredi P L, Inturrisi C E, DiGuglielmo G, Hanania T, Bernstein G, DeMartin S, Fogaca M, Duman R, Traversa S. Development of the N-Methyl-D-Aspartate Receptor (NMDAR) Antagonist d-Methadone (REL 1017) for the Treatment of Depression and Other CNS Disorders. American Society of Clinical Psychopharmacology annual meeting, May 2019; Fogaga M V, Fukumoto K, Franklin T, et al. N-Methyl-D-aspartate receptor antagonist d-methadone produces rapid, mTORC1-dependent antidepressant effects. Neuropsychopharmacology. 2019; 44(13):2230-2238).

Thus, the therapeutic potential of NMDAR antagonists at dosages that do not cause psychedelic or psychotomimetic effects, has been established for select drugs and select diseases (memantine, adamantine and dextromethorphan/quinidine are FDA respectively approved for Alzheimer's dementia, Parkinson disease and emotional lability secondary to pseudobulbar palsy). Of note, the esketamine's dosage recently approved by the FDA for the treatment of depression remains high enough to cause some degree of psychedelic/psychotomimetic effects (dissociative effects) and at this time the treatment with esketamine is restricted to treatment resistant depression and requires supervision in the physician's office.

Further of note, the mechanisms underlying the potential effects of 5-HT2A agonists for the treatment of depression (Ly et al., 2018), and the mechanism underlying the potential effectiveness of NMDAR antagonists for a multiplicity of disorders and conditions, are both thought to be MTorR and BDNF dependent (International Patent Application No. PCT/US2018/016159; De Martin S, Vitolo O V, Bernstein G, Alimonti A, Traversa S, Inturrisi C E, Manfredi P L. The NMDAR Antagonist Dextromethadone Increases Plasma BDNF levels in Healthy Volunteers Undergoing a 14-day In-Patient Phase 1 Study. ACNP annual meeting, Dec. 9-13, 2018; Hollywood, Florida; Li N, Lee B, Liu R J, et al. mTOR-dependent synapse formation underlies the rapid antidepressant effects of NMDA antagonists. Science. 2010; 329(5994):959-964. doi:10.1126/science.1190287; Fogaga M V, Fukumoto K, Franklin T, et al. N-Methyl-D-aspartate receptor antagonist d-methadone produces rapid, mTORC1-dependent antidepressant effects. Neuropsychopharmacology. 2019; 44(13):2230-2238). These mechanisms for inducing neural plasticity were however thought to be distinct, one mechanism mediated via 5-HT2A receptors and the other mechanism mediated by open channel block of NMDARs.

SUMMARY OF THE INVENTION

Certain exemplary aspects of the invention are set forth below. It should be understood that these aspects are presented merely to provide the reader with a brief summary of certain forms the invention might take and that these aspects are not intended to limit the scope of the invention. Indeed, the invention may encompass a variety of aspects that may not be explicitly set forth below.

One aspect of the present invention is directed to a compound comprising a structural analogue to psilocin, norpsilocin, psilocybin, baeocystin, norbaeocystin or N,N-dimethyltryptamine, according to formula I:

(I)

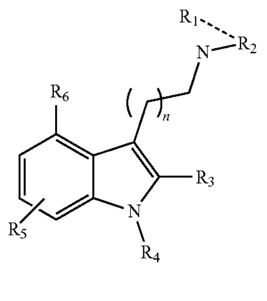

wherein (1) R1 and R2 are, independently, hydrogen, deuterium, C1-C8 alkyl, C2-C8 alkenyl, C2-C8 alkynyl, C3-C8 cycloalkyl (independently or ring close with the nitrogen), C3-C8 cycloalkenyl (independently or ring close with the nitrogen), aryl or heterocyclyl, optionally substituted at one or more positions by deuterium, halogen, alkyl, alkyl ester, hydroxy, alkoxy, carboxy, formyl, aryl, aryloxy, heterocyclyl, amino, alkylamino, arylamido, alkylamido, thiol, thioalkyl, thioaryl, alkylsulfonyl, alkylcarbamoyl, arylcarbamoyl, nitro, cyano, nitrate; (2) R3 is hydrogen, deuterium, C1-C8 alkyl, C2-C8 alkenyl, C2-C8 alkynyl, C3-C8 cycloalkyl, C3-C8 cycloalkenyl, aryl or heterocyclyl, optionally substituted at one or more positions by deuterium, halogen, alkyl, alkyl ester, hydroxy, alkoxy, carboxy, formyl, aryl, aryloxy, heterocyclyl, amino, alkylamino, arylamido, alkylamido, thiol, thioalkyl, thioaryl, alkylsulfonyl, alkylcarbamoyl, arylcarbamoyl, nitro, cyano, nitrate; or R3 is selected from the group consisting of halogen, alkyl ester, hydroxy, alkoxy, carboxy, formyl, aryloxy, amino, alkylamino, arylamido, alkylamido, thiol, thioalkyl, thioaryl, alkylsulfonyl, alkylcarbamoyl, arylcarbamoyl, nitro, cyano, nitrate; (3) R4 is hydrogen, deuterium, C1-C8 alkyl, C2-C8 alkenyl, C2-C8 alkynyl, C3-C8 cycloalkyl, C3-C8 cycloalkenyl, aryl or heterocyclyl, any of which are optionally substituted at one or more positions by deuterium, halogen, alkyl, alkyl ester, hydroxy, alkoxy, carboxy, formyl, aryl, aryloxy, heterocyclyl, amino, alkylamino, arylamido, alkylamido, thiol, thioalkyl, thioaryl, alkylsulfonyl, alkylcarbamoyl, arylcarbamoyl, nitro, cyano, nitrate; or R4 is selected from the group consisting of alkyl ester, formyl, hydroxy, arylamido, alkylamido, alkylcarbamoyl, arylcarbamoyl, amino, alkylsulfonyl, alkylamino; (4) R5 represents 1-3 substituents selected from the group consisting of hydrogen, deuterium, halogen, C1-C8 alkyl, C2-C8 alkenyl, C2-C8 alkynyl, C3-C8 cycloalkyl, C3-C8 cycloalkenyl, aryl or heterocyclyl, optionally substituted at one or more positions by deuterium, halogen, alkyl, alkyl ester, hydroxy, alkoxy, carboxy, formyl, aryl, aryloxy, heterocyclyl, amino, alkylamino, arylamido, alkylamido, thiol, thioalkyl, thioaryl, alkylsulfonyl, alkylcarbamoyl, arylcarbamoyl, nitro, cyano, nitrate; (5) R6 is hydrogen, deuterium, C1-C8 alkyl, C2-C8 alkenyl, C2-C8 alkynyl, C3-C8 cycloalkyl, C3-C8 cycloalkenyl, aryl or heterocyclyl any of which are optionally substituted at one or more positions by deuterium, halogen, alkyl, alkyl ester, hydroxy, alkoxy, carboxy, formyl, aryl, aryloxy, heterocyclyl, amino, alkylamino, arylamido, alkylamido, thiol, thioalkyl, thioaryl, alkylsulfonyl, alkylcarbamoyl, arylcarbamoyl, nitro, cyano, nitrate; or R6 is selected from the group consisting of halogen, alkyl ester, hydroxy, alkoxy, carboxy, formyl, aryloxy, amino, alkylamino, arylamido, alkylamido, thiol, thioalkyl, thioaryl, alkylsulfonyl, alkylcarbamoyl, arylcarbamoyl, nitro, cyano, nitrate, —OP(O)(OH)2, —OC(O)R7, —OSO2OH, —OC(O)NHR7, —OC(O)NR7R8 or —SONH; and (6) n is 1 to 5.

Another aspect of the present invention is directed to a compound comprising a structural analogue to 2,5-Dimethoxy-4-iodoamphetamine, according to formula II:

(II)

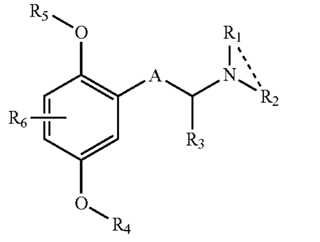

wherein (1) A is C1-C6 alkylene, C2-C6 alkenylene, or C2-C6 alkynylene; (2) R1 and R2 are, independently, hydrogen, deuterium, C1-C8 alkyl, C2-C8 alkenyl, C2-C8 alkynyl, C3-C8 cycloalkyl (independently or ring close with the nitrogen), C3-C8 cycloalkenyl (independently or ring close with the nitrogen), aryl or heterocyclyl, optionally substituted at one or more positions by deuterium, halogen, alkyl, alkyl ester, hydroxy, alkoxy, carboxy, formyl, aryl, aryloxy, heterocyclyl, amino, alkylamino, arylamido, alkylamido, thiol, thioalkyl, thioaryl, alkylsulfonyl, alkylcarbamoyl, arylcarbamoyl, nitro, cyano, nitrate; (3) R3 is hydrogen, deuterium, C1-C8 alkyl, C2-C8 alkenyl, C2-C8 alkynyl, C3-C8 cycloalkyl, C3-C8 cycloalkenyl, aryl or heterocyclyl, optionally substituted at one or more positions by deuterium, halogen, alkyl, alkyl ester, hydroxy, alkoxy, carboxy, formyl, aryl, aryloxy, heterocyclyl, amino, alkylamino, arylamido, alkylamido, thiol, thioalkyl, thioaryl, alkylsulfonyl, alkylcarbamoyl, arylcarbamoyl, nitro, cyano, nitrate; or R3 is selected from the group consisting of halogen, alkyl ester, hydroxy, alkoxy, carboxy, formyl, aryloxy, amino, alkylamino, arylamido, alkylamido, thiol, thioalkyl, thioaryl, alkylsulfonyl, alkylcarbamoyl, arylcarbamoyl, nitro, cyano, nitrate; (4) R4 and R5 are, independently, hydrogen, C1-C8 alkyl, C2-C8 alkenyl, C2-C8 alkynyl, C3-C8 cycloalkyl, C3-C8 cycloalkenyl, aryl or heterocyclyl, optionally substituted at one or more positions by deuterium, halogen, alkyl, alkyl ester, hydroxy, alkoxy, carboxy, formyl, aryl, aryloxy, heterocyclyl, amino, alkylamino, arylamido, alkylamido, thiol, thioalkyl, thioaryl, alkylsulfonyl, alkylcarbamoyl, arylcarbamoyl, nitro, cyano, nitrate. or R4 and R5 are, independently for each occurrence, selected from the group consisting of alkyl ester, alkylsulfonyl, alkylcarbamoyl, arylcarbamoyl, nitrate; and (5) R6 represents 1-3 substituents selected from the group consisting of hydrogen, deuterium, halogen, C1-C8 alkyl, C2-C8 alkenyl, C2-C8 alkynyl, C3-C8 cycloalkyl, C3-C8 cycloalkenyl, aryl or heterocyclyl, optionally substituted at one or more positions by deuterium, halogen, alkyl, alkyl ester, hydroxy, alkoxy, carboxy, formyl, aryl, aryloxy, heterocyclyl, amino, alkylamino, arylamido, alkylamido, thiol, thioalkyl, thioaryl, alkylsulfonyl, alkylcarbamoyl, arylcarbamoyl, nitro, cyano, nitrate.

Another aspect of the present invention is directed to a compound comprising a structural analogue to Lysergic acid diethylamide, according to formula III:

(III)

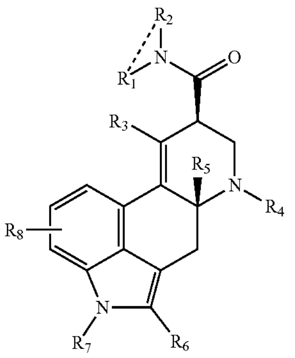

wherein (1) R1 and R2 are, independently, hydrogen, deuterium, C1-C8 alkyl, C2-C8 alkenyl, C2-C8 alkynyl, C3-C8 cycloalkyl (independently or ring close with the nitrogen), C3-C8 cycloalkenyl (independently or ring close with the nitrogen), aryl or heterocyclyl, optionally substituted at one or more positions by deuterium, halogen, alkyl, alkyl ester, hydroxy, alkoxy, carboxy, formyl, aryl, aryloxy, heterocyclyl, amino, alkylamino, arylamido, alkylamido, thiol, thioalkyl, thioaryl, alkylsulfonyl, alkylcarbamoyl, arylcarbamoyl, nitro, cyano, nitrate; (2) R3 is hydrogen, deuterium, C1-C8 alkyl, C2-C8 alkenyl, C2-C8 alkynyl, C3-C8 cycloalkyl, C3-C8 cycloalkenyl, aryl or heterocyclyl, optionally substituted at one or more positions by deuterium, halogen, alkyl, alkyl ester, hydroxy, alkoxy, carboxy, formyl, aryl, aryloxy, heterocyclyl, amino, alkylamino, arylamido, alkylamido, thiol, thioalkyl, thioaryl, alkylsulfonyl, alkylcarbamoyl, arylcarbamoyl, nitro, cyano, nitrate; or R3 is selected from the group consisting of halogen, alkyl ester, hydroxy, alkoxy, carboxy, formyl, aryloxy, amino, alkylamino, arylamido, alkylamido, thiol, thioalkyl, thioaryl, alkylsulfonyl, alkylcarbamoyl, arylcarbamoyl, nitro, cyano, nitrate; (3) R4 and R7 are, independently, hydrogen, deuterium, C1-C8 alkyl, C2-C8 alkenyl, C2-C8 alkynyl, C3-C8 cycloalkyl, C3-C8 cycloalkenyl, aryl or heterocyclyl, optionally substituted at one or more positions by deuterium, halogen, alkyl, alkyl ester, hydroxy, alkoxy, carboxy, formyl, aryl, aryloxy, heterocyclyl, amino, alkylamino, arylamido, alkylamido, thiol, thioalkyl, thioaryl, alkylsulfonyl, alkylcarbamoyl, arylcarbamoyl, nitro, cyano, nitrate; (4) R5 and R6 are, independently, hydrogen, deuterium, C1-C8 alkyl, C2-C8 alkenyl, C2-C8 alkynyl, C3-C8 cycloalkyl, C3-C8 cycloalkenyl, aryl or heterocyclyl, optionally substituted at one or more positions by deuterium, halogen, alkyl, alkyl ester, hydroxy, alkoxy, carboxy, formyl, aryl, aryloxy, heterocyclyl, amino, alkylamino, arylamido, alkylamido, thiol, thioalkyl, thioaryl, alkylsulfonyl, alkylcarbamoyl, arylcarbamoyl, nitro, cyano, nitrate; or R5 and R6 are, independently for each occurrence, selected from the group consisting of halogen, alkyl ester, hydroxy, alkoxy, carboxy, formyl, aryloxy, amino, alkylamino, arylamido, alkylamido, thiol, thioalkyl, thioaryl, alkylsulfonyl, alkylcarbamoyl, arylcarbamoyl, nitro, cyano, nitrate; and (5) R8 represents 1-3 substituents selected from the group consisting of hydrogen, deuterium, halogen, C1-C8 alkyl, C2-C8 alkenyl, C2-C8 alkynyl, C3-C8 cycloalkyl, C3-C8 cycloalkenyl, aryl or heterocyclyl, optionally substituted at one or more positions by deuterium, halogen, alkyl, alkyl ester, hydroxy, alkoxy, carboxy, formyl, aryl, aryloxy, heterocyclyl, amino, alkylamino, arylamido, alkylamido, thiol, thioalkyl, thioaryl, alkylsulfonyl, alkylcarbamoyl, arylcarbamoyl, nitro, cyano, nitrate.

Another aspect of the present invention is directed to a compound comprising a structural analogue to ibogaine, according to formula IV:

(IV)

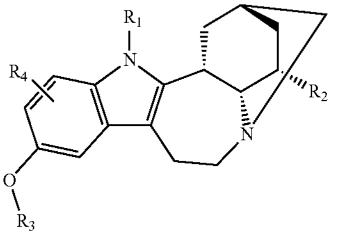

wherein (1) R1 is deuterium, C1-C8 alkyl, C2-C8 alkenyl, C2-C8 alkynyl, C3-C8 cycloalkyl, C3-C8 cycloalkenyl, aryl or heterocyclyl, optionally substituted at one or more positions by deuterium, halogen, alkyl, alkyl ester, hydroxy, alkoxy, carboxy, formyl, aryl, aryloxy, heterocyclyl, amino, alkylamino, arylamido, alkylamido, thiol, thioalkyl, thioaryl, alkylsulfonyl, alkylcarbamoyl, arylcarbamoyl, nitro, cyano, nitrate; (2) R2 is hydrogen, deuterium, C1-C8 alkyl, C2-C8 alkenyl, C2-C8 alkynyl, C3-C8 cycloalkyl, C3-C8 cycloalkenyl, aryl or heterocyclyl, optionally substituted at one or more positions by deuterium, halogen, alkyl, alkyl ester, hydroxy, alkoxy, carboxy, formyl, aryl, aryloxy, heterocyclyl, amino, alkylamino, arylamido, alkylamido, thiol, thioalkyl, thioaryl, alkylsulfonyl, alkylcarbamoyl, arylcarbamoyl, nitro, cyano, nitrate; or R2 is selected from the group consisting of halogen, alkyl ester, hydroxy, alkoxy, carboxy, formyl, aryloxy, amino, alkylamino, arylamido, alkylamido, thiol, thioalkyl, thioaryl, alkylsulfonyl, alkylcarbamoyl, arylcarbamoyl, nitro, cyano, nitrate; (3) R3 is hydrogen, C1-C8 alkyl, C2-C8 alkenyl, C2-C8 alkynyl, C3-C8 cycloalkyl, C3-C8 cycloalkenyl, aryl or heterocyclyl, optionally substituted at one or more positions by deuterium, halogen, alkyl, alkyl ester, hydroxy, alkoxy, carboxy, formyl, aryl, aryloxy, heterocyclyl, amino, alkylamino, arylamido, alkylamido, thiol, thioalkyl, thioaryl, alkylsulfonyl, alkylcarbamoyl, arylcarbamoyl, nitro, cyano, nitrate; or R3 is selected from the group consisting of alkyl ester, alkylsulfonyl, alkylcarbamoyl, arylcarbamoyl, nitrate; and (4) R4 represents 1-3 substituents selected from the group consisting of hydrogen, deuterium, halogen, C1-C8 alkyl, C2-C8 alkenyl, C2-C8 alkynyl, C3-C8 cycloalkyl, C3-C8 cycloalkenyl, aryl or heterocyclyl, optionally substituted at one or more positions by deuterium, halogen, alkyl, alkyl ester, hydroxy, alkoxy, carboxy, formyl, aryl, aryloxy, heterocyclyl, amino, alkylamino, arylamido, alkylamido, thiol, thioalkyl, thioaryl, alkylsulfonyl, alkylcarbamoyl, arylcarbamoyl, nitro, cyano, nitrate.

Formulae I-IV also appear in Table 1A (below).

Another aspect of the present invention is directed to a method for preventing or treating diseases and conditions or improving functions in patients or subjects, the method comprising administration of a compound as described for Formulae I-IV at doses, dosages, posology, or formulations devoid of clinically meaningful psychedelic or psychotomimetic actions or effects, and having clinical effects comparable to those exerted by human plasma psilocin Cmax of 4 ng/ml or less, or human 5-HT2A CNS receptor occupancy of 50% or less, or PD effects comparable to those exerted by human plasma psilocin Tmax in excess of 60 minutes.

Another aspect of the present invention is directed to a method for preventing or treating diseases and conditions or improving functions in patients or subjects, the method comprising administration of a 5-HT2A agonist substance at doses, dosages, posology, or formulations devoid of clinically meaningful psychedelic or psychotomimetic actions or effects, and having clinical effects comparable to those exerted by human plasma psilocin Cmax of 4 ng/ml or less, or human 5-HT2A CNS receptor occupancy of 50% or less, or PD effects comparable to those exerted by human plasma psilocin Tmax in excess of 60 minutes.

BRIEF DESCRIPTION OF THE DRAWINGS

The accompanying drawings, which are incorporated in and constitute a part of this specification, illustrate embodiments of the invention and, together with the general description of the invention given above and the detailed description of the embodiments given below, serve to explain the principles of the present invention.

FIG. 4B shows IL-10; FIG. 4C shows CCL2). *p<0.001 and **p<0.0001; one-way ANOVA followed by Tukey's post hoc test.

FIG. 11B showing NMDAR2A; FIG. 11C showing NMDAR2B). ***$p<0.001$ vs control (untreated cells), ##$p<0.01$ vs cells treated with psilocin 10 μM for 24 hours; one-way ANOVA followed by Tukey's post hoc test.

FIG. 11E showing NMDAR2A; FIG. 11F showing NMDAR2B). **$p<0.01$ vs control (untreated cells); one-way ANOVA followed by Tukey's post hoc test.

FIG. 11H showing NMDAR2A; FIG. 11I showing NMDAR2B). *$p<0.05$, ****$p<0.0001$ vs control (untreated cells); one-way ANOVA followed by Tukey's post hoc test.

FIG. 12B showing 5-HT2C). ##$p<0.01$ vs cells treated with psilocin 10 μM for 24 hours; one-way ANOVA followed by Tukey's post hoc test.

FIG. 16A shows IL-1β expression after 4, and 10 h from treatment with activated U937 CM. FIG. 16B shows IL-8 expression after 4 and 10 h from treatment with activated U937 CM. FIG. 16C shows IL-12 expression after 4 and 10 h from treatment with activated U937 CM. FIG. 16D shows TNF-α expression after 4 and 10 h from treatment with activated U937 CM.

FIG. 18A shows IL-1β expression after 4, and 10 h from treatment with activated U937 CM. FIG. 18B shows IL-8 expression after 4 and 10 h from treatment with activated U937 CM. FIG. 18C shows IL-12 expression after 4 and 10 h from treatment with activated U937 CM. FIG. 18D shows TNF-α expression after 4 and 10 h from treatment with activated U937 CM.

DETAILED DESCRIPTION OF THE INVENTION

Figure 1A:
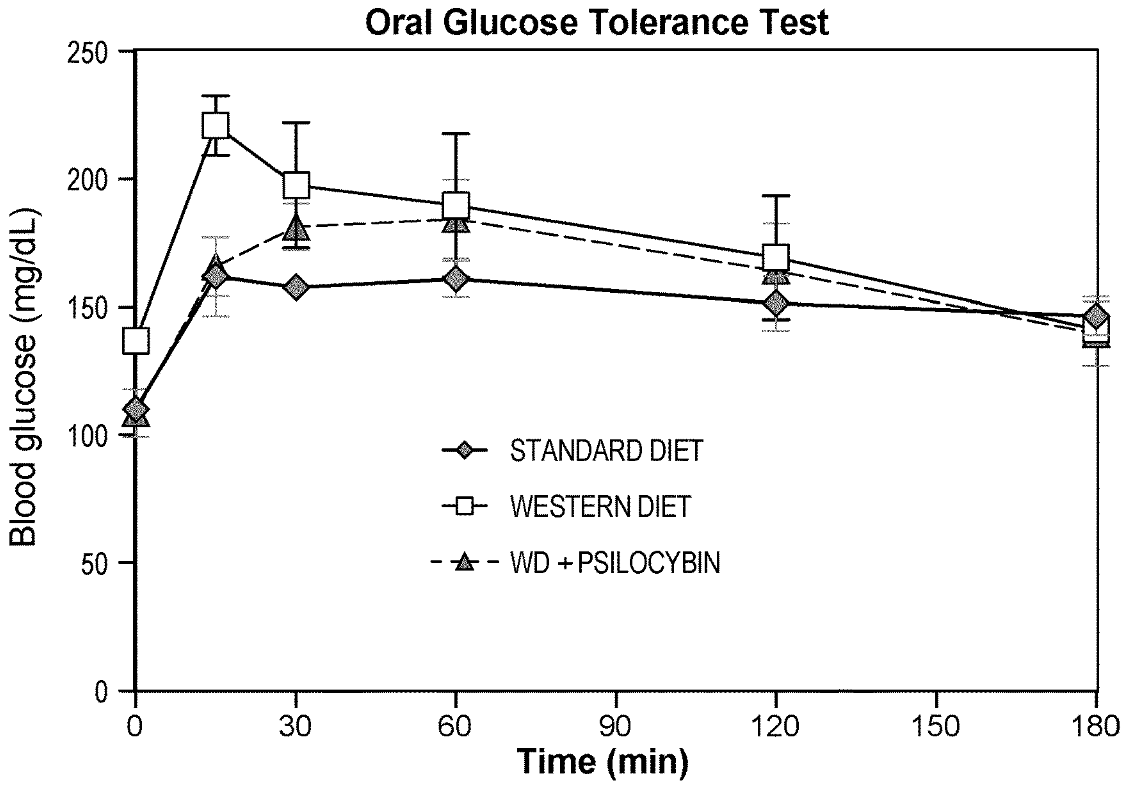
FIG. 1A is a graph showing effect of psilocybin on oral glucose tolerance test. ***p<0.001; one-way ANOVA followed by Tukey's post hoc test.

One or more specific embodiments of the present invention will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Definitions

For the purposes of this disclosure, the present inventors define "diseases" as human and veterinary diseases/disorders/syndromes/symptoms in their different stages, from preclinical stages to advanced stages, (including symptoms and signs of diseases, including prodromes and other manifestations of diseases).

For the purposes of this disclosure, the present inventors define "symptoms" as manifestations of diseases as defined above.

For the purposes of this disclosure, the present inventors define "conditions" as underperformance relatively to the individual's potential and goals in cognitive, motor and social abilities and underperformance in special senses relatively to the individual's potential and goals.

For the purposes of this disclosure, the present inventors define "functions" as functions of special senses (vision, olfaction, taste, hearing and balance), including for improvement of vision.

For the purpose of this disclosure the present inventors define "aging or ageing" as the accumulation of changes in a living being over time, leading to a deficit or deterioration in physical, psychological, and social abilities. The present inventors include in this definition accelerated aging and diseases due to physical and chemical factors, including environmental factors, toxins, and drugs, foods and lack of nutrients and vitamins and drug treatments. Osteoporosis as a form of aging of bones is of particular relevance because of the known presence of NMDARs on osteoblasts and osteoclasts (Chenu C, Serre C M, Raynal C, Burt-Pichat B and Delmas P D (1998) Glutamate receptors are expressed by bone cells and are involved in bone resorption. Bone 22:295-299).

For the purposes of this disclosure, the present inventors define "treatment" as treatment and or prevention, including primary and secondary prevention, and amelioration of conditions, symptoms, disorders, syndromes and diseases.

For the purpose of this disclosure, the present inventors define "neural plasticity" as structural an functional changes in the nervous system occurring at any time during the life span, including neurogenesis, modulation of neuron or astrocyte soma or neurite size, shape and length, synaptic plasticity, including synaptogenesis, synaptic strengthening, spinogenesis, loss of synaptic spines, "pruning", changes in synaptic spine volume, changes in synaptic densities, including changes in specific synaptic proteins and pathways (including PD95, PD93,synapsin, GLUR1, including especially mRNA coding for synaptic density protein and receptor subunits, including especially protein subunits of the AMPAR and NMDAR, and including modulation of the mTOR pathway and TrkB pathway and changes in neurotrophic factors' pathways, including especially BDNF.

For the purpose of this disclosure, the present inventors define "neuroplastogen drugs" or "neuroplastogens" as drugs with the potential for modulating neural plasticity, as defined above. In order for a neuroplastogen drug to be potentially useful for the treatment of diseases and conditions, the drug should be safe and well tolerated and the modulating action on neural plasticity should occur in the absence of clinically meaningful side effects, including, especially, in the absence of psychedelic/psychotomimetic effects. Neuroplastogen drugs should be administered at neuroplastogen doses, dosages, posology and or formulations, as defined below.

For the purpose of this disclosure, the present inventors define "neuroplastogen dose" and in particular "neuroplastogen dose of drugs classified as 5-HT2A agonists", as a dose, dosage, posology or formulation, including modified release formulations, of a substance with 5-HT2A agonist actions and actions on neural plasticity, including modulation of NMDARs, that is well tolerated, safe, when administered at doses, dosages, posology and or formulations, that does not cause clinically meaningful psychedelic/psychotomimetic effects. Neuroplastogen drugs modulate NMDARs via gene regulation for NMDAR subunits and gene regulation for trophic factors, including BDNF, at doses dosages, posology and or formulation do that do not cause clinically meaningful off target effects, including without causing clinically meaningful alterations in consciousness, emotion, and cognition, including positive and negative psychotomimetic symptoms (psychedelic effects, psychedelic experience, psychotomimetic effects). The novel mechanism of action of neuroplastogen drugs for their uses in the treatment of diseases and conditions proposed by the inventors consists in differential down regulation of excessive $Ca^{2+}$ influx through only hyperactive NMDARs (selective open channel block) subtypes A-D in select cellular populations and or cellular networks. The block of excessive $Ca^{2+}$ influx reinstates cellular functions, including functions essential for physiological neural plasticity (e.g., mobilization and synthesis of synaptic proteins, including NMDAR subunits, and synthesis of neurotrophic factors, including BDNF).

Description of Various Aspects of the Invention

The present inventors now provide new experimental evidence showing NMDAR modulating actions of neuroplastogen 5-HT2A agonists (see Example 3, below). This experimental evidence signals that neural plasticity can occur from low doses of 5-HT2A agonists, in the absence of psychedelic/psychotomimetic effects, and thus these psychedelic/psychotomimetic effects may be viewed as side effects rather than therapeutic effects (as is the case with some NMDAR antagonists).

The potential therapeutic effects of substances in the triptan family (5-HT agonists, including 5-HT2A agonists), administered chronically, continuously or intermittently, at dosages and formulations that do not cause psychedelic/psychotomimetic effects, has not previously been adequately explored. While there is a limited body of scientific literature on administration of low doses of psychedelics, available scientific publications, to date, teach away from the use of these agents for the treatment of diseases. The findings from Anderson et al., (Anderson T, Petranker R, Rosenbaum D, Weissman C R, Dinh-Williams L A, Hui K, Hapke E, Farb N A S. Microdosing psychedelics: personality, mental health, and creativity differences in microdosers. Psychopharmacology (Berl). 2019 Jan. 20) and the review and studies from Polito and Stevenson, 2019 (Polito V, Stevenson R J (2019) A systematic study of microdosing psychedelics. PLOS ONE 14(2): e0211023. https://doi.org/10.1371/journal.pone.0211023). https://doi.org/10.1371/journal.pone.0211023), by underscoring that the "beneficial" effects of low doses of psychedelic substances can be defined at the most as a generic "increase in psychological functions", teach away from the use of small doses of psychedelic substances as neuroplastogens for the treatment of diseases, including neurological or ophthalmological diseases or for deficits associated with aging and senescence or even for a generic improvement in cognitive function (nootropic effect). In particular Polito and Stevenson conclude: "The current findings suggest that popular accounts of the effects of microdosing may not match the experience of long term microdosers, and that promising avenues for future investigation are the impacts of microdosing on improved mental health, attentional capabilities, and neuroticism". The study by Fadiman and Korb (Fadiman J, Korb S. Might Microdosing Psychedelics Be Safe and Beneficial? An Initial Exploration. J Psychoactive Drugs. 2019 Mar. 29:1-5) suggests that microdoses were followed by improvements in negative moods. These conclusions underscore how the current research focus and understanding on "microdosing" of psychedelic substances to this day remains confined to the psychiatric experimental arena, teaching away from the potential uses of 5-HT agonists substances at dosages devoid of psychedelic effects as neuroplastogen for the treatment and prevention of neurological and ophthalmological diseases and metabolic diseases and other clinical indications and conditions listed in this application, including the treatment of psychiatric disorders as defined by the Diagnostic and Statistical Manual of Mental Disorders (DSM-5). The potential for treatment of mental disorders is not anticipated by a potential improvement on "negative moods" as hypothesized by Fadiman.

Furthermore, the current knowledge of non-psychedelic/psychotomimetic dosages of 5-HT agonists teaches away from their uses for therapeutic indications, including psychiatric indications: the potential effectiveness for 5-HT agonists for the treatment of diseases, and specifically psychiatric diseases, is presently entwined with their ability to cause psychedelic/psychotomimetic symptoms. The potential therapeutic efficacy of psychedelic substances presently under investigation remains thus within the boundaries of their ability to cause the "psychedelic experience" and psychedelic substance are administered in single doses, together with psychotherapy and pre, during and post drug administration counseling/talk therapy, in special settings, under close supervision, for the treatment of certain psychiatric diseases and symptoms. Psychedelics administered in such a specific manner are presently in different phases of development, including in phase 2 clinical studies. The potential for 5-HT agonists for the treatment diseases and conditions and aging at dosages that do not cause psychedelic/psychotomimetic effects is not presently under clinical investigation and the current scientific knowledge teaches away from the therapeutic uses of 5-HT2A agonists at nonpsychedelic/psychotomimetic dosages.

Patients particularly sensitive to the mind altering and psychedelic/psychotomimetic effects of 5-HT2A agonists may benefit from neuroplastogen 5-HT2A agonists including modified release (MR) formulations as detailed below, so the 5-HT2A agonist can be potentially administered repeatedly over days or months or even chronically, without the need for a particular setting or the need for counseling and or psychotherapy, or the need for close monitoring and supervision because psychedelic/psychotomimetic would not occur with the appropriate posology and formulation.

The repeated administration of 5-HT2A drugs over time, days to months, or chronically, continuously or intermittently potentially allows for the effective treatment of conditions, symptoms, disorders, syndromes and diseases that may benefit from induction of neural plasticity, especially in patients for whom repeated induction psychotomimetic and psychedelic effects would be contraindicated and or detrimental. The therapeutic window for psilocybin and other 5-HT2A agonist drugs could be widened by changing the drug formulation to modified release, as disclosed in more detail below. Of note, the present inventors also present experimental evidence that intermittent repeated therapy, including intermittent chronic therapy, e.g., every other day, every three days, every week, every two weeks, every other month, may offer advantages over continuous chronic therapy (daily therapy).

5-HT2A agonist administered chronically at low non-psychedelic doses (neuroplastogen doses), may therefore be therapeutic for a multiplicity of diseases and conditions, not only for psychiatric indications, which are the focus of researchers studying psychedelic dosages of 5-HT2A agonists.

There may be potential reciprocal allosteric effects with potential synergy of effects among select molecules in these two drug classes, as shown by some of the novel experimental work detailed below.

The present inventors therefore disclose that for many patients that could benefit from 5-HT receptor agonist with neural plasticity effects, in particular for patients that potentially benefit from neural plasticity effects maintained over time, the psychedelic experience and the psychotomimetic and other mind-altering effects of these drugs are problematic and detrimental side effects of a relative drug overdose and not a therapeutic intrinsic activity, as viewed by ongoing research activities in the field of 5-HT2A agonists.

In summary, drugs or drug formulations, with neural plasticity effects but devoid of psychedelic effects, could benefit patients and individuals and improve or prevent conditions, symptoms, disorders, syndromes and diseases in human subjects. Furthermore, a particular setting and close personal supervision/counseling/psychotherapy are unnecessary for the actions of 5-HT2A agonists on neural plasticity when non-psychedelic dosages and formulations are administered. The present inventors disclose potential benefits from these novel compositions and uses of 5-HT2A agonists for the treatments a multiplicity of conditions, symptoms, disorders, syndromes and diseases, including ophthalmological, neurological, psychiatric, metabolic and for the treatments of deficits associated with aging.

While psychedelic drugs by their very definition determine psychedelic/psychotomimetic effects and their potential intended therapeutic benefits for psychiatric disorders are intrinsically linked to these psychedelic/psychotomimetic effects, and their therapeutic uses, currently under investigation, are focused on psychiatric diseases and conditions that may benefit from the "psychedelic experience", which is generally induced in single sessions with high doses of 5-HT agonists in a particular setting and preceded and followed by counseling and or psychological therapy (Griffiths R R, Richards W A, Johnson M W, McCann U D, Jesse R. Mystical-type Experiences Occasioned by Psilocybin Mediate the Attribution of Personal Meaning and Spiritual Significance 14 Months Later. J Psychopharmacol. 2008

August; 22(6):621-32). The compositions and uses described in the current application are instead characterized by their ability to modulate neural plasticity as outlined above, at dosages and formulations that do not cause psychedelic/psychotomimetic effects, and are administered in repeated doses over time, daily or intermittently, for periods of several days to months, or even chronically, in order to potentially be therapeutic for a multiplicity of conditions, symptoms, disorders, syndromes and diseases, including those requiring ongoing, days or months, or even chronic modulation of neural plasticity, including neuropsychiatric, metabolic and ophthalmological conditions, symptoms, disorders, syndromes and diseases. Thus, in the case of 5-HT2A neuroplastogens, the psychedelic effects are not therapeutic effects but are unwanted side effects and these side effects make these drugs contraindicated for patients and subjects that could otherwise benefit from the neural plasticity actions of these drugs.

Posology, including dosage and frequency and timing of administration (dosages), the formulations, including modified release formulations, the duration of therapy, days or chronically as opposed to one time, and in certain cases the route and methods of administrations, and thus the PK parameters (in particular Cmax, Tmax) and PD parameters, including acute and chronic receptor occupancy, receptor downregulation effects, and downstream effects, including trophic effects on cells including effects on neurogenesis, promotion of arborization, neurite growth, synaptogenesis, synaptic strengthening, spinogenesis, increased synaptic spine volume, augmentation of synaptic densities, including modulation of specific synaptic proteins, including PD95, synapsin, GLUR1, including especially mRNA, and protein subunits of the NMDARs different subtypes, subunits and subtypes of AMPARs, and including modulation of the mTOR pathway and TrkB pathway and modulation of neurotrophins, including BDNF, including anti-inflammatory effects, including effects on TNF-α, IL-10, IL-6 and other markers of inflammation and markers of neural plasticity described in the present inventors' experiments, in neurons, astrocytes, oligodendrocytes, Schwann cells, and potentially exert trophic effects on additional select cells, e.g., including especially retinal pigment cells and other cells that support sensory receptors, including auditory, vestibular, olfactory, gustatory and tactile receptors, and ultimately the clinical effects, are very different. Furthermore, ancillary therapies and treatment-associated precautions and, ultimately, clinical indications and therapeutic indications are likely to substantially differ from current uses and misuses by researchers, therapists and laymen.

Based on the present inventors' observations and findings the present inventors disclose that for many patients and for a multiplicity of conditions, symptoms, disorders, syndromes and diseases, the psychedelic experience and psychotomimetic effects are side effects of an overdose of substances with potential neuroplastogen effects that are therapeutic at non-psychedelic lower doses. Furthermore, while the psychedelic effect/psychotomimetic effects may be therapeutic for select indications and select patients and under certain circumstances, outside of the scope of this disclosure, such as for subsets of patients suffering from disorders currently under investigation with psychedelics (depression, PTSD, anxiety, addiction), the present inventors disclose that for a multiplicity of conditions, symptoms, disorders, syndromes and diseases that may benefit from neuroplastogen effects, including subsets of patients suffering from the same psychiatric disorders (depression, PTSD, anxiety, addiction), (the complete list of these potential indications is disclosed below), the psychedelic experience/psychotomimetic effects are side effects of overdosages of drugs administered at super-therapeutic doses. For further clarification, the psychedelic experience and the psychotomimetic symptoms are generally caused by overdosing with 5-HT2A agonist and or NMDAR antagonist neuroplastogens, while the therapeutic neuroplastogen effects are exerted by much lower and safer doses (approximately 1/10th) of the same drugs and these neuroplastogen effects, in the absence pf psychedelic effects, and are potentially therapeutic for a multiplicity of conditions, symptoms, disorders, syndromes and diseases as listed below. Furthermore, the tolerability, safety and effectiveness of select neuroplastogens can be enhanced by novel MR formulations. The present inventors here disclose the potential neuroplastogen actions of serotonin agonist substances, in particular substances with actions at the 5-HT2A receptor and other serotonin receptors, in particular psilocin carbamate, psilocybin and baeocystin and their derivatives. Additionally, the present inventors disclose the neuroplastogen actions of psilocin, norpsilocin, norbaeocystin and their derivatives at doses and formulations that do not cause psychedelic or psychotomimetic symptoms. Furthermore, the present inventors disclose the potentially therapeutic actions of select Structurally Modified derivatives of Serotonin Neuroplastogens (SMSNs, including nitro-derivatives of 5-HT2A receptor agonists, as described below) as having neuroplastogen effects, according to the neuroplastogen definition outlined above.

These neuroplastogen effects may be modulation of transcription and synthesis of glutamate receptors, as described in the present inventors' novel experiments, and may be secondary to or facilitated by anti-inflammatory actions on neural tissues and other mammalian tissues, again as signaled by the present inventors' experiments. These neuroplastogen effects may be of particularly importance for preventing, alleviating and treating a multiplicity of conditions, symptoms, disorders, syndromes and diseases at dosages and formulations that do not produce psychedelic effects, or psychotomimetic effects or other clinically meaningful side effects on thought, emotion and cognition. Thus, in the case of neuroplastogens, psychedelic and psychotomimetic effects are side effects and not therapeutic effects, while their potential effects on learning, including scholar/academic learning, learning of motor and social skills, and emotional pathway dysfunction influenced by learning, are instead potentially therapeutic targets.

The present inventors therefore disclose that in the case of neuroplastogens, not only the effects on neural plasticity, but also cellular trophic effects and anti-inflammatory effects, when appropriate dosages and formulations and posology are followed, are present in the absence of psychedelic/psychotomimetic symptoms, and furthermore the present inventors disclose that neuroplastogen effects, aside for improving neuropsychiatric, metabolic an ophthalmological symptoms, diseases and conditions may result in improvement in various functions, including sensory functions, including vision, and that these improvements may outlast the pharmacological action at the 5-HT2A receptor and other receptors, i.e., the therapeutic effects are due to their effects on neural plasticity and therefore the therapeutic effects of these drugs may be present and maintained after virtually all of the clinically active amount of drug has been eliminated. The present inventors furthermore disclose that multiple doses, over the course of days or months, rather than single doses, are needed for the treatment of a multiplicity of diseases and conditions (e.g., 1-4 doses per day over 2-3 or more days or weeks or months or indefinitely or even one dose every 2 days or every 3 days or every week or every two weeks or every other months for several weeks or months or indefinitely); different indications are likely to require different posology, but the treatment of chronic conditions, symptoms, disorders, syndromes and diseases that may benefit from drugs that modulate neural plasticity are likely to require repeated administration over time of non-psychedelic/psychotomimetic dosages and formulations, as shown in the present inventors' experimental work.

In select circumstances, the administration of a single non-psychedelic-psychotomimetic dose of neuroplastogen, e.g., intranasal for social anxiety or for panic attack or for acute enhancement of vision, may be useful. The potential therapeutic and beneficial effects of neuroplastogen drugs for the treatment of a multiplicity of conditions, symptoms, disorders, syndromes and diseases are however potentially due to continuous effects over time on neural plasticity and other trophic and anti-inflammatory actions of neuroplastogens administered in multiple doses for prolonged periods (days to months or chronically). The effects of certain 5-HT2A agonists administered at multiple doses repeated over time, intermittently (e.g., every other day or every 3 days or every other week) or continuously (e.g., daily or several times a day) at dosages and formulations that do not cause psychedelic symptoms, by combining neural plasticity effects, trophic effects on neurons and other cells and anti-inflammatory actions, are potentially useful for the treatment of a multiplicity of conditions, symptoms, disorders, syndromes and diseases including for the improvement of functions, including ophthalmological, neurological, psychiatric and metabolic diseases and for the treatment of ageing including senescence and deficits associated with ageing, including accelerated aging and senescence induced by noxious agents, including medical treatments, including cancer treatments, including chemotherapy and radiation therapy, including the improvement of special senses (vision, olfaction, taste, hearing and balance) and in particular for improving vision in ophthalmological diseases (e.g., macular degeneration) and brain diseases (e.g., CVA) and for improving vision in subjects with normal visual acuity (visual acuity enhancement).

The present inventors' novel experimental and observational work outlined below and the present inventors' disclosures about neuroplastogen drugs, uncover the potential of substances and drugs acting via 5-HT2A receptors, and potentially acting also via other serotonin receptors and other receptors and transporters (DAT, NET, SERT) and other mechanisms, including other 5-HT receptors, DA receptors, and sigma receptors, CB1, NOP for the treatment of a multiplicity of diseases and conditions, including ophthalmological, neurological, psychiatric and metabolic diseases and for the treatment of aging including senescence and deficits associated with aging, including accelerated senescence induced by noxious agents, including medical treatments, including deficits of special senses (vision, olfaction, taste, hearing and balance) caused by ageing, drug treatments or other causes. Of particular importance are drugs that act both at the 5-HT system and glutamate system, in particular 5-HT2A agonists and open channel NMDAR antagonists, glutamate receptors, including AMPARs and or S-nitrosylation activity at NMDARs receptor. Modulation of neural plasticity, anti-inflammatory actions and neuroprotective and trophic actions on retinal, olfactory and inner ear, including supporting cells, including retinal pigment cells, and cells of the nervous system, including neurons, astrocytes, and oligodendrocytes and Schwann cells are potential mechanisms and targets for the therapeutic actions of neuroplastogen substances and drugs, as detailed throughout this application. The above listed therapeutic actions are especially obtained with neuroplastogen drugs acting primarily as 5-HT2A receptor agonists administered repeatedly, continuously or intermittently, over a course of days or months or chronically.

Indoleamines and phenethylamines, in particular psilocybin, administered in single sessions at doses causing psychedelic symptoms, are presently under clinical investigation for a multiplicity of psychiatric diseases and symptoms. Depression, anxiety, PTST, end of life angst, and addiction are some of the psychiatric diseases and symptoms that may be improved by psychedelics [Kvam $T_M$, Stewart L H, Andreassen O A. Psychedelic drugs in the treatment of anxiety, depression and addiction. Tidsskr Nor Laegeforen. 2018 Nov. 12; 138(18)].

Despite the renovated interest of the scientific psychiatric community in 5-HT2A agonists for the treatment of psychiatric indications, the recreational abuse of these substances and drugs poses a significant barrier to their development as pharmaceuticals. Strong public safety and regulatory concerns remain about the use of substances with the potential for inducing psychedelic effects, including concerns for their uses as treatment of diseases, and these substances and drugs remain illegal in most countries. In the USA and in many other countries, psychedelic substances, natural and synthetic, including plants and fungi, are classified as schedule I substances with high abuse potential and no clinical uses. While the relative safety and low addiction potential of these substances have been underscored in recent scientific publications (Brown R T, Nicholas C R, Cozzi N V, Gassman M C, Cooper K M, Muller D, Thomas C D, Hetzel S J, Henriquez K M, Ribaudo A S, Hutson P R. Pharmacokinetics of Escalating Doses of Oral Psilocybin in Healthy Adults. Clin Pharmacokinet. 2017 December; 56 (12):1543-1554; Studerus E, Kometer M, Hasler F, Vollenweider F X. Acute, subacute and long-term subjective effects of psilocybin in healthy humans: a pooled analysis of experimental studies. J Psychopharmacol. 2011 November; 25(11):1434-52; Johnson M W, Griffiths R R, Hendricks P S, Henningfield J E. The abuse potential of medical psilocybin according to the 8 factors of the Controlled Substances Act. Neuropharmacology. 2018 November; 142:143-166), due to their potential for abuse, which remains a concern despite the low addiction potential, and due to strong and multi-faceted socio-cultural and legal barriers (which vary widely across countries), the development of psychedelic substances for the treatment of diseases remains problematic to this day, and more studies are needed to better define the role of these substances as therapeutic agents. In addition, the current popular and scientific understanding to this day teaches that the psychotomimetic effects and or the holistic "psychedelic experience" are integral to the potential therapeutic activity of these substances.

While the importance of the psychedelic experience as a therapeutic tool may hold promise for some psychiatric indications and for subsets of patients, the present inventors disclose that dosages, posology and formulations of 5-HT2A agonists administered repeatedly, chronically or intermittently, over days or months, defined here as 5-HT neuroplastogens, because of their actions on neural plasticity in the absence of psychotomimetic/psychedelic effects, and the potentially psychotomimetic-free effects of novel chemical compounds with neuroplastogen actions, specifically synthetically modified serotonin agonists neuroplastogen (SMSNs), also disclosed in this application, may be therapeutic for diseases and conditions of the nervous system, including deficits of special senses, including ophthalmological, olfactory and inner ear conditions and a multiplicity of neurological, psychiatric, ophthalmological and metabolic condition and diseases, and for the treatment of aging and senescence associated deficits and for the betterment of cognition (nootropic effects) and social skills, motor skills and for the betterment of vision, olfaction, taste, hearing and balance and including for betterment of vision in subjects with inadequate visual acuity in relation to their potential or preference.

Aside from disclosing that the at least one mechanism (modulation of BDNF and mToR dependent pathways) for inducing neural plasticity is shared by NMDAR antagonists, Fogaga et al., 2019 (dextromethadone), and 5-HT2A agonists, Ly et al., 2018 (5-HT2A agonists), the present inventors performed an extensive review the literature and found the following reports signaling possible interactions and overlapping actions between 5-HT2A agonists and NMDAR open channel blockers. The following reports, taken together with the present inventors' observations and experimental results (including Example 3) lend support to the present application:

First, certain 5-HT2A agonists were found to inhibit NMDA receptor activity (Arvanov V L, Liang X, Russo A, Wang R Y. LSD and DOB: interaction with 5-HT2A receptors to inhibit NMDA receptor-mediated transmission in the rat prefrontal cortex. European Journal of Neuroscience, Vol. 11, pp. 3064-3072, 1999; Berger M L, Palangsuntikul R, Rebernik P, Wolschann P, Berner H. Tryptamines at NMDA, 5-HT1A, and 5-HT2A Receptors: A Comparative Binding and Modeling Study. Current Medicinal Chemistry, 2012, 19, 3044-3057). When combined with the present inventors' disclosures and experimental findings, the results by Arvanov et al., suggest that a complementary and synergistic action at the two pharmacological targets could potentially enhance biological responses, such as neural plasticity and thus influence therapeutic outcomes for a multiplicity of diseases and conditions.

Second, a study by Ceglia and others (Ceglia I, Carli M, Baviera M, Renoldi G, Calcagno E. The 5-HT2A receptor antagonist M100,907 prevents extracellular glutamate rising in response to NMDA receptor blockade in the mPFC. Journal of Neurochemistry, 2004, 91, 189-199) suggests that 5-HT2A antagonists prevent the effects of NMDAR block which may suggest that 5-HT2A receptor activation may be needed for NMDAR antagonist actions: this finding is also potentially supportive of the present inventors' findings and disclosures for allosteric interactions and possibly synergy between NMDA antagonists and serotonin agonists.

Third, a 1998 report by Farber et al., (Farber N B, M. D., Hanslick J, Kirby C, McWilliams L, Olney J W. Serotonergic agent that activate 5-HT2A receptors prevent NMDA antagonist neurotoxicity. Neuropsychopharmacology 1998—Vol. 18, No. 1) suggest a potential protective action of b 5-HT52A agonists against toxicity induced by the high affinity NMDAR antagonist MK-801. This finding together with the present inventors' disclosure suggests a potential safety advantage for concomitant administration of agent with 5-HT agonist actions and agents with NMDAR antagonist action.

Fourth, work by Zhong and others (Zhong P, Yuen E Y, Zhen Yan. Modulation of Neuronal Excitability by Serotonin-NMDA Interactions in Prefrontal Cortex. Mol Cell Neurosci. 2008 June; 38(2): 290-299) suggests that the effects on membrane depolarization of neurons of 5-HT2A receptors agonists is dependent on NMDA receptors, suggesting a co-dependency of these receptors for at least part of their effects.

And fifth, metabotropic glutamate receptors interact with 5-HT2A receptors to form functional complexes in brain cortex (Gonzalez-Maeso J, Ang R L, Yuen T, et al. Identification of a serotonin/glutamate receptor complex implicated in psychosis. Nature. 2008; 452(7183):93-97. doi: 10.1038/nature06612).

Based on the pooling of the observations by the authors cited above, suggesting indirect interactions between the serotonin receptor and the NMDAR pathways, the present inventors hypothesized and then demonstrated experimentally a direct action of 5-HT2A on NMDAR modulation, i.e., the induction by 5-HT2A agonists of the synthesis of NMDAR subunits in ARPE-19 cells. This novel finding and other experimental results detailed in Examples 1-3, below, unexpectedly signal the potential efficacy of 5-HT2A agonists not only when administered as single large pulse doses for the treatment of depression and other psychiatric indications, as hypothesized by several researchers (phase 2 studies are in progress), but also when administered as neuroplastogens (at doses devoid of psychedelic/psychotomimetic effects), chronically, continuously or intermittently, for the treatment diseases and conditions for which modulation of NMDARs is potentially therapeutic, such as diseases and conditions disclosed in International Patent Application No. PCT/US2018/016159, and in the current application.

Furthermore, the present inventors disclose that novel drugs, with both 5-HT2A agonist actions and NMDAR antagonist actions may offer additional efficacy and safety compared to the combination of two agents. The present inventors have therefore designed a first set of serotoninergic agonists with 5-HT2A affinity containing novel molecular features which may confer added modulatory activity at NMDARs. To this effect, among others, the present inventors designed novel 5-HT agonist derivatives characterized by the introduction of a nitric acid ester group and plan to test the effects of these novel molecules for their affinity for blocking NMDAR subtypes in addition to their agonist effects on 5-HT2A receptors. The postulated mechanism for the NMDAR antagonistic actions of these novel compounds is modulation of NMDA receptor activity by S-nitrosylation of the sulfhydryl group of the cysteine residue on the N-terminus (or extracellular domain) of the NMDAR, while maintaining the serotonergic activity of the parent compounds. The present inventors are in the process of testing these novel agents both for serotoninergic activity at select 5-HT receptor families and subtypes and at NMDARs and their subtypes. These novel compounds are also undergoing testing for their ability to prevent excitotoxicity, inflammatory cellular damage and for neurotrophic effects.

Table 1A (below) includes the modifications of psilocybin, psilocin, DMT, DOI, and LSD (5-HT2A agonists) to obtain novel derivatives with novel and improved pharmacokinetics (PK) and/or pharmacodynamics (PD) parameters and in particular deuterated derivatives to modulate PK and or PD, fluoro-derivatives to modulate lipo-solubility/cell membrane permeability and thus PK and PD properties, nitro-derivatives to modify PK and PD parameters and potentially provide additional neuro-protective actions, including additional NMDAR modulation, and combinations thereof, including deuterated fluoro-nitro-derivatives.

TABLE 1A

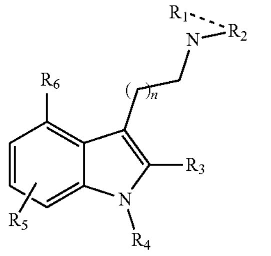
(I)

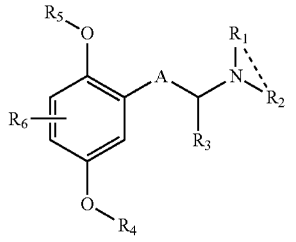
(II)

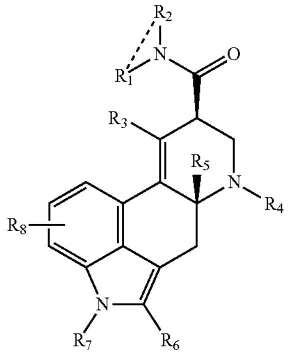
(III)

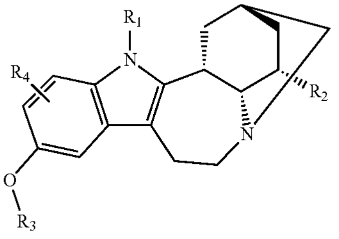
(IV)

Formula I of Table 1 A represents a structural analogue to psilocin, norpsilocin, psilocybin, baeocystin, norbaeocystin or N,N-dimethyltryptamine, wherein (1) R1 and R2 are, independently, hydrogen, deuterium, C1-C8 alkyl, C2-C8 alkenyl, C2-C8 alkynyl, C3-C8 cycloalkyl (independently or ring close with the nitrogen), C3-C8 cycloalkenyl (independently or ring close with the nitrogen), aryl or heterocyclyl, optionally substituted at one or more positions by deuterium, halogen, alkyl, alkyl ester, hydroxy, alkoxy, carboxy, formyl, aryl, aryloxy, heterocyclyl, amino, alkylamino, arylamido, alkylamido, thiol, thioalkyl, thioaryl, alkylsulfonyl, alkylcarbamoyl, arylcarbamoyl, nitro, cyano, nitrate; (2) R3 is hydrogen, deuterium, C1-C8 alkyl, C2-C8 alkenyl, C2-C8 alkynyl, C3-C8 cycloalkyl, C3-C8 cycloalkenyl, aryl or heterocyclyl, optionally substituted at one or more positions by deuterium, halogen, alkyl, alkyl ester, hydroxy, alkoxy, carboxy, formyl, aryl, aryloxy, heterocyclyl, amino, alkylamino, arylamido, alkylamido, thiol, thioalkyl, thioaryl, alkylsulfonyl, alkylcarbamoyl, arylcarbamoyl, nitro, cyano, nitrate; or R3 is selected from the group consisting of halogen, alkyl ester, hydroxy, alkoxy, carboxy, formyl, aryloxy, amino, alkylamino, arylamido, alkylamido, thiol, thioalkyl, thioaryl, alkylsulfonyl, alkylcarbamoyl, arylcarbamoyl, nitro, cyano, nitrate; (3) R4 is hydrogen, deuterium, C1-C8 alkyl, C2-C8 alkenyl, C2-C8 alkynyl, C3-C8 cycloalkyl, C3-C8 cycloalkenyl, aryl or heterocyclyl, any of which are optionally substituted at one or more positions by deuterium, halogen, alkyl, alkyl ester, hydroxy, alkoxy, carboxy, formyl, aryl, aryloxy, heterocyclyl, amino, alkylamino, arylamido, alkylamido, thiol, thioalkyl, thioaryl, alkylsulfonyl, alkylcarbamoyl, arylcarbamoyl, nitro, cyano, nitrate; or R4 is selected from the group consisting of alkyl ester, formyl, hydroxy, arylamido, alkylamido, alkylcarbamoyl, arylcarbamoyl, amino, alkylsulfonyl, alkylamino; (4) R5 represents 1-3 substituents selected from the group consisting of hydrogen, deuterium, halogen, C1-C8 alkyl, C2-C8 alkenyl, C2-C8 alkynyl, C3-C8 cycloalkyl, C3-C8 cycloalkenyl, aryl or heterocyclyl, optionally substituted at one or more positions by deuterium, halogen, alkyl, alkyl ester, hydroxy, alkoxy, carboxy, formyl, aryl, aryloxy, heterocyclyl, amino, alkylamino, arylamido, alkylamido, thiol, thioalkyl, thioaryl, alkylsulfonyl, alkylcarbamoyl, arylcarbamoyl, nitro, cyano, nitrate; (5) R6 is hydrogen, deuterium, C1-C8 alkyl, C2-C8 alkenyl, C2-C8 alkynyl, C3-C8 cycloalkyl, C3-C8 cycloalkenyl, aryl or heterocyclyl any of which are optionally substituted at one or more positions by deuterium, halogen, alkyl, alkyl ester, hydroxy, alkoxy, carboxy, formyl, aryl, aryloxy, heterocyclyl, amino, alkylamino, arylamido, alkylamido, thiol, thioalkyl, thioaryl, alkylsulfonyl, alkylcarbamoyl, arylcarbamoyl, nitro, cyano, nitrate; or R6 is selected from the group consisting of halogen, alkyl ester, hydroxy, alkoxy, carboxy, formyl, aryloxy, amino, alkylamino, arylamido, alkylamido, thiol, thioalkyl, thioaryl, alkylsulfonyl, alkylcarbamoyl, arylcarbamoyl, nitro, cyano, nitrate, —OP(O)(OH)2, —OC(O)R7, —OSO2OH, —OC(O)NHR7, —OC(O)NR7R8 or —SONH; and (6) n is 1 to 5.

Formula II of Table 1A represents a compound comprising a structural analogue to 2,5-Dimethoxy-4-iodoamphetamine, wherein (1) A is C1-C6 alkylene, C2-C6 alkenylene, or C2-C6 alkynylene; (2) R1 and R2 are, independently, hydrogen, deuterium, C1-C8 alkyl, C2-C8 alkenyl, C2-C8 alkynyl, C3-C8 cycloalkyl (independently or ring close with the nitrogen), C3-C8 cycloalkenyl (independently or ring close with the nitrogen), aryl or heterocyclyl, optionally substituted at one or more positions by deuterium, halogen, alkyl, alkyl ester, hydroxy, alkoxy, carboxy, formyl, aryl, aryloxy, heterocyclyl, amino, alkylamino, arylamido, alkylamido, thiol, thioalkyl, thioaryl, alkylsulfonyl, alkylcarbamoyl, arylcarbamoyl, nitro, cyano, nitrate; (3) R3 is hydrogen, deuterium, C1-C8 alkyl, C2-C8 alkenyl, C2-C8 alkynyl, C3-C8 cycloalkyl, C3-C8 cycloalkenyl, aryl or heterocyclyl, optionally substituted at one or more positions by deuterium, halogen, alkyl, alkyl ester, hydroxy, alkoxy, carboxy, formyl, aryl, aryloxy, heterocyclyl, amino, alkylamino, arylamido, alkylamido, thiol, thioalkyl, thioaryl, alkylsulfonyl, alkylcarbamoyl, arylcarbamoyl, nitro, cyano, nitrate; or R3 is selected from the group consisting of halogen, alkyl ester, hydroxy, alkoxy, carboxy, formyl, aryloxy, amino, alkylamino, arylamido, alkylamido, thiol, thioalkyl, thioaryl, alkylsulfonyl, alkylcarbamoyl, arylcarbamoyl, nitro, cyano, nitrate; (4) R4 and R5 are, independently, hydrogen, C1-C8 alkyl, C2-C8 alkenyl, C2-C8 alkynyl, C3-C8 cycloalkyl, C3-C8 cycloalkenyl, aryl or heterocyclyl, optionally substituted at one or more positions by deuterium, halogen, alkyl, alkyl ester, hydroxy, alkoxy, carboxy, formyl, aryl, aryloxy, heterocyclyl, amino, alkylamino, arylamido, alkylamido, thiol, thioalkyl, thioaryl, alkylsulfonyl, alkylcarbamoyl, arylcarbamoyl, nitro, cyano, nitrate. or R4 and R5 are, independently for each occurrence, selected from the group consisting of alkyl ester, alkylsulfonyl, alkylcarbamoyl, arylcarbamoyl, nitrate; and (5) R6 represents 1-3 substituents selected from the group consisting of hydrogen, deuterium, halogen, C1-C8 alkyl, C2-C8 alkenyl, C2-C8 alkynyl, C3-C8 cycloalkyl, C3-C8 cycloalkenyl, aryl or heterocyclyl, optionally substituted at one or more positions by deuterium, halogen, alkyl, alkyl ester, hydroxy, alkoxy, carboxy, formyl, aryl, aryloxy, heterocyclyl, amino, alkylamino, arylamido, alkylamido, thiol, thioalkyl, thioaryl, alkylsulfonyl, alkylcarbamoyl, arylcarbamoyl, nitro, cyano, nitrate.

Formula III of Table 1A represents a structural analogue to Lysergic acid diethylamide, wherein (1) R1 and R2 are, independently, hydrogen, deuterium, C1-C8 alkyl, C2-C8 alkenyl, C2-C8 alkynyl, C3-C8 cycloalkyl (independently or ring close with the nitrogen), C3-C8 cycloalkenyl (independently or ring close with the nitrogen), aryl or heterocyclyl, optionally substituted at one or more positions by deuterium, halogen, alkyl, alkyl ester, hydroxy, alkoxy, carboxy, formyl, aryl, aryloxy, heterocyclyl, amino, alkylamino, arylamido, alkylamido, thiol, thioalkyl, thioaryl, alkylsulfonyl, alkylcarbamoyl, arylcarbamoyl, nitro, cyano, nitrate; (2) R3 is hydrogen, deuterium, C1-C8 alkyl, C2-C8 alkenyl, C2-C8 alkynyl, C3-C8 cycloalkyl, C3-C8 cycloalkenyl, aryl or heterocyclyl, optionally substituted at one or more positions by deuterium, halogen, alkyl, alkyl ester, hydroxy, alkoxy, carboxy, formyl, aryl, aryloxy, heterocyclyl, amino, alkylamino, arylamido, alkylamido, thiol, thioalkyl, thioaryl, alkylsulfonyl, alkylcarbamoyl, arylcarbamoyl, nitro, cyano, nitrate; or R3 is selected from the group consisting of halogen, alkyl ester, hydroxy, alkoxy, carboxy, formyl, aryloxy, amino, alkylamino, arylamido, alkylamido, thiol, thioalkyl, thioaryl, alkylsulfonyl, alkylcarbamoyl, arylcarbamoyl, nitro, cyano, nitrate; (3) R4 and R7 are, independently, hydrogen, deuterium, C1-C8 alkyl, C2-C8 alkenyl, C2-C8 alkynyl, C3-C8 cycloalkyl, C3-C8 cycloalkenyl, aryl or heterocyclyl, optionally substituted at one or more positions by deuterium, halogen, alkyl, alkyl ester, hydroxy, alkoxy, carboxy, formyl, aryl, aryloxy, heterocyclyl, amino, alkylamino, arylamido, alkylamido, thiol, thioalkyl, thioaryl, alkylsulfonyl, alkylcarbamoyl, arylcarbamoyl, nitro, cyano, nitrate; (4) R5 and R6 are, independently, hydrogen, deuterium, C1-C8 alkyl, C2-C8 alkenyl, C2-C8 alkynyl, C3-C8 cycloalkyl, C3-C8 cycloalkenyl, aryl or heterocyclyl, optionally substituted at one or more positions by deuterium, halogen, alkyl, alkyl ester, hydroxy, alkoxy, carboxy, formyl, aryl, aryloxy, heterocyclyl, amino, alkylamino, arylamido, alkylamido, thiol, thioalkyl, thioaryl, alkylsulfonyl, alkylcarbamoyl, arylcarbamoyl, nitro, cyano, nitrate; or R5 and R6 are, independently for each occurrence, selected from the group consisting of halogen, alkyl ester, hydroxy, alkoxy, carboxy, formyl, aryloxy, amino, alkylamino, arylamido, alkylamido, thiol, thioalkyl, thioaryl, alkylsulfonyl, alkylcarbamoyl, arylcarbamoyl, nitro, cyano, nitrate; and (5) R8 represents 1-3 substituents selected from the group consisting of hydrogen, deuterium, halogen, C1-C8 alkyl, C2-C8 alkenyl, C2-C8 alkynyl, C3-C8 cycloalkyl, C3-C8 cycloalkenyl, aryl or heterocyclyl, optionally substituted at one or more positions by deuterium, halogen, alkyl, alkyl ester, hydroxy, alkoxy, carboxy, formyl, aryl, aryloxy, heterocyclyl, amino, alkylamino, arylamido, alkylamido, thiol, thioalkyl, thioaryl, alkylsulfonyl, alkylcarbamoyl, arylcarbamoyl, nitro, cyano, nitrate.

Formula IV of Table 1 A represents a structural analogue of ibogaine, wherein (1) R1 is deuterium, C1-C8 alkyl, C2-C8 alkenyl, C2-C8 alkynyl, C3-C8 cycloalkyl, C3-C8 cycloalkenyl, aryl or heterocyclyl, optionally substituted at one or more positions by deuterium, halogen, alkyl, alkyl ester, hydroxy, alkoxy, carboxy, formyl, aryl, aryloxy, heterocyclyl, amino, alkylamino, arylamido, alkylamido, thiol, thioalkyl, thioaryl, alkylsulfonyl, alkylcarbamoyl, arylcarbamoyl, nitro, cyano, nitrate; (2) R2 is hydrogen, deuterium, C1-C8 alkyl, C2-C8 alkenyl, C2-C8 alkynyl, C3-C8 cycloalkyl, C3-C8 cycloalkenyl, aryl or heterocyclyl, optionally substituted at one or more positions by deuterium, halogen, alkyl, alkyl ester, hydroxy, alkoxy, carboxy, formyl, aryl, aryloxy, heterocyclyl, amino, alkylamino, arylamido, alkylamido, thiol, thioalkyl, thioaryl, alkylsulfonyl, alkylcarbamoyl, arylcarbamoyl, nitro, cyano, nitrate; or R2 is selected from the group consisting of halogen, alkyl ester, hydroxy, alkoxy, carboxy, formyl, aryloxy, amino, alkylamino, arylamido, alkylamido, thiol, thioalkyl, thioaryl, alkylsulfonyl, alkylcarbamoyl, arylcarbamoyl, nitro, cyano, nitrate; (3) R3 is hydrogen, C1-C8 alkyl, C2-C8 alkenyl, C2-C8 alkynyl, C3-C8 cycloalkyl, C3-C8 cycloalkenyl, aryl or heterocyclyl, optionally substituted at one or more positions by deuterium, halogen, alkyl, alkyl ester, hydroxy, alkoxy, carboxy, formyl, aryl, aryloxy, heterocyclyl, amino, alkylamino, arylamido, alkylamido, thiol, thioalkyl, thioaryl, alkylsulfonyl, alkylcarbamoyl, arylcarbamoyl, nitro, cyano, nitrate; or R3 is selected from the group consisting of alkyl ester, alkylsulfonyl, alkylcarbamoyl, arylcarbamoyl, nitrate; and (4) R4 represents 1-3 substituents selected from the group consisting of hydrogen, deuterium, halogen, C1-C8 alkyl, C2-C8 alkenyl, C2-C8 alkynyl, C3-C8 cycloalkyl, C3-C8 cycloalkenyl, aryl or heterocyclyl, optionally substituted at one or more positions by deuterium, halogen, alkyl, alkyl ester, hydroxy, alkoxy, carboxy, formyl, aryl, aryloxy, heterocyclyl, amino, alkylamino, arylamido, alkylamido, thiol, thioalkyl, thioaryl, alkylsulfonyl, alkylcarbamoyl, arylcarbamoyl, nitro, cyano, nitrate.

Another aspect of the present invention may involve the molecules disclosed in Table 1A for the treatment of diseases and conditions in mammals with NMDARs used according to the method below for preventing and treating diseases and conditions or improving functions in patients or subjects, the method comprising of repeated administration of Table 1 A substances or Table 1B (below) substances at doses, dosages, posology, and or formulations devoid of clinically meaningful psychedelic/psychotomimetic actions (neuroplastogen doses) and with clinical effects comparable to those exerted by human plasma psilocin Cmax of 4 ng/ml or less and or human 5-HT2A CNS receptor occupancy of 50% or less and preferably result in PD effects comparable to those exerted by human plasma psilocin Cmax of 2 ng/ml or less and or 5-HT2A human CNS receptor occupancy of 40% or less and preferably result in PD effects comparable to those exerted by human plasma psilocin Cmax of 1 ng/ml or less and or 5-HT2A human CNS receptor occupancy of 30% or less and/or in PD effects comparable to those exerted by human plasma psilocin Tmax in excess of 60 minutes and preferably in excess of 120 minutes and preferably in excess of 180 minutes.

This method may occur wherein the administering of the substance occurs under conditions that may modulate NMDARs and their subunits in addition to modulate 5-HT2A receptors; wherein the administering of the substance may provide excitotoxicity protection; wherein the administering of the substance may modulate neurogenesis; wherein the administering of the substance occurs under conditions effective for the substance to exert neuroplastogen effects, including modulation of neural plasticity; wherein the administering of the substance is safe and well tolerated, and, in particular, is devoid of clinically meaningful psychedelic and or psychotomimetic effects; wherein the administration of the substance is repeated over days or months or is chronic; wherein the administration of the substance is intermittent and occurs every second day, every third day or every other week or every 2 weeks or every other month; and/or wherein a blister package or other suitable packaging is used for the purpose of facilitating compliance when an intermittent (not daily) administration is used.

Another aspect of the invention may include a method for preventing and treating diseases and conditions or improving functions in patients or subjects, the method comprising of repeated administration of 5-HT2A agonist substances at doses, dosages, posology, and or formulations devoid of clinically meaningful psychedelic/psychotomimetic actions (neuroplastogen doses) and with clinical effects comparable to those exerted by human plasma psilocin Cmax of 4 ng/ml or less and or human 5-HT2A CNS receptor occupancy of 50% or less and preferably result in PD effects comparable to those exerted by human plasma psilocin Cmax of 2 ng/ml or less and or 5-HT2A human CNS receptor occupancy of 40% or less and preferably result in PD effects comparable to those exerted by human plasma psilocin Cmax of 1 ng/ml or less and or 5-HT2A human CNS receptor occupancy of 30% or less and/or in PD effects comparable to those exerted by human plasma psilocin Tmax in excess of 60 minutes and preferably in excess of 120 minutes and preferably in excess of 180 minutes;

This method may occur wherein the administering of the substance occurs under conditions that may modulate NMDARs and their subunits in addition to modulate 5-HT2A receptors; wherein the administering of the substance may provide excitotoxicity protection; wherein the administering of the substance may modulate neurogenesis; wherein the administering of the substance occurs under conditions effective for the substance to exert neuroplastogen effects, including modulation of neural plasticity; wherein the administering of the substance is safe and well tolerated, and, in particular, is devoid of clinically meaningful psychedelic and or psychotomimetic effects; wherein the administration of the substance is repeated over days or months or is chronic; wherein the administration of the substance is intermittent and occurs every second day, every third day or every other week or every 2 weeks or every other month; and/or wherein a blister package or other suitable packaging is used for the purpose of facilitating compliance when an intermittent (not daily) administration is used.

Another aspect may include a method for preventing and treating diseases and conditions in a subject, the method comprising of administering 5-HT2A agonists derivative, including carbamate derivatives, fluoro-derivatives and including nitro-derivatives and their deuterated versions including deuterated carbamate derivatives, deuterated fluoro-derivatives and including nitro-derivatives and deuterated fluoro-nitroderivatives, including substances listed in Table 1 A and Table 1B.

Any of the methods may include the treatment of the metabolic syndrome and its complications; the treatment of impaired glucose tolerance, diabetes and their complication; the treatment of NAFL, NAFLD, NASH and their complications; the treatment of obesity and its complications; the treatment of vision impairment and visual loss including macular degeneration and retinopathies; the treatment of neurological diseases, including neurodevelopmental diseases and neurodegenerative diseases that may benefit from modulation of neural plasticity, including: Neurological diseases and their symptoms and signs that may respond to neuroplastogen drugs and SMSNs include: Alzheimer's disease; presenile dementia; senile dementia; vascular dementia; Lewy body dementia; cognitive impairment, including mild cognitive impairment associated with aging and with chronic disease and its treatment, including chemotherapy, immunotherapy and radiotherapy, Parkinson's disease and Parkinsonian related disorders including but not limited to Parkinson dementia; disorders associated with accumulation of beta amyloid protein (including but not limited to cerebrovascular amyloid angiopathy, posterior cortical atrophy); disorders associated with accumulation or disruption of tau protein and its metabolites including but not limited to frontotemporal dementia and its variants, frontal variant, primary progressive aphasias (semantic dementia and progressive non fluent aphasia), corticobasal degeneration, supranuclear palsy; epilepsy; NS trauma; NS infections; NS inflammation, including inflammation from autoimmune disorders, including NMDAR encephalitis, and cytopathology from toxins, (including microbial toxins, heavy metals, and pesticides etc.); stroke; multiple sclerosis; Huntington's disease; mitochondrial disorders; Fragile X syndrome; Angelman syndrome; hereditary ataxias; neuro-otological and eye movement disorders; neurodegenerative diseases of the retina like glaucoma, diabetic retinopathy and age-related macular degeneration; amyotrophic lateral sclerosis; tardive dyskinesias; hyperkinetic disorders; attention deficit hyperactivity disorder and attention deficit disorders; restless leg syndrome; Tourette's syndrome; schizophrenia; autism spectrum disorders; tuberous sclerosis; Rett syndrome; cerebral palsy; disorders of the reward system including eating disorders [including anorexia nervosa ("AN") and bulimia nervosa ("BN"); and binge eating disorder ("BED"), trichotillomania, dermotillomania, nail biting; migraine; fibromyalgia; and peripheral neuropathy of any etiology. Symptoms or manifestations of nervous system disorders that may be treated or prevented by neuroplastogen substances and drugs include: a decline, impairment, or abnormality in cognitive abilities including executive function, attention, cognitive speed, memory, language functions (speech, comprehension, reading and writing), orientation in space and time, praxis, ability to perform actions, ability to recognize faces or objects, concentration, and alertness; abnormal movements including akathisia, bradykinesia, tics, myoclonus, dyskinesias, including dyskinesias relate to Huntington's disease, levodopa induced dyskinesias and neuroleptic induced dyskinesias, dystonias, tremors, including essential tremor, and restless leg syndrome; parasomnias, insomnia, disturbed sleep pattern; psychosis; delirium; agitation; headache; motor weakness, spasticity, impaired physical endurance; sensory impairment, including impairment of vision and visual field defects, smell, taste, hearing and balance, and dysesthesias; dysautonomia; and ataxia, impairment of balance or coordination, tinnitus, neuro-otological and eye movement impairments, neurological symptoms of alcohol withdrawal, including delirium, headache, tremors, hallucinations, hypertension; the treatment of psychiatric diseases as defined by DMS5 and ICD11 that may benefit from modulation of neural plasticity, including Schizophrenia spectrum and other psychotic disorders, Bipolar and related disorders, Depressive disorders, Anxiety disorders, Obsessive-compulsive and related disorders, Trauma- and stressor-related disorders, Dissociative disorders, Somatic symptom and related disorders, Feeding and eating disorders, Elimination disorders, Sleep-wake disorders, Sexual dysfunctions, Gender dysphoria, Disruptive, impulse-control, and conduct disorders, Substance-related and addictive disorders, Neurocognitive disorders, Personality disorders, Paraphilic disorders; the treatment of systemic inflammatory states and autoimmune disorders; the treatment of aging, senescence and associated deficits, including osteoporosis; the treatment of dry eye syndrome; the treatment of restless leg syndrome.

In any of these methods, the function may be chosen from visual, auditory, sense of balance, olfactory, gustatory.

In any of these methods, the substance may be psilocybin, psilocin, norpsilocin, baeocystin, nor-baeocystin or a mixture thereof; and/or the substance is a modified release formulation of psilocybin, psilocin, norpsilocin, baeocystin, nor-baeocystin or a mixture thereof. In certain embodiments, the drug is a combination of at least two drugs, the first drug chosen among 5-HT2A agonists, including psilocybin or psilocin or norpsilocin or baeocystin or norbaeocystin at doses of 0.01-24 mg and the second drug chosen among an open-channel low-affinity uncompetitive NMDAR antagonist, including dextromethorphan, dextromethadone, ketamine and its isomers, memantine, amantadine, noribogaine at doses of 0.01-50 mg; wherein the administering of the combination substance provides synergistic effects and or improved safety over the administration of either substance alone.

Further, any of the methods may occur in combination with magnesium and or zinc and or lithium and salts thereof; wherein the administering of the combination substance provides synergistic effects and or improved safety over the administration of either substance alone.

The method may include daily oral administration psilocybin and or psilocin and or baeocystin containing fungi and or extracts thereof.

In any of the methods, the substance may be coated with an emetic drug to lower the abuse potential of the substance.

And, the administering of substance is performed orally, buccally, sublingually, rectally, vaginally, nasally, via aerosol, trans-dermally, trans-mucosal, parenterally (e.g., intravenous, intradermal, subcutaneous, and intramuscular injection), epidurally, intrathecally, intra-auricularly, intraocularly, including implanted depot formulations, or topically, including creams, lotions, gels and ointments for the skin or for the eyes and eye drops.

It is known that fluorine can increase the lipophilicity of a molecule to allow higher partitioning into membranes and facilitate hydrophobic interactions with a target receptor. In the case of psychedelics, ring fluorination results in a loss of psychedelic effects, while maintaining 5-HT2A affinities, suggesting that activity at this receptor, while necessary, may not be sufficient for the psychedelic effects. (Blair J B1, Kurrasch-Orbaugh D, Marona-Lewicka D, Cumbay M G, Watts V J, Barker E L, Nichols D E. Effect of ring fluorination on the pharmacology of hallucinogenic tryptamines. J Med Chem. 2000 Nov. 30; 43(24):4701-10). Neural plasticity effects and neuroprotective effects may instead be maintained despite loss of psychedelic effects, and therefore, in light of the present inventors' disclosure, certain fluoro-derivatives may be of particular interest for the present inventors' neuroplastogen therapeutic programs, for which, as disclosed above in more detail, psychedelic/psychotomimetic effects are undesired side effects rather than therapeutic effects. Novel designed drugs characterized by 5-HT2A affinity and loss of psychedelic effects obtained with ring fluorination, may thus be particularly desirable for the therapeutic indications disclosed in this application, and particularly for condition and diseases that may benefit from modulation of NMDARs and or neural plasticity effects.

Furthermore, if a nitro-derivative of a psychedelic drug should prove itself effective for a specific disease, this therapeutic effect might derive from S-nitrosylation of overactive NMDARs with NO induced channel closure, as may be the case for nitro-memantines (Tomohiro Nakamura and Stuart A. Lipton. Protein S-Nitrosylation as a Therapeutic Target for Neurodegenerative Diseases. Trends in Pharmacological Sciences, January 2016, Vol. 37, No. 1) or it might be for another reason altogether (Stamler et al., US patent number U.S. Pat. No. 5,593,876A; Inturrisi, CE. NMDA receptors, nitric oxide and opioid tolerance. Regulatory Peptides, 1994, Volume 54, Issue 1), including, as revealed in this application, because of a differential modulation of 5-HT receptor subtypes or other receptors.

Furthermore, while reactive radicals—ROS and reactive nitrogen species (RNS) are normal components of cellular metabolism, overproduction of these types of radicals leads to inability of the cell to regulate them, which leads to redox imbalance and formation of oxidative stress. A nitro-derivative of a psychedelic drug with potential neural plasticity and neuro-protective actions may regulate these reactive radicals and prevent or decrease cellular damage by this or other mechanisms. Simply increasing the affinity for 5-HT2A receptors is not necessarily therapeutically advantageous for the indications disclosed in this application: LSD is a very potent psychedelic (the effective dose for inducing psychedelic effects is measured in micrograms) but it may not offer improved neuro-protection over other neuroplastogen molecules administered at comparable dosages devoid of psychedelic/psychotomimetic effects; a very high potency may instead pose safety concerns, as in the case of LSD. On the other hand, changes in molecular structure of select neuroplastogens that determine changes in their PK and PD functions might prove advantageous for select diseases and thus the synthesis of fluoro-derivatives and nitro-derivatives, and deuterated compounds, including a combinations of these modifications (including deuterated fluoro-nitro-derivatives), among other possible structural modifications, may result in novel potentially effective molecules therapeutic for the indications disclosed in this application.

Finally, the present inventors postulate that there is close proximity of 5-HT2A receptors and NMDARs within post-synaptic mega-complexes. This proximity may determine allosteric interactions, therefore, the activation of 5-HT2A by certain agonists at this receptor might also modulate, e.g., inhibit (close), the open NMDAR channel, and vice versa, NMDAR blockers may also interact with 5-HT2A receptors [(furthermore, some NMDAR blockers also inhibit the SERT and NET pathway (Codd et al., 1995) and more importantly the NMDAR antagonist dextromethadone exerts affinity of 5-HT-2A receptors in the nanomolar range (Rickli et al., 2017)]. The present inventors are currently testing these interactions in electrophysiological models to determine relations within receptor NMDAR subtype and 5-HT receptor subtype affinities and affinities to other select receptors, including dopamine receptors, sigma 1 receptors, histamine receptors of different molecules within both of these pharmaceutical classes (NMDAR antagonists and 5-HT2A agonists, including novel designer drugs) 5-HT1A; 5-HT1 B; 5-HT1 D; 5-HT2A; 5-HT2B; 5-HT2C; 5-HT5; 5-HT6; 5-HT7; D1; D2L; D3; D4; D5; SERT; NET; MOP; DOP; KOP; H1 Sigma 1; NMDAR2A, 2 B, 2C, 2D subtypes). The present inventors are also testing the affinity of nitro-derivatives that might be agonists at the 5-HT2A receptors and determine NMDA block by interacting with the open channel outer domain, as described above for nitro-derivatives.

Derivatives of 5-HT2A agonists of particular interest include psilocybin, psilocin carbamate, psilocin, norpsilocin, DMT, DMO, LSD, baeocystin, norbaeocystin, noribogaine derivatives; fluoro-derivatives (F), including fluoro-psilocybin; nitro derivatives (NO), including nitro-psilocybin; fluoro-nitro-derivatives, including fluoro-nitro-psilocybin; deuterated 5-HT2A agonist derivatives modified as above for psilocybin, including deuterated fluoro-derivatives (F), including fluoro-psilocybin, deuterated nitro derivatives (NO), including nitro-psilocybin, and deuterated fluoro-nitro-derivatives, including fluoro-nitro-psilocybin.

The same derivatives listed above for psilocybin are disclosed for psilocin, norpsilocin, DMT, DMO, LSD, baeocystin, norbaeocystin, noribogaine and carbamate derivatives thereof. See also Table 1A.

For the purposes of this disclosure, the present inventors define "prodrugs" or "pro-drugs" as compounds with moieties that can be hydrolyzed in vivo, both chemically or enzymatically, to release the active compound. Examples of prodrugs and their uses are well known in the art (See, e.g., Rautio et al. (2018) Nature Reviews Drug Discovery volume 17, pages 559-587). The prodrugs can be prepared in situ during the final isolation and purification of the compounds, or by separately reacting the purified compound with a suitable derivatizing agent. Examples of prodrug moieties include substituted and unsubstituted, branch or unbranched alkyl ester moieties, (e.g., propionoic acid esters), alkenyl esters, dialkylamino alkyl esters (e.g., dimethylaminoethyl ester), acylamino alkyl esters (e.g., acetyloxymethyl ester), acyloxy alkyl esters (e.g., pivaloyloxymethyl ester), aryl esters (e.g. phenyl ester), aryl alkyl esters (e.g., benzylester), aryl and arylalkyl esters, amides, alkylamides, dialkyl amides, and hydroxy amides, alkyl carbamates, dialkyl carbamates each optionally substituted at one or more positions by deuterium, halogen, alkyl, alkyl ester, hydroxy, alkoxy, carboxy, formyl, aryl, aryloxy, heterocyclyl, amino, alkylamino, arylamido, alkylamido, thiol, thioalkyl, thioaryl, alkylsulfonyl, alkylcarbamoyl, arylcarbamoyl, nitro, cyano, nitrate. Preferred prodrug moieties of the invention are N-monosubstituted amino acid carbamates (e.g. L-Isoleucyl, L-Leucyl, L-Alanyl, β-Alanyl, L-Valinyl etc.).

The invention may include a compound of any of formula in Table 1A, salts, and prodrugs thereof.

Psilocybin (PSY) is believed to act as prodrug for the corresponding Psilocin (PSI in vivo (Jacob III, P.; Shulgin, A. T. in NIDA Research Monograph 146 (Hallucinogens, an Update), 2000, Eds. Lin, G. C.; Glennon, R. A., pp. 74). PSY is dephosphorylated by alkaline phosphatase to active PSI. Furthermore, PSI chemically degrades quickly in the presence of air, heat, and/or light. This is due to the presence of the free 4-hydroxy group on the tryptamine scaffold, which is susceptible to oxidation. On the other hand, PSY is far more stable than PSI due to the presence of a phosphate ester, which protects the 4-OH group from degradation, both chemical and metabolic. Thus, the prodrug approach has been proven to be a successful tool for the exploitation of PSI pharmacological activity.

The invention also relates to new PSI carbamate prodrugs (4-carbamoyl indoles) and derivatives, also substituted at the 5-, 6-, and/or 7-positions in which the 4-hydroxyl moiety is reversibly protected as a carbamate ester linked to the N-terminus of a natural amino acid. It has been shown that lipophilic amino acid carbamate ester prodrugs of phenolic compounds strongly improve the bioavailability increasing absorption after oral administration, reducing metabolism and leading to a sustained release, up to 24 hours, of low concentrations of the active compound particularly in brain tissue (See, e.g., Azzolini et al. (2017) Eur J Pharm Biopharm volume 115, pages 149-158). A sustained release of the active compound at low concentration could represent an advantage for the PSI (and derivatives) pharmacological safe uses by avoiding the psychedelic/psychotomimetic effects after PSY (and derivatives) administration while maintaining the ability to promote both structural and functional plasticity in brain tissue.

For further clarification, the pro-drug concept is relative to the target effect, e.g. agonistic action at the 5-HT2A receptor. However, for a different target effect (e.g. NMDAR modulation) at a different postulated site (e.g., pore channel of the NMDAR), as postulated for drugs classified as 5-HT2A agonists and their derivatives listed in Table 1A, the pro-drug for the 5-HT2A receptor may also function as a drug for the pore channel block, as suggested by the present inventors' docking results (see Table 1B, below) for psilocybin and carbamate "prodrugs".

TABLE 1B

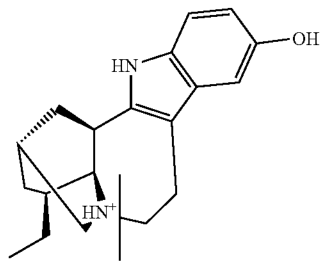

title: IBO
glide gscore: -7.58

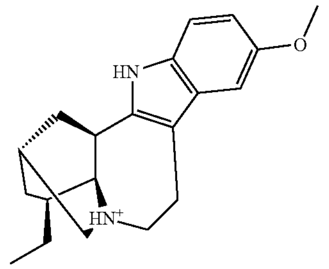

title: NIBO
glide gscore: -7.27

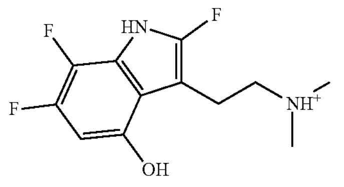

title: PSI14
glide gscore: -7.077

TABLE 1B-continued
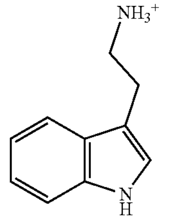
title: DDMT
glide gscore: -6.989
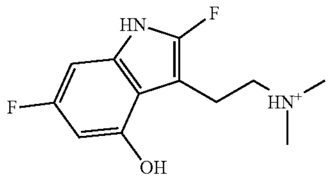
title: PSI10
glide gscore: -6.897
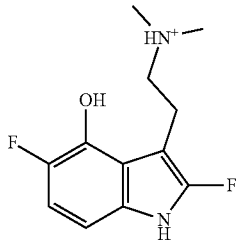
title: PSI9
glide gscore: -7.163
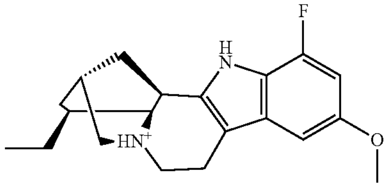
title: IBO1
glide gscore: -6.861
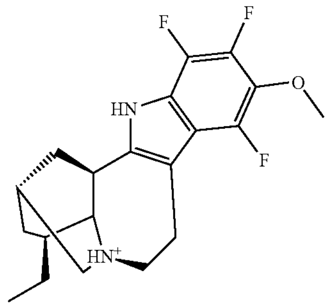
title: IBO7
glide gscore: -6.853
TABLE 1B-continued
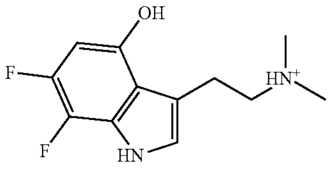
title: PSI6
glide gscore: -6.803
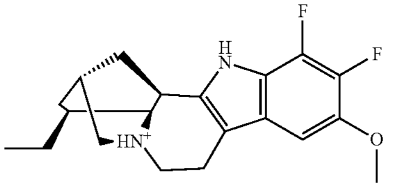
title: IBO4
glide gscore: -6.797
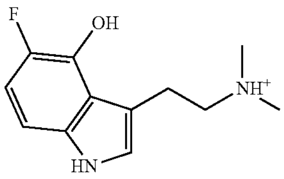
title: PSI1
glide gscore: -6.87
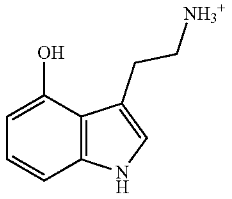
title: DPSI
glide gscore: -6.722
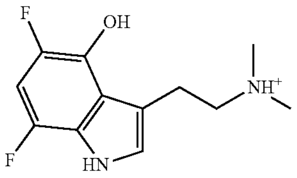
title: PSI7
glide gscore: -6.811
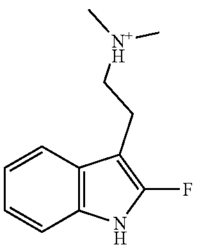
title: DMT4
glide gscore: -6.682

TABLE 1B-continued
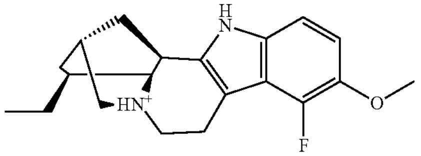
title: IBO3
glide gscore: -6.675
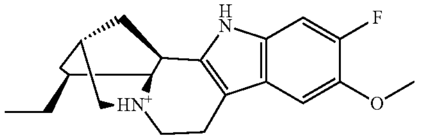
title: IBO2
glide gscore: -6.661
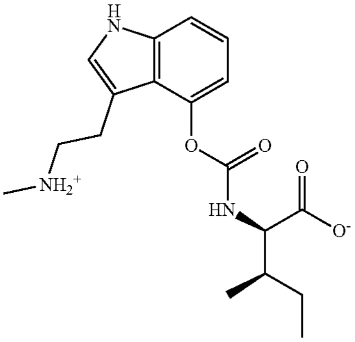
title: NPCARB
glide gscore: -6.641
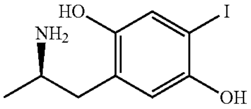
title: DDOI
glide gscore: -6.654
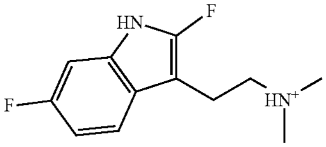
title: DMT12
glide gscore: -6.615
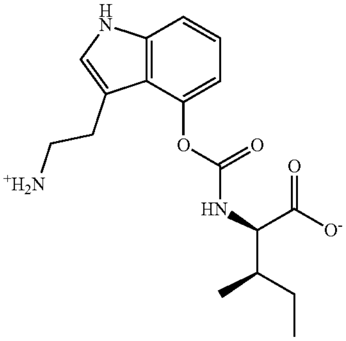
title: DPCARB
glide gscore: -6.604
TABLE 1B-continued
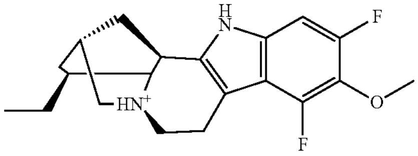
title: IBO6
glide gscore: -6.596
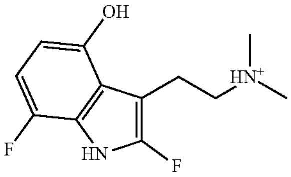
title: PSI8
glide gscore: -6.574
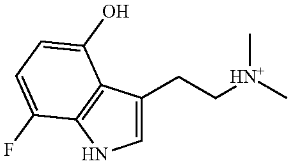
title: PSI3
glide gscore: -6.573
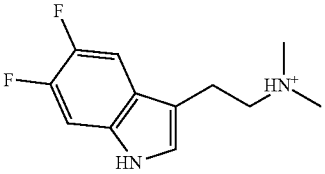
title: DMT5
glide gscore: -6.569
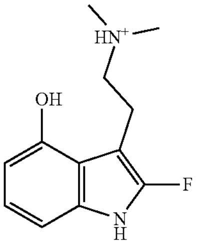
title: PSI4
glide gscore: -6.556
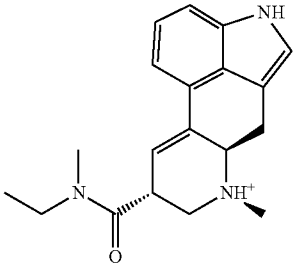
title: LSD
glide gscore: -7.286

TABLE 1B-continued
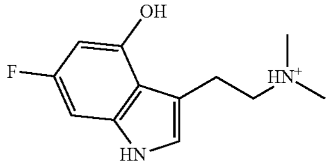
title: PSI2
glide gscore: -6.424
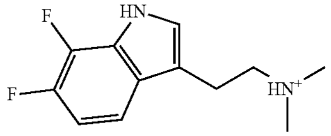
title: DMT6
glide gscore: -6.385
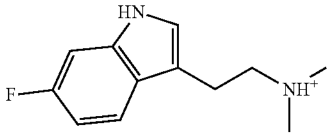
title: DMT2
glide gscore: -6.38
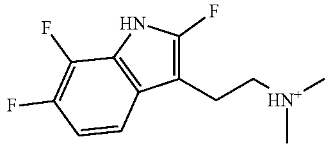
title: DMT14
glide gscore: -6.374
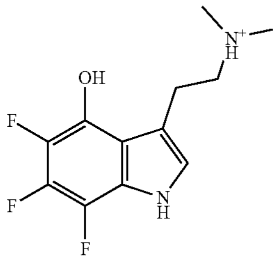
title: PSI11
glide gscore: -6.85
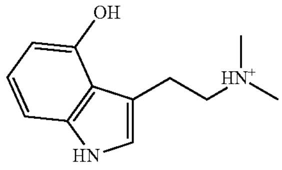
title: PSI
glide gscore: -6.292
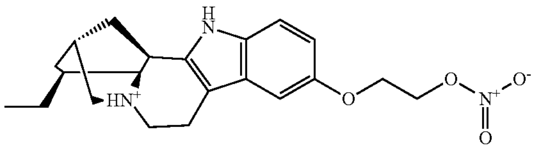
title: IBO8
glide gscore: -6.291
TABLE 1B-continued
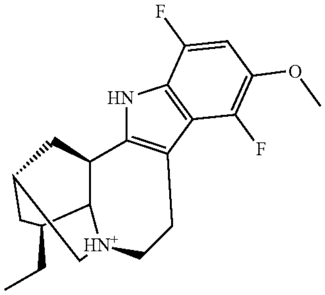
title: IBO5
glide gscore: -6.276
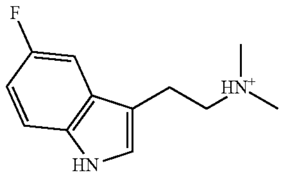
title: DMT1
glide gscore: -6.278
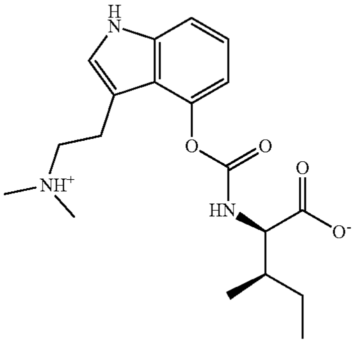
title: PCARB
glide gscore: -6.251
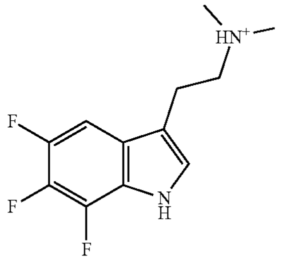
title: DMT10
glide gscore: -6.223

TABLE 1B-continued
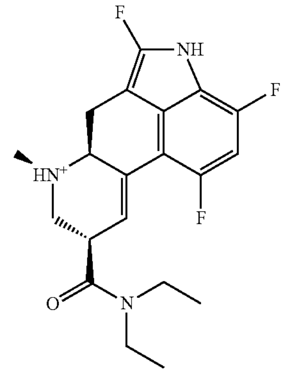
title: LSD11
glide gscore: -7.081
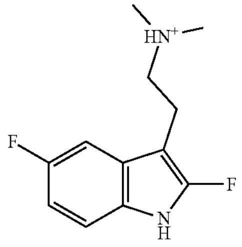
title: DMT9
glide gscore: -6.189
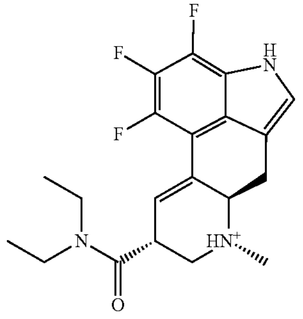
title: LSD10
glide gscore: -7.045
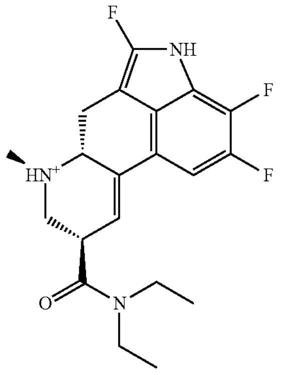
title: LSD12
glide gscore: -7.042
TABLE 1B-continued
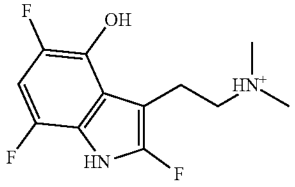
title: PSI13
glide gscore: -6.404
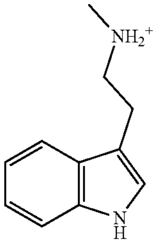
title: NDMT
glide gscore: -6.153
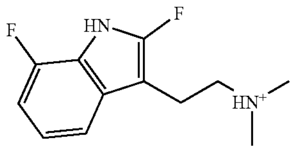
title: DMT8
glide gscore: -6.157
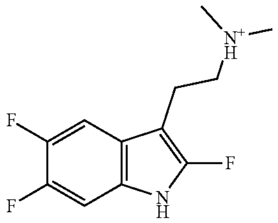
title: DMT11
glide gscore: -6.14
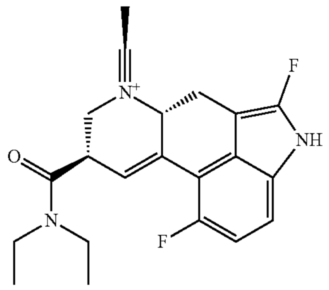
title: LSD6
glide gscore: -6.94

TABLE 1B-continued
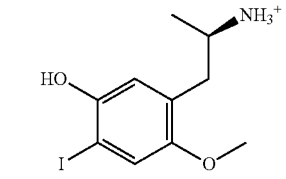
title: N2DOI
glide gscore: -6.146
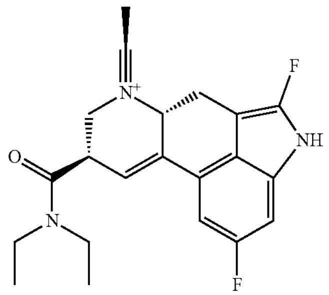
title: LSDB
glide gscore: -7.089
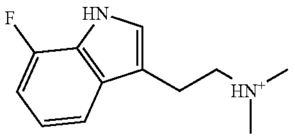
title: DMT3
glide gscore: -6.078
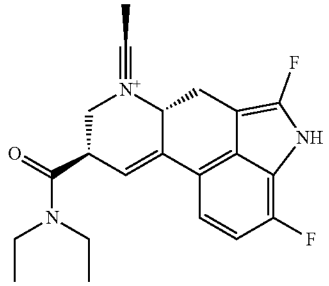
title: LSD3
glide gscore: -6.925
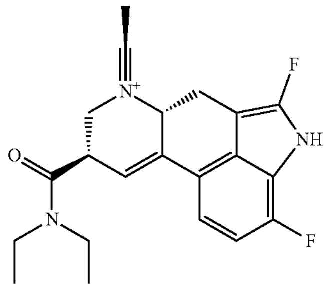
title: LSD9
glide gscore: -6.925
TABLE 1B-continued
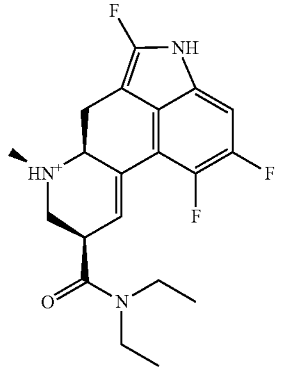
title: LSD13
glide gscore: -7.016
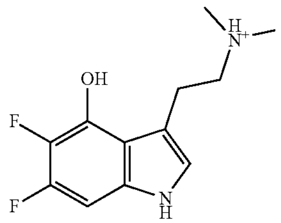
title: PSI5
glide gscore: -6.584
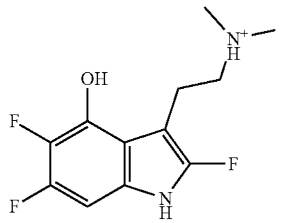
title: PSI12
glide gscore: -6.901
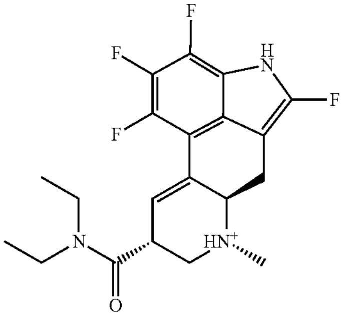
title: LSD14
glide gscore: -6.838

TABLE 1B-continued
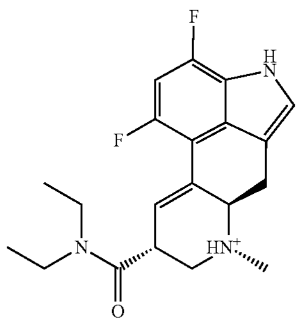
title: LSD5
glide gscore: -6.828
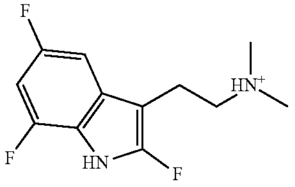
title: DMT13
glide gscore: -5.936
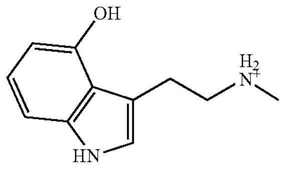
title: NPSI
glide gscore: -5.86
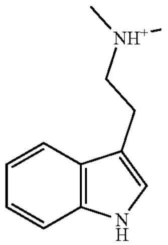
title: DMT
glide gscore: -5.853
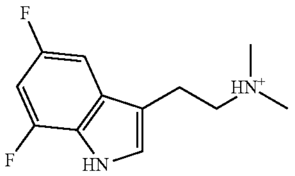
title: DMT7
glide gscore: -5.839
TABLE 1B-continued
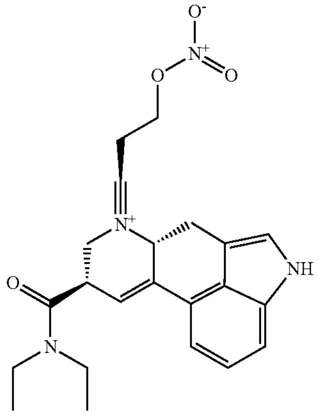
title: LSD15
glide gscore: -6.128
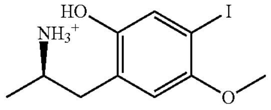
title: N1DOI
glide gscore: -5.813
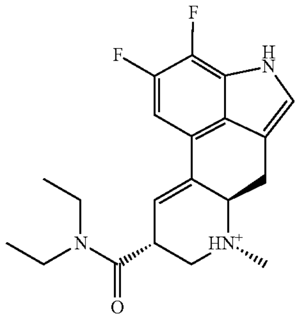
title: LSD7
glide gscore: -6.662
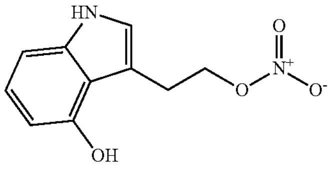
title: PSI15
glide gscore: -5.76
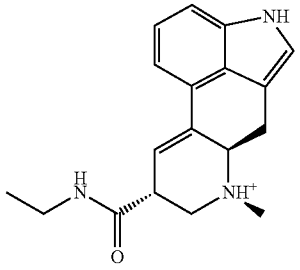
title: NLSD
glide gscore: -6.326

TABLE 1B-continued
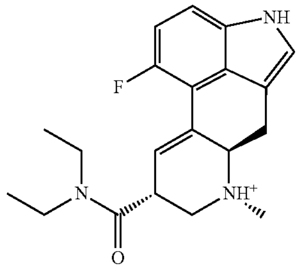
title: LSD1
glide gscore: -6.496
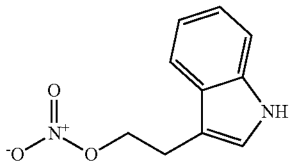
title: DMT15
glide gscore: -5.633
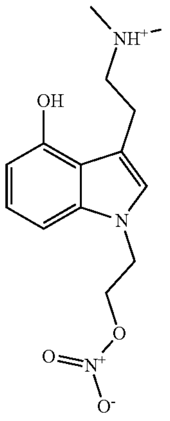
title: PSI16
glide gscore: -5.27
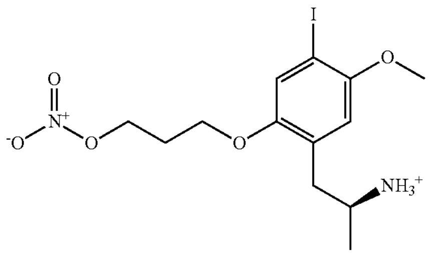
title: DOI2
glide gscore: -5.257
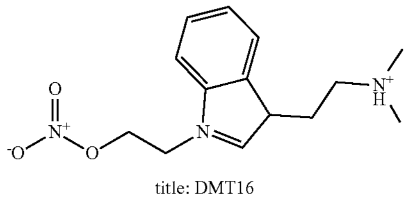
title: DMT16
glide gscore: -5.213
TABLE 1B-continued
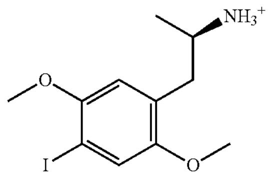
title: DOI
glide gscore: -5.159
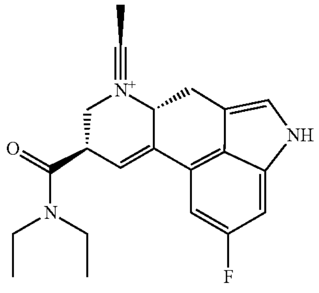
title: LSD2
glide gscore: -6.143
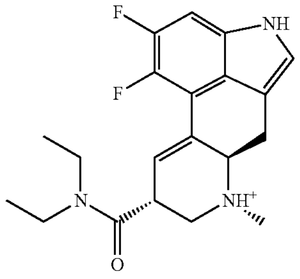
title: LSD4
glide gscore: -6.05
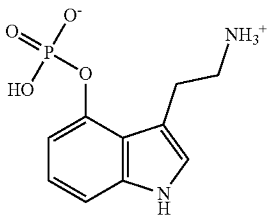
title: NBAE
glide gscore: -5.845
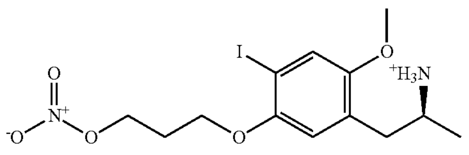
title: DOI1
glide gscore: -4.066

TABLE 1B-continued

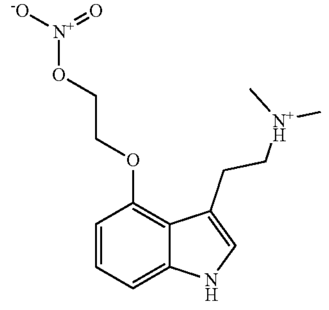

title: PSI17
glide gscore: -3.907

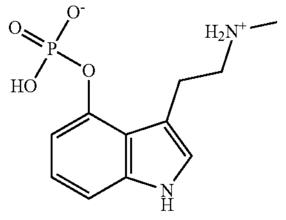

title: BAE
glide gscore: -5.15

The typical effects of psychedelic substances at moderately high doses [e.g., 12-20 mg (0.178-0.254 mg/Kg) of psilocybin resulting in plasma psilocin Cmax levels of 4.8-12.3 ng/ml.

(Hasler F, Bourquin D, Brenneisen R, Bär T, Vollenweider F X. Determination of psilocin and 4-hydroxyindole-3-acetic acid in plasma by HPLC-ECD and pharmacokinetic profiles of oral and intravenous psilocybin in man. Pharm Acta Helv. 1997; 72(3):175-184. doi:10.1016/s0031-6865(97)00014-9) include increased intensity and increased lability of affective responses and distortions of perceptual processes, visual, auditory and tactile. In another study by Hasler et al. 2004 (Hasler F, Grimberg U, Benz M A, Huber T, Vollenweider F X. Acute psychological and physiological effects of psilocybin in healthy humans: a double-blind, placebo-controlled dose-effect study. Psychopharmacology (Berl). 2004; 172(2):145-156. doi:10.1007/s00213-003-1640-6) looking at effects of different doses of psilocybin, the threshold dose of 0.045 mg/kg defined as "very low dose" (high dose in this study was close to ten times as much, 0.315 mg/kg) was rated clearly psychoactive by most of the study subjects. Slight drowsiness and increased sensitivity and intensification of pre-existing mood states were the most prominent effects at this "very low dose" of psilocybin. The findings by Hasler et al, 1994 and 2004, teach away from the potential uses of 5-HT2A agonists for non-psychiatric diseases and symptoms and also teach away from potential uses of 5-HT2A agonists for potential use for psychiatric diseases and symptoms when psychedelic and psychotomimetic effects are contraindicated or not necessary for the therapeutic activity. Furthermore, the findings of increased intensity and lability of affective responses by Hasler with "very low dose" and the findings of the Polito study on microdosing cited above teach away from potential neuropsychiatric therapeutic actions, including teaching away from positive effects on cognitive abilities (nootropic effects) or on enhancement of special senses, including vision. In fact, the production of distortion of visual, auditory and tactile processes teaches away from the use of these substances for the treatment of ophthalmological diseases and from their potential for bettering vision in general or for improving other special senses, including loss of hearing and tinnitus. Also, for subsets of psychiatric patients, including those suffering from the diseases and symptoms presently under clinical investigation (depression, addiction, post-traumatic stress disorder, anxiety), the current mode of administration of 5-HT agonists and in particular of psilocybin, which includes a single session during which a large psychedelic dose is administered, may be detrimental rather than therapeutic. As per the present inventors' current disclosure, these psychiatric patients could instead potentially benefit from small, non-psychedelic, repeated doses (neuroplastogen dosages, posology and formulations). The potentially effective doses tested in the present inventors' experimental models (0.01 mg/Kg) correspond to less than ¼ of the "very low dose" defined by Hasler (0.045 mg/Kg) (see experimental details below).

The psychotomimetic/psychedelic effects of psychedelic substances appear to be primarily but not solely mediated by serotonin receptors and in particular 5-HT2A receptors, based on experimental studies with moderately selective 5-HT2A antagonists (e.g., ketanserin, which blocks psychedelic effects), selective agonists (e. g., lorcaserin, selective for 5-HT2C and devoid of psychedelic effects) and based on the correlation of relative potency of psychedelic effects with the 5-HT2A affinity of different drugs (Ki for LSD, psilocin, DMT: 3.5; 107; 127). Aside for their affinity for 5-HT2A receptors, most psychedelic substances show moderate to high affinity towards several other receptors, including other serotonin receptors but also dopamine receptors and histamine receptors (Halberstadt A L, Geyer M A. Multiple receptors contribute to the behavioral effects of indoleamine hallucinogens. Neuropharmacology. 2011 September; 61(3):364-81). While the mind-altering effects, including the effects on sensory distortion induced by psychedelic substances appear to correlate with 5-HT2A receptor affinity, actions at other receptors, including 5-HT1, and or dopamine receptors are likely to contribute to these effects and other factors related to PK characteristics are also important (Blair J B, Kurrasch-Orbaugh D, Marona-Lewicka D, Cumbay M G, Watts V J, Barker E L, Nichols D E. Effect of ring fluorination on the pharmacology of hallucinogenic tryptamines. J Med Chem. 2000 Nov. 30; 43(24):4701-10). Based on the present inventors' novel experimental work detailed below and a thorough review of available data from the literature, the present inventors disclose a novel mechanism for the neuroplasticity induced by 5-HT2A agonists: 5-HT2A agonist induced neural plasticity may be secondary to modulation of synthesis of NMDAR subunits, an action possibly mediated via NMDAR blocking effects via allosteric interactions. This effect may be initiated and maintained by the acute downregulation of 5-HT2A receptors, which is the basis for the known acute tolerance that develops from administration of 5-HT2A agonists at high (psychedelic) doses. The chronic downregulation of 5-HT2A receptors determined by chronic doses (multiple doses administered for days or months) may thus be at the basis of the neural plasticity effects mediated by NMDAR modulation, which is potentially therapeutic for a multiplicity of conditions and disorders.

Potential neurological, metabolic and ophthalmic therapeutic effects discussed below may also be determined at least in part by actions at receptors other than 5-HT2A and or mediated by other mechanisms, including yet uncovered mechanisms, including those that may be consequential to the binding to 5-HT2A receptors, and which may be present, or differentially present, at dosages that do not produce psychotomimetic/psychedelic effects and are thus potentially therapeutic for a multiplicity of diseases and conditions for which psychotomimetic and psychedelic effects are detrimental side effects. Furthermore, other properties may also be important in determining psychotomimetic effects, such as on-set and off-set receptor time, thus offering potential parameters for improvement of clinical efficacy for newly designed SMSNs with neuroplastogen effect but devoid of psychotomimetic effects even at higher dosages, thus widening the therapeutic window for non-psychedelic novel 5-HT2A agonist drugs.

While the findings of the potential for modulation of neural plasticity by indoleamines and other psychedelics is becoming better understood (Ly et al., 2018), the potential therapeutic value of these substances and drugs beyond psychiatric diseases, and the concept that modulation of neural plasticity and the potential for neuro-protective effects can be achieved without psychedelic/psychotomimetic effects, needs to be studied beyond the current research focus which presently remains centered around the administration of 5-HT2A agonists in isolated treatment sessions at doses that cause intense psychedelic/psychotomimetic effects for the treatments of psychiatric diseases. In summary, the psychedelic experience and its strong psychotomimetic effects are still thought to be integral and necessary for the psychiatric therapeutic effects, by the layman, the user as well as by the scientific community. The heavy sociocultural weight carried by these substances and the current scientific view centered on psychiatric diseases and primarily on psychedelic treatments for depression, are so strong as to define them as narrowly as psychedelics or at the most psychoplastogens (Ly et al., 2018), with reference to their ability to induce a potentially therapeutic psychedelic experience, with potentially therapeutic effects limited to the psychiatric field, without acknowledging that therapeutic effects can be present at "neuroplastogen doses" administered chronically, as shown by the present inventors' novel research, and can be therapeutic outside of the psychiatric field for metabolic, ophthalmological and neurological diseases and conditions. Thus, the present inventors disclose here that 5-HT2A agonist drugs devoid of psychedelic effects (e.g., psilocybin 0.1-4 mg), have neuroplastogen effects, and are potentially therapeutic for a multiplicity of diseases and conditions, which may include but are not limited to psychiatric disorders, as disclosed throughout this application.

The importance of administering neuroplastogen doses of drugs with effects on neural plasticity repeated over time is instead well acknowledged for NMDAR antagonists with the potential for treatment of neurological diseases. The present inventors reviewed the available publications for the open channel NMDAR blocker dextromethadone in several published studies and in published patent applications in the light of the present inventors' present observations, results and disclosures: in a single ascending dose study (SAD) where doses of 5-200 mg were tested, only the lowest tested dose of 5 mg of dextromethadone elicited a nootropic signal (International Patent Application No. PCT/US2018/016159). In this study the MTD was set at 150 mg (nausea and vomiting), so the supposedly nootropic dose was 1/30 of the MTD. In a multiple ascending dose test (MAD) where doses of 25, 50 and 75 mg were tested over a 14-day period, only the lower dose (25 mg daily) resulted in a statistically significant increase in plasma BDNF (De Martin et al., 2018).

A recent study compared the cognitive effects of psilocybin 10,20,30 mg and dextromethorphan 400 mg. This study found dose-dependent negative effects of psilocybin on psychomotor performance, working memory, episodic memory, associative learning, and visual perception, which again teach away from the current disclosure. The effects of the 400 mg dose of dextromethorphan on psychomotor performance, visual perception, and associative learning were in the range of effects of a moderate to high dose (20 to 30 mg/70 kg) of psilocybin. This was the first study of the dose effects of psilocybin and dextromethorphan on a large battery of neurocognitive assessments. Psilocybin had greater effects than DXM on working memory. DXM had greater effects than all psilocybin doses on balance, episodic memory, response inhibition, and executive control (Barrett F S, Carbonaro $T_M$, Hurwitz E, Johnson M W, Griffiths R R. Double-blind comparison of the two hallucinogens psilocybin and dextromethorphan: effects on cognition. Psychopharmacology (Berl). 2018 October; 235(10):2915-2927). Notably, the tested dose of dextromethorphan, 400 mg, is much higher than the dose used in approved formulations with neurological therapeutic effects (the dextromethorphan dose FDA approved for pseudobulbar affect is 20 mg, a much smaller dose compared to 400 mg used in the above study, even when accounting for the metabolic block afforded by quinidine).

Based on the above observations for the NMDAR open channel blocker dextromethadone (International Patent Application No. PCT/US2018/016159; De Martin et al., 2018) and the dose dependent cognitive effects observed in the Barrett 2018 study for dextromethorphan and psilocybin, the present inventors disclose not only that the effects of 5-HT agonists and NMDAR antagonists are similar in their potential for inducing neural plasticity, as seen in vitro and in vivo studies, but that the clinically advantageous therapeutic actions of these drugs may be present only at low "neuroplastogen doses" and not necessarily at higher doses, and that there is a ceiling to the therapeutic dose and that psychedelic effects may represent the ceiling for therapeutic effects, at least for the majority of disorders and patients that may benefit from non-psychedelic neuroplastogens: when the doses of NMDAR antagonists and the doses of 5-HT2A agonist are high enough to result in psychedelic, dissociative, psychotomimetic symptoms and in the type of neurocognitive impairments described by Barrett et al, 2018, the therapeutic effect of these substances for some or all of the indications here disclosed is likely compromised. The same is true for ketamine that at high doses is anesthetic and at lower doses is an FDA approved antidepressant (esketamine).

However, based on the present inventors' observations and findings, the present inventors disclose that at lower doses devoid of the psychedelic experience side effects (at doses approximately 1/10-1/20 of the psychedelic dose), drugs in both classes, 5-HT2A agonists and NMDAR open channel blockers, exert neuroplastogen actions with potential therapeutic effects for a multiplicity of diseases and conditions. The psychedelic experience and the psychotomimetic symptoms induced by these drugs, which in the current scientific view are essential for the therapeutic actions, particularly for certain psychiatric disorders, may therefore be a side effect avoidable by administering a lower dose in a repeated, daily, every other day, every three days, weekly, biweekly or monthly or chronic daily schedule for most of the indications disclosed in this application.

For further clarification, neuroplastogen effects adequate for exerting clinically meaningful effects for a multiplicity of diseases are induced by doses of 5-HT agonists much lower than the doses in current use by laymen, including traditional tribal users, recreational users and therapists and the doses employed in ongoing clinical trials for psychiatric disorders, including those at major US university centers.

Finally, the effects on neural plasticity, and not the "psychedelic experience", are the basis for the main potential therapeutic actions of neuroplastogens, including the potential therapeutic effects for nervous system disorders and conditions, metabolic disorders, ophthalmological disorders, including the effects on special senses, the effects on aging and including some of the effects on psychiatric disorders for which the psychedelic effects may not be necessary and thus represent detrimental side effects. While the present inventors cannot exclude that for certain patients the psychedelic experience may be therapeutic (clinical trials are underway), the present inventors disclose that there is a large group of psychiatric patients that may benefit from neuroplastogens (non-psychedelic repeated doses of 5-HT agonists) for whom the psychedelic experience is detrimental and thus for these patients a much lower and safer dose of drug may be needed, e.g., 0.1 mg-4 mg of psilocybin or psilocybin equivalent, and administered on a regular basis (continuous or intermittent)n for days or months or chronically, instead of the currently used doses of 8-50 mg administered in one isolated session. Furthermore, at lower neuroplastogen doses, the agonist effect at 5-HT2A receptors is not clinically meaningful, especially if this 5-HT2A effect is defined by its ability to induce psychedelic/psychotomimetic effects. As shown in the present inventors' Example 3 experiment, the neuroplastogen effects of these drugs classified as 5-HT2A agonists may be secondary to modulating actions at the NMDAR.

The same concept stands for NMDAR antagonists, but for these drugs the concept is already understood by the scientific community and the approved therapeutic dose for dextromethorphan is well below the dose that causes dissociative symptoms and the doses of dextromethadone under clinical investigation do not cause psychotomimetic effects (International Patent Application No. PCT/US2018/016159; Relmada.com).

Furthermore, the present inventors hypothesize that at least some of the neuroplastogen effects may not be induced by the direct agonist interaction with the 5-HT2A receptors and subsequent downstream cascade but may be secondary to other mechanisms including down regulation/modulation of 5-HT receptor expression, including 5-HT52A receptors, following exposure to 5-HT agonists and to potential effects on other receptors such as NMDARs and AMPA receptors and DA and histamine and sigma 1 and opioid receptors. Some of the neuroplastogen effects, including those potentially therapeutic for a multiplicity of diseases and conditions, may therefore be best achieved with the administration of repeated small doses of drugs devoid of psychedelic/psychotomimetic effects, rather than administered as a single large dose with psychedelic/psychotomimetic effects.

Ly et al., 2018, studied in vitro and in vivo the acute effects of large doses of several compounds with 5-HT2A agonist activity (however, Ly et al. 2018, did not specifically study psilocin/psilocybin and did not study NMDAR antagonists and did not disclosed possible actions of drugs classified as 5-HT2A agonists at NMDARs). The studies by Ly et al., 2018 were designed to assess the mechanisms underlying the clinical findings of the effects of large doses of select drugs producing psychedelic and psychotomimetic effects in patients with psychiatric disorders and in particular the effects of these drugs in patients with depression and anxiety. The findings by Ly et al. 2018, support their hypothesis: large doses (doses expected to produce psychedelic and psychotomimetic effects in humans) of psychedelics potentially promote functional neural plasticity in prefrontal cortical neurons and this effect potentially results in the antidepressant and anxiolytic effects seen in patients currently undergoing investigations in phase 2 clinical trials. The present inventors performed a different subset of experiments as detailed below, to study a different hypothesis: low neuroplastogen dosages, administered chronically, of drugs classified as 5-HT2A agonists and modulators, exert neuroplastogen effects by modulating NMDARs and thus may be potentially therapeutic for diseases and conditions and for improvement of functions, including vision.

While the current DEA scheduling (schedule I) for 5-HT2A agonist drugs may change as therapeutic indications and range of effects are better defined by the clinical studies that are underway for psychiatric uses, abuse concerns, partly driven by sociocultural forces, still make these drugs unappealing for development as pharmaceutical agents (Sellers E M, Romach M K, Leiderman D B. Studies with psychedelic drugs in human volunteers. Neuropharmacology. 2018 November; 142:116-134). Presently, researchers of psychedelic drugs for the treatment of psychiatric diseases have only considered their use at high doses (psychedelic) in single session in supervised settings. This requirement for in-patient and or supervised administration may reduce the abuse potential because the drug is directly administered in a supervised setting, generally by a therapist, with reduced risk for diversion.

The relative safety and low addiction potential of these substances have been underscored in recent scientific publications (Johnson M W, Griffiths R R, Hendricks P S, Henningfield J E. The abuse potential of medical psilocybin according to the 8 factors of the Controlled Substances Act. Neuropharmacology. 2018 November; 142:143-166.), however, potential for abuse of pharmaceutical 5-HT2A agonists is realistic and the potential for harmful effects when these drugs are taken for recreational purposes, while generally not severe, is well documented, with nearly 6000 cases with psilocybin-containing mushrooms reported to United States poison centers from 1 Jan. 2000 to 31 Dec. 2016 (Leonard J B, Anderson B, Klein-Schwartz W. Does getting high hurt? Characterization of cases of LSD and psilocybin-containing mushroom exposures to national poison centers between 2000 and 2016. J Psychopharmacol. 2018 December; 32(12):1286-1294). Therefore, the potential for abuse of 5-HT agonists with neuroplastogen effects poses safety questions, especially if these drugs with neuroplastogen actions are intended for prolonged outpatient therapy, in relatively unsupervised settings: recreational users, in search for the psychedelic experience, could potentially abuse the drug by self-administering several tablets at once, rather than the non-psychedelic/psychotomimetic prescribed dose.

In order to minimize the potential for abuse of these substances the present inventors disclose formulation strategies that introduce anti-abuse features that have the potential to lower their abuse potential, even when administered in an outpatient setting.

The present inventors therefore disclose the combination of a neuroplastogen with an emetic drug, including an emetic embedded in the capsule or in the coating of a tablet, including emetic drugs acting at the CTZ in the medulla and or gastrointestinal irritants. The present inventors disclose an abuse deterrent formulation which comprises the combination of a neuroplastogen with the potential for causing psychedelic effects when abused (e.g., ingestion of 10 times the prescribed neuroplastogen dose may potentially induce psychedelic effects) with a low dose emetic drug: the emetic drug dose is ineffective when the drug is taken as prescribed (e.g., one or two tablets at once) but the emetic dose becomes effective if a subject attempts to abuse the drug and ingests a larger dose (multiple tablets, e.g. over three tablets at once) with the intention of inducing psychedelic effects (e.g., 5-10 tablets at once would potentially induce psychedelic effects). Of note, even without the induction of emesis, which may occur only when higher doses are ingested (e.g., 10 times or more of the prescribed dose) less severe but still deterring nauseating effects might occur when the abuse is limited to 3-5 times the prescribed dose and these deterring effects may be sufficient for limiting future abuse (even the weak psychedelic experience searched by a potential drug abuser would be greatly impoverished by concomitant nausea).

Along the same lines the present inventors also disclose other forms of abuse deterrent drugs and methods that can be combined with MR 5-HT neuroplastogens, including when combined to emetic drugs, including when formulated as long-acting and or slow release pharmaceutical compositions: (1) incorporation of an excipient that gels when mixed with water, alcohol, or other common solvents; (2) incorporation of a physical barrier that resists crushing, dissolving, melting, or chemical extraction; (3) formulation of very strong tablets that are extremely hard to brake or tamper; (4) chemically engineering prodrugs that require in vivo enzymatic cleavage to produce a pharmacological effect (e.g., an amidic linkage formed between the drug molecule and a single amino acid like lysine or a small (up to 15 amino acids) oligopeptide, an ester linkage formed between a hydroxyl group on the drug and a carboxylic group on the carrier, complexation with an ion exchange resin, complexation with a metal cation, complexation with a fatty acid); (5) incorporation of another aversive ingredient, in addition or in alternative to the emetic drug: (e.g., a flushing agent [niacin], a diuretic, a laxative, or irritant [capsaicin]; nasal irritants, emetic agents, bittering agents, and effervescent agents; and/or (6) co-formulation with a sequestered antagonist or aversive agent that is released upon product tampering.

Modified Release (MR) Formulations

While some patients/diseases and condition may benefit from IR psilocybin at non-psychedelic/psychotomimetic doses (e.g., 2-4 mg or less), subsets of patients or select diseases and conditions may require a slightly higher dose of psilocybin or other 5H-2a agonist (e.g., baeocystin MR) for optimal neuroplastogen action. However, for these patients the psychedelic/psychotomimetic effects would be detrimental. In fact, large subsets of patients, in particular those that could benefit the most from neuroplastogens (such as patients with neurodevelopmental and neurodegenerative disorders, and elderly patients, and all patients with some form of cognitive impairment, including minimal cognitive impairment, and many patients with psychiatric disorders as defined by DSM5), are likely more susceptible to experiencing detrimental psychedelic and psychotomimetic side effects if doses higher than 2-4 mg of IR psilocybin are administered.

The inter-individual variability in experiencing psychedelic/psychotomimetic is well documented. Pharmacological inter-subject PK variability factors and non-pharmacological variability factors, both play an important role on inter-subject susceptibility to psychedelic/psychotomimetic side effects of neuroplastogens. Therefore, while psychedelic/psychotomimetic effects of 5-HT2A agonists are directly related to the dose administered [Studerus E, Kometer M, Hasler F, Vollenweider F X. Acute, subacute and long-term subjective effects of psilocybin in healthy humans: a pooled analysis of experimental studies. J Psychopharmacol. 2011 November; 25(11):1434-52]; Studerus E, Gamma A, Kometer M, Vollenweider F X. Prediction of Psilocybin Response in Healthy Volunteers. PLoS ONE. 2012; 7], and plasma levels, which also correlate with 5H2A receptor occupancy [Madsen, M. K; Burmester, D; Stenbåk, D. S. Psilocybin occupancy of brain serotonin 2A receptors correlates with psilocin levels and subjective experience: a (11C) Cimbi-36 PET study in humans. European Neuropsychopharmacology, 2019, Volume 29], some patients will be unable to tolerate even the very low (e.g., less than 1 mg of psilocybin or psilocybin equivalent) potentially effective IR psilocybin dose without incurring in cognitive side effects, including psychedelic/psychotomimetic side effects. Properly designed MR formulations of 5-HT2A agonists, able to target specific PK parameters (Cmax, AUC, Tmax) and PD effects (receptor occupancy and psychedelic/psychotomimetic effects or lack of thereof) as detailed below, may be instead effective for these patients.

Aside from the dose, and individual PK and psychiatric variables, the difference in pharmacokinetic parameters caused by the route of administration of psilocybin also plays an important role in the psychedelic/psychotomimetic effects: the high Cmax (12.9+−5.6 ng/ml) and short Tmax (1.9+−1 min) of 1 mg of IV psilocybin compared to oral psilocybin 10-20 mg (similar Cmax: 8.2+−2.8 ng/ml; longer Tmax: 105+−37 min) elicited similar psychedelic effects despite a much smaller AUC for the IV administered drug (240+−55 versus 1963+−659) (Hasler F, Bourquin D, Brenneisen R, Bar T, Vollenweider F X. Determination of psilocin and 4-hydroxyindole-3-acetic acid in plasma by HPLC-ECD and pharmacokinetic profiles of oral and intravenous psilocybin in man. Pharm Acta Helv. 1997 June; 72(3):175-84). Cmax and Tmax are also likely enhanced (Cmax) and shortened (Tmax), similarly to IV administration, when the drug is inhaled intranasally, instead of taken orally. Bearing the importance of dose and route, PK parameters and other variables related to subsets of patients and or select diseases and conditions, a modified release formulation (oral or transdermal) may optimize the PK parameters (and PD effects) for neuroplastogen actions without cognitive side effects, rather than for psychedelic effects, by allowing the administration of higher daily doses without the side effects of psychedelic/psychotomimetic effects, by maintaining a lower Cmax and longer Tmax and a larger or equal AUC compared to IR 5-HT2A agonists.

As discussed above, patients who may benefit the most from neuroplastogen drugs, such as patients with neurodevelopmental and neurodegenerative disorders and elderly patients, and patients with even minimal cognitive impairments, are also those with the lower tolerance and at higher risk for psychedelic and psychotomimetic effects. The present inventors, therefore, disclose the use of modified release formulations of 5-HT2A agonists (e.g., psilocybin MR and baeocystin MR) that optimize PK parameters compared to the same dose of 5-HT2A IR: lower Cmax, slower Tmax, increased T½ and comparable or larger AUC. This modified release formulation will allow administration of dosages of psilocybin higher than those that would be tolerated with the IR formulation, thus avoiding psychedelic/psychotomimetic side effects, allowing for example doses up to 32 mg of psilocybin, a dose that in the IR formulation will cause psychedelic/psychotomimetic effects in the majority of patients, and also allowing for very small doses, e.g. 0.5 mg psilocybin, which in select clinical settings (e.g., dementia) or for very sensitive individual patients, may only be tolerated in a MR formulation and not in IR formulations. The paper by Madsen et al., cited above, correlates psychedelic/psychotomimetic symptoms with psilocin plasma levels and 5-HT2A receptor occupancy. In this study an oral dose of 3 mg of IR psilocybin (the lowest dose tested in the study) determined psychedelic/psychotomimetic effects, psilocin Cmax of 2.4 ng/ml and 42.9% 5-HT2A receptor occupancy. The intensity of the psychedelic/psychotomimetic symptoms was mild compared to the tested higher doses which resulted in more intense psychedelic/psychotomimetic effects, higher Cmax (up to 19.3) and higher receptor occupancy (up to 72.4%). Of note, the subject with the highest receptor occupancy (72.4%) was not the subject with the highest psilocin plasma levels, suggesting additional potential inter-individual variables, other than Cmax, in determining receptor occupancy (e.g., CNS penetration of the drug, receptor variables, including affinity state of receptors). Additionally, especially as technology progresses and test costs decrease, the assessment of receptor occupancy might aid in predicting tolerability of neuroplastogen doses of 5-HT2A agonists without psychedelic/psychotomimetic side effects [e.g., receptor occupancy equal or less than 40% (or less than 50% or less than 30%) may predict good tolerability to the tested neuroplastogen dose. Thus, a 5-HT2A receptor occupancy test may aid the clinician in prescribing the appropriate neuroplastogen dose for an individual patient.

Finally, because of PK and or PD effects, including receptor modulation and receptor occupancy, the combination of 5-HT2A agonists and NMDA antagonists, including the combination of psilocybin and dextromethadone, may offer synergic advantages while decreasing the potential for psychedelic/psychotomimetic and other side effects, as discussed throughout this application.

It is known that the different subtypes of NMDARs change across the lifespan: NMDAR2B are more prevalent at a younger developmental age and later in development are substituted by NMDAR2A. NMDAR2B appear to have a longer "on" time and thus this receptor subtype has been associated with enhanced long-term potentiation (LTP) and some phases of life (young age) are characterized by facilitated learning, e.g., language learning. This naturally occurring NMDAR subtype shift (2B→2A) could potentially be physiologically modulated by actions at 5-HT2A receptors by endogenous agonists (e.g., DMT). Low dose 5-HT2A agonists could exert enhanced neuroplastogen modulatory actions, as seen in the present inventors' in vitro experiments in ARPE-19 cells.

While the present inventors cannot exclude that psychedelic symptoms may be therapeutic in select diseases and for select psychiatric symptoms or for select patients, as hypothesized by some researchers (clinical trials to answer this question are underway), the current view of the layman and of scientific community that the psychedelic/psychotomimetic effects are always necessary for the potential therapeutic activity of 5-HT2A agonists is challenged by the present inventors' observations, experimental results and disclosures.

The present inventors therefore disclose that neuroplastogens, as defined above, and which comprise 5-HT agonists, including 5-HT agonist with potential modulating activity on NMDARs and their subtypes, potentially exert their neuroplastogen therapeutic effects at doses that do not produce psychedelic/psychotomimetic/dissociative effects and do not produce negative neurocognitive side effects and may actually result in nootropic effects, especially if neurocognitive tests are performed after the drug has had the time to exert its modulating CNS plasticity actions (chronic dosing). To this effect, the present inventors are verifying, both in vitro and in vivo, the changes in NMDAR receptor expression and 5-HT receptor expression, including their subtypes and their subunits, induced by neuroplastogen drugs.

Based on the present inventors' experimental results (described in the Examples, below) the present inventors disclose that select 5-HT agonists, including those with activity at the 5-HT2A receptor, including psilocybin, may modulate endogenous receptors, including 5-HT2A receptors and or NMDARs, in a manner similar to endogenous neurotransmitters, including DMT. The direct actions of 5-HT2A agonists at 5-HT2A receptors, and direct or indirect actions at NMDARs disclosed in this application, and or the actions on down regulation of serotonin receptors caused by the exogenous 5-HT2A neuroplastogens, potentially modulate the expression of NMDARs (increase in mRNA and subunit proteins shown in the present inventors' experiments) and in particular, drugs in this pharmacological class may modulate expression of NMDARs, and specifically protein transcription and synthesis of subunits that form NMDAR subtypes NR1-2A, NR1-2B, NR1-2C and NR1-2D, including NR1-2A-2B and other tri-heteromeric combinations.

It is known that NMDARs of the 2B subtype are more prominent during early development and are thought to have an important role in the learning capabilities of the developing brain. During development the NMDAR subtype 2B is progressively replaced by subtype 2A which eventually predominates in the adult brain. Thus, it is conceivable that neuroplastogens by modulating NMDARs subtypes could potentially recreate the level of neural plasticity seen during early development and thus favor and promote new neural circuits and or neural repair and thus be potentially therapeutic for a multiplicity of diseases and conditions, especially diseases and conditions affecting sensory pathways and memory and learning (learning is not limited to memory and cognition but also determines, motor skills, social skills and emotional functions). Finally, neuroplastogens in the 5-HT2A agonist class may improve the outcomes of rehabilitation programs, including neuro-rehabilitation programs, including those focused on cognitive aspects, language, vision and including rehabilitation programs for substance use disorders, including physical therapy focused rehabilitation. The rehabilitation outcome improvement is achieved by enhancing and modulating neural plasticity and neural circuits involved in learning.

Furthermore, while there may be subsets of patients among those that suffer from psychiatric disorders that might benefit from the psychedelic experience (as there are psychiatric patients that benefit from ECT), based on the present inventors' in vitro and in vivo and clinical results, the present inventors disclose that other patients, including subsets of psychiatric patients, will likely benefit from treatment with continuous ongoing treatment with non-psychedelic neuroplastogen administered at low doses, including intermittent doses and including in modified release formulations.

Treatment with neuroplastogens at non-psychedelic doses are likely to determine additional benefits when associated with appropriate psychotherapy and neuro-rehabilitation programs.

Finally the fact that ketamine, a neuroplastogen in the NMDAR antagonist pharmacologic class is FDA approved for depression at doses that are psychedelic/psychotomimetic or doses bordering the psychedelic/psychotomimetic window (dissociative symptoms), and that psilocybin is in clinical trials at psychedelic doses, suggests that there may be a subset of patients that benefits from the higher psychedelic/psychotomimetic doses or, alternatively, it may signify that these patients could also benefit (or alternatively, could benefit in fact even more) from much lower, non-psychedelic doses and formulations of the same drugs administered for prolonged periods, when tested in appropriately designed clinical trials.

Furthermore, magnesium and zinc are both modulators at the NMDAR. Magnesium is a NMDAR blocker and thus for the reasons and results disclosed above the combination of magnesium with 5-HT2A agonists may be synergistic. Zinc is a NMDAR modulator, and thus, for the reasons and results disclosed above, the combination of zinc with or without magnesium with 5-HT2A agonists may be synergistic. Magnesium supplementation has been shown to the potential of improving hypertension, insulin sensitivity, hyperglycemia, diabetes mellitus, left ventricular hypertrophy, and dyslipidemia; in addition, magnesium can treat certain types of seizures (e.g., those occurring as part of eclampsia) and can be used for arrhythmias such as torsades de pointes. [Houston M. The role of magnesium in hypertension and cardiovascular disease. J Clin Hypertens (Greenwich). 2011 November; 13(11):843-7]; [Rosanoff A. Magnesium and hypertension. Clin Calcium. 2005 February; 15(2):255-60]. The combination of 5-HT2A agonists with magnesium and or zinc and salts thereof may potentially be synergistic for the treatment of diseases and conditions that may benefit from modulation of neural plasticity and may result in drugs with not only improved efficacy but also improved safety. In the case of blister packages for intermittent dosing, magnesium and or zinc could be substituted for inactive doses on "off therapy" days (e.g., every three days).

Chronic NMDA administration causes mitochondrial dysfunction in rats [Kim, H. K. et al., Mitochondrial dysfunction and lipid peroxidation in rat frontal cortex by chronic NMDA administration can be partially prevented by lithium treatment. J Psychiatr Res. 2016 May; 76:59-65]. Thus, lithium combined with NMDAR antagonists may offer enhanced safety over NMDAR antagonists alone. According to Leslie and others, 1993, the combination of 5-HT2A agonists with lithium may enhance the potential antidepressant actions of 5-HT2A agonists (Leslie R A, Moorman J M, Grahame-Smith D G. Lithium enhances 5-HT2A receptor-mediated c-fos expression in rat cerebral cortex. Neuroreport. 1993 Dec. 13; 5(3):241-4). Taken together with the present inventors' new evidence for potential neuroplastogen actions of non-psychedelic doses of 5-HT2A agonist, the increase in c-fos expression induced by lithium seen by Leslie and other may also be suggestive of a potential for synergy not only for anti-depressant effects but also for neuro-modulatory effects (neuroplastogen effects).

According to the present inventors' observations, findings and disclosures, and ongoing and planned in vitro, in vivo, and clinical studies, low doses, non-psychotomimetic, of known 5-HT2A agonists and novel drugs listed in Table 1A (SMSNs), here defined neuroplastogens, administered repeatedly over days, months or chronically, may activate serotonin and other receptors, including 5-HT2A receptors, on different cell lines, including retinal pigment cells (thereby also influencing photoreceptor activity and vitality), other retinal cells, and specialized olfactory, auditory, balancing cells, and neurons and astrocytes (including astrocyte like cells in the retina, e.g., Muller cells) and specific neuronal populations, including retinal ganglion cells and other neurons involved in visual pathways, including cortical neurons, including hippocampal neurons, and exert trophic functions, and modulate and generate new and or stronger synaptic activity and new connections, thereby improving the function of special senses, improving memory and learning, in subjects and patients with sensory impairment from a multitude of diseases and conditions and improve neurological functions, including visual function, other sensory functions and cognitive functions, in subjects with neurological impairments from a multiplicity of diseases and conditions, including neurological, psychiatric, metabolic diseases and deficits from aging, including senescence. In particular, the trophic and protective effects on retinal pigment epithelial cells and astrocytes may be of particular importance for their role in gating the blood retinal barrier and the BBB and thus in supplying nutrients, neurotransmitters and other crucial molecules to CNS neurons and receptors that are part of the visual pathways and other sensory pathways, including photoreceptors, and for their scavenger role and other important roles in neural plasticity.

Because of their neural plasticity effects, including trophic effects on cells, and because of anti-inflammatory effects, the effects of 5-HT2A agonist substances and SMSNs may not only outlast their clearance from the body, but under some circumstances, the positive effects may be more evident or only evident after the substance has been substantially eliminated. This may be particularly relevant for some visual and cognitive improvements, especially when the dose of the NMDAR antagonists and or 5-HT2A agonist drugs and or their combination is sufficient to cause CNS symptoms such as psychotomimetic or psychedelic symptoms.

The work on inflammation and serotonin by Banganz (Baganz, N. L.& Blakely, R. D. A dialogue between the immune system and brain, spoken in the language of serotonin. ACS Chem. Neurosci. 4, 48-63 (2013) and Arreola (Arreola, R. et al. Immunomodulatory effects mediated by serotonin J Immunol Res. 2015, 354957 (2015) and the work by Flanagan and Nichols (Flanagan T W, Nichols C D. Psychedelics as anti-inflammatory agents. Int Rev Psychiatry. 2018 Aug. 13:1-13), are all in accordance with the present inventors' clinical observations and experimental results and with the present inventors' findings and disclosures: the agonist actions of psychedelics at serotonin receptors, mainly 5-HT2A receptors but also actions at other receptors, including non-serotonin receptors, may curtail inflammation, including TNF-α mediated inflammation. Based on the present inventors' experimental results, these anti-inflammatory effects potentially have a role in improving neurological functions, including vision, or may prevent neurological deficits, including neurological and ophthalmological deficits associated with aging and cell senescence, including visual deficits in diseases of the CNS where inflammation potentially plays a role, such as in neurodegenerative and neurodevelopmental diseases, including diseases where inflammation of visual pathways (anywhere from retinal pigment cells to cortical structures) is involved. A modulation of systemic indicators of inflammation may also improve psychiatric symptoms and syndromes, including depression, which has been associated with systemic inflammation.

The results of the recent study by Madsen et al. [Madsen, M. K; Burmester, D; Stenbåk, D. S. Psilocybin occupancy of brain serotonin 2A receptors correlates with psilocin levels and subjective experience: a (11C) Cimbi-36 PET study in humans. European Neuropsychopharmacology, 2019, Volume 29] suggest that the psilocybin psychedelic effects correlate with the dose and thus a lower dose will not produce psychotomimetic/psychedelic effects, in accordance with the present inventors' observations and disclosures. Furthermore, also in accordance with the present inventors' clinical observations, experimental results and disclosures for safety and potential therapeutic indications, not only the psychotomimetic effects, but also other side effects of psychedelic substances, such as headache, fatigue and increases in blood pressure are dose-dependent (MW Johnson, Sewell A R. Griffiths R R. Psilocybin dose-dependently causes delayed, transient headaches in healthy volunteers Drug and Alcohol Dependence, 2011, Volume 123, Issue 1; Studerus E, Kometer M, Hasler F, Vollenweider F X. Acute, subacute and long-term subjective effects of psilocybin in healthy humans: a pooled analysis of experimental studies. J Psychopharmacol. 2011 November; 25(11):1434-52), confirming that relatively lower doses of psychedelic substances are likely to be not only safe but also well tolerated and devoid of psychotomimetic and other side effects. On the other hand, the anti-inflammatory actions appear to be active at very low doses (Nichols D E et al., 2016 Psychedelics as medicines; an emerging new paradigm), again supporting the present inventors' novel observations in patients and the present inventors' novel experimental data and thus supporting the development of psychedelics as medicines for neurological and ophthalmological and metabolic indications, and not only for psychiatric indications, as disclosed throughout this application, at non-psychedelic doses and with non-psychedelic formulations.

In the 2011 study by Studerus et al., (Studerus E, Kometer M, Hasler F, Vollenweider F X. Acute, subacute and long-term subjective effects of psilocybin in healthy humans: a pooled analysis of experimental studies. J Psychopharmacol. 2011 November; 25(11):1434-52) the present inventors noted an improvement of symptoms of "restless legs" in 2 patients treated with psilocybin (see table 2 in the Studerus et al., 2011 paper). The present inventors also noted a similar improvement in one of the present inventors' patients (CF). This observation, while limited to three patients, indicating that three patients with possibly suffering from restless leg syndrome improved after treatment with 5-HT-agonists, taken together with the present inventors' new data on the NMDAR antagonistic actions of select 5-HT agonists and the effects of these drugs on glutamatergic pathways and excitotoxicity, suggests a possible therapeutic activity for 5-HT2A agonists in restless leg syndrome (RLS). A hyperglutamatergic state has been postulated as a mechanism for RLS.

The present inventors' clinical observations, experimental results and disclosures teach that relatively low doses of 5-HT agonist substances administered repeatedly over days or months or even chronically, continuously or intermittently, have the potential to be safe and well tolerated and devoid of clinically significant side effects, including psychotomimetic effects and other typical psychedelic effects, and cognitive side effects. Thus, neuroplastogens and SMSNs, when dosed properly, may be safe and effective for management of diseases and conditions listed throughout this application and for improving vision and cognition, a multiplicity of neuropsychiatric diseases and conditions and metabolic disorders, including the metabolic syndrome. The psychedelic effects of 5-HT2A agonists to this day have been seen as inherent to the potential for therapeutic benefits (centered around psychiatric diseases) of 5-HT2A agonist drugs and not as side effects. In the present inventors' disclosure the psychotomimetic effects are side effects caused by an overdosage, while neuroplasticity and the improvement of diseases and conditions seen with lower, appropriate, dosages and formulations are therapeutic effects. Psychotomimetic effects may be minimized or avoided altogether by using non-psychedelic dosages and formulations of these substances administered repeatedly over time and or by applying structural molecular modifications to known 5-HT2A agonists (see Table 1A), resulting in SMSNs with improved PK and PD parameters.

Based on the present inventors' disclosures, observations and experimental results, doses of IR psilocybin equal or lower than 4 mg (or psychedelic-potency-equivalent doses of other 5-HT2A agonists and NMDAR antagonists) may be sufficient for modulating neuroplasticity that potentially could treat the multiplicity of disorders and conditions listed in this application. In fact according to the present inventors' observations and results, neuroplastogen effects are potentially more prominent when lower concentrations maintained over time rather than when higher concentration are administered in single sessions [see also the cited BDNF results for dextromethadone's phase 1 study where the increase in BDNF reached statistical significance only in the 25 mg group and not in the 50 or 75 mg groups, (De Martin et al., 2018)]. However, for select diseases and or select patient subgroups or individuals, a higher dose of a neuroplastogen drug may be required in order to exert the appropriate modulation of neural plasticity that will improve a particular disease or condition: in such patient the administration of a modified release or long acting or slow release preparation of a 5-HT2A agonist may be appropriate as detailed below. Psychedelic effects are known to be linked to dose, plasma levels and to receptor occupancy: higher doses correspond to higher blood levels and to higher the receptor occupancy and to more prominent psychedelic symptoms [Madsen, M. K; Burmester, D; Stenbåk, D. S. Psilocybin occupancy of brain serotonin 2A receptors correlates with psilocin levels and subjective experience: a (110) Cimbi-36 PET study in humans. European Neuropsychopharmacology, 2019, Volume 29]; (Brown R T, Nicholas C R, Cozzi N V, Gassman M C, Cooper K M, Muller D, Thomas C D, Hetzel S J, Henriquez K M, Ribaudo A S, Hutson P R. Pharmacokinetics of Escalating Doses of Oral Psilocybin in Healthy Adults. Clin Pharmacokinet. 2017 December; 56(12):1543-1554). Neuroplastogen effects are instead potentially driven by additional and consequential mechanisms and not solely by the direct binding of the drug to 5-HT2A receptors. The neuroplastogen effects, as shown by the present inventors' in vitro work, in vivo work and clinical observations, may actually be enhanced by lower doses/concentration compared to higher doses (e.g., psychedelic/psychotomimetic dosages) and thus present at non-psychedelic/psychotomimetic dosages. Modified release, long acting and or slow release formulation of a neuroplastogen drug will allow for administration of a relatively higher amount of drug while still avoiding the psychedelic and or psychotomimetic side effects caused by a peak in blood levels of the drug (the psychedelic effects caused by a high Cmax and short Tmax). The present inventors therefore also disclose modified release long-acting and or slow-release formulations of neuroplastogens, including long-acting oral or transdermal formulations and or slow-release formulations of psilocybin and or baeocystin at doses up to 30 mg per 24 hours (or a dose of other 5-HT2A agonists and NMDAR antagonists with equivalent psychedelic/psychotomimetic potency, and thus also devoid of these effects). The modified release long acting/slow release formulation is designed to maintain plasma levels of psilocin below the 4-6 ng/ml window that causes psychedelic/psychotomimetic effects for psilocin (or a psychedelic-potency-equivalent plasma level of other 5-HT2A agonists and or NMDAR antagonists) so they will not determine plasma levels sufficient for psychedelic effects.

Finally, modified release long-acting and or slow-release preparation may allow the administration of larger doses of 5-HT agonists which may be indicated for select diseases and conditions among those listed above, and or may be indicated for select subjects, e.g., subjects who may be more sensitive to the psychedelic/psychotomimetic effects of these drugs than average, thus allowing effective treatment by widening the therapeutic window for these drugs.

The same reasoning behind the potential therapeutic role of psychedelic substances for ophthalmologic disorders can be applied to other pathological conditions of other sensory organs and pathways such as hearing/balance—otologic disorders and disorders of olfaction/smell and or gustatory/taste deficits and disorders of tactile sensations, including certain sexual disorders, in particular those associated with senescence. These substances and drugs could potentially safely improve or prevent or delay the sensory loss (vision, hearing, balance, olfaction, gustation and somatosensory) associated with senescence.

The present inventors further disclose that the neural plasticity effects of these drugs may involve extra-neuronal cells, such as retinal pigment cells, and astrocytes and neurons outside of the prefrontal cortex and thus result in effects and potentially therapeutic effect on a multitude of neurological and ophthalmological syndromes (beyond psychiatric disorders), not only by promoting neurite growth but also via neuro-protective mechanisms, including excitotoxicity protection, and anti-inflammatory mechanisms, as detailed in the present inventors' clinical observations, experiments and disclosures. In particular the present inventors' disclosures reveal that these effects of 5-HT agonists are not limited to neurons but also involve retinal epithelial pigment cells, and potentially other cells such as liver and pancreatic cell as shown and signaled in the present inventors' novel experiments (see Examples 1-3). Furthermore, the present inventors underscore the potential role of astrocytes, as these cells have been found to express 5-HT2A receptors [Xu T1, Pandey S C. Cellular localization of serotonin(2A) (5-HT2A) receptors in the rat brain. Brain Res Bull. 2000 April; 51(6):499-505], in lending support to the present inventors' disclosure: as mentioned above, the effects of psychedelics on astrocytes and retinal pigment cells may be of particular importance for their role in gating the blood retinal barrier and the BBB and thus in supplying nutrients, neurotransmitters and other crucial molecules to CNS neurons and photoreceptors that are part of the visual pathways, and for their scavenger role and other important roles in neural plasticity.

The current scientific understanding of psychedelics effects on cognitive function, teaches away from the use of psychedelics to improve cognitive function (Bayne T, Carter O. Dimensions of consciousness and the psychedelic state. Neurosci Conscious. 2018; 2018(1)): "The findings are grouped into three broad categories (sensory perception, cognitive function, and experiences of unity) and demonstrate that although certain aspects of consciousness are improved or enhanced in the psychedelic state, many of the functional capacities that are associated with consciousness are seriously compromised".

Finally, as the mechanisms of modulation of neural plasticity by psychedelic substances may be experience driven, the present inventors disclose the importance of timing the administration of these substances and drugs (known 5-HT2A agonists and the modified novel molecules detailed in Table 1A) with specific activities (including activities of daily living and specific mental activities and specific neuro-rehabilitation programs, including visual rehabilitation programs). This coupling of drug and activity may be offer additional advantages for the use of these drugs as neurological and ophthalmological treatments, including neurological and ophthalmological rehabilitation treatments. Timing of neuroplastogen treatment in order to achieve relatively high levels during specific activities and progressive lowering of plasma and tissue levels of drug in the evening hours, which may potentially result in consolidation of neural plasticity during physiological sleep (with very low or non-effective drug levels), may thus be of importance. This reasoning would point towards the administration of the 5-HT2A serotonin agonist substance in a manner as to achieve higher serum levels during the day and during specific neuro-rehabilitation sessions and lower levels during sleep. In the present inventors' reported subjects the administration of psilocybin containing substances was timed with intensive visual testing and the present inventors postulate that this timing may have had a potentially beneficial effect for the positive outcomes of day 5, after the clearance of substantially all of the psychedelic substance (48 hours after the last dose).

Based on immunohistochemical and morphologic results suggesting neural plasticity effects for 5-HT2A agonists administered repeatedly and at low doses, the present inventors disclose that substances acting at 5-HT2A receptors and other CNS receptors and SMSNs may not only be useful for the treatment of psychiatric diseases and symptoms, including depression in all its forms, anxiety in all its forms, PTSD, addictive behaviors and addiction to drugs, but may potentially prevent these diseases and symptoms when administered in anticipation of life stressors or during stress or shortly following the stressful events, prior to the development of psychiatric diseases or symptoms. By promoting neural plasticity and by other mechanisms, such as modulating 5-HT2A receptors, NMDARs, SERT and NET pathways, and BDNF, 5-HT2A agonists and SMSNs may increase resilience to developing psychiatric diseases and symptoms when administered during periods of life burdened by mental stressors or when a mental stressor is anticipated and thus may be useful for prevention of psychiatric diseases and symptoms, including those triggered by mental stress from a multiplicity of causes including social stress, grief, disease, personal loss, marital and family related stress, financial stress, war, natural- and man-induced disasters, et cetera. This disclosure is supported by the experimental results by Brachman for ketamine, (Brachman R A, McGowan J C, Perusini J N, et al. Ketamine as a Prophylactic Against Stress-Induced Depressive-like Behavior. Biol Psychiatry. 2015; 79(9):776-786): ketamine is an NMDAR antagonist that potentially shares neuroplasticity effects with select 5-HT2A agonists.

In the USA, the metabolic syndrome prevalence increased from 1988 to 2012 for every sociodemographic group; by 2012, more than a third of all US adults met the definition and criteria for metabolic syndrome agreed to jointly by several international organizations. (Moore J X, Chaudhary N, Akinyemiju T. Metabolic Syndrome Prevalence by Race/Ethnicity and Sex in the United States, National Health and Nutrition Examination Survey, 1988-2012. Prev Chronic Dis 2017; 14:160287. DOI: http://dx.doi.org/10.5888/pcd14.160287) The metabolic syndrome is associated with cardiovascular disease, obesity, arthritis, NAFL, NASH, MDD, schizophrenia, dementia and cancer. The present inventors' results suggest that neuroplastogen 5-HT2A agonists, e.g., low chronic dose psilocybin, as a stand-alone therapy or with low dose NMDAR antagonist, may improve one or more features of the metabolic syndrome. Based on the present inventors' experimental findings, 5-HT2A neuroplastogen drugs signal strong therapeutic potential for the treatment of the metabolic syndrome, not only as an appetite suppressant and anti-obesity drug but as a potentially disease modifying treatment with actions and influences at the molecular level on hepatocytes (decrease in steatosis), Langherhans cells (decrease in glycemic peak), and on immune cells (decrease in inflammatory markers).

Metabolic disorders that may be treated or prevented by neuroplastogen substances and drugs include: the metabolic syndrome, obesity, hyperglycemia, type 2 diabetes mellitus, high blood pressure, coronary artery disease including myocardial infarction and unstable angina, nonalcoholic fatty liver disease (NAFLD) and nonalcoholic steatohepatitis (NASH), hypogonadism, testosterone insufficiency, hypothalamic-pituitary axis disorders, and BDNF insufficiency, including WAGR syndrome, 11p deletion, and 11p inversion, and Prader-Willi, Smith-Magenis, and ROHHAD syndromes.

In 2015, a total of 1.02 million people were blind, and approximately 3.22 million people in the United States had visual impairment (best-corrected visual acuity in the better-seeing eye). By 2050, the numbers of these conditions are projected to double to approximately 2.01 million people with blindness, 6.95 million people with visual impairment (Varma R1, Vajaranant TS2, Burkemper B3, Wu S3, Torres M3, Hsu C3, Choudhury F3, McKean-Cowdin R4. Visual Impairment and Blindness in Adults in the United States: Demographic and Geographic Variations From 2015 to 2050. JAMA Ophthalmol. 2016 Jul. 1; 134(7):802-9).

Currently available medications are inadequate for the treatment of eye diseases and conditions associated with visual impairment; there has been little innovation in this area in the last decades. The need for better treatments remains, especially for visual impairment associated to retinal diseases, including those associated with aging.

Sight or vision (adjectival form: visual/optical) is the capability of the eye(s) to focus and detect images of visible light on photoreceptors in the retina of each eye that generates electrical nerve impulses for varying colors, hues, and brightness. There are two types of photoreceptors: rods and cones. Rods are very sensitive to light but do not distinguish colors. Cones distinguish colors but are less sensitive to dim light. Stereopsis, the perception of depth using both eyes, is generally a cognitive (that is, post-sensory) function of the visual cortex of the brain where patterns and objects in images are recognized and interpreted based on previously learned information (visual memory).

People who are blind from degradation or damage to the visual cortex, but still have functional eyes, are actually capable of some level of vision and reaction to visual stimuli but not a conscious perception; this is known as blindsight. People with blindsight are usually not aware that they are reacting to visual sources, and instead just unconsciously adapt their behavior to the stimulus.

Neuroplastogens may have a role in the improvement of vision affected by diseases and injury at all levels of the visual pathways from the retina to the cortical areas and for all levels of vision loss, including patients with partial or complete cortical blindness where they might prevent retinal pathology and restore some vision or at least maintain "blindsight". The multifactorial decline of vision secondary to aging may also be slowed or improved by neuroplastogen substances. Improvement in vision from neuroplastogens include improvements in visual acuity, contrast sensitivity, color vision, visual fields and stereopsis.

Neurodegenerative, neurodevelopmental and inflammatory diseases of the retina like glaucoma, diabetic retinopathy, age-related macular degeneration, retinitis pigmentosa, optic neuritis and LHON and refractive disorders are among the diseases that could be potentially improved by neuroplastogen substances, including SMSNs. Ophthalmological diseases and their symptoms and signs that may respond to neuroplastogen drugs and SMSNs include all of the above cited disorders.

In neurodegenerative diseases of the retina such as glaucoma, diabetic retinopathy and age-related macular degeneration, during metabolic stress, glutamate is released, initiating dysfunction and death of neurons containing ionotropic NMDA receptors such retinal ganglion cells and a specific type of amacrine cells. The major causes for cell death following activation of NMDA receptors is the influx of calcium into cells, the generation of free radicals linked to the formation of advanced glycation end products (AGEs) and/or advanced lipoxidation end products (ALEs), as well as defects in the mitochondrial respiratory chain. Macular edema represents the end-stage of multiple pathophysiological pathways in a multitude of vascular, inflammatory, metabolic and other diseases; novel treatments such as neuroprotective agents like nerve growth factors and NMDA antagonists may inhibit neuronal cell death in the retina (Wolfensberger T J. Macular Edema—Rationale for Therapy. Dev Ophthalmol. 2017; 58:74-86). Similar NMDA induced nerve cell damage can occur in glaucoma and optic neuritis. Memantine, an NMDA antagonist, has been found to potentially benefit glaucoma in an experimental study (Celiker H et al., Neuroprotective Effects of Memantine in the Retina of Glaucomatous Rats: An Electron Microscopic Study. J Ophthalmic Vis Res. 2016 April-June; 11(2):174-82); the authors concluded that when started in the early phase of glaucomatous process, memantine may help to preserve the retinal ultrastructure and thus prevent neuronal injury in experimentally induced glaucoma. Memantine was also found to be effective in reduction of retinal nerve fiber layer (RNFL) thinning in patients with optic neuritis (Esfahani M R et al., Memantine for axonal loss of optic neuritis. Graefes Arch Clin Exp Ophthalmol. 2012 June; 250(6):863-9), although it did not improve vision.

A previously decontextualized observation by Honyglo and others on the distribution of psilocin in the human body after the ingestion of psilocybin mushrooms, lends now further weight to the present inventors' disclosure of potential ophthalmological therapeutic activity. After the ingestion of psilocybin mushrooms, psilocin was quantified in peripheral and cardiac blood as 60 and 67 ng/mL, respectively, and in urine (2230 ng/mL), bile (3102 ng/mL), and vitreous humor (57 ng/mL). (Honyiglo, E Franchi A; Cartiser: Unpredictable Behavior Under the Influence of "Magic Mushrooms": A Case Report and Review of the Literature. Journal of Forensic Sciences, 12/2018). The comparable levels of psilocin in blood and vitreous humor seen in this report, taken together with the present inventors' novel clinical observations and experimental results, suggest that after systemic intake of 5-HT-agonists, the retina may be exposed to psilocin at levels comparable with levels reaching the systemic circulation. These relatively high levels in the vitreous humor are potentially adequate to exert a biological effect on retinal pigment cells (homologous to ARPE-19 cells used in the present inventors' experiments, see Example 3) and other retinal cells and thus modulate and improve important connections and cellular activities within the visual pathways, starting from the retina. This finding supports the present inventors' clinical observations and confirms the present inventors' experimental findings and disclosures: with vitreal concentration of psilocin comparable to concentration seen in blood it is possible that the visual effects of psilocin observed in the present inventors' clinical observations (see Example 1) could be also secondary to retinal exposure from local vitreal diffusion and not only from exposure via blood retinal barrier or exposure across BBB for more central NS structures. The long-lasting positive effects on vision seen in the present inventors' subjects may therefore be secondary to modulation of neural plasticity via different mechanisms, including the dampening of inflammation anywhere in the nervous system pathways, including the retina and the visual pathways, including cells composing the retinal pigment cells within the retina and up to the cortical areas.

Substances preventing excito-cytotoxic events (excitotoxicity) are considered to be potentially neuroprotective. Experimental studies demonstrate that several drugs reduce or prevent the death of retinal neurons deficient of nutrients. These agents generally block NMDA receptors to prevent the action of glutamate or halt the subsequent pathophysiologic cycle resulting in cell death (Schmidt K G et al., Neurodegenerative diseases of the retina and potential for protection and recovery. Curr Neuropharmacol. 2008 June; 6(2):164-78.). Glutamate induced optic atrophy toxicity has also been found to be associated with alterations in BDNF expression (Ito Y et al., Degenerative alterations in the visual pathway after NMDA-induced retinal damage in mice. Brain Res. 2008 May 30; 1212:89-101). Excitotoxic injury has been postulated as a concurrent pathogenic factor in Leber Hereditary Optic Neuropathy (Howell N. Leber hereditary optic neuropathy: respiratory chain dysfunction and degeneration of the optic nerve. 1988 Vis Res 38:1495-1504. Sala G. Antioxidants Partially Restore Glutamate Transport Defect in Leber Hereditary Optic Neuropathy Cybrids. Journal of Neuroscience Research 2008 86:3331-3337). Alterations in glutamate metabolism have been described in different models of retinitis pigmentosa; glutamate-mediated excitotoxic mechanisms were found to contribute to rod photoreceptor death in the retinal degeneration mouse model (Delyfer M N et al., Evidence for glutamate-mediated excitotoxic mechanisms during photoreceptor degeneration in the rd1 mouse retina. Mol Vis. 2005 Sep. 1; 11:688-96). The novel findings by the applicants on the modulating effects of 5-HT2A agonists on NMDARs open new perspective for their potential uses to prevent excitotoxic neural damage.

Psilocybin at neuroplastogen dosages shown to be devoid of psychotomimetic effects and potentially improve visual parameters in human subjects (see Example 1) may potentially treat and or prevent the worsening of many neurological and ophthalmological conditions where altered neuronal plasticity or modulation of neural plasticity may play a role and to treat and prevent the worsening of conditions, including diseases where BDNF regulates neuronal plasticity, including diseases of the retina, optic nerve and optic pathways, whether administered systemically, topically via eye drops, and/or intra-ocularly, including intra-vitreal depot formulations. The inventors discovered that sclerotia of psilocybe atlantis improves visual parameters. 5-HT2A agonists stimulate neuroplasticity via BDNF and mToR pathways (Ly et al., 2018). The effects of BDNF on nerve cells of the eye, including retinal ganglion cells, may prevent or treat neurodegenerative and inflammatory diseases of the retina and the eye.

Currently available medications are inadequate for the treatment of nervous system disorders, their symptoms, and/or their manifestations; there has been little innovation in this area in the last decades. The need for better treatments remains.

Neurological diseases and their symptoms and signs that may respond to neuroplastogen drugs and SMSNs include: Alzheimer's disease; presenile dementia; senile dementia; vascular dementia; Lewy body dementia; cognitive impairment, including mild cognitive impairment associated with aging and with chronic disease and its treatment, including chemotherapy, immunotherapy and radiotherapy, Parkinson's disease and Parkinsonian related disorders including but not limited to Parkinson dementia; disorders associated with accumulation of beta amyloid protein (including but not limited to cerebrovascular amyloid angiopathy, posterior cortical atrophy); disorders associated with accumulation or disruption of tau protein and its metabolites including but not limited to frontotemporal dementia and its variants, frontal variant, primary progressive aphasias (semantic dementia and progressive non fluent aphasia), corticobasal degeneration, supranuclear palsy; epilepsy; NS trauma; NS infections; NS inflammation, including inflammation from autoimmune disorders, including NMDAR encephalitis, and cytopathology from toxins, (including microbial toxins, heavy metals, and pesticides etc.); stroke; multiple sclerosis; Huntington's disease; mitochondrial disorders; Fragile X syndrome; Angelman syndrome; hereditary ataxias; neuro-otological and eye movement disorders; neurodegenerative diseases of the retina like glaucoma, diabetic retinopathy and age-related macular degeneration; amyotrophic lateral sclerosis; tardive dyskinesias; hyperkinetic disorders; attention deficit hyperactivity disorder and attention deficit disorders; restless leg syndrome; Tourette's syndrome; schizophrenia; autism spectrum disorders; tuberous sclerosis; Rett syndrome; cerebral palsy; disorders of the reward system including eating disorders [including anorexia nervosa ("AN") and bulimia nervosa ("BN"); and binge eating disorder ("BED"), trichotillomania, dermotillomania, nail biting; migraine; fibromyalgia; and peripheral neuropathy of any etiology.

Symptom or manifestation of nervous system disorders that may be treated or prevented by neuroplastogen substances and drugs include: a decline, impairment, or abnormality in cognitive abilities including executive function, attention, cognitive speed, memory, language functions (speech, comprehension, reading and writing), orientation in space and time, praxis, ability to perform actions, ability to recognize faces or objects, concentration, and alertness; abnormal movements including akathisia, bradykinesia, tics, myoclonus, dyskinesias, including dyskinesias relate to Huntington's disease, levodopa induced dyskinesias and neuroleptic induced dyskinesias, dystonias, tremors, including essential tremor, and restless leg syndrome; parasomnias, insomnia, disturbed sleep pattern; psychosis; delirium; agitation; headache; motor weakness, spasticity, impaired physical endurance; sensory impairment, including impairment of vision and visual field defects, smell, taste, hearing and balance, and dysesthesias; dysautonomia; and ataxia, impairment of balance or coordination, tinnitus, neuro-otological and eye movement impairments, neurological symptoms of alcohol withdrawal, including delirium, headache, tremors, hallucinations, hypertension.

Psychiatric disorders and symptoms that may be improved by neuroplastogens include those listed on the DSM5 and ICD11, and furthermore include disorders such as Schizophrenia spectrum and other psychotic disorders, Bipolar and related disorders, Depressive disorders, Anxiety disorders, Obsessive-compulsive and related disorders, Trauma- and stressor-related disorders, Dissociative disorders, Somatic symptom and related disorders, Feeding and eating disorders, Elimination disorders, Sleep-wake disorders, Sexual dysfunctions, Gender dysphoria, Disruptive, impulse-control, and conduct disorders, Substance-related and addictive disorders, Neurocognitive disorders, Personality disorders, Paraphilic disorders.

Aging related disorders and deficits that may be treated or prevented by neuroplastogen substances and drugs include: disorders associated with physiologic or accelerated aging (including aging accelerated by noxious agents, including medical treatments, including cancer treatments and its symptoms and manifestations is chosen from: cognitive impairments, sarcopenia, osteoporosis, sexual dysfunction, skin aging, loss and or graying of hair, impaired physical endurance, sensory impairment, including impairment of hearing, balance, smell, taste, and or vision; fatigue.

Hearing

Hearing or audition is the sense of sound perception. Mechanoreceptors in the inner ear turn motion—vibration—into electrical nerve pulses. Since sound is vibration, propagating through a medium, the detection of these vibrations, that is the sense of the hearing, is a mechanical sense because these vibrations are mechanically conducted from the eardrum through a series of tiny bones to hair-like fibers in the inner ear, which detect mechanical motion of the fibers within a range of about 20 to 20,000 hertz, with substantial variation between individuals. Hearing at high frequencies declines with an increase in age. Inability to hear is called deafness or hearing impairment. Sound can also be detected as vibrations conducted through the body by touch.

Neuroplastogens may have a role in the improvement of hearing affected by diseases and their treatments and injury at all levels of the auditory pathways from the inner ear hair cells to the cortical areas. The decline of hearing secondary to aging may also be slowed or improved by neuroplastogens.

Neuroplastogens for improvement of hearing and balance or to relieve tinnitus could be administered topically in the form of ear drops, via iontophoresis to increase inner ear penetration, via trans-tympanic injection, including as an inner ear depot form, or could be administered systemically.

Taste and Flavor

Taste or gustation refers to the capability to detect the taste of substances such as food, certain minerals, and poisons, etc. The sense of taste is often confused with the "sense" of flavor, which is a combination of taste and smell perception.

Flavor depends on odor, texture, and temperature as well as on taste. Humans receive tastes through sensory organs called taste receptors, or gustatory caliculi, concentrated on the upper surface of the tongue. There are five basic tastes: sweet, bitter, sour, salty and umami. Other tastes such as calcium and free fatty acids may also be basic tastes but have yet to receive widespread acceptance. The inability to taste is called ageusia.

Neuroplastogens may have a role in the improvement of deficits in the perception of taste and flavor affected by diseases, treatment of diseases and other injury at all levels of the gustatory pathways from the gustatory calyculi to the cortical areas. The decline in the perception of taste secondary to aging may also be slowed or improved by neuroplastogens.

Smell

Smell or olfaction is a chemical sense, like taste. Unlike taste, there are hundreds of olfactory receptors (388 according to one source), each binding to a particular molecular feature. Odor molecules possess a variety of features and, thus, excite specific receptors more or less strongly. This combination of excitatory signals from different receptors makes up what the present inventors perceive as the molecule's smell.

In the brain, olfaction is processed by the olfactory system. Olfactory receptor neurons in the nose differ from most other neurons in that they die and regenerate on a regular basis. The inability to smell is called anosmia. Some neurons in the nose are specialized to detect pheromones. Loss of smell is a prodrome to neurodegenerative diseases, including Alzheimer's disease and Parkinson disease.

Neuroplastogens may have a role in the improvement of deficits of olfaction affected by diseases, their treatments, and injuries at any and all levels of the olfactory pathways, from the olfactory receptors to the cortical areas. The decline in the perception of olfaction secondary to aging may also be slowed or improved by neuroplastogens. The prevention of anosmia or the improvement in hyposmia by neuroplastogen drugs, aside from improving the quality of life of patients, may be therapeutic for select neurological diseases and conditions, including neurodegenerative diseases, including Alzheimer's disease and Parkinson disease.

Neuroplastogens for improvement of the sense of smell could be administered topically in the form of intranasal spray, aerosols, via iontophoresis to increase penetration, including as an intranasal depot form, or could be administered systemically.

Touch

Touch or somatosensation or mechanoreception, is a perception resulting from activation of neural receptors, generally in the skin including hair follicles, but also in the tongue, throat, cornea and mucosa. A variety of pressure receptors respond to variations in pressure (firm, brushing, sustained, etc.). The touch sense of itching caused by insect bites or allergies involves special itch-specific neurons in the skin and spinal cord. The loss or impairment of the ability to feel anything touched is called tactile anesthesia. Paresthesia is a sensation of tingling, pricking, or numbness of the skin that may result from nerve damage and may be permanent or temporary.

Neuroplastogens may have a role in the improvement of deficits in sense of touch, affected by diseases, medical treatments and injury at all levels of the somatosensory pathways from the neural receptors in the skin including hair follicles, tongue, throat, cornea and mucosa to the cortical areas. The decline in the perception of touch, secondary to aging may also be slowed or improved by neuroplastogens.

Balance and Acceleration, Vestibular System

Balance, equilibrioception, or vestibular sense is the sense that allows an organism to sense body movement, direction, and acceleration, and to attain and maintain postural equilibrium and balance. The organ of equilibrioception is the vestibular labyrinthine system found in the inner ear. In technical terms, this organ is responsible for two senses of angular momentum acceleration and linear acceleration (which also senses gravity), but they are known together as equilibrioception.

The vestibular nerve conducts information from sensory receptors in three ampulla that sense motion of fluid in three semicircular canals caused by three-dimensional rotation of the head. The vestibular nerve also conducts information from the utricle and the saccule, which contain hair-like sensory receptors that bend under the weight of otoliths (which are small crystals of calcium carbonate) that provide the inertia needed to detect head rotation, linear acceleration, and the direction of gravitational force.

Neuroplastogens may have a role in the improvement of deficits balance affected by diseases and injury at all levels of the somatosensory pathways from the neural receptors in the inner ear to the cortical areas. The decline in the sense of balance secondary to aging may also be slowed or improved by neuroplastogens.

Proprioception

Proprioception, the kinesthetic sense, provides the parietal cortex of the brain with information on the movement and relative positions of the parts of the body. Neuroplastogens may have a role in the improvement of deficits in proprioception affected by diseases their treatment and injury at all levels of the somatosensory pathways from the receptors to the cortical areas. The decline in the sense of proprioception secondary to aging may also be slowed or improved by neuroplastogens.

Sexual Stimulation and Sexual Function

Sexual stimulation is any stimulus (including bodily contact) that leads to, enhances and maintains sexual arousal, and may lead to orgasm. Distinct from the general sense of touch, sexual stimulation is strongly tied to hormonal activity and chemical triggers in the body. Although sexual arousal may arise without physical stimulation, achieving orgasm usually requires physical sexual stimulation, stimulation of the Krause-Finger corpuscles found in erogenous zones of the body.

Neuroplastogens may have a role in the improvement of sexual dysfunction affected by diseases and injury at all levels of the sexual stimulation pathways, from the neural receptors in the skin including hair follicles, tongue, throat, and mucosa to the cortical areas. The decline in sexual function and bladder control secondary to aging or oncologic treatments, including radiation therapy and chemotherapy, may also be slowed or improved by neuroplastogens.

Furthermore, by enhancing and or restoring the senses of olfaction, vision, hearing and touch, neuroplastogens may also enhance libido and sexual function affected by diseases and aging.

Time Perception

Chronoception refers to how the passage of time is perceived and experienced. Although the sense of time is not associated with a specific sensory system, the work of psychologists and neuroscientists indicates that human brains do have a system governing the perception of time, composed of a highly distributed system involving the cerebral cortex, cerebellum and basal ganglia. One particular component, the suprachiasmatic nucleus, is responsible for the circadian (or daily) rhythm, while other cell clusters appear to be capable of shorter-range (ultradian) timekeeping. One or more dopaminergic pathways in the central nervous system appear to have a strong modulatory influence on mental chronometry, particularly interval timing.

Psychedelics are known for their potential to profoundly affect the sense of time. When this sense is disrupted by CNS disease or injury, including eye disorder, neuroplastogens may have a role in restoring physiological chronometry. The impairment in chronometry secondary to aging may also be slowed or improved by neuroplastogens.

Sense of Agency

The sense of agency refers to the subjective feeling of having chosen a particular action. Some neurological diseases or injuries can lead to a loss of this sense, causing a person to feel like a machine or even leading to delusions of being controlled from some outside source. The opposite extreme occurs too, with some people experiencing everything in their environment as if they had decided that it would happen. When this sense is disrupted by CNS disease or injury, neuroplastogens may have a role in restoring this sense. The impairment of sense of agency secondary to aging may also be slowed or improved by neuroplastogens.

Familiarity

Recognition memory is sometimes divided into two functions by neuroscientists: familiarity and recollection. A strong sense of familiarity can occur without any recollection, for example in cases of deja vu. The temporal lobe, in particular the perirhinal cortex, responds differently to stimuli which feel novel than to things which feel familiar. Firing rates in the perirhinal cortex are connected with the sense of familiarity in humans and other mammals.

When this sense is disrupted by CNS disease or injury, and or eye disease or injury, neuroplastogens may have a role in restoring this sense. The impairment of sense of familiarity secondary to aging may also be slowed or improved by neuroplastogens.

Additional literature support for the experimental results disclosed in this application:

According to recent research, these two classes of compounds, NMDAR antagonists (De Martin et al., 2018; Fogaca et al., 2019) and 5-HT2A agonists (Ly et al, 2018) share the ability to promote neural plasticity, to induce trophic actions and may have anti-inflammatory actions and some of these effects may be mediated via modulation of BDNF but other mechanisms may potentially play a role. Select molecules from both classes may thus offer neural protection and cellular protection which may be therapeutic for a multiplicity of clinical disorders. Furthermore, due to distinct and potentially synergic mechanisms of actions, respectively at NMDAR and 5-HT2A receptors, and the potential interactions between these two receptor classes disclosed throughout this application, including allosteric interactions, and reciprocal induction (synthesis of proteins) and modulation (allosteric or intra-channel blocking actions) of receptors, including induction of select protein subunits selective for certain receptor subtypes, these two classes of drugs, NMDAR antagonists and 5-HT2A agonists may have the potential of acting synergistically, i.e. their effects may be additive and advantageous for select patients and or diseases. Furthermore, when administered together these drugs may be safer than either drug administered alone. For example, their co-administration may allow even lower doses to be effective, compared to treatment with a single agent from each class administered alone, for the treatment of certain diseases and conditions. Furthermore, the neuroplasticity modulatory effects of some of the NMDA open channel blockers such as ketamine, dextromethadone and dextromethorphan may be mediated via 5-HT receptors for which these drugs have affinities [inhibition of NET and SERT or agonists actions at 5-HT receptors [Kapur S, Seeman P. NMDA receptor antagonists ketamine and PCP have direct effects on the dopamine D(2) and serotonin 5-HT(2)receptors—implications for models of schizophrenia. Mol Psychiatry. 2002; 7(8):837-44; Codd et al., Serotonin and Norepinephrine activity of centrally acting analgesics: Structural determinants and role in antinociception. IPET 1995; 274 (3)1263-1269); Rickli et al., 2017].

Both serotonin agonists and NMDAR antagonists potentially determine neural plasticity effects possibly by modulation of BDNF (Ly et al., 2018 and De Martin et al., 2018; Fogaca et al. 2019). While the present inventors disclose a potential synergy among these two distinct classes of drugs, drugs in both classes and select drugs within each of the two classes potentially may have distinct target clinical indications.

The study by Catlow et al., 2013 (Catlow B, Song S, Paredes D A, Kirstein C L, Sanchez-Ramos J) Effects of psilocybin on hippocampal neurogenesis and extinction of trace fear conditioning. Exp Brain Res. 2013 August; 228 (4):481-91) showed that psilocybin reduced hippocampal neurogenesis at high doses while noting that there was an opposite trend towards an increase in hippocampal neurogenesis at lower doses. This observation lends further support to the present inventors' findings and disclosures, underscoring the importance of dosing when aiming towards neural modulatory effects and in particular pointing toward the potential therapeutic effects of lower doses of 5-HT2A agonists administered chronically for modulation of plasticity, neurogenesis and neuroprotection, as demonstrated by the present inventors' experiments (in particular Example 3). The 2018 study by Ly et al., (Ly C, Greb A C, Cameron L P, et al. Psychedelics Promote Structural and Functional Neural Plasticity. Cell Rep. 2018; 23(11):3170-3182) confirms the potential for psychedelics for promoting neural plasticity and suggests a mechanism based on activation of 5-HT2A receptors through BDNF, TrkB and mToRC1-dependent mechanisms. This paper focuses on the potential neuronal plasticity effects of psychedelics on a particular neuronal population (prefrontal neurons) known to be affected in depression and other psychiatric syndromes (PTSD, anxiety, addiction), administered acutely (24 hours) at high concentration, and thus suggests hypotheses for better understanding the potential uses and effects of large doses of psychedelics in the treatment of depression. This study supports the currently investigated single large dose (psychedelic experience) therapeutic approach, combined with psychotherapy/counseling, for the uses of 5-HT2A agonists for the treatment of depression and other psychiatric symptoms and syndromes(addiction, anxiety, PTSD). The present inventors' studies instead support the hypothesis of safety and effectiveness of neuroplastogen doses administered chronically, continuously or intermittently.

EXAMPLES

Example 1

The following clinical observations were made in the Netherlands in subjects who self-administered sclerotia of Psilocibe atlantis (magictruffles.com). Psilocybe atlantis is a species containing psilocybin, psilocin, baeocystin, and norbaeocystin (Guzman G, Hanlin R T, White C. Another new bluing species of Psilocybe from Georgia, U.S.A. Mycotaxon 2003; 86: 179-183).

Of note, the sale and use of sclerotia of psychedelic mushrooms are legal in the Netherlands and the producer of the particular brand and species of sclerotia self-administered by the described subjects indicates the intake of 15 grams for a "psychedelic dose" [the amount taken by the first subject, CF, (1.5 grams) was 1/10 of the suggested "psychedelic dose" and the amount taken by the other two subjects, GG and PM, (3 grams) was 1/5 of the suggested "psychedelic dose"].

The present inventors describe CF, an 85-year-old with a history of mild myopia (−2 diopters, RE and LE) corrected at the time of cataract surgery (age 82) with intraocular lens insertion, who reported improvement in vision (improved vision at a distance, specifically improved detection of objects at a distance) after occasional intake of low dose (non-psychotomimetic) psilocybe fungi.

Upon request from the patient, after an interval of at least three months without intake of mushrooms, drugs or other substances, including prescription drugs, vitamins and supplements, the present inventors performed visual testing and psychometric testing (baseline day-0) and on day 3, 2 hours after (acute effects) oral intake of 1.5 grams of psilocybe atlantis sclerotia daily for three days (day-3), and on day 4, 24 hours after the last dose of psilocybe atlantis sclerotia (day 4).

| Visual Acuity Testing, Subject CF: |
|---|
| RE: from 10/10 day-0 baseline to 12/10 on day-3 and day-4 follow-up<br>LE: from 10/10 day-0 baseline to 12/10 on day-3 and day-4 follow-up<br>OU (both eyes): from 10/10 day-0 baseline to 12/10 on day-3 and day-4 follow-up |
| Ishihara Color Test: |
| OD (right eye): pre-treatment baseline 2 mistakes; day-3 and post treatment follow-up day-4, 1 mistake<br>OS (left eye): pre-treatment baseline 2 mistakes; day-3 and post treatment follow-up day-4, 1 mistake<br>OO (both eyes): pre-treatment baseline 2 mistakes; day-3 and post treatment follow-up day-4, 0 mistakes |
| MMMSE: |
| 3 0/30, no changes, day 0, day-3 acute (2 hours after the first dose) and day-4 follow-up, except for improved geometrical drawing in the follow-up test 24 hours after the last treatment dose |

These results suggest persistent visual improvement (up to 24 hours) after repeated doses (daily for three days) of very low dose psilocybin containing sclerotia (Psilocybe atlantis sclerotia/1.5 grams daily for 3 days).

The present inventors describe below two subjects. The first subject, GG, is a 56-year-old healthy male. The second subject, PM, is a 57-year-old healthy male with moderate myopia since childhood (−9 diopters), well corrected with contact lenses. Neither subject had taken drugs, including prescription drugs, food-supplements or vitamin-supplements for at least three months prior to baseline evaluation.

Visual parameters before (day-0, baseline) and after (day-4, 24 hours post-intake of the third and last dose) intake of 3 grams of Psilocybe atlantis sclerotia/day for 3 days. Spatial Contrast sensitivity was measured by means of randomized Snellen letters of contrast decreasing according to a logarithmic scale of 0.15 for a constant visual acuity of 0.3.

| Subject 1 (GG): |
|---|
| RE: 3.2% 3/7* day-0 to 3.2% day-4<br>LE: 3.2% day-0 to 1.1% 6/7* day-4<br>OU (both eyes): 1 .1% day-0 to 0.8% 6/7 day-4 |

-continued

| Subject 2 (PM): |
| --- |
| RE: 3.2% 2/7* day-0 to 3.2% day-4 |
| LE: 4.5% 2/7* day-0 to 3.2% day-4 |
| OU (both eyes): 3.2% 4/7* day-0 to 3.2% day-4 |

*Number of letters correctly identified among those shown on the corresponding letter row composed by seven letters

| Visual Acuity Testing: |
| --- |
| Subject 1 (GG): |
| RE: 12/10 day-0 to 14/10 day-4 |
| LE: 14/10 day-0 to 16/10 day-4 |
| OU (both eyes): 14/10 day-0 to 16/10 day-4 |
| Subject 2 (PM): |
| RE: 10/10 day-0 to 12/10 day-4 |
| LE: 9/10 day-0 to 10/10 day-4 |
| OU (both eyes): 10/10 day-0 to 12/10 day-4 |

The present inventors administered the Farnsworth-Munsell 100 Hue Color Vision Test 100 and generated TES values. TES is an automated, generated value that calculates the number of tiles placed incorrectly and scales the value for uniform analysis. Average TES scores range from thirty to forty in series tests; while scores exceeding seventy can point to a marker for color blindness. Lower scores are intended to point to significantly increased color vision accuracy, as the TES score is directly correlated to the number of tiles incorrectly identified. https://www.color-munki.com/game/huetest_kiosk

| Subject 1 (GG): |
| --- |
| OU (both eyes): 70 day-0 to 16 day-4 |
| Subject 2 (PM): |
| OU (both eyes): 73 day-0 to 40 day-4 |

In order to obtain a measure of global behaviour of visual performances, the present inventors evaluated Visual Field Testing by means of Humphrey computerised perimetry program 30-2 which offers a standardized, widely accepted static measurement of light perception over a consistent reproducible illumination background, and determined the classic indicators given by the system, Visual field index (in %), Mean defect (in dB):

| Subject 1 (GG): | | | |
| --- | --- | --- | --- |
| Day-0 | | Day-4 | |
| Visual Field Index (VFI): | | | |
| RE: 97% | LE: 100% | RE: 98% | LE: 100% |
| Mean Defect (MD) | | | |
| RE: −1.78 | LE: −0.33 | RE: +0.41 | LE: +0.04 |
| Subject 2 (PM): | | | |
| Day-0 | | Day-4 | |

-continued

| Visual Field Index (VFI): | | | |
| --- | --- | --- | --- |
| RE: 99% | LE: 93% | RE: 100% | LE: 99% |
| Mean Defect (MD) | | | |
| RE: −1.4 | LE: −3.61 | RE: −0.16 | LE: −0.14 |

As the highest concentration of photoreceptors is concentrated in the macular area, Central (macular and perimacular area) Visual field testing by means of Humphrey computerised perimetry program 10-2 was evaluated by taking into account the Mean defect (in dB):

| Mean Defect (MD) | | | |
| --- | --- | --- | --- |
| Day-0 | | Day-4 | |
| Subject 1 (GG): | | | |
| RE: −0.50 | LE: +0.45 | RE: +0.72 | LE: +1.19 |
| Subject 2 (PM): | | | |
| RE: −0.95 | LE: −0.50 | RE: −0.16 | LE: −0.14 |

The sensitivity (in dB) of the point of fixation, usually corresponding to the location of the sharpest visual performance, was also tested at the Humphrey perimeter (data in dB):

| Day-0 | | Day-4 | |
| --- | --- | --- | --- |
| Fixation sensitivity | | | |
| Subject 1 (GG): | | | |
| RE: 39 dB | LE: 38 dB | RE: 39 dB | LE: 42 dB |
| Subject 2 (PM): | | | |
| RE: 35 dB | LE: 36 dB | RE: 37 dB | LE: 41dB |

Pupillometry (scotopic, mesopic and photonic) was performed on both subjects on day-3, 2 hours post-dose:

| Subject 1 (GG): |
| --- |
| RE: Scotopic 4.41 day-0 to 5.38 day-3 |
| Mesopic 3.45 day-0 to 4.45 day-3 |
| Photopic 3.26 day-0 to 3.50 day-3 |
| Dynamic: +2.86 day-0 to +3.37 day-3 |
| LE: Scotopic 4.30 day-0 to 5.00 day-3 |
| Mesopic 3.27 day-0 to 4.49 day-3 |
| Photopic 2.67 day-0 to 3.44 day-3 |
| Dynamic: +2.88 day-0 to +3.0.0 day-3 |
| Subject 2 (PM): |
| RE: Scotopic 6.09 day-0 to 6.54 day-3 |
| Mesopic 4.60 day-0 to 4.46 day-3 |
| Photopic 3.60 day-0 to 3.65 day-3 |
| Dynamic: +3.37 day-0 to 3.90 day-3 |
| LE: Scotopic 5.94 day-0 to 5.99 day-3 |
| Mesopic 4.72 day-0 to 4.26 day-3 |
| Photopic 3.98 day-0 to 3.45 day-3 |
| Dynamic: +4.08 day-0 to |

The present inventors performed baseline (day 0) and post-dose on day-1 and on day-4 the 5-dimensional Altered State of Consciousness Rating Scale. Results below in the Summary of Results.

Summary of Results: Compared to baseline, day-0, on day 4, 24 hours after the last dose of three days of daily administration of 3 grams pf psilocybe atlantis sclerotia, the present inventors detected an improvement in measurements of contrast sensitivity, visual acuity and color vision compared to baseline-day-0 in both tested subjects. Visual field indicators also indicated improvement both subjects. A mild increase in mydriatic tone was noted in both subjects on day-3, 2 hours post-dose, compared to baseline day-0 (pupillometry). The 5-dimensional Altered State of Consciousness Rating Scale in both subjects showed normal state of consciousness in all tested areas at all tested times (day-0, day-1, day-4), confirming the absence of psychedelic/psychotomimetic effects, both acutely (day-1, 2 hours post-dose) and, expectedly, 24 hours after the last of three daily doses.

The above results suggest that repeated low doses (non—psychedelic/non-psychotomimetic) of psilocybe atlantis sclerotia, resulting in low, non-psychedelic plasma levels of psilocybin, psilocin, baeocystin, potentially determine sustained clinically meaningful effects on different visual parameters. The present inventors disclose that these therapeutic effects are potentially mediated by the neuroplastogen actions of these molecules, potentially at different levels of the visual pathways, from the retinal pigment layer (see ARPE-19 test results, Annex 3) to the visual cortex (see in vitro results on neurogenesis, Annex 2).

Thus, based on the present inventors' observational work, the following conclusions were reached:

a) The repeated daily administration of neuroplastogen doses of 5-HT2A agonist substances is potentially safe and effective for the improvement of vision;
b) The repeated daily administration of neuroplastogen doses of 5-HT2A agonist substances is potentially safe and effective for the treatment of ophthalmological diseases and conditions associated with visual impairment;
c) 5-HT2A agonists at neuroplastogen doses may be therapeutic as sole agents (e.g., psilocybin or psilocin or baeocystin) or may be therapeutic as a mixture of molecules, e.g., the mixture contained in Psilocybe Atlantis fungi: psilocybin and or psilocin and or baeocystin and mixtures thereof, including mixtures of other molecules contained in the psilocybe atlantis sclerotia;
d) Clinically meaningful and measurable potentially therapeutic effects of chronic neuroplastogen doses of 5-HT2A agonists outlast the effects expected from receptor occupancy, signalling a potential effect on modulation of neural plasticity rather than an effect based on extemporary receptor occupancy; and
e) Clinically meaningful measurable effects of chronic neuroplastogen doses of 5-HT2A agonists outlast the effects expected from receptor occupancy, signalling a potential therapeutic effect of chronic intermittent neuroplastogen doses of 5-HT2A agonists. [*Drugs acting directly on neurotransmitters and their pathways, including transporter pathways, such as for example benzodiazepines and opioids (and also SSRI), exert their effects by interacting with specific receptors and their effects cease or even rebound when the drugs are discontinued. A persistence of effects, as noted in the present inventors' cases of chronic neuroplastogen dose administration of 5-HT2A agonist substances, signal a potential effect modulated through other mechanisms (e.g., neural plasticity mechanisms or biological pathways) that outlast receptor occupancy.]

In the case of drugs with a very short half-life in humans, as is the case with many 5-HT2A drugs, while large doses (psychedelic doses) may result in rapid downregulation of 5-HT2A receptors and loss of effect (e.g., loss of the psychedelic effect) on repeated dosing, chronic dosing with low (non-psychedelic doses) may result in continued efficacy because of less or no downregulation of receptors due to 1) less receptor occupancy 2) rapid clearance of the drug 3) effects on NMDARs (see Example 3, below). The above mechanisms might suggest a reverse U curve when 5-HT2A agonists are used as neuroplastogens (for modulating neural plasticity in the absence of psychedelic/psychotomimetic effects): doses on the top of the inverted U curve (neuroplastogen doses) are more effective than very extremely doses on the upslope of the inverted U curve and also more effective than higher doses on the downslope of the inverted U curve.

These observations signal that clinically measurable effects on visual parameters can be obtained with repeated neuroplastogen doses (non-psychedelic/non-psychotomimetic) of 5-HT2A agonist substances at doses that do not cause psychedelic/psychotomimetic symptoms and said doses resulting in plasma levels of said substances much lower than plasma levels generally required for psychedelic/psychotomimetic effect.

Example 2—In Vivo Studies

The available scientific literature, both in clinical settings (safety and efficacy studies) and in experimental settings (in vitro and in vivo experimental settings, including work by Ly et al., 2018), thus far, has remained focused on acute, pulse treatments with "large" doses of drugs expected and intended to produce clinically meaningful psychedelic/psychotomimetic effects (Johnson M1, Richards W, Griffiths R. Human hallucinogen research: guidelines for safety. J Psychopharmacol. 2008 August; 22(6):603-20). A similar approach (pulse exposure to high concentrations) has been taken in experimental trials (Ly et al., 2018) which thus support the use of psychedelic doses of 5-HT2A agonists.

In order to assess whether repeated chronic low-dose (non-psychedelic/psychotomimetic) administration of 5-HT2A agonists potentially modulate neural plasticity and or modulate neuroinflammation, and in order to assess whether these effects are potentially cytoprotective, and whether these effects may result in potentially clinically meaningful therapeutic effects, the present inventors performed a series of preclinical in vivo experiments. These tests were designed specifically to assess the potential therapeutic effects of neuroplastogen chronic dosages of 5-HT2A agonists.

1. Effects of Psilocybin on Western Diet Fed Rats

Hypothesis: Low dose chronic treatment with psilocybin counteracts the negative effects of western diet (WD) on metabolic parameters.

Background: The modern western lifestyle is characterized by the consumption of a hypercaloric diet rich in fats and simple carbohydrates. This diet is associated with obesity, type 2 diabetes mellitus (T2D) and the metabolic syndrome (Lozano I, Van der Werf R, Bietiger W, Seyfritz E, Peronet C, Pinget M, Jeandidier N, Maillard E, Marchioni E, Sigrist S, Dal S. High-fructose and high-fat diet-induced disorders in rats: Impact on diabetes risk, hepatic and vascular complications. Nutrition & Metabolism 2016, 13: 15). These metabolic disorders have been associated to other diseases, e.g. non-alcoholic fatty liver disease (NAFLD), but also with pathologic conditions characterized by a low-grade inflammatory state, that could lead to severe immunologic and neuro-psychiatric dysfunctions (Castanon N, Lasselin J, Capuron L. Neuropsychiatric Comorbidity in Obesity: Role of Inflammatory Processes. Frontiers in Endocrinology, 2014, 5: 74).

In the liver, lipid accumulation may be due to the increased delivery of fatty acids or de novo lipogenesis, and/or decreased lipid clearance due to a drop of lipid secretion or oxidation (Musso G, Cassader M, Gambino R. Non-alcoholic steatohepatitis: Emerging molecular targets and therapeutic strategies. Nature Review Drug Discovery 2016, 15: 249-274). The accumulation of fatty acids in the liver results in the development of NAFLD, which currently represents one of the most common causes of chronic liver disease worldwide and one of the major causes of liver-related morbidity and mortality, and, as stated before, is strongly associated to the development of obesity, type 2 diabetes and metabolic syndrome (Byrne C D, Targher, G. NAFLD: A multisystem disease. Journal of Hepatology 2015, 62: S47-S64). Although the relative contribution of the different pathways described above to the development of NAFLD is only partially known, a number of preclinical studies and clinical trials have demonstrated that the de novo lipogenesis plays a pivotal role in the development of NAFLD (Lambert J E, Ramos-Roman M A, Browning J D, Parks E J. Increased de novo lipogenesis is a distinct characteristic of individuals with nonalcoholic fatty liver disease. Gastroenterology 2014, 146: 726-735). To date, although the prevalence of NAFLD and its complication, non-alcoholic steatohepatitis (NASH), are increasing worldwide, no therapeutic options are currently available (Alkhouri N, Lawitz E, Noureddin M. Looking Into the Crystal Ball: Predicting the Future Challenges of Fibrotic NASH Treatment. Hepatology Communications 2019, 3: 605-613).

Methods: 30 male Sprague-Dawley rats (200±50 g) were housed 3 per cage at a temperature of 21° C., alternating 12 hours of light and 12 hours of dark and after a period of acclimatization were randomized into two groups. The control group (N: 10) continued on Standard Diet (SD, Altromin, Italy), while the Western Diet (WD) group (N: 20) was switched to High Fat Diet (HFD) (60% kcal from fat, Altromin, Italy), enriched with fructose in drinking water, at a concentration of 30% (w/V). The combination of HFD and 30% fructose in drinking water is a model of the so-called WD. After 26 weeks, the rats on the WD were randomly divided into 2 subgroups (N=10) treated daily for 15 days by gastric gavage respectively with aqueous vehicle or psilocybin (0.05 mg/kg body weight).

All procedures involving animals were performed in compliance with institutional guidelines in compliance with national and international laws and policies (Council Directive of the European Economic Community 86/609, OJ L 358, 1, Dec. 12, 1987; NIH Guide for the Care and Use of Laboratory Animals, NIH Publication No. 85-23, 1985). The study design was approved by the Ethics Committee of the University of Padua for the care and use of laboratory animals and by the Italian Ministry of Health.

Results:

Oral Glucose Tolerance Test

Figure 1B:
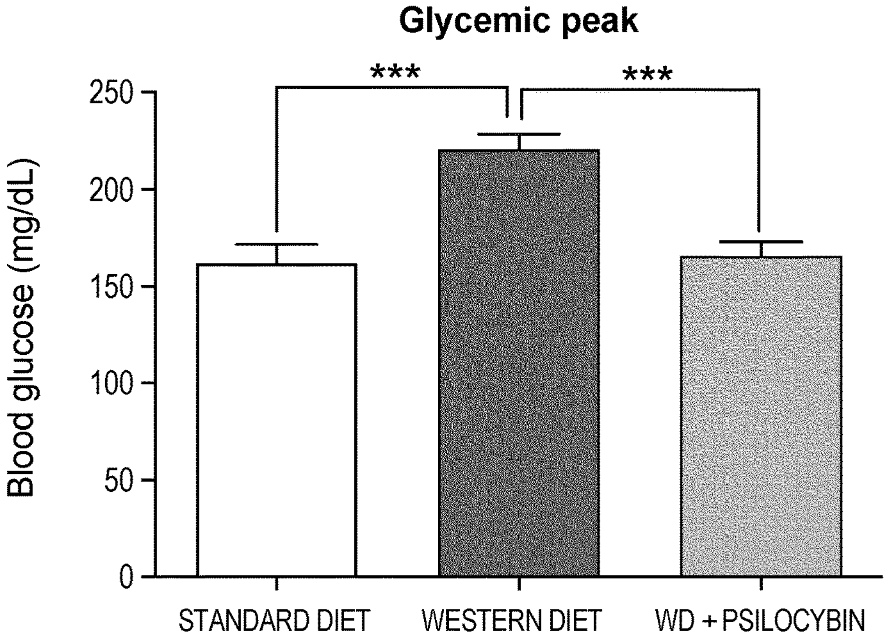
FIG. 1B is a graph showing effect of psilocybin on glycemic peak. ***p<0.001; one-way ANOVA followed by Tukey's post hoc test.

The oral glucose tolerance test was performed the day before sacrifice to evaluate the glycemic response after the oral administration of glucose (2 g/Kg body weight). Referring to FIGS. 1A and 1B, in the WD+vehicle group, the oral glucose tolerance test induced a significant increase of glycemic peak after 15 minutes from glucose gavage compared to the SD group, while the curve of WD+psilocybin animals was comparable to the SD group. Accordingly, after oral glucose tolerance test, the increase of glycemic peak caused by WD was counteracted by 15 days by gastric gavage with psilocybin 0.05 mg/kg body weight compared to gastric gavage with vehicle.

Body and Liver Weight

Figure 2A:
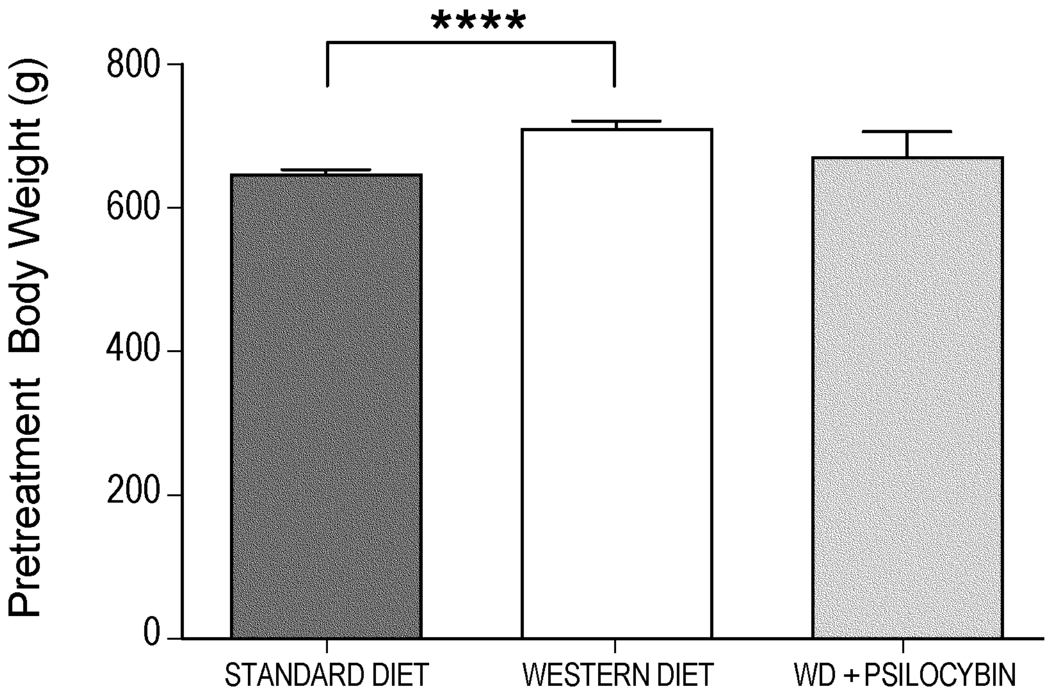
FIG. 2A is a graph showing body weight (pre-treatment with psilocybin). *P<0.05, p<0.01; one-way ANOVA followed by Tukey's post hoc test.
Figure 2B:
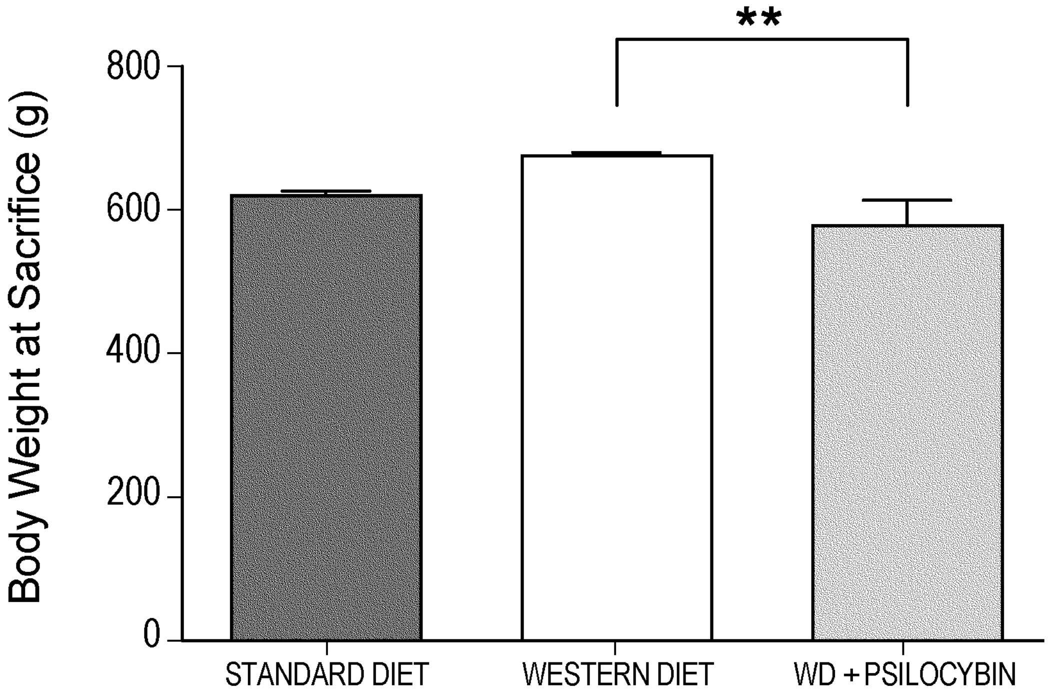
FIG. 2B is a graph showing the effect of psilocybin on body weight (after treatment) at sacrifice. *P<0.05, **p<0.01; one-way ANOVA followed by Tukey's post hoc test.
Figure 2C:
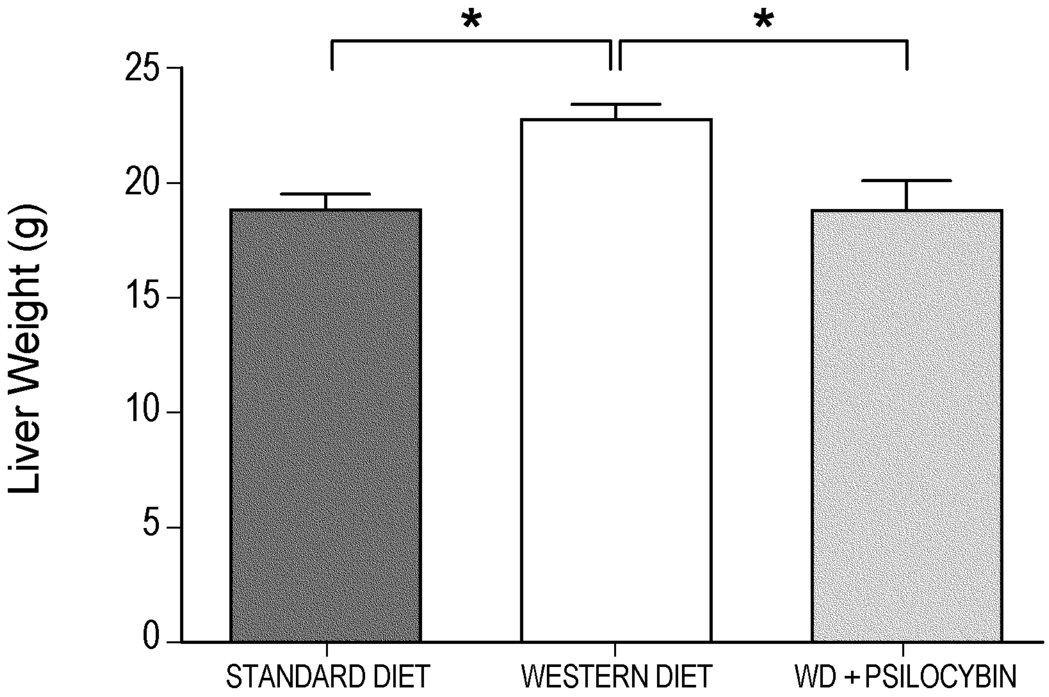
FIG. 2C is a graph showing the effect of psilocybin on liver weight (after treatment) at sacrifice. *P<0.05, **p<0.01; one-way ANOVA followed by Tukey's post hoc test.

Referring now to FIGS. 2A-2C, at sacrifice, the present inventors observed an increase in body and liver weight in WD+vehicle rats compared to SD fed rats and WD+psilocybin rats. Notably, the treatment with psilocybin 0.05 mg/Kg for 15 days was able to counteract this WD-induced body and liver weight increase.

Liver Histology and Hepatic Inflammation

Figure 3B:
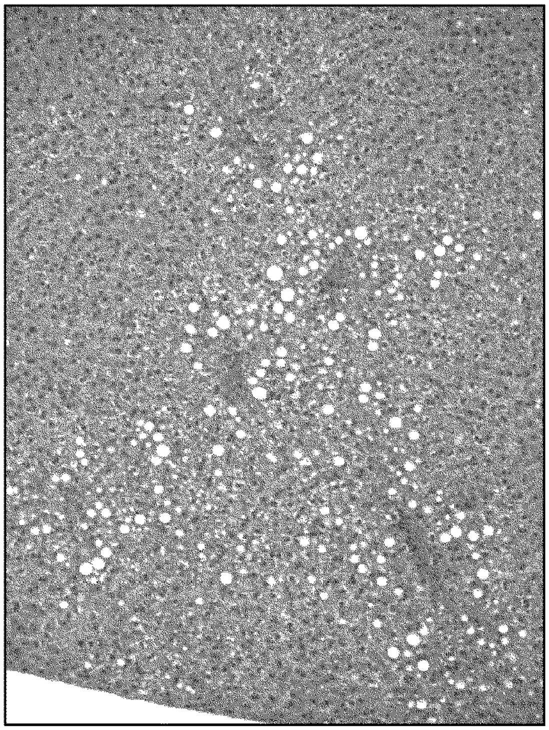
FIG. 3B is a photograph showing liver histology via H&E staining of liver tissue obtained from a WD+vehicle rat, 10× magnification.
Figure 3C:
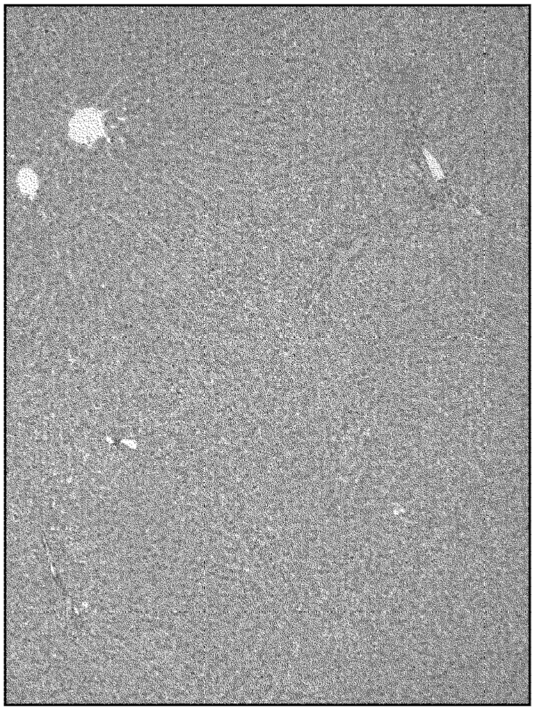
FIG. 3C is a photograph showing liver histology via H&E staining of liver tissue obtained from a WD+psilocybin rat, 10× magnification.
Figure 3A:
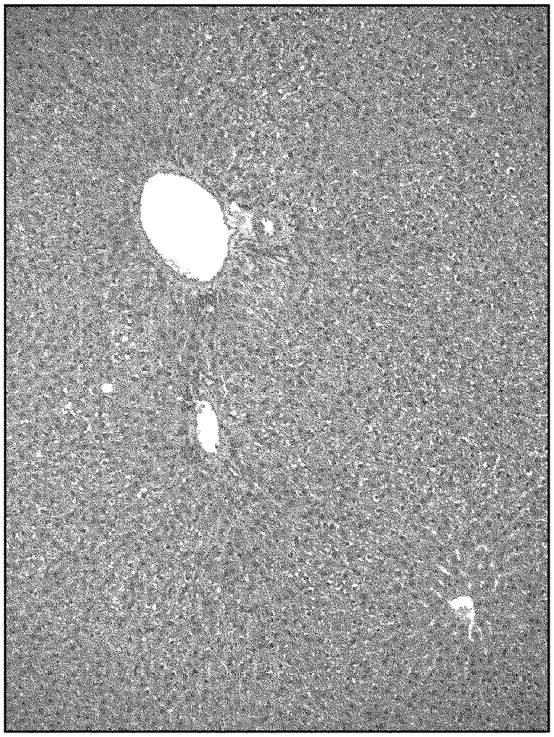
FIG. 3A is a photograph showing liver histology via H&E staining of liver tissue obtained from a SD fed rat, 10× magnification.

In order to evaluate liver status, the present inventors performed a histological analysis of liver tissue by hematoxylin-eosin staining of paraffine-embedded liver slices. At histology, SD fed rats showed a normal liver architecture (FIG. 3A), whereas lipid accumulation leading to hepatic steatosis was observed in WD fed rats, where lipid accumulation could be observed in 15% of the hepatocytes (median) (FIG. 3B, white fat vesicles, see also Table 2, below), while a dramatic reduction of steatosis could be observed in the WD rats treated with psilocybin (FIG. 3C, Table 2).

TABLE 2

Liver histology: degree of liver steatosis. Data are expressed as median (range).

| Group | % Hepatic macrovescicular steatosis |
|---|---|
| Standard Diet | 0 (0) |
| Western Diet | 15 (5-20) |
| Western Diet + Psilocybin | 5 (<5-15) |

Figure 4A:
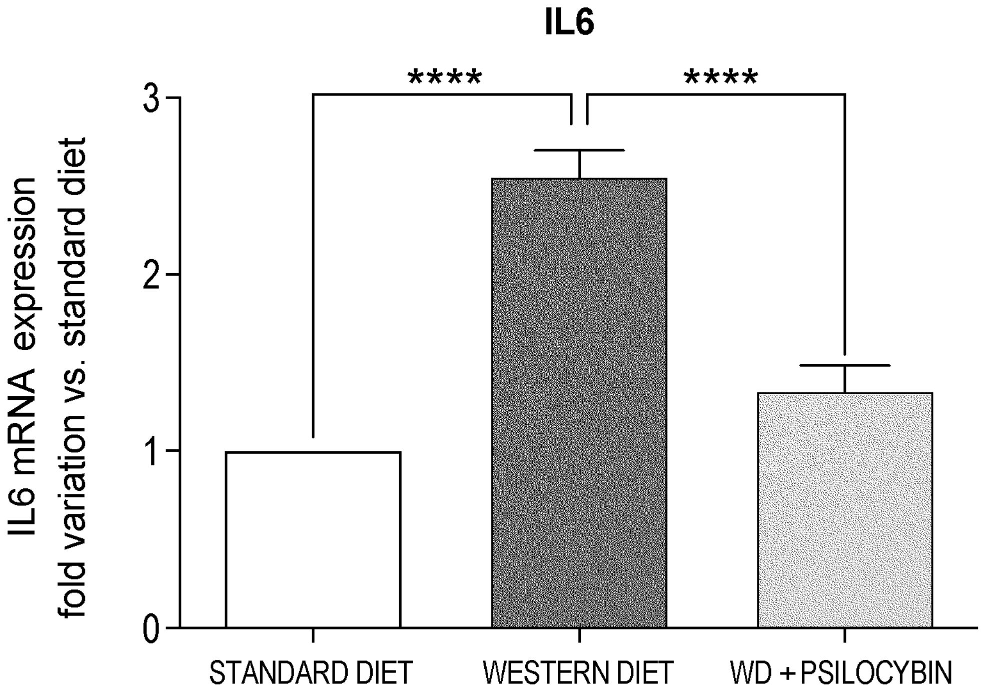
FIGS. 4A-4C are graphs related to hepatic inflammation by showing the gene expression of three interleukins involved in inflammatory pathways (FIG. 4A shows IL-6.
Figure 4B:
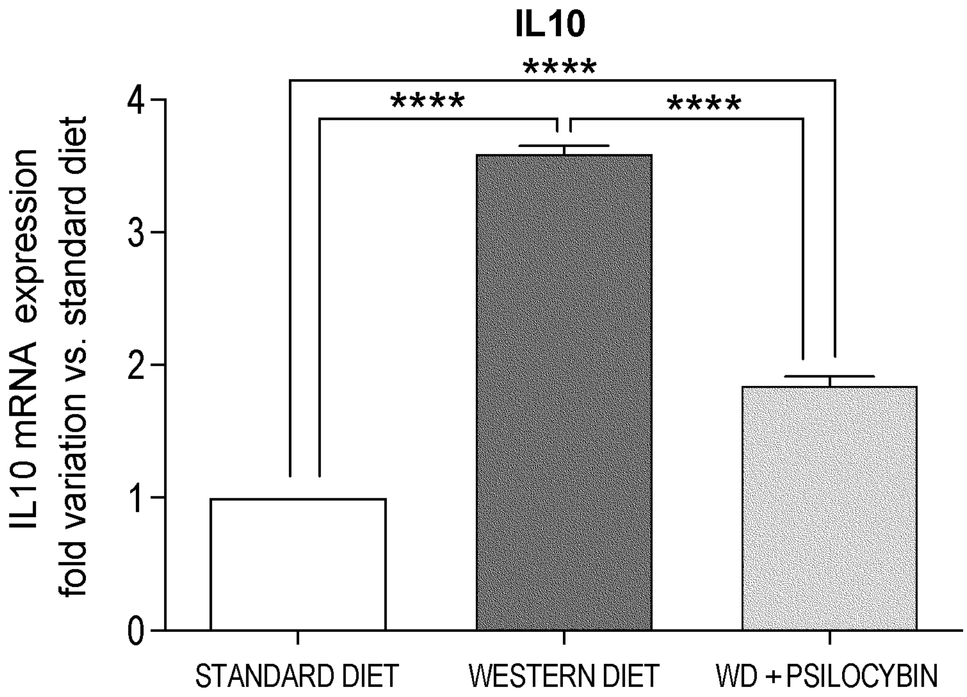
Figure 4C:
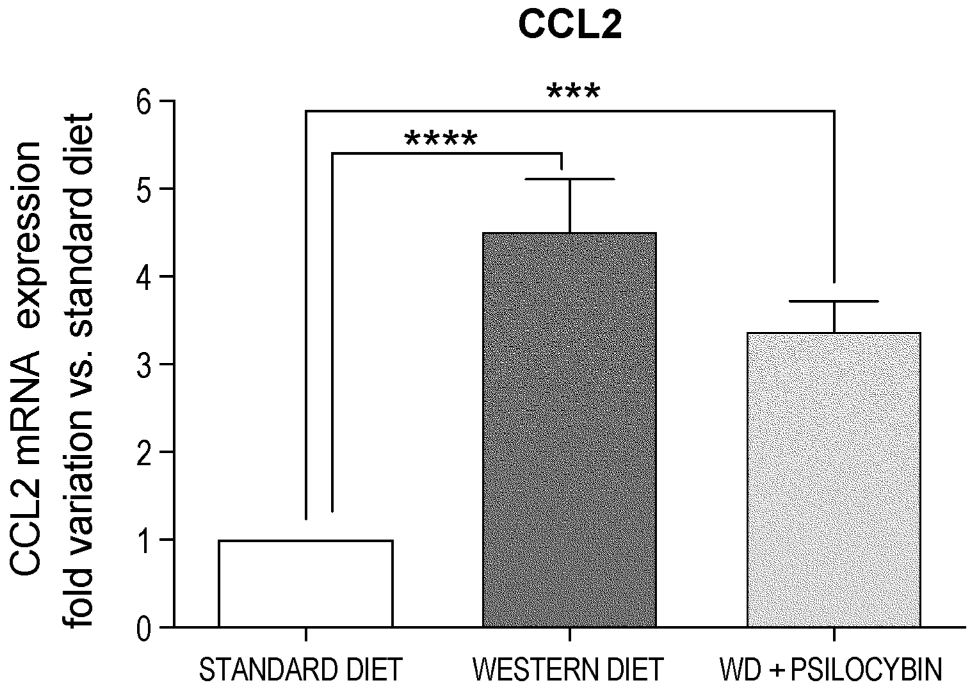

The gene expression of three interleukins involved in inflammatory pathways was measured by qRT-PCR in the rat livers. Results are shown in FIGS. 4A-4C. The gene expression of the pro-inflammatory interleukin IL-6 and was significantly increased by WD administration, indicating an increase of hepatic inflammation, and psilocybin treatment was able to counteract this effect, restoring the physiological IL-6 levels. As far as the anti-inflammatory interleukin IL-10 is concerned, its gene expression was increased in rats fed with WD, and decreased significantly in rats treated with psilocybin, without reaching normal levels. Furthermore, the gene expression of CCL2, a chemokine involved in inflammation and in the recruitment of immune cells in the liver, was increased by WD with respect to SD, and psilocybin treatment didn't affect this increase significantly, although a decreasing tendency could be observed in psilocybin-treated animals compared to untreated WD fed rats.

Reactive Oxygen Species

Figure 5:
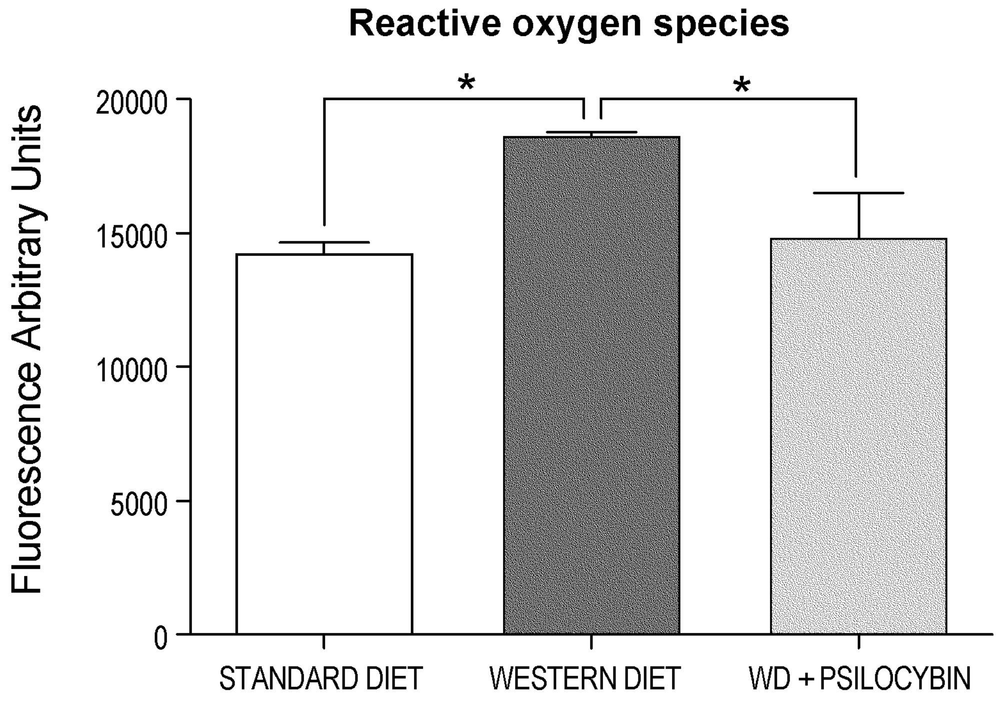
FIG. 5 is a graph showing the production of reactive oxygen species in rat livers. *p<0.05; one-way ANOVA followed by Tukey's post hoc test.

Since the production of reactive oxygen species (ROS) is related to hepatic oxidative and metabolic stress, e.g. hepatic lipid deposition, the present inventors evaluated ROS production in rat livers by means of the 2',7'-dichlorofluorescin diacetate (DCFDA) method. Results are shown in FIG. 5, and it was shown that hepatic ROS production was significantly increased by WD+vehicle administration, while WD+psilocybin treatment was able to restore physiological ROS levels.

Hepatic Lipid Metabolism

Figure 6A:
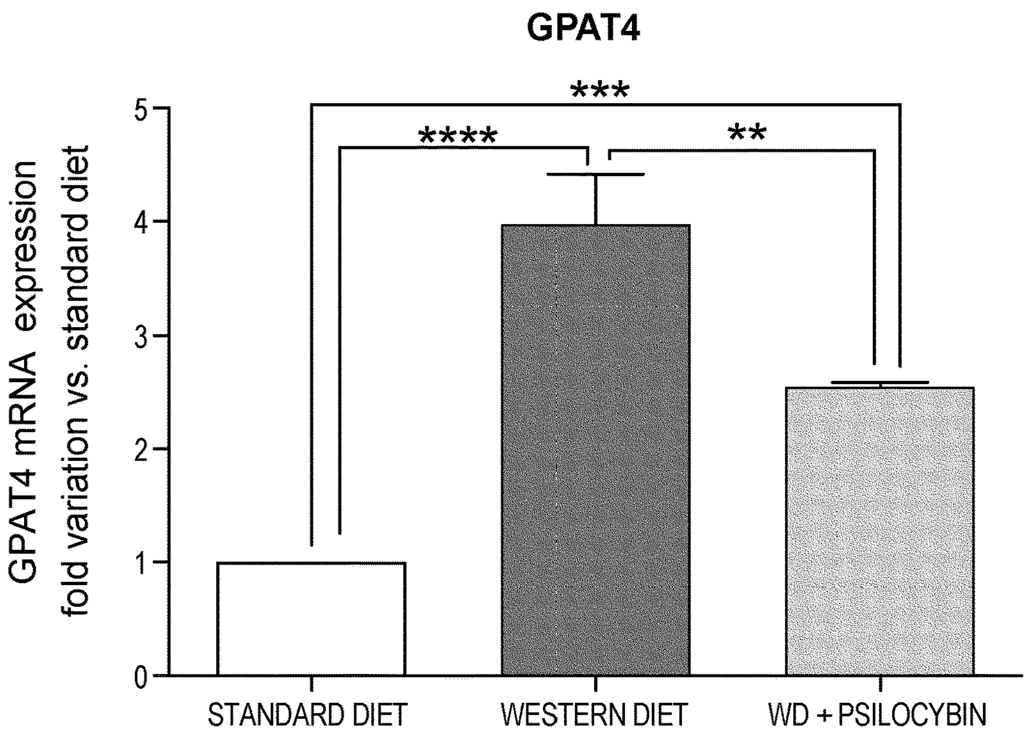
FIG. 6A is a graph showing gene expression of GPAT4 in rat livers. p<0.01, *p<0.001 and ****p<0.0001; one-way ANOVA followed by Tukey's post hoc test.
Figure 6B:
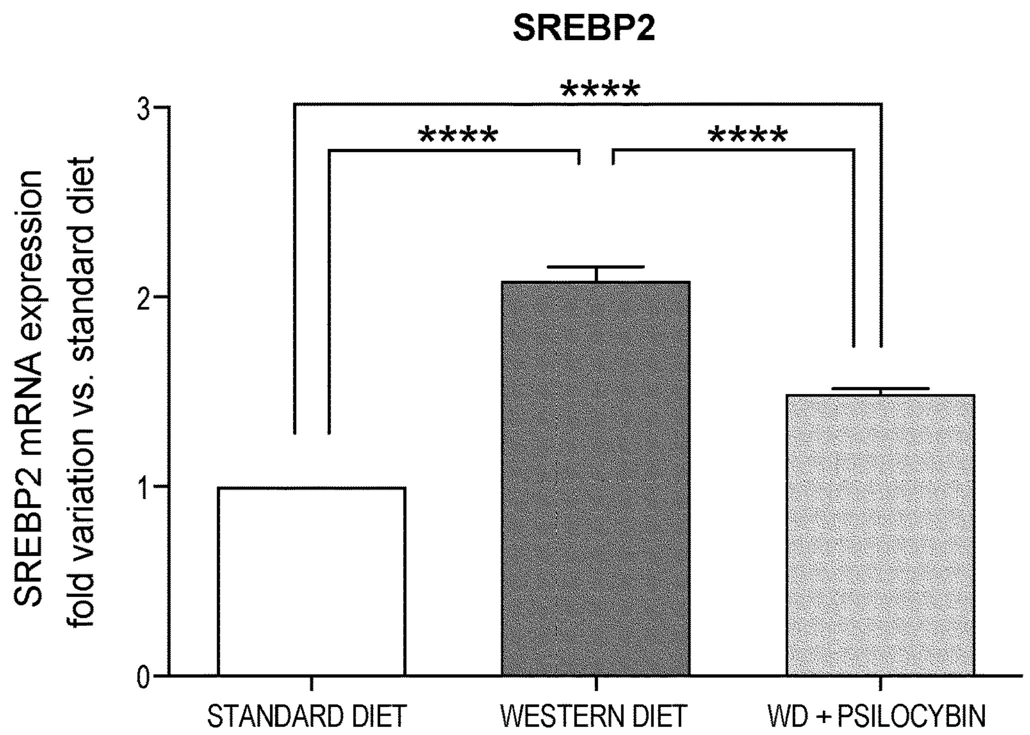
FIG. 6B is a graph showing gene expression of SREPB2 in rat livers. p<0.01, *p<0.001 and ****p<0.0001; one-way ANOVA followed by Tukey's post hoc test.

In order to confirm the histological data indicating the presence of hepatic steatosis, the present inventors measured the expression of two genes involved in lipid metabolism, i.e., GPAT4 and SREPB2 by qRT-PCR. Referring to FIGS. 6A and 6B, the gene expression of both GPAT4 and SREPB2 was significantly increased by WD+vehicle administration, while WD+psilocybin treatment was able to cause a significant drop of their expression, even if this decrease didn't restore their physiological levels. This may indicate that psilocybin leads to a reduction of liver steatosis by reducing lipid accumulation and de novo lipogenesis in hepatocytes.

Behavioral Testing

Figure 7C:
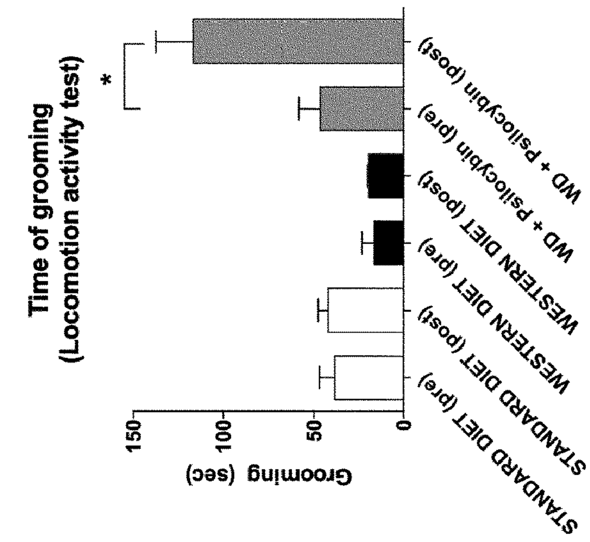
FIGS. 7A-7C are graphs showing the results for a Locomotion Activity Test for crossings (FIG. 7A), rearing (FIG. 7B), and grooming (FIG. 7C).
Figure 7B:
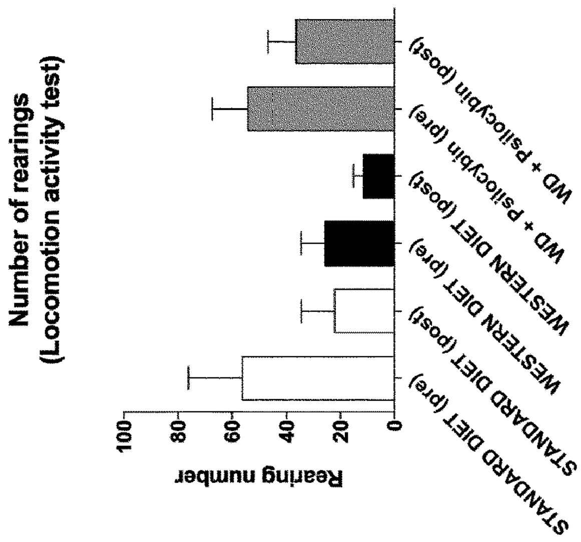
Figure 7A:
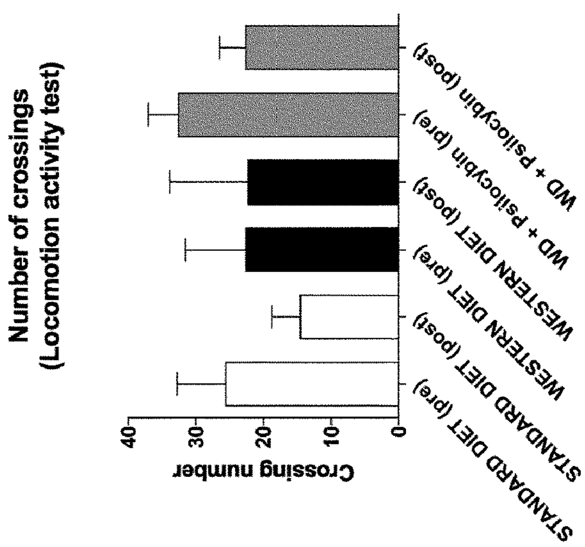

In order to ascertain whether the chronic administration of low dose psilocybin alters behavior in WD fed rats, the present inventors performed the Locomotion Activity Test (LMA) before and after the psilocybin treatment (see FIGS. 7A-7C). This test has the aim of assessing spontaneous locomotor activity in laboratory animals. This test is performed in a gray arena (open field) exposed to light of regulated intensity (24 and 30 lux), avoiding light-shadow zones within the perimeter in which the experiment takes place. Along the base of the open field, 4 standard sized squares have been drawn, clearly visible even in the dark and large enough to allow the animal to remain inside them in all its length. The LMA test has been preceded by one hour of habituation, at the end of which the rat was inserted inside the open field, in one of the previously designed squares. The movements and behaviors in reaction to the environment were then recorded for 10 minutes.

In the LMA test, three fundamental aspects were assessed: 1. the number of crossings, i.e., the number of crossings made by the animal from one square to another, passing the line defining it with both legs. This value gives an indication of the distance traveled by the animal during the test and of its locomotor activity; 2. the number of rearings, i.e, the number of times the animal lifts up on the two posterior legs. This value is proportional to the state of anxiety experienced; 3. the time of grooming, i.e., the interval of time spent by the animal in washing itself, another indicative value of the state of anxiety experienced during the test.

As far as the number of crossings is concerned, the present inventors observed a decreasing tendency in psilocybin-treated animals, which resembles the results obtained with rats fed with SD. This is probably due to the repetition of the test after 2 weeks, but this effect could not be observed in rats fed with WD. The present inventors also observed a significant increase of the time of grooming only in psilocybin-treated rats.

Of note, there was no evidence of psychedelic behavioral effects from chronic (15 day) low dose 0.05 mg/Kg psilocybin administration.

Inflammatory Cytokines

In order to ascertain whether the observed hepatic inflammation is correlated to a systemic increase of inflammatory markers, we measured the plasma levels of two cytokines (IL-6 and TNF-α) involved in inflammatory processes by ELISA kits (RayBiotech), following the manufacturer's instructions.

Figure 8A:
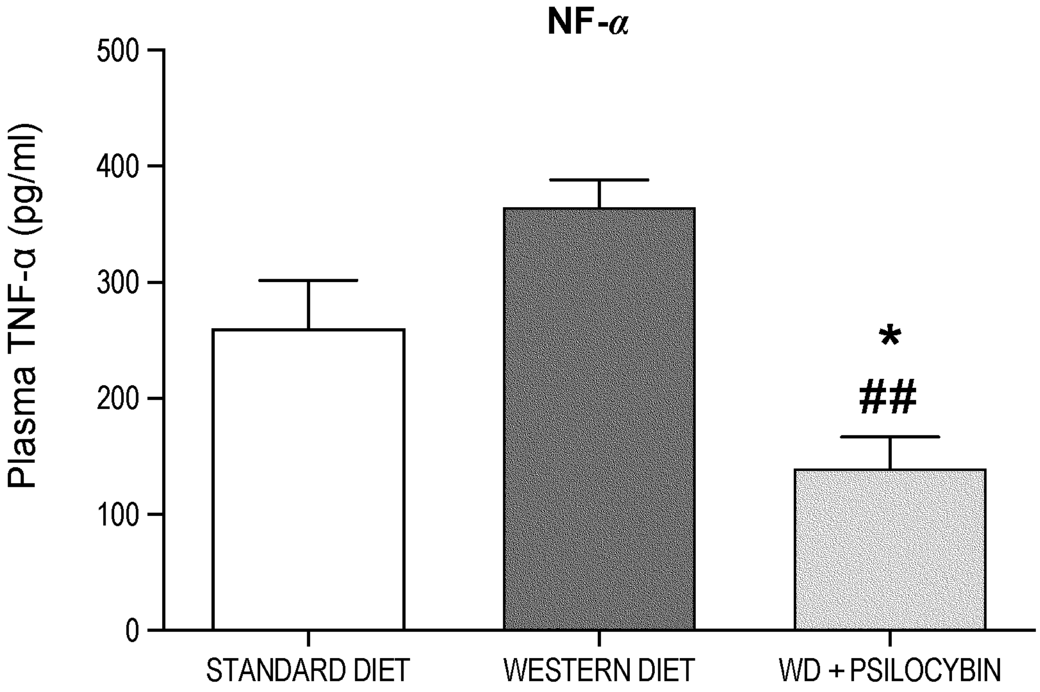
FIGS. 8A and 8B are graphs showing the plasma levels of two cytokines, TNF-α (FIG. 8A) and IL-6 (FIG. 8B), involved in inflammatory processes. *$p<0.05$ vs rats fed with Standard Diet, ##$p<0.01$ vs rats fed with Western Diet; one-way ANOVA followed by Tukey's post hoc test.
Figure 8B:
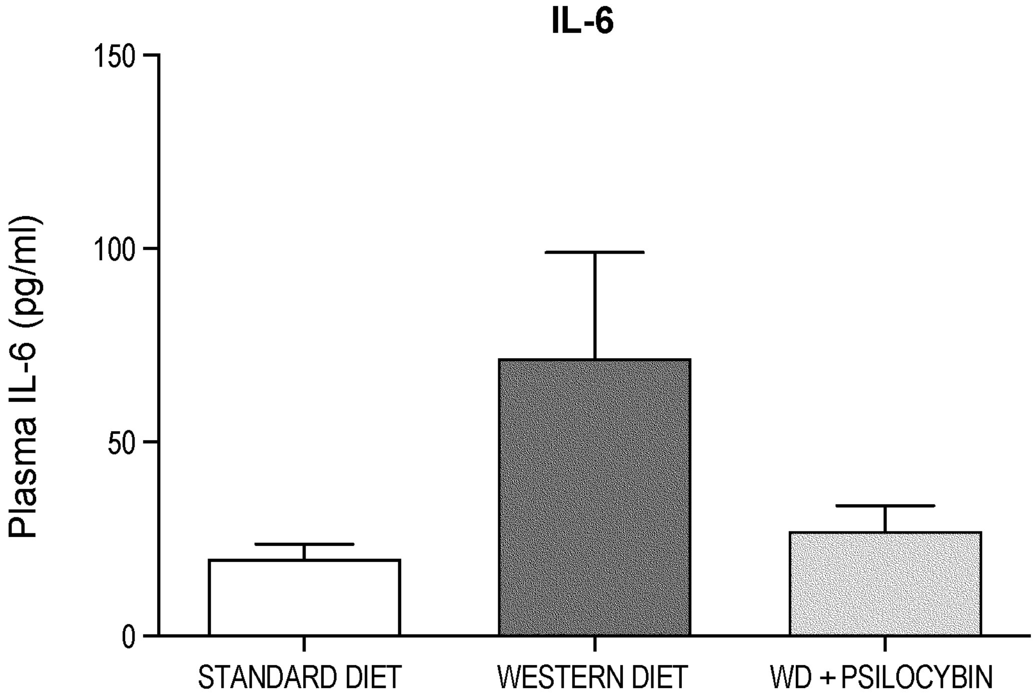

As shown in FIGS. 8A and 8B, the administration of psilocybin dramatically decreased TNF-α plasma concentration with respect to rats fed both with standard ($p<0.05$) and Western diet ($p<0.01$). Due to the high interindividual variability, no significant differences could be detected in IL-6 plasma levels in the different groups, but a tendency similar to the results observed for TNF-α levels was observed.

2. Effects on Neurogenesis

Hypothesis: Low dose chronic treatment with psilocybin counteracts the negative effects of western diet (WD) on neurogenesis Background: Neurogenesis persists in two niches of the adult brain: the dentate gyrus of the hippocampus and along the lateral walls of the lateral ventricles, in the subventricular zone (SVZ) (Lepousez G, Nissant A, Lledo P M Adult neurogenesis and the future of the rejuvenating brain circuits. Neuron 2015; 86:387-401; Lledo P M, Alonso M, Grubb M S Adult neurogenesis and functional plasticity in neuronal circuits. Nature reviews Neuroscience 2006; 7:179-193).

Neurogenesis represents a mechanism of neuronal plasticity and can be affected by several factors (Redolfi N, Galla L, Maset A, Murru L, Savoia E, Zamparo I, Gritti A, Billuart P, Passafaro M, Lodovichi C. Oligophrenin-1 regulates number, morphology and synaptic properties of adult-born inhibitory interneurons in the olfactory bulb. Human Molecular Genetics 2016; 25:5198-5211. Rochefort C, Gheusi G, Vincent J D, Lledo P M. Enriched odor exposure increases the number of newborn neurons in the adult olfactory bulb and improves odor memory. The Journal of neuroscience: the official journal of the Society for Neuroscience 2002; 22:2679-2689. Lepousez G, Nissant A, Lledo P M. Adult neurogenesis and the future of the rejuvenating brain circuits. Neuron 2015; 86:387-401. Lledo P M, Saghatelyan A. Integrating new neurons into the adult olfactory bulb: joining the network, life-death decisions, and the effects of sensory experience. Trends in Neurosciences 2005; 28:248-254.

Recent studies report that obesity accelerates the aging process and suppress neurogenesis, potentially leading to neuro-psychiatric effects. The effect seems specific for the SVZ, since the generation of new neurons in the hippocampus does not appear to be affected (Ogrodnik M, Zhu Y, Langhi L G P, Tchkonia T, Kruger P, Fielder E, Victorelli S, Ruswhandi R A, Giorgadze N, Pirtskhalava T, Podgorni O, Enikolopov G, Johnson K O, Xu M, Inman C, Palmer A K, Schafer M, Weigl M, Ikeno Y, Burns T C, Passos J F, von Zglinicki T, Kirkland J L, Jurk D Obesity-Induced Cellular Senescence Drives Anxiety and Impairs Neurogenesis. Cell Metabolism 2019, 29:1233).

Methods: To perform immunohistochemistry, rats were euthanized and then perfused with 0.9% saline followed by 4% paraformaldehyde (PFA) in 1× phosphate saline buffer (PBS) (rats n tot=8, n=2 for each condition). Rats brains were promptly dissected and then post-fixed in 4% PFA for 48 hours. Brains were embedded in 2.5% agarose (Sigma-Aldrich) and then sectioned in sagittal sections (40 μm thick) at the vibratome (Vibratome VT1000S, Leica). Sagittal brain sections including the subventricular zone, were treated with a blocking solution of 10% normal goat serum (Jackson ImmunoResearch) in 1×PBS for 1 hour and then stained with rabbit anti-Ki67 monoclonal antibody (Abcam, AB 16667) (1:200) overnight. The primary antibody was revealed with Alexa Fluor 488-conjugated goat anti-rabbit (1:500, Jackson ImmunoResearch), applied for 2 hours at room temperature. Brain sections were mounted with Aqua-Poly/Mount (Polysciences). Images of the sagittal sections containing the subventricular zone were acquired at the confocal microscope (Zeiss LSM 700) equipped with an EC Plan-Neofluar 20×/0.50 M27 objective (Zeiss). Ki67 positive cells were counted along the lateral wall of the lateral ventricles in rat brain sagittal sections, using ImageJ software (RRID: nif-000030467).

Results

Figure 8C:
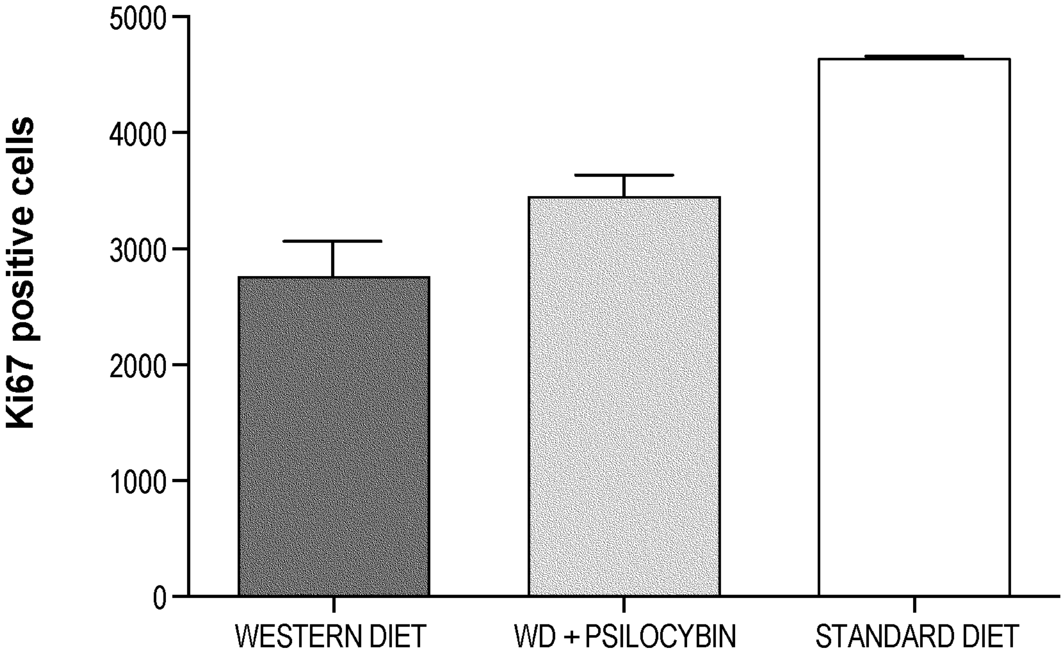
FIG. 8C is a graph showing neurogenesis in SVZ evaluated by the number of Ki67 positive cells.
Figure 9A:
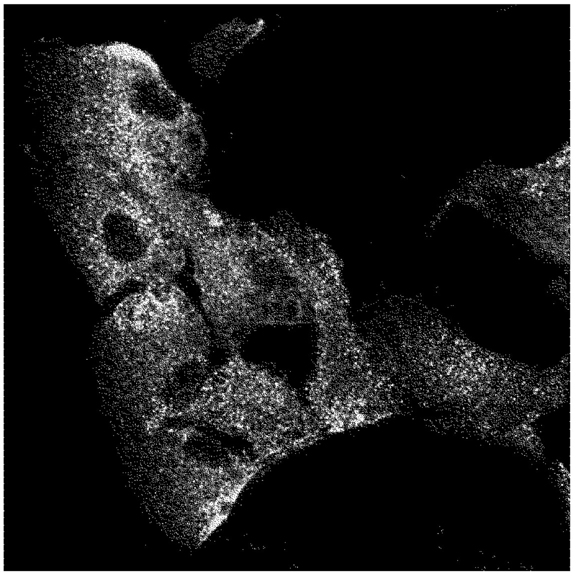
FIGS. 9A-9E are photographs showing expression of NMDAR subunits and 5-HT2 receptor subtypes in ARPE-19 cells.
Figure 9B:
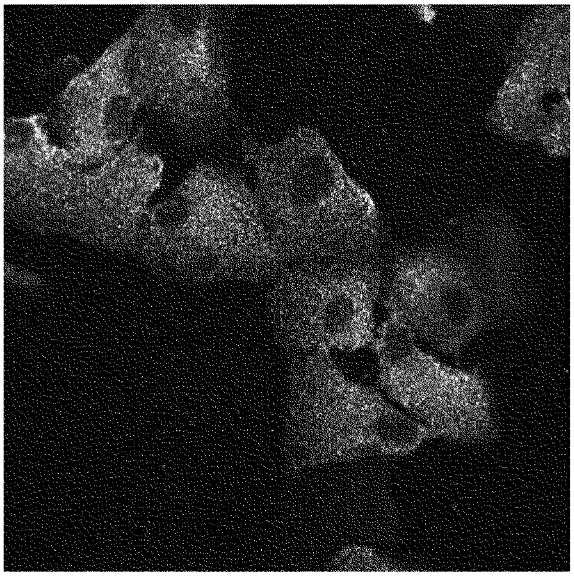
Figure 9C:
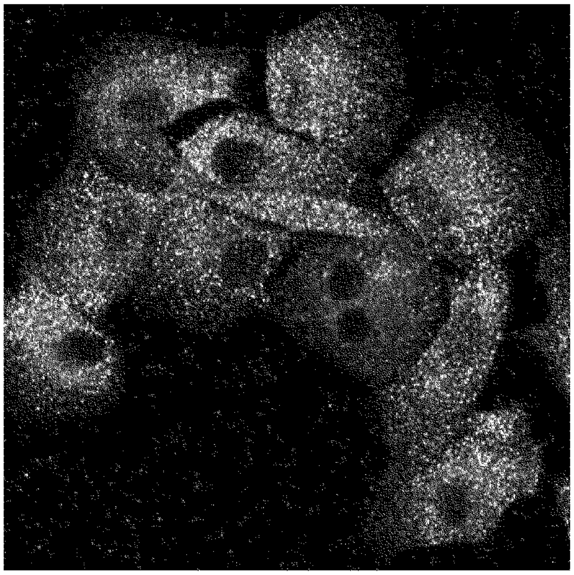
Figure 9E:
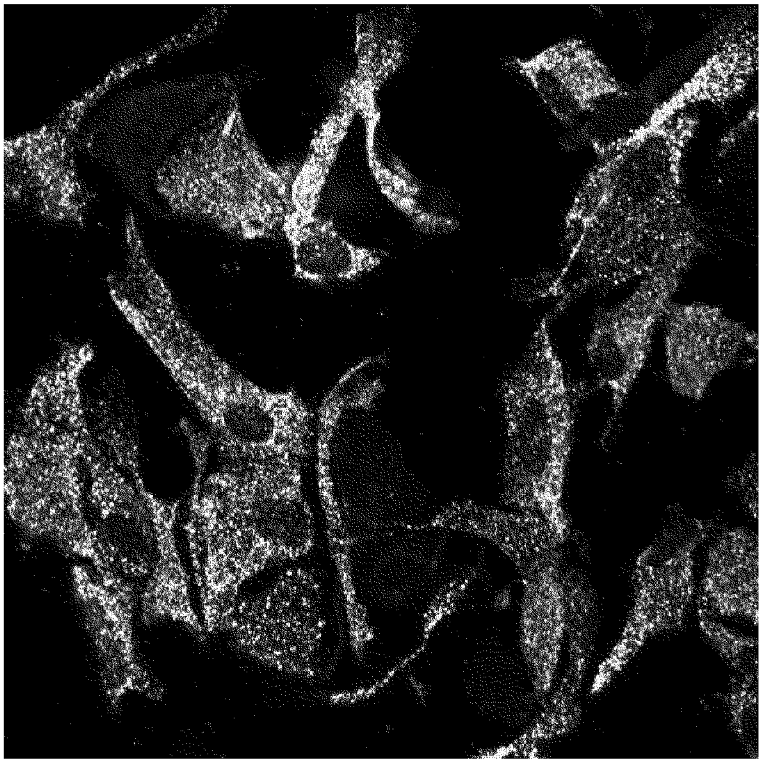
Figure 9D:
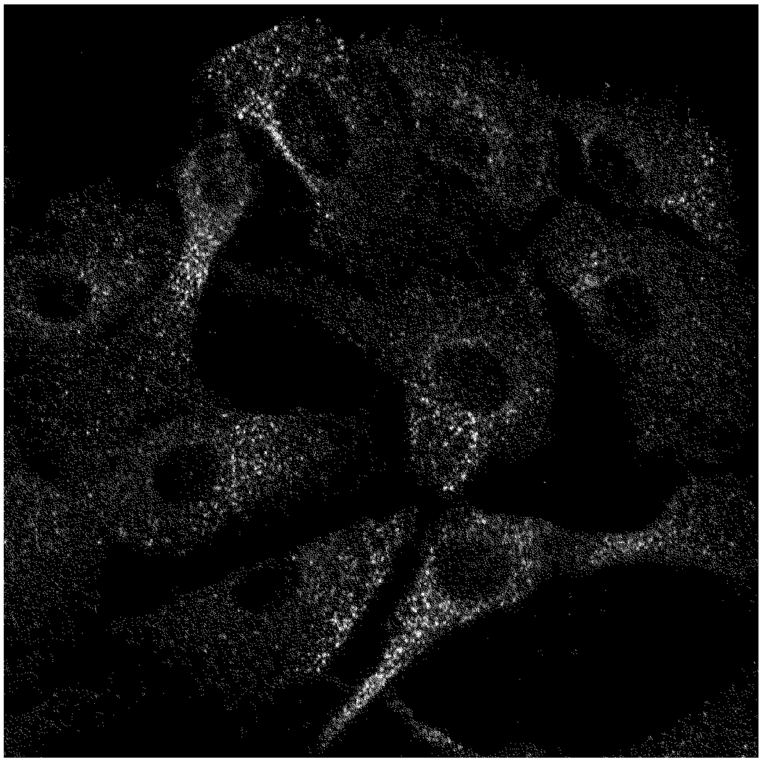

Referring to FIG. 8, the present inventors found that neurogenesis was significantly reduced in WD fed rats fed compared to SD fed rats (WD fed rats, new cells n=2722±225; SD fed rats, new cells n=4601±17; WD rats versus SD rats, unpaired t-test, $p=0.01$). Psilocybin 0.05 mg/Kg via gastric gavage for 15 days was able to partially preserve the number of newly generated cells in WD fed rats (Psilocybin treated rats, new cells n=3404±199) compared to WD fed rats treated with vehicle.

Conclusions

The results showed that that low dose chronic treatment with low dose psilocybin administered to WD fed rats had a positive effect on various metabolic parameters, including glycemic control, lipid accumulation in the liver, body weight and inflammatory markers. The results also confirm that WD reduces significantly the number of newly generated cells in the SVZ. Furthermore, chronic treatment with low doses psilocybin is able to partially rescue the number of newly generated neurons in the SVZ of WD fed rats and did not cause signs of anxiety or psychedelic behavioral effects in rats. The following further conclusions were also reached:

a) The chronic administration of neuroplastogen doses of 5-HT2A agonists is potentially safe and effective for the treatment of diseases and conditions;
b) The chronic administration of neuroplastogen doses of 5-HT2A agonists is potentially safe and effective for the treatment of diseases and conditions associated with impaired neurogenesis;
c) The chronic administration of neuroplastogen doses of 5-HT2A agonist is potentially safe and effective for the treatment of diseases and conditions associated with learning disabilities, including scholar/academic underachievement, underachievement in motor skills, underachievement in social skills and dysfunctional emotional patterns (based on b);
d) The chronic administration of neuroplastogen doses of 5-HT2A agonist is potentially safe and effective for the treatment of psychiatric diseases, including psychiatric disorders as defined by DSM5 and ICD11 (based on b);
e) The chronic administration of neuroplastogen doses of 5-HT2A agonist is potentially safe and effective for the treatment of neurological diseases and conditions, including neurodevelopmental and neurodegenerative diseases (based on b);
f) The chronic administration of neuroplastogen doses of 5-HT2A agonist is potentially safe and effective for the treatment of diseases and conditions associated with impaired glucose tolerance, including diabetes mellitus;
g) The chronic administration of neuroplastogen doses of 5-HT2A agonist is potentially safe and effective for the treatment of diseases and conditions associated with obesity, including its complications;
h) The chronic administration of neuroplastogen doses of 5-HT2A agonist is potentially safe and effective for the treatment of diseases and conditions associated with NAFLD and NASH;
i) The chronic administration of neuroplastogen doses of 5-HT2A agonist is potentially safe and effective for the treatment of diseases and conditions associated with liver inflammatory states, including NASH; and
j) The chronic administration of neuroplastogen doses of 5-HT2A agonist is potentially safe and effective for the treatment of diseases and conditions associated with systemic inflammatory states.

The human equivalent dose (HED) to the rat dose used in the Example 2 study (0.05 mg/Kg) is 0.0094 mg/Kg (Nair A B, Jacob S. A simple practice guide for dose conversion between animals and human. J Basic Clin Pharm. 2016; 7(2):27-31), approximately 0.66 mg of psilocybin for a 70-Kg human, well below even the lower doses shown to be psychedelic: 0.045 mg/Kg, approximately 3.2 mg for a 70 kg human (Hasler F, Grimberg U, Benz M A, Huber T, Vollenweider F X. Acute psychological and physiological effects of psilocybin in healthy humans: a double-blind, placebo-controlled dose-effect study. Psychopharmacology (Berl). 2004; 172(2):145-156. doi:10.1007/s00213-003-1640-6).

In an experiment by Davis et al., 1977, the startle reflex was measured in 7 groups of 10 rats each after intraperitoneal injection of saline or 0.25, 0.50, 0.75, 1.0, 2.0, 4.0 or 8.0 mg/kg psilocybin. At 0.75-2.0 mg/kg but not at lower doses, psilocybin increased startle amplitude whereas high doses (4.0-8.0 mg/kg) depressed startle. (Davis M, Walters J K. Psilocybin: biphasic dose-response effects on the acoustic startle reflex in the rat. Pharmacol Biochem Behav. 1977; 6(4):427-431). In a study by Rambousek et al., 2014, psilocin subcutaneously significantly impaired the acquisition of the Carousel maze at both doses (1 and 4 mg/kg) (Rambousek L, Palenicek T, Vales K, Stuchlik A. The effect of psilocin on memory acquisition, retrieval, and consolidation in the rat. Front Behav Neurosci. 2014; 8:180). In both of these studies (Davis et al., 1977 and Rambousek et al., 2014), the doses administered to rats were much higher than the low chronic doses of psilocybin tested in the present inventors' study, 0.05 mg/Kg daily for 15 days. The present inventors' much lower doses, 0.05 mg/Kg did significantly not alter rat behavior, except for increasing grooming time as detailed in the behavioral section of Example 2. While increased grooming time in rodents has been associated with anxiety, in the case of rats, and in the absence of other anxiety related behavior, the increase in grooming time can also be associated with a relief from an anxiety provoking stimulus (Nazareth Veloso A W, Filgueiras G B, Lorenzo P, and Estanislau C. Psychology & Neuroscience 2016, Vol. 9, No. 1, 91-104). In the case of the present inventors' study this relief could have been provided by low dose pslocybin treatment.

Sengupta P. The Laboratory Rat: Relating Its Age With Human's. Int J Prev Med. 2013; 4(6):624-630. According to Sagupta P, 2013, the rats are well into the maturity stages of life and thus neurogenesis preservation in the WD+psilocybin group compared to the WD+vehicle group potentially suggests activity against senescence of the nervous system accelerated by western diet.

The present inventors' experiment, detailed in Example 2, is especially groundbreaking as it is the first in vivo experiment showing that the chronic neuroplastogen dose administration of 5-HT2A agonists is potentially therapeutic for the treatment of diseases and conditions.

Example 3—In Vitro Studies

In order to assess the mechanisms of potentially therapeutic effects and whether repeated chronic low-dose treatments with 5-HT2A agonists potentially modulate neural plasticity and or modulate neuroinflammation, and in order to assess whether these effects are potentially cytoprotective, including against excitotoxicity and against inflammatory mediators, and, ultimately, whether these effects may result in potentially clinically meaningful therapeutic effects, the present inventors performed a series of preclinical in vitro experiments. These tests were designed specifically to assess the potential therapeutic effects of repeated neuroplastogen dose (low concentration) of drugs classified as 5-HT2A agonists.

1. Effect of Psilocin and Psilocin Carbamate on NMDAR Subunits and 5-HT2 Receptor Subtypes in ARPE19 Cells Hypothesis:

The membrane of retinal pigment cells (ARPE-19 cell line) expresses NMDARs and 5-HT2A and 5-HT2C receptors. Psilocin reduces L-glutamate-induced cytotoxicity and modulates transcription and synthesis of select NMDAR protein subunits.

Background:

The mechanisms underlying the potential effectiveness of 5-HT2A agonists administered in large "psychedelic/psychotomimetic" dosages (single sessions) for depression has been recently linked to BDNF and mToR pathways and has been potentially related to neural plasticity: Ly et al. demonstrate that psychedelic compounds such as LSD, DMT, and DOI increase dendritic arbor complexity, promote dendritic spine growth, and stimulate synapse formation. These cellular effects are similar to those produced by the fast-acting antidepressant ketamine and highlight the potential of psychedelics for treating depression and related disorders (Ly C, Greb A C, Cameron L P, et al. Psychedelics Promote Structural and Functional Neural Plasticity. Cell Rep. 2018; 23(11):3170-3182). However, Ly et al., did not test psilocin/psilocybin, and did not test low doses or low doses in relation to higher doses.

Methods and Results:

Expression of NMDAR and 5-HT Subtypes in ARPE-19 Cells

First, the present inventors assessed the expression of three NMDAR subunits (NMDAR1, NMDAR2A, NMDAR2B) and two 5-HT2 subtypes (5-HT2A, 5-HT2C) by immunofluorescence coupled to confocal microscopy. 7,500 cells/well were plated in a 24-well plate on sterile glass coverslips. The next day, the immunofluorescence analysis was performed. The following primary antibodies were used: anti-NMDAR1A (Abcam, ab68144), NMDAR2A (Bioss, bs-3507R-TR), NMDAR2B (Bioss, bs-0222R-TR), 5-HT2A (Bioss, bs-12049R), 5-HT2C (Bioss, 2959R), and the secondary antibody goat anti-rabbit IgG (GeneTex, GTX213110-04). The images of the immunostained cells were acquired by means of a confocal microscope Zeiss LSM 800, using a 63× magnification and can be seen in FIGS. 9A-9E. ImageJ software was used to quantify the intensity of the fluorescent signal.

Effect of Psilocin on Glutamate-Induced Cytotoxicity

Figure 10:
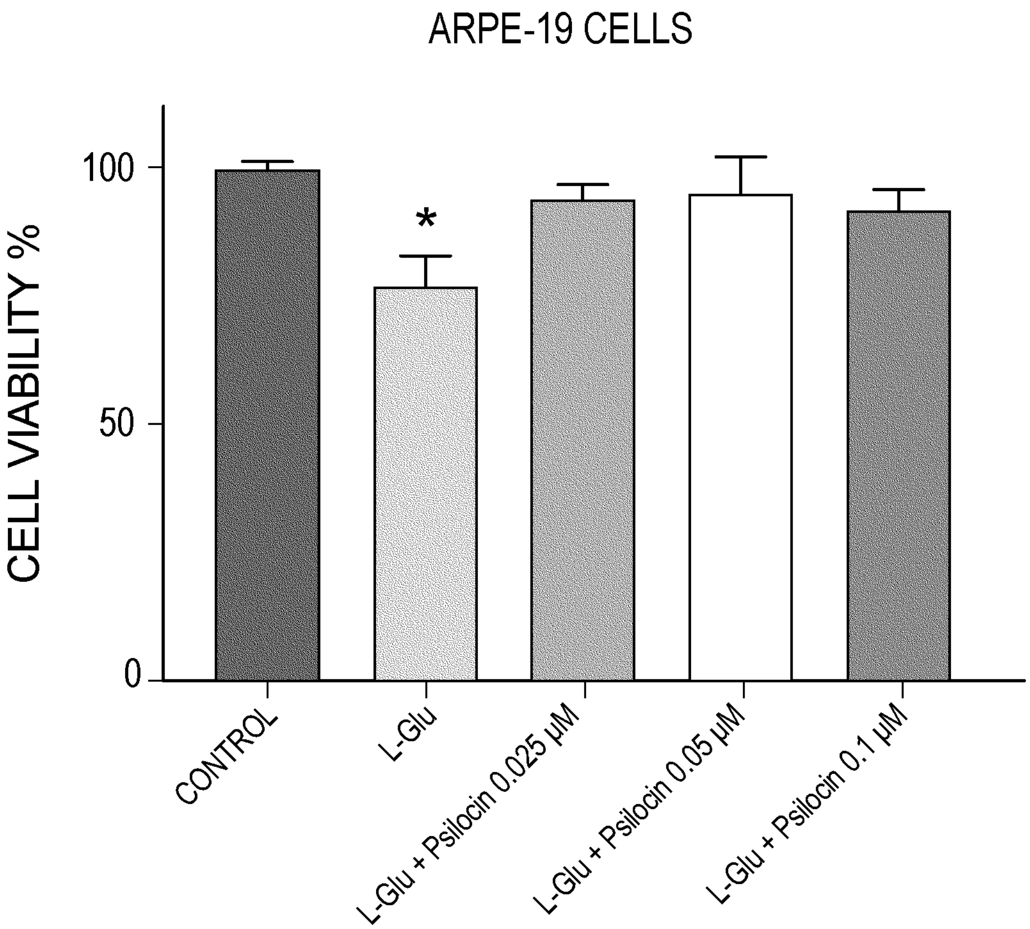
FIG. 10 is a graph showing cell viability of ARPE-19 cells after treatment with the NMDAR agonist L-glutamate alone (1 mM L-Glu) or in combination with the 5-HT2A agonist psilocin at different concentrations. * $P<0.05$ vs control cells treated with vehicle (one-way ANOVA followed by Dunnett's post hoc test.

In order to ascertain the effect of psilocin on L-glutamate-induced cytotoxicity in ARPE-19 cells, the present inventors performed a cell viability assay. For this experiment, the ARPE-19 cells were seeded in a 96 wells plate (7000 cells/well). They were left overnight in a 37° incubator with 5% CO2. The following day, the cells were pretreated with the solutions of psilocin. After six hours all the wells (with the exception of control cells) were replaced with the L-glutamate solution dissolved in a Tris-buffered control salt solution (CSS). After 5 min, the exposure solution was washed out thoroughly and replaced with standard culture medium, according to an already described protocol (Choi D W, Viseskul V., 1988. Opioids and non-opioid enantiomers selectively attenuate N-methyl-D-aspartate neurotoxicity on cortical neurons. Eur J Pharmacol 155, 27-35). After 24 hours of resting time, cell viability was assessed by means of the ATPlite kit following the manufacturer's instructions. The results can be seen in FIG. 10, and the present inventors observed that psilocin, tested at 3 different concentrations (ranging from 0.025 to 0.1 μM) counteracted the observed reduction of cell viability induced by L-glutamate treatment.

Effect of Psilocin on the Protein Expression of NMDAR Subunits and 5-HT2 Receptor Subtypes The present inventors performed additional immunocytochemical studies to ascertain whether psilocin induces synthesis of select proteins that form NMDARs and select 5-HT receptor subtypes (5-HT2A and 5-HT2C).

7,500 cells/well were plated in a 24-well plate on sterile glass coverslips. The next day, cells were treated with either 10 μM psilocin for 24 hours followed by 5 days of rescue in standard culture medium or 0.5 μM of psilocin for 6 consecutive days. After 6 days an immunofluorescence analysis coupled to confocal microscopy was performed with the primary and secondary antibodies described above.

Figure 11A:
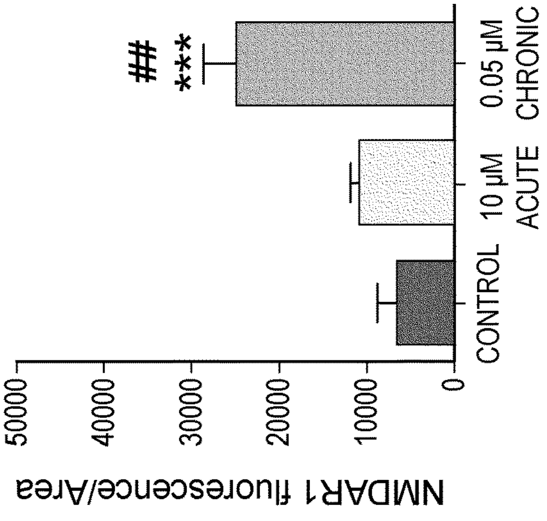
FIGS. 11A-11C are graphs showing protein expression of NMDAR subunits (FIG. 11A showing NMDAR1.
Figure 11B:
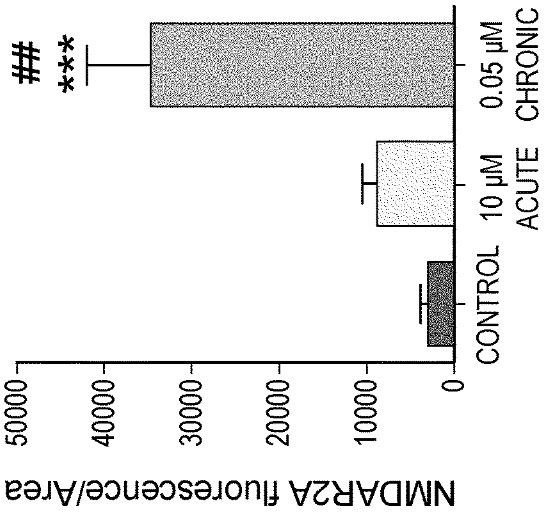
Figure 11C:
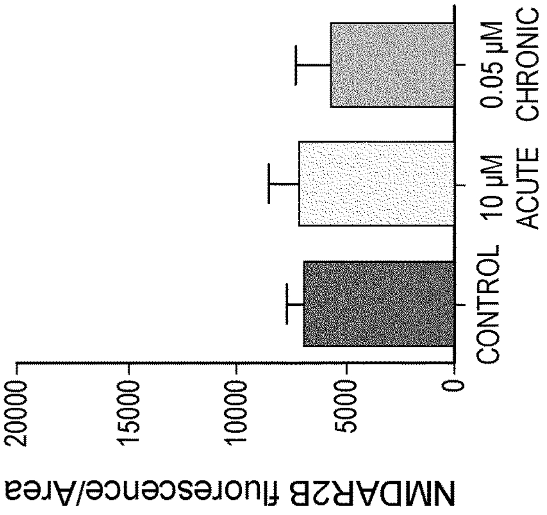

Referring to FIGS. 11A-11C, ARPE-19 cells exposed to psilocin 0.05 μM for 6-days showed a dramatic increase in NMDAR1 and NMDAR2A subunits. NMDAR2B subunits did not change. Conversely, ARPE-19 cells exposed to psilocin 10 μM for 24 hours showed only a slight, not significant increase of NMDAR1 and NMDAR2A. NMDAR2B subunits did not change.

Figure 11F:
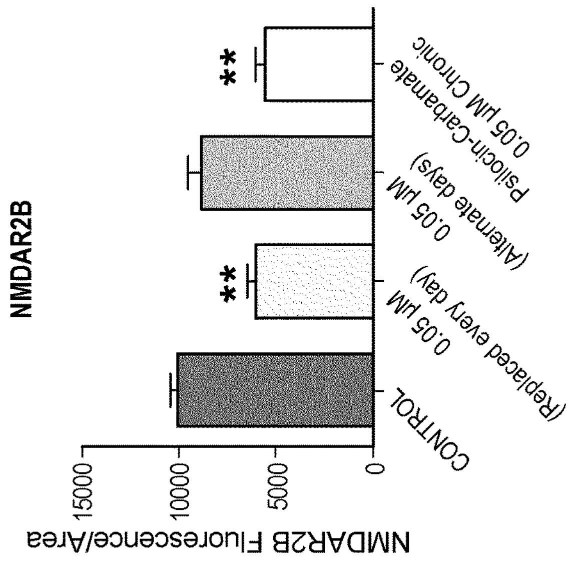
FIGS. 11D-11F are graphs showing protein expression of NMDAR subunits (FIG. 11D showing NMDAR1.
Figure 11E:
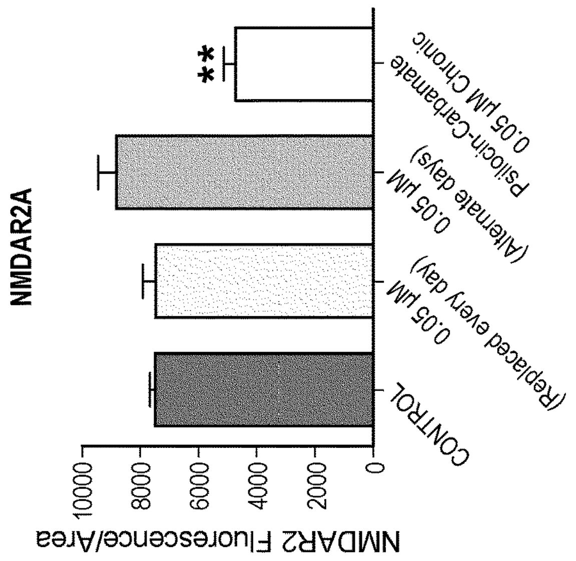
Figure 11D:
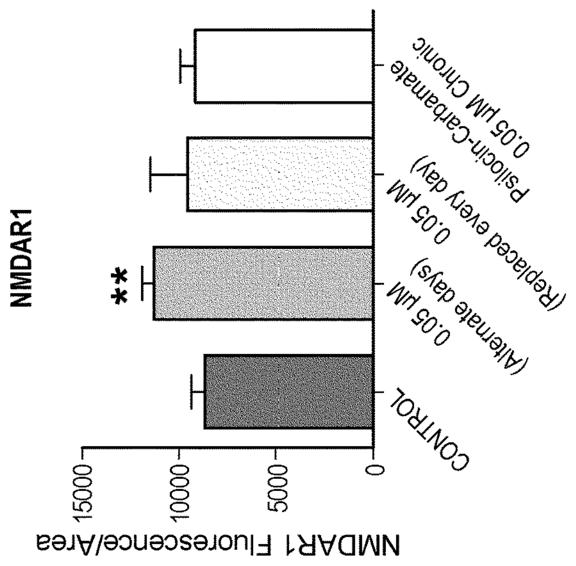

Referring now to FIGS. 11D-11F, in general, a less evident effect of the treatment on the expression of NMDAR subunits could be observed when the cell medium containing psilocybin was replaced every day (96 hours in total) or cells were treated alternating medium with/without psilocin every 24 hours (96 hours in total). In particular, an increase of NMDAR1 expression and a decrease of NMDAR2B expression could be observed with a 0.05 μM incubation was performed alternating medium with/without psilocin every 24 hours. Furthermore, the effect of a chronic treatment with psilocin carbamate for 96 hours on NMDAR subunits was evaluated. As shown in FIGS. 11D-11F, a reduction of NMDAR2A and NMDAR2B expression was observed.

Figure 11I:
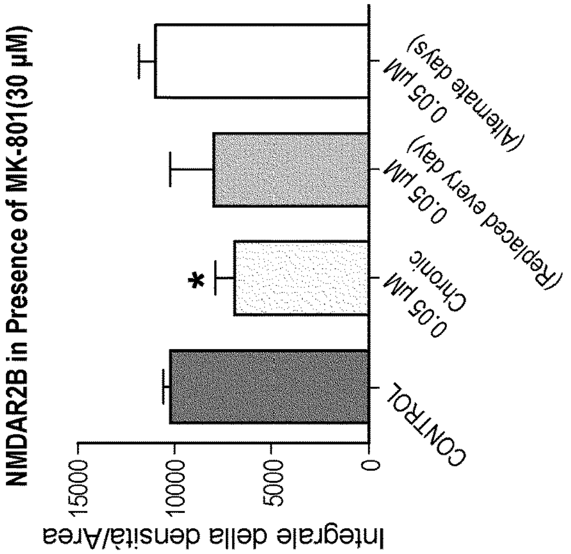
FIGS. 11G-11I are graphs showing protein expression of NMDAR subunits after co-incubation with psilocin and MK-801 (FIG. 11G showing NMDAR1.
Figure 11H:
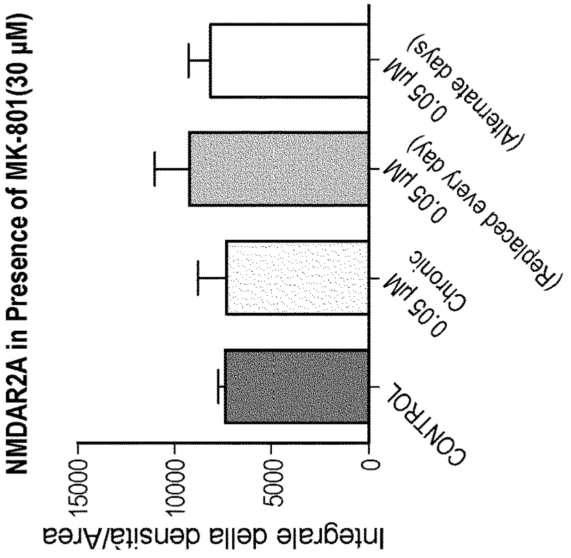
Figure 11G:
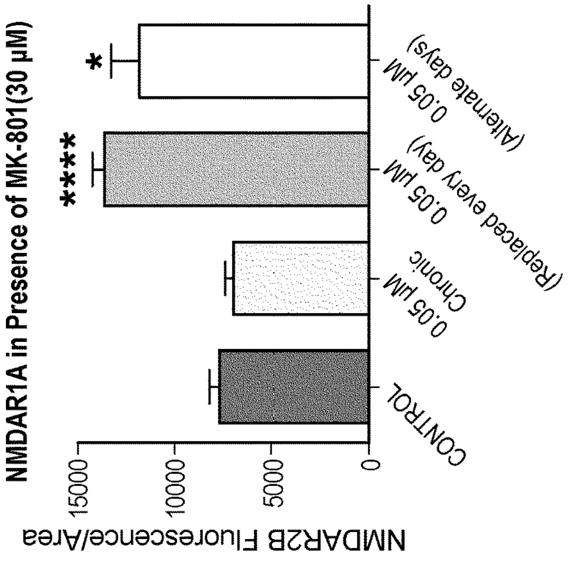

Referring now to FIGS. 11G-11I, the effect of co-incubation of 0.05 μM psilocin with an excess (30 μM) of the prototypical NMDAR antagonist MK-801 was evaluated. In particular, as far as NMDAR1 and NMDAR2A expression is concerned, the increase reported after chronic psilocin treatment (FIGS. 11A-11C) was counteracted by MK-801-mediated inhibition (FIGS. 11G-11I). Conversely, a drop of NMDAR2B expression was observed in the same conditions. NMDAR1 expression increased significantly in case of alternate incubation or when psilocin-containing culture medium was replaced every day.

Figure 12A:
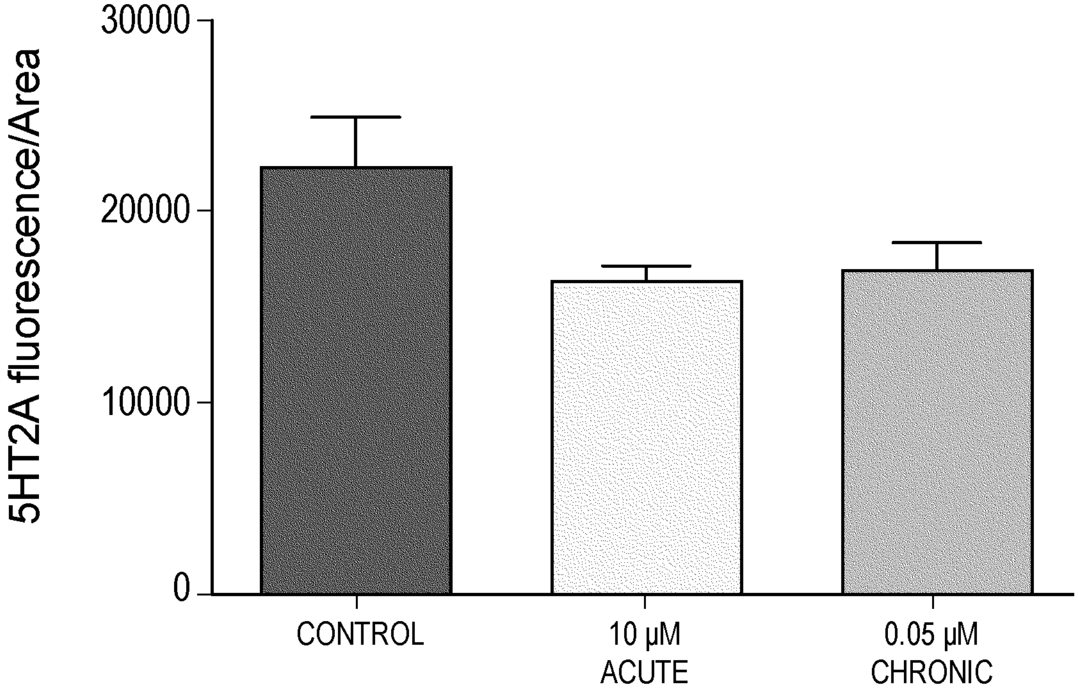
FIGS. 12A and 12B are graphs showing protein expression of % HT2 receptors (FIG. 12A showing 5-HT2A.
Figure 12B:
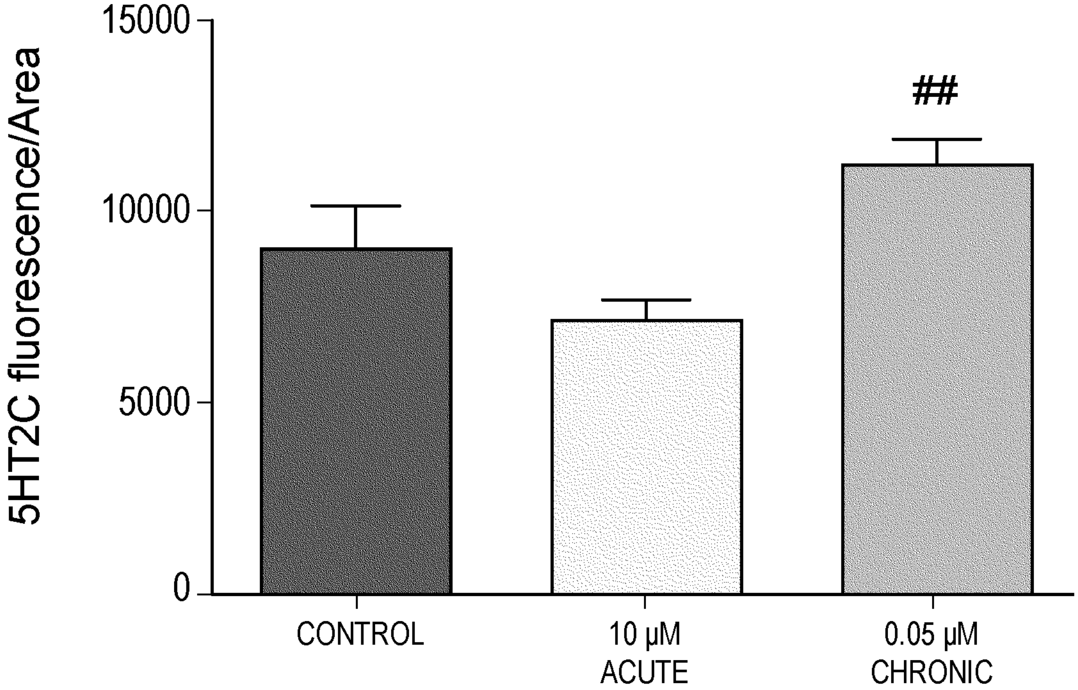

Referring now to FIGS. 12A and 12B, conversely, psilocin has virtually no effect on the expression of 5-HT2A receptor in ARPE-19 cells, although a decreasing tendency could be noticed after both acute and chronic exposure. The expression of 5-HT2C expression was increased after chronic treatment with psilocin.

Conclusions:

The prevention of excitotoxicity and the induction of NMDAR subunits by exposure to psilocin in ARPE-19 cells signals modulation (down regulation) of Ca2+ influx. The induction of selected NMDAR subunits signal effects on NMDAR membrane expression (NMR1 subunits are necessary for membrane expression of NMDARs) and signal other selective actions of 5-HT agonists on NMDAR subtypes (A-D). These actions of psilocin signal potential therapeutic uses for low dose chronic therapy (continuous or intermittent) with 5-HT2A receptor agonists via modulation of NMDARs for diseases and conditions that potentially benefit from prevention of excitotoxicity and/or benefit from NMDAR modulation and/or from modulation of neural plasticity, including diseases and conditions listed in the present application, including ophthalmic, psychiatric, metabolic and neurologic disease and conditions.

The following conclusions were also reached regarding ARPE 19 cells:

a) ARPE 19 cells express NMDARs (qPCR and immunofluorescence analysis);
b) ARPE 19 cells express 5-HT2A receptors (qPCR and immunofluorescence analysis);
c) 5-HT2A agonists are not cytotoxic for ARPE-19 cells;
d) High concentration glutamate is toxic to ARPE-19 cells;
e) 5-HT2A agonists exert cellular protection against excitotoxicity induced by high dose glutamate;
f) 5-HT2A agonists modulate NMDARs by modulating mRNA for NMDAR subunits and modulating synthesis of NMDAR subunits;
g) 5-HT2A agonist modulate NMDAR subunits at chronic neuroplastogen doses and at intermittent chronic neuroplastogen doses (low concentrations) more effectively compared to large doses (high concentrations) applied once only (high pulse concentrations);
h) The chronic administration of neuroplastogen doses of 5-HT2A agonist and the chronic administration of intermittent neuroplastogen doses of 5-HT2A agonists are potentially effective for the treatment of diseases and conditions associated with NMDAR dysfunction;
i) The chronic administration of neuroplastogen doses of 5-HT2A agonist is potentially effective for the treatment of diseases and conditions associated with learning disabilities, including scholar/academic underachievement, underachievement in motor skills, underachievement in social skills and dysfunctional emotional patterns (NMDAR modulation, based on e and f);
j) The chronic administration of neuroplastogen doses of 5-HT2A agonist is potentially safe and effective for the treatment of psychiatric diseases, including psychiatric disorders as defined by DSM5 and ICD11 (NMDAR modulation, based on e and f);
k) The chronic administration of neuroplastogen doses of 5-HT2A agonist is potentially safe and effective for the treatment of neurological diseases and conditions, including neurodevelopmental and neurodegenerative diseases (NMDAR modulation, based on e and f); and
l) The chronic administration of neuroplastogen doses of 5-HT2A agonist is potentially effective for the treatment of ophthalmological diseases and conditions (effects on ARPE-19, retinal pigment epithelial cells, based on e and f).

Example 3 potentially suggests therapeutic uses for 5-HT receptor agonists via modulation of NMDARs and prevention of excitotoxicity. The finding that the synthesis of select NMDAR subunits is modulated by 5-HT2A agonists and their protective effects on excitotoxicity signals a potential allosteric block of open NMDAR channels by these drugs, with a reduction of excessive Ca2+ influx towards physiologic levels, prevention of excitotoxicity, and resumption of cellular function, e.g., resumption of synthesis of NR-1 subunits. The present inventors also disclose that even before induction of mRNA and synthesis occur, mobilization from ER of NMDAR1 subunits induced by modulation of Ca2+ influx via NMDARs may result in cellular membrane expression of new NMDARs as also signaled in the review by Baez et al., 2018 (Baez M V, Cercato M C, Jerusalinsky D A. NMDA Receptor Subunits Change after Synaptic Plasticity Induction and Learning and Memory Acquisition. Neural Plast. 2018). The present inventors have obtained additional signals of allosteric modulation of the NMDAR pore (see Example 5) and are in the process of confirming this postulated mechanism of action by performing a FLIPR calcium assay experiments. The increase in NMDARs at the post-synaptic cleft may also be associate with a decrease in perk synaptic/extra-synaptic NMDARs. While post-synaptic NMDARs located at synapses are associated with LTP and cellular survival, extra-synaptic NMDARs have been associated with excito-toxicity and apoptosis. The positive effects of 5-HT2A agonists on cellular survival (described in Example 3 and Example 4) and the positive effects of the combination of psilocin and dextromethadone on senescence induced by UV radiation (see Example 6) may be due to down regulation of Ca2+ influx. Additional experiments are being performed to test this mechanism for cellular protection and enhanced survival.

The new experiments presented with this application signal excitotoxicity protection from 5-HT2A agonists and confirm the NMDAR1 mRNA increases in retinal cells exposed to 5-HT2A agonists and also show that 5-HT2A agonists induce the synthesis of NR-2A subunits but not NR-2B subunits, signaling a potentially selective "repair mechanism" (selective for NMDAR subtypes) with synthesis of new NMDAR select subunits and expression of new NMDAR select subtypes and potential synapse strengthening mechanisms (post-synaptic modulation of NMDARs), in addition to the BDNF dependent effects described by Ly et al., 2018 that provide a mechanism for retrograde presynaptic strengthening and neurite growth effects. Both pre-synaptic neuroplasticity effects, as shown by Ly et al., 2018, and post-synaptic strengthening, as signaled by the present inventors' experiments on modulation of NMDAR subunits, are essential for LTP, memory formation, and learning.

Example 4—Further In Vitro Studies—Corneal Cells

In Vitro Study on the Cytotoxicity and Anti-Inflammatory Effects of Psilocin

Aims

The study aims to verify:

a) the effects of psilocin on cell viability
b) the expression of NMDAR and HT2A subunits in corneal epithelial cells and keratocytes
c) the anti-inflammatory effects of psilocin on corneal epithelial cells treated with the culture medium of activated human monocytes (line U937) which differentiate to macrophages
d) the anti-VEGF and anti-fibrotic effects of psilocin in keratocyte cultures exposed to the inflammatory conditioned medium of activated U937 cells

Materials and Methods

Cell cultures. Human corneal epithelial (HCE) cells were obtained from the American Type Culture Collection. U937 human monocytes cell line was purchased from Thermo Scientific.

Primary corneal keratocytes were obtained after digestion of human corneas from healthy donors purchased at the Veneto Eye Bank Foundation (Venezia Mestre, Italy). After the corneal epithelium was removed with a cell scraper and the endothelium was enzymatically detached using 0.05% trypsin/0.02% EDTA-solution for 15 minutes at 37° C., the stroma was then cut into 3- to 4-mm pieces and treated overnight at 37° C. with type I collagenase (100 U/ml) and hyaluronidase (2 mg/ml) solutions in Dulbecco's Modified Eagle's Medium (DMEM). Isolated keratocytes were then seeded in monolayer and cultured at 37° C. with 5% CO2 in DMEM containing 10% FBS, 1% penicillin-streptomycin (P/S) and 1% L-glutamine (otherwise known as complete medium). Expanded cells were trypsinized and sub-cultured at a ratio of 1:2. Corneal cells were grown under standard cell culture practices in complete DMEM medium at 37° C., in a 5% CO2 atmosphere. U937 human monocytes were grown in suspension in complete RPMI 1640 medium and passaged twice weekly by dilution using a seeding density of $10^6$ cells/ml.

Psilocin cytotoxicity and viability evaluations. Different concentrations of psilocin were added to corneal cells and cytotoxicity was determined 3 days later. Cell viability was assessed by the MTT test (3-4,5-dimethylthiazol-2-yl-2,5-diphenyltetrazolium bromide, Sigma, MO, USA) at 1, 3 and 6 days after psilocin treatment, using a modified Denizot method. With this procedure, only viable cells with functioning mitochondria can oxidize MTT to a violet-red reaction product.

Immunofluorescence coupled to confocal microscopy. 7,500 cells/well were plated in a 24-well plate on sterile glass coverslips. The next day, the immunofluorescence analysis was performed. The following primary antibodies were used: anti-NMDAR1A (Abcam, ab68144), 5-HT2A (Bioss, bs-12049R), 5-HT2C (Bioss, 2959R), and the secondary antibody goat anti-rabbit IgG (GeneTex, GTX213110-04). The images of the immunostained cells were acquired by means of a confocal microscope Zeiss LSM 800, using a 63× magnification. The ImageJ software was used to quantify the intensity of the fluorescent signal.

Anti-inflammatory and anti-fibrotic effects evaluations. Cytokines expression was analyzed in human keratocytes and HCE cells exposed to the inflammatory conditioned medium (CM) of activated U937 cells.

U937 human monocytes were differentiated to macrophages by treatment with 50 ng/mL phorbol myristate acetate (PMA) for 48 h followed by the exposure to 1 μL/mL lipopolysaccharide (LPS) for 1 hour. Cells were then washed and cultivated with complete RPMI for 24 hours to produce the inflammatory CM. The CM was collected, filtered and stored at −80° C. The differentiation of monocytes to macrophages was examined under an inverted phase-contrast microscope and the mRNA expression of the macrophage differentiation marker CD68 was analysed by quantitative real time PCR (qPCR). Cells were then washed and cultivated with complete DMEM for 24 hours to produce the CM. The CM was collected, filtered and stored at −80° C.

Corneal cell cultures were exposed for 24 h to the CM of activated U937 cells and then treated in the presence or absence of different concentrations of psilocin.

Cytokines expression was analyzed in human keratocytes and HCE cells exposed to CM for 24 h and then treated in the presence or absence of psilocin at different concentrations, using untreated cultures as controls. At 4 and 10 or at 4, 10 and 24 h cells were detached and mRNA and mRNA extracted to analyze the expression of pro-inflammatory cytokines (IL-1β, TNF-α, IL-8, IL-12, IFNγ). The expression of type collagen I and VEGF was analysed on mRNA extracted from keratocyte cell cultures. The experiments were performed three times.

Statistical analysis. Graphpad Prism 8 was used for statistical analysis. The comparison between groups was made using Student's unpaired t-test. Data are presented as mean and standard error. For the statistical significance, differences were indicated at $P<0.05$ (*), $P<0.01$ () and $P<0.001$ (*).

Results

Figure 13A:
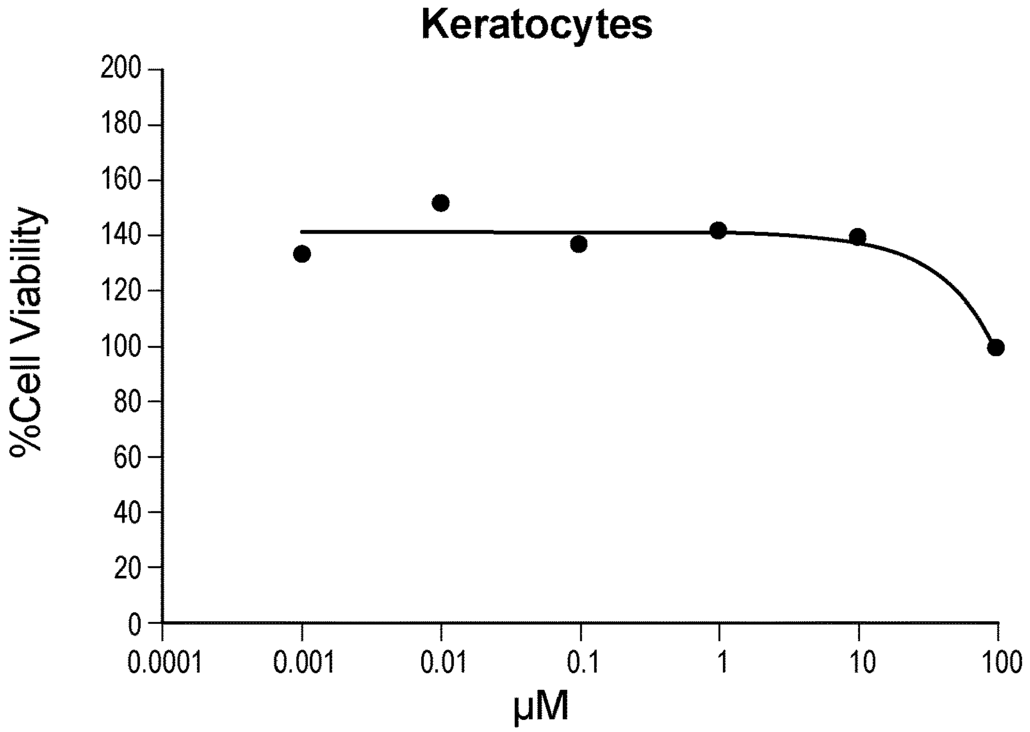
FIG. 13A is a graph showing the cytotoxicity of psilocin in keratocytes.
Figure 13B:
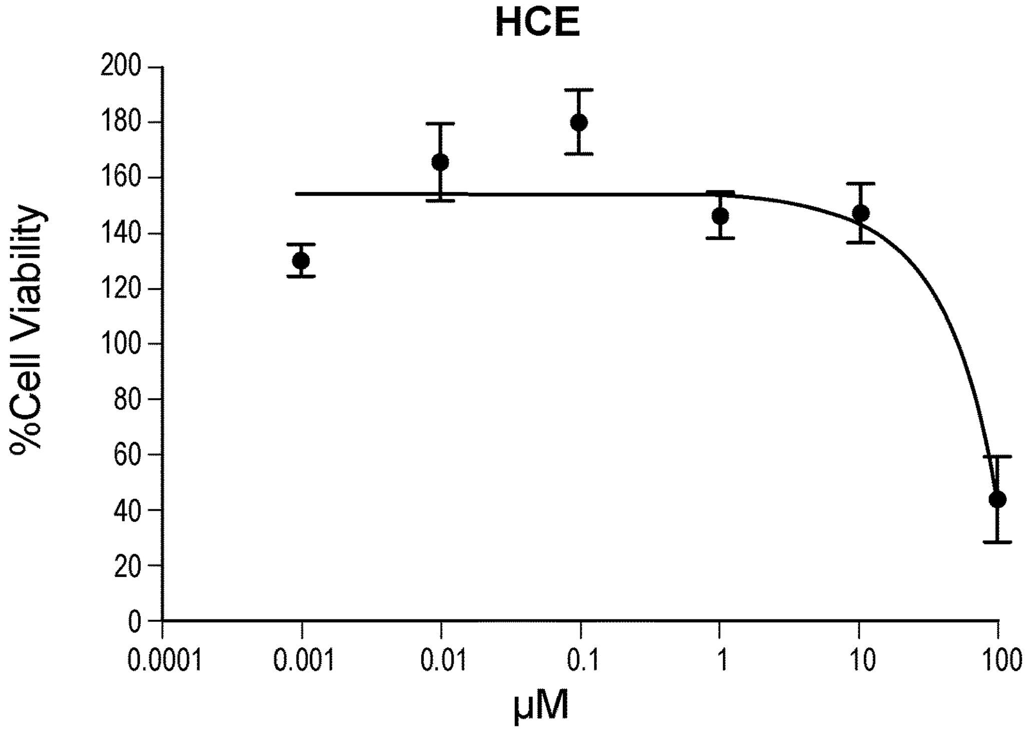
FIG. 13B is a graph showing the cytotoxicity of psilocin in human corneal epithelial (HCE) cells.
Figure 14A:
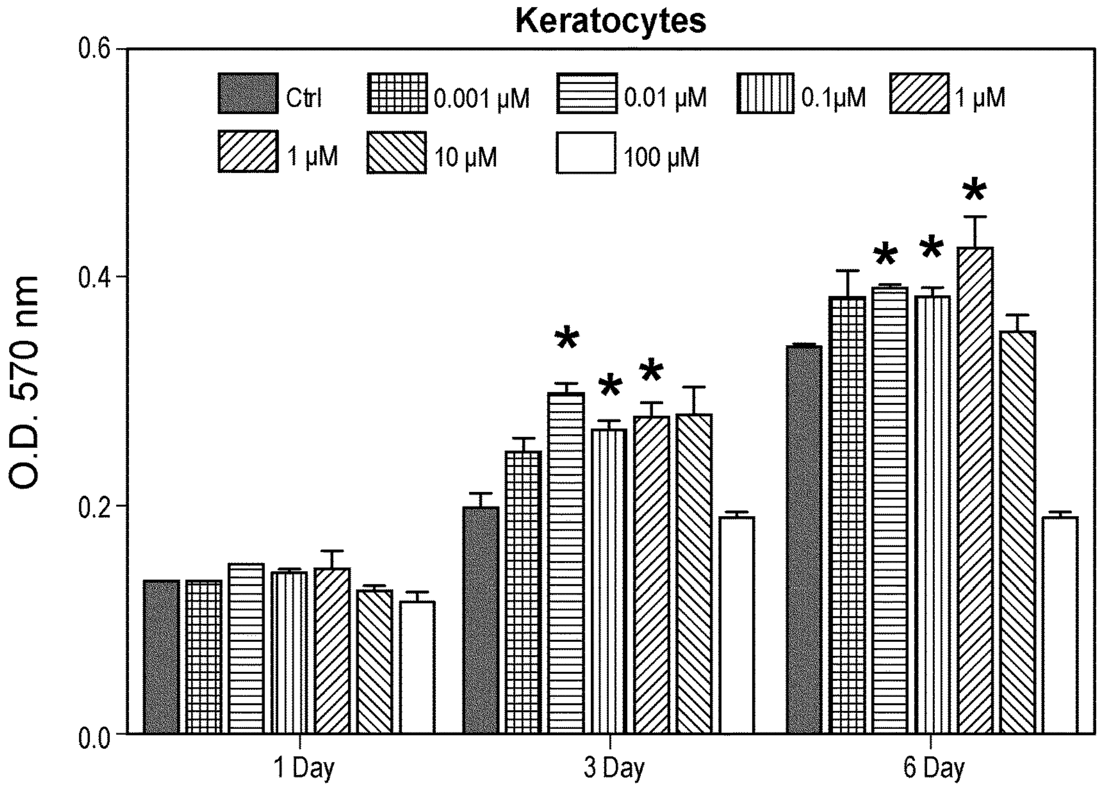
FIG. 14A is a graph showing corneal cell viability (keratocytes) in the presence of psilocin at different concentrations.
Figure 14B:
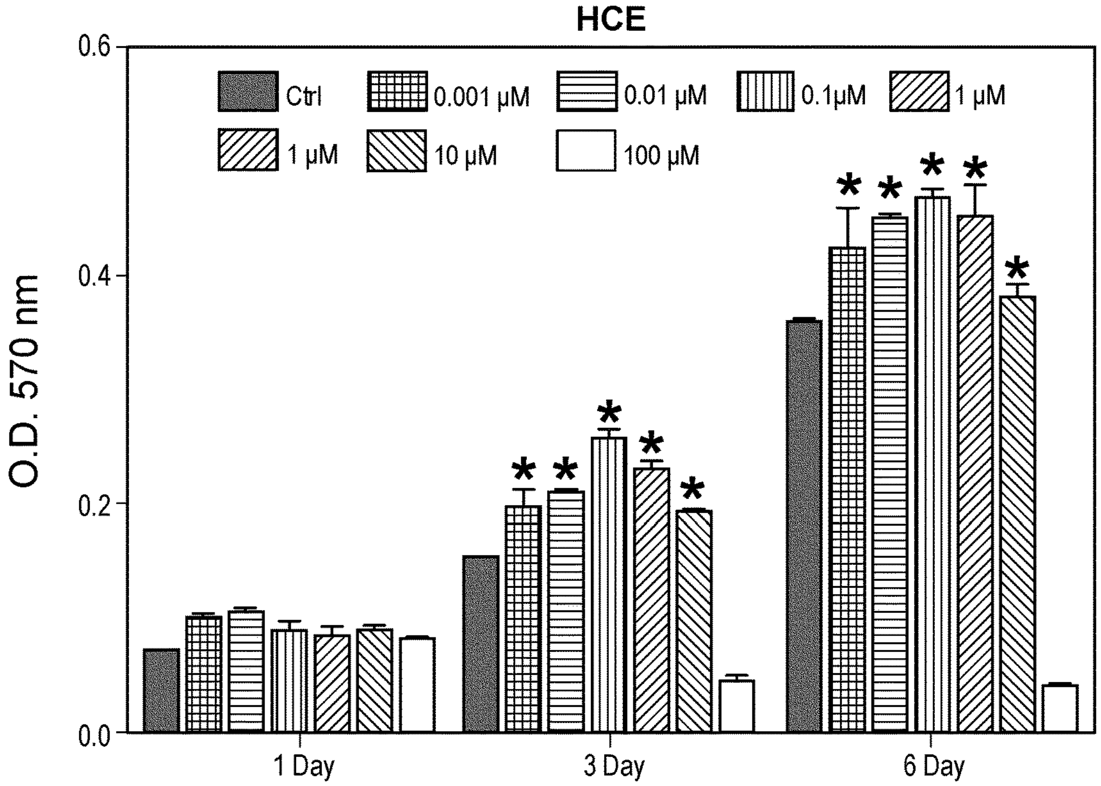
FIG. 14B is a graph showing corneal cell viability (HCE cells) in the presence of psilocin at different concentrations.
Figure 15B:
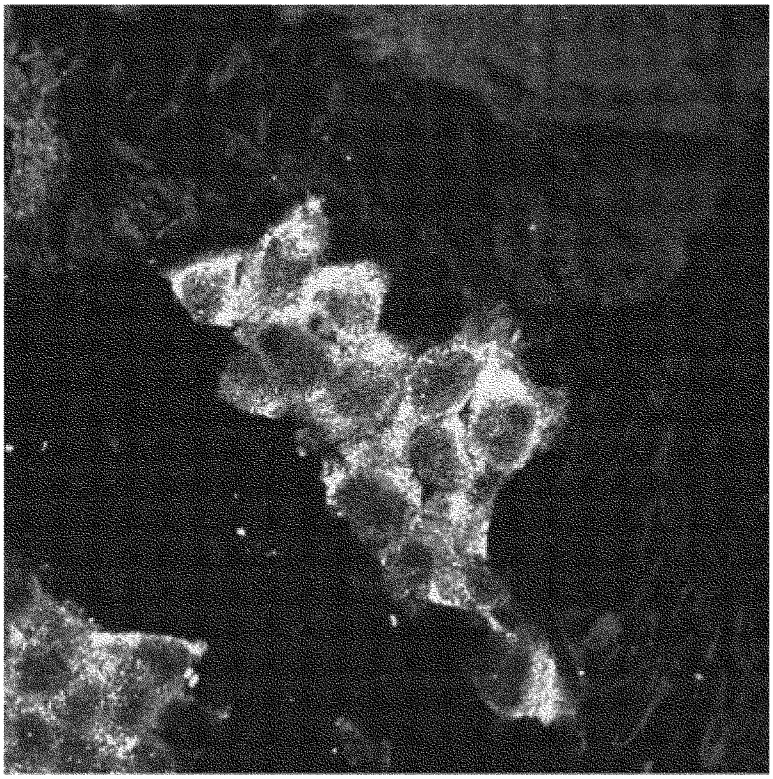
FIG. 15B is a photograph showing expression of NMDAR1 in HCE.
Figure 15A:
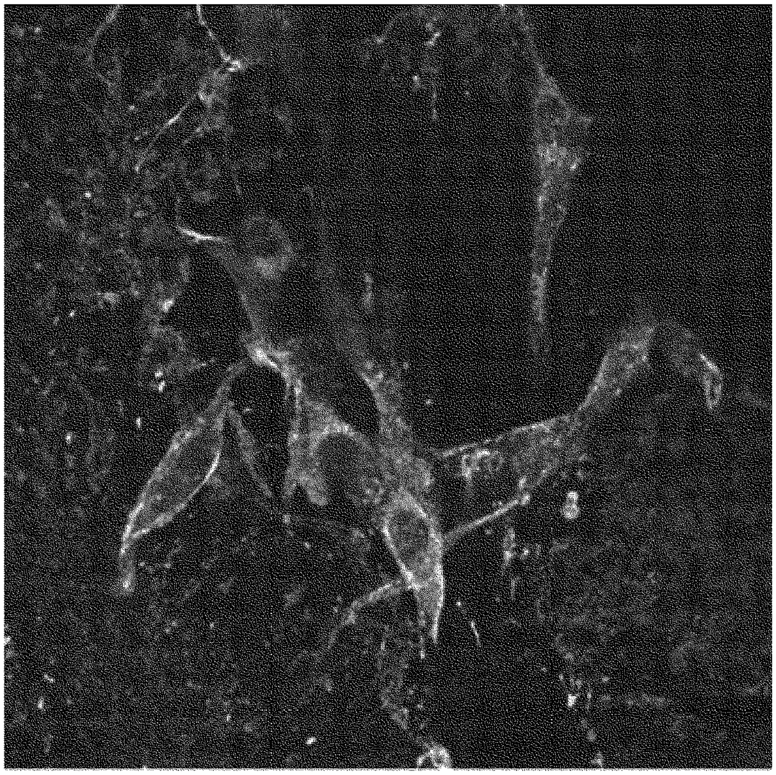
FIG. 15A is a photograph showing expression of 5-HT2A in keratocytes.
Figure 15D:
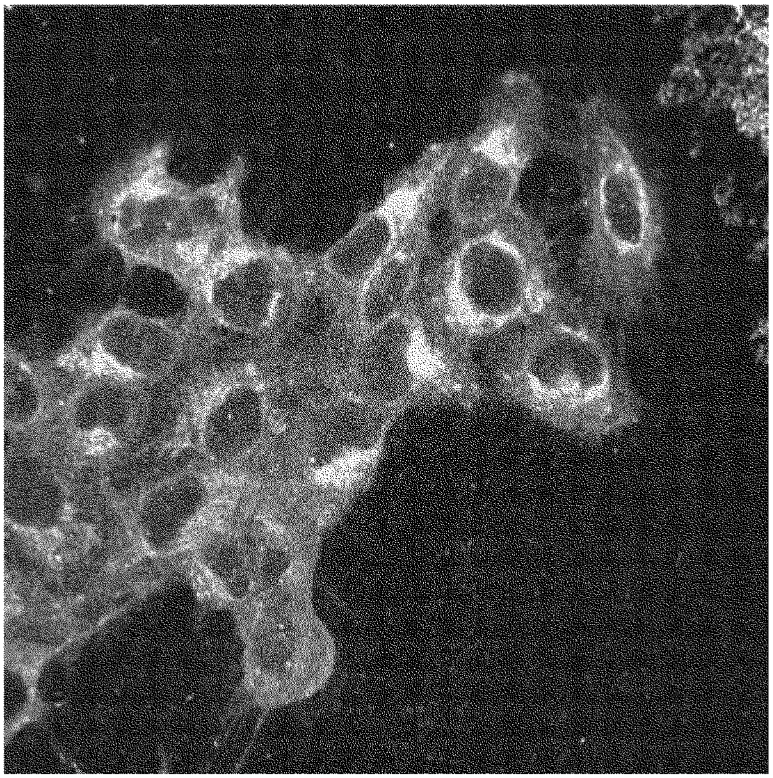
FIG. 15D is a photograph showing expression of 5-HT2C in HCE.
Figure 15C:
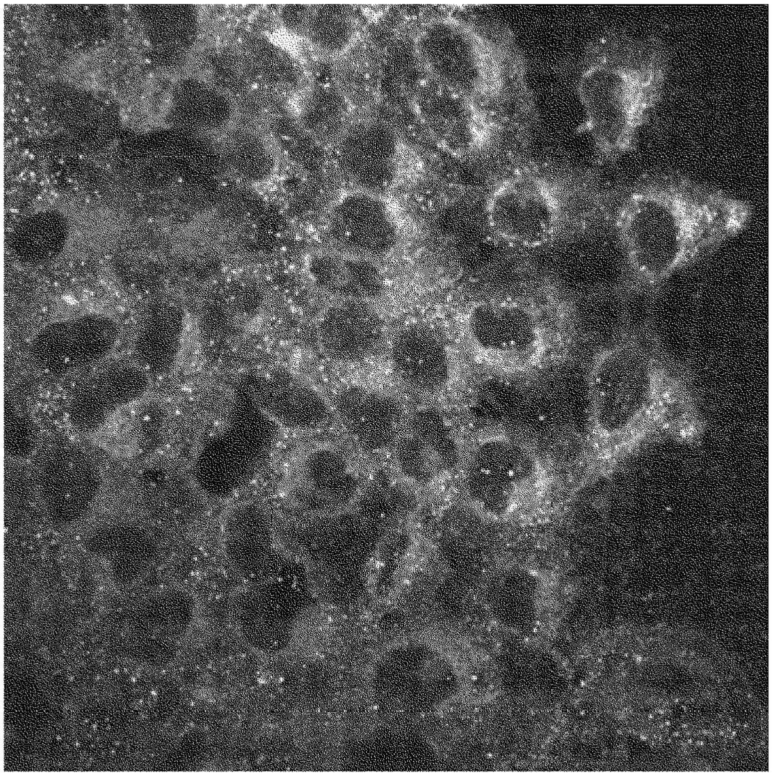
FIG. 15C is a photograph showing expression of 5-HT2A in HCE.

Effects of psilocin cytotoxicity and viability on HCE cells and keratocytes. Corneal cells were separately cultured with different concentrations of psilocin (from 000.1 to 100 μM) and cytotoxicity was assessed at 3 days after treatment (FIGS. 13A and 13B). Cell viability was analysed by the MTT test up to 6 days and as shown in FIGS. 14A and 14B, a significant increased viability was found in both HCE cells and keratocytes in the range of concentrations from 0.1 to 1 μM of psilocin.

Expression of the proteins NMDAR1, 5-HT2A and 5-HT2C in HCE cells and keratocytes. HCE cells express NMDAR1 and the two serotoninergic receptors 5-HT2A and 5-HT2C whereas keratocytes do not express NMDAR1 and 5-HT2C at significant levels (see FIGS. 15A-15D).

Effect of psilocin on the expression of some pro-inflammatory cytokines by corneal cells grown in the conditioned medium (CM) of PMA-activated 0937 monocytes. Since it has been demonstrated that native corneal cells are activated upon stromal injury and inflammation, the present inventors analyzed the expression of some pro-inflammatory cytokines in corneal cells treated with the CM of activated U937 monocytes (macrophages). qPCR analysis of mRNA extracted from PMA-activated U937 cells showed highly increased expression levels of the macrophage differentiation marker CD68.

Figure 16A:
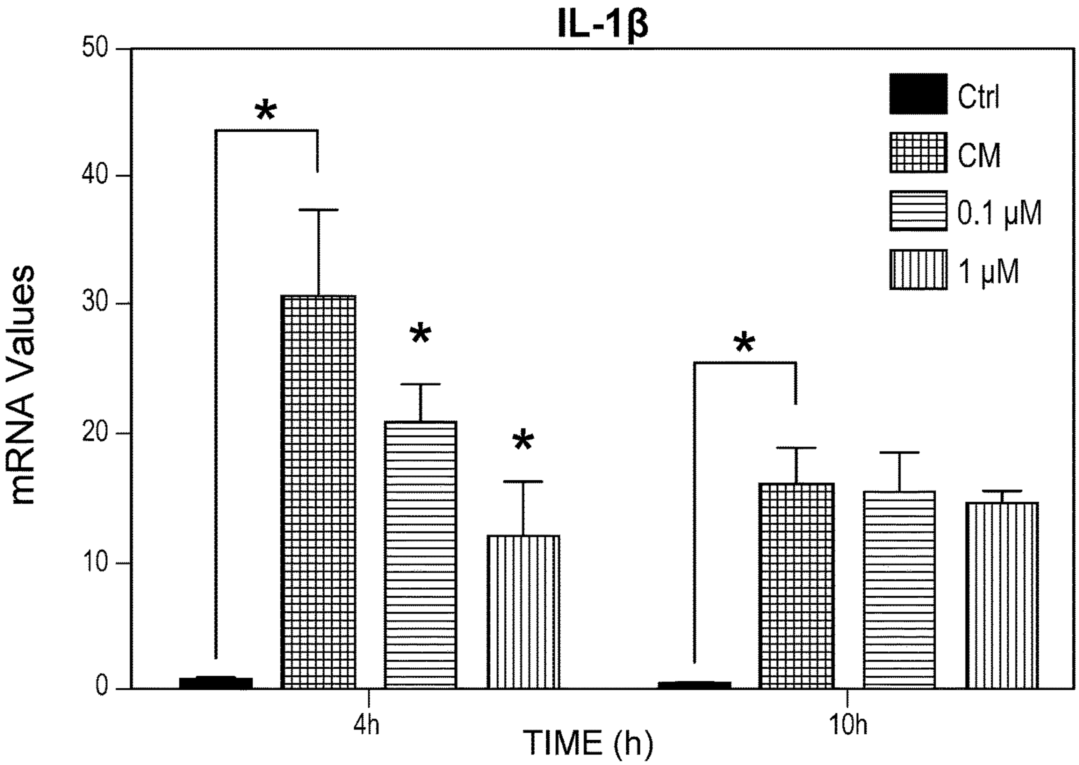
FIGS. 16A-16D are graphs showing cytokine expression by keratocytes cells treated with the conditioned medium (CM) of U937 activated monocyte for 24 h and cultured in the presence or in the absence of psilocin.
Figure 16B:
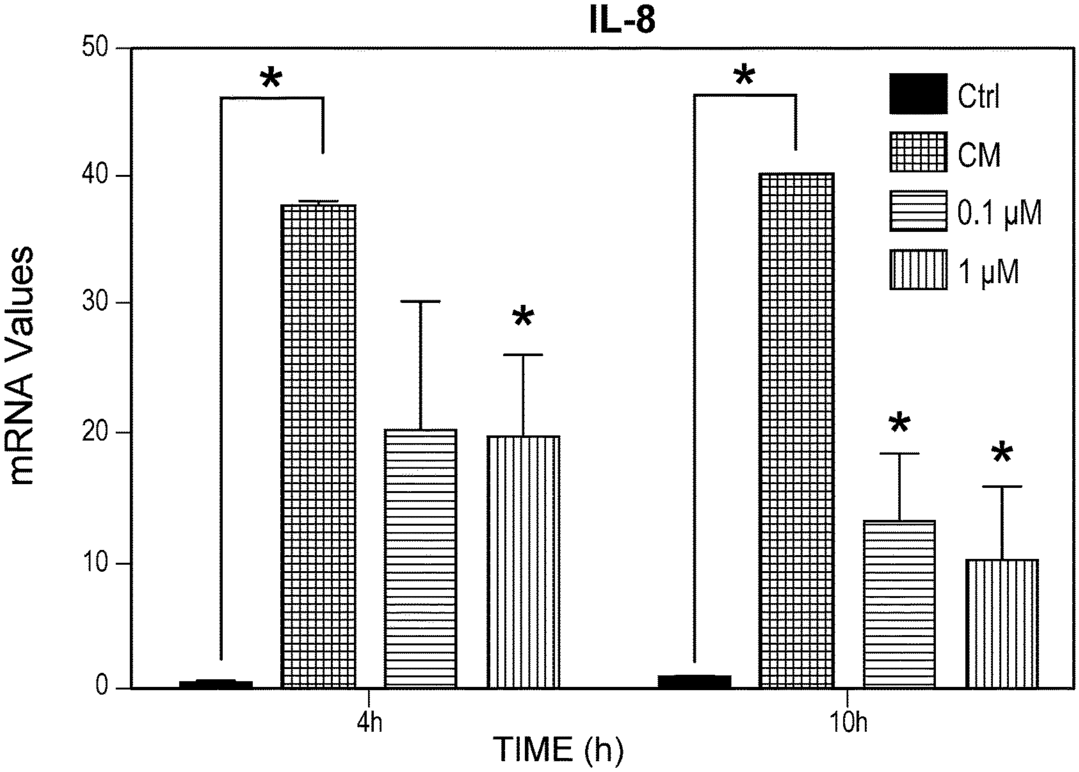
Figure 16C:
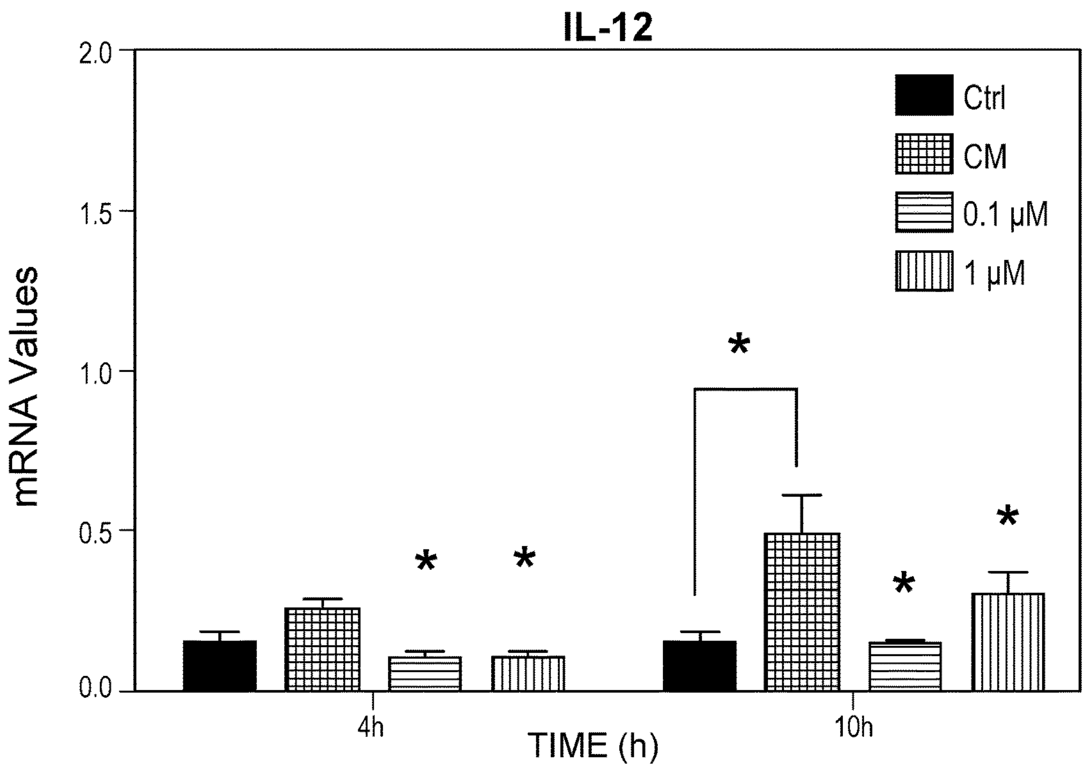
Figure 16D:
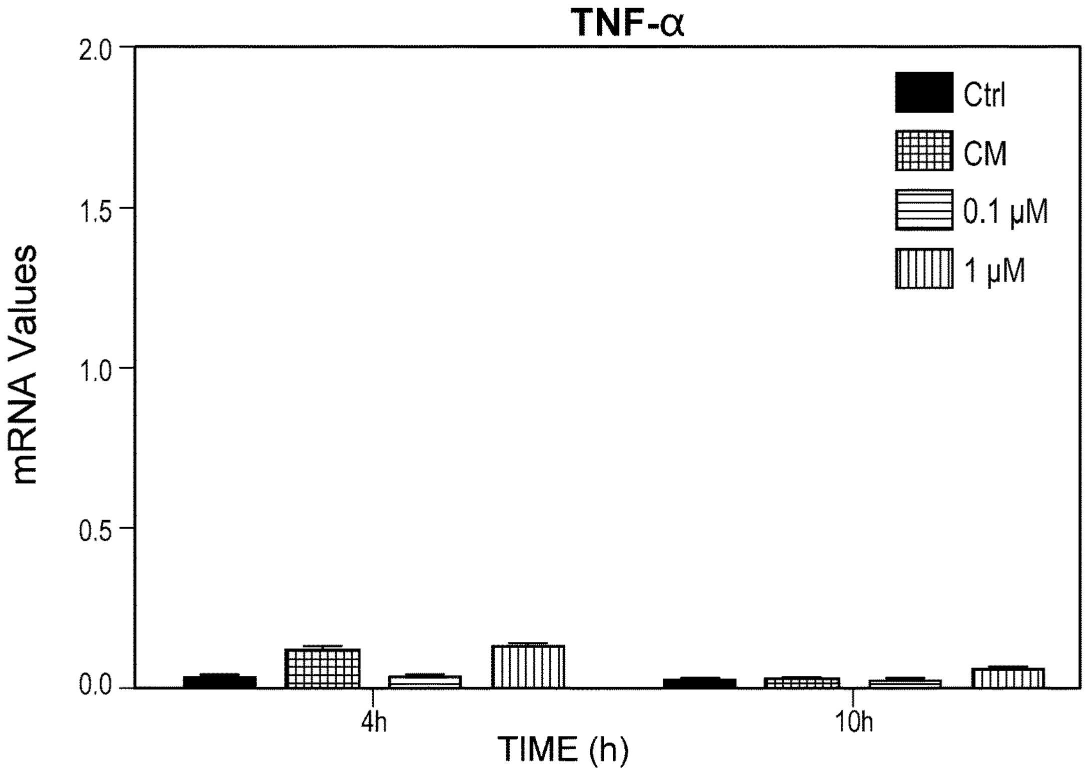

The exposure of corneal cells to the CM of macrophages confirmed that the environment created by macrophages highly enhanced the pro-inflammatory cytokines expression in corneal cell cultures. Subsequently, to verify the influence of psilocin on pro-inflammatory cytokines production, the molecule was added to cells at the concentration of 0.1 or 1 μM. qPCR analysis demonstrated that the treatment of keratocytes with the CM of PMA-activated U937 cells induced a significant over-expression of IL-1β, IL-8 and IL-12 mRNA (FIGS. 16A-16D). The presence of 0.1 and 1 μM psilocin induced a significant decrease of IL-1β at 4 h (FIG. 16A) and of IL-8 (FIG. 16B) and IL-12 (FIG. 16C) expression at 4 and 10 h post-treatment. The expression of TNF-α was very low and comparable to that of cells treated only with CM (FIG. 16D). IFNγ expression was not detectable in the present inventors' qPCR analysis.

Figure 17:
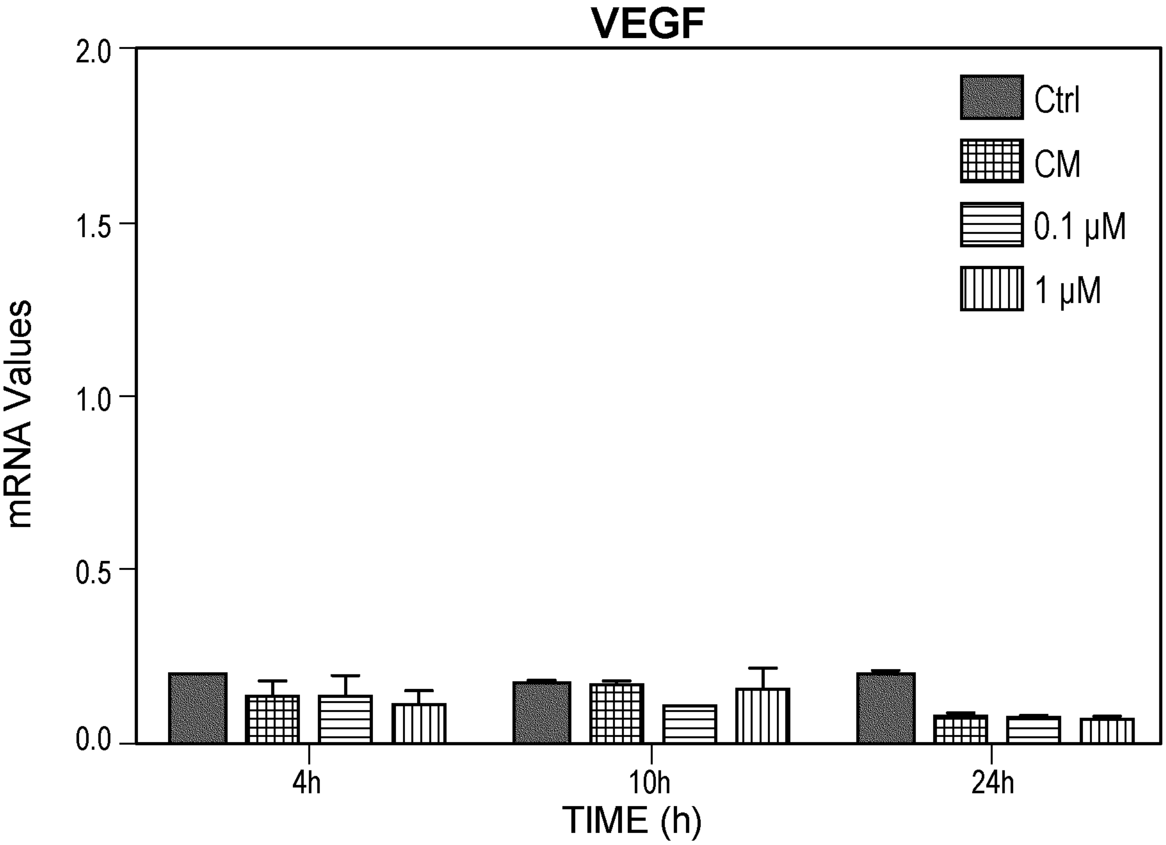
FIG. 17 is a graph showing VEGF expression by keratocytes cells treated with the conditioned medium (CM) of U937 activated monocyte for 24 h and cultured in the presence or in the absence of psilocin, after 4, 10 and 24 h from treatment with activated U937 CM.
Figure 18A:
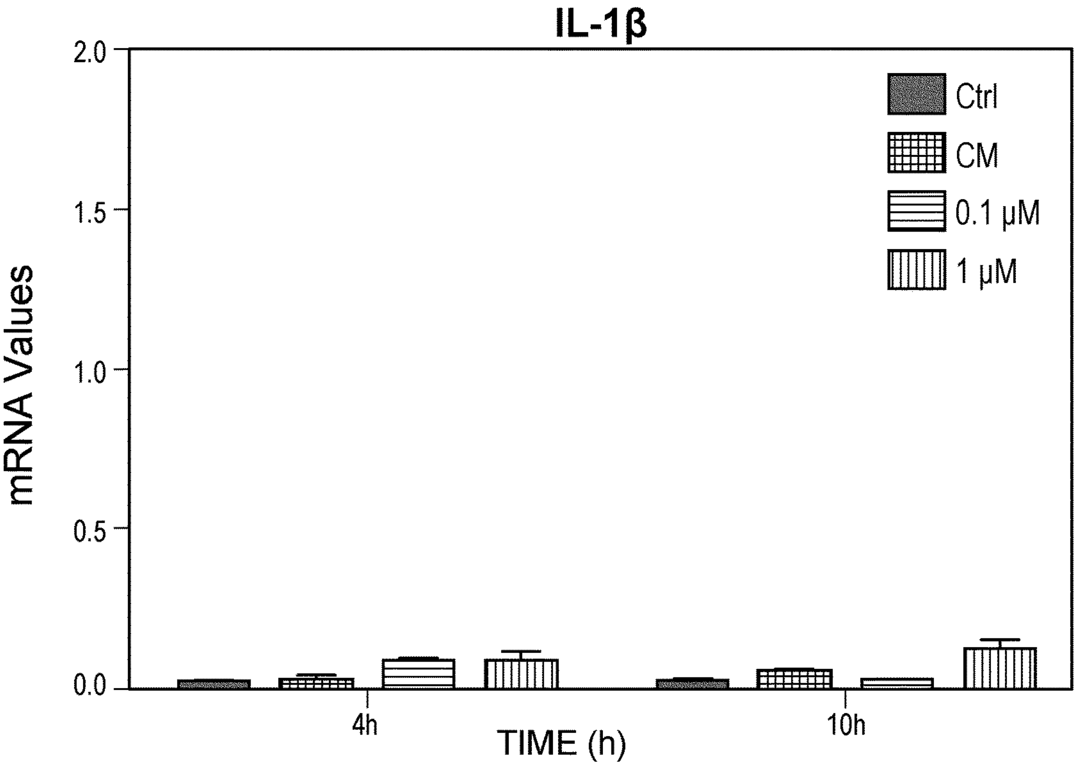
FIGS. 18A-18D are graphs showing cytokine expression by HCE cells treated with conditioned medium (CM) of U937 activated monocyte for 24 h and cultured in the presence or absence of psilocin.
Figure 18B:
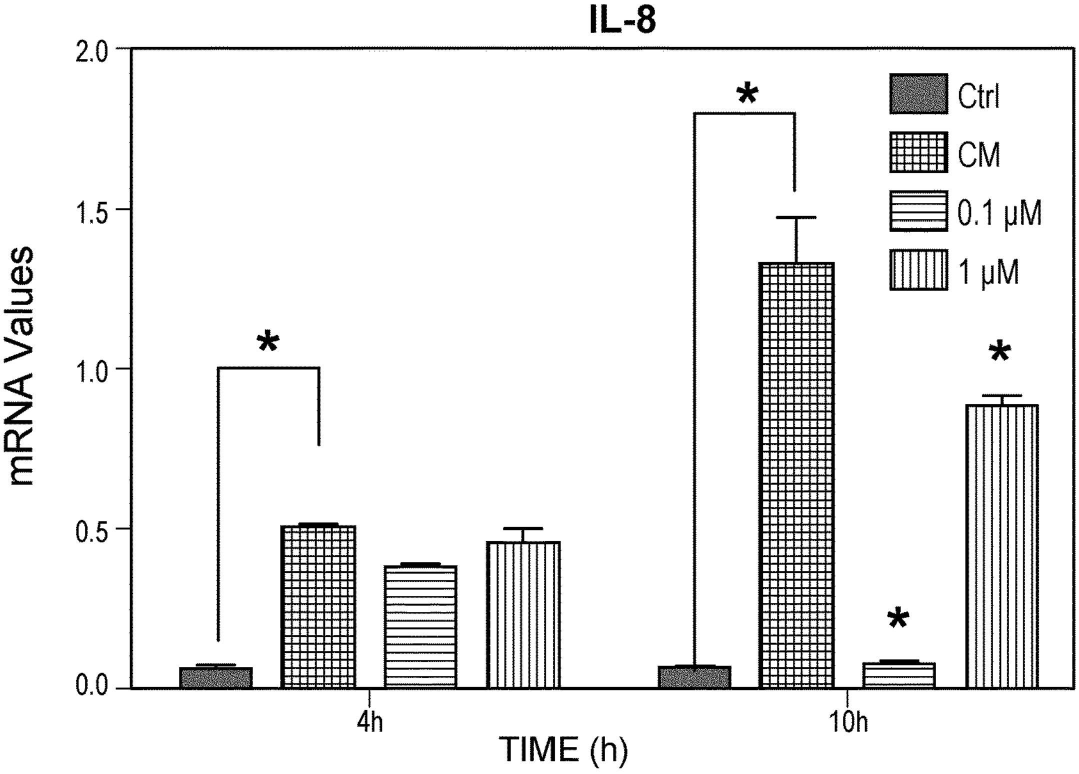
Figure 18C:
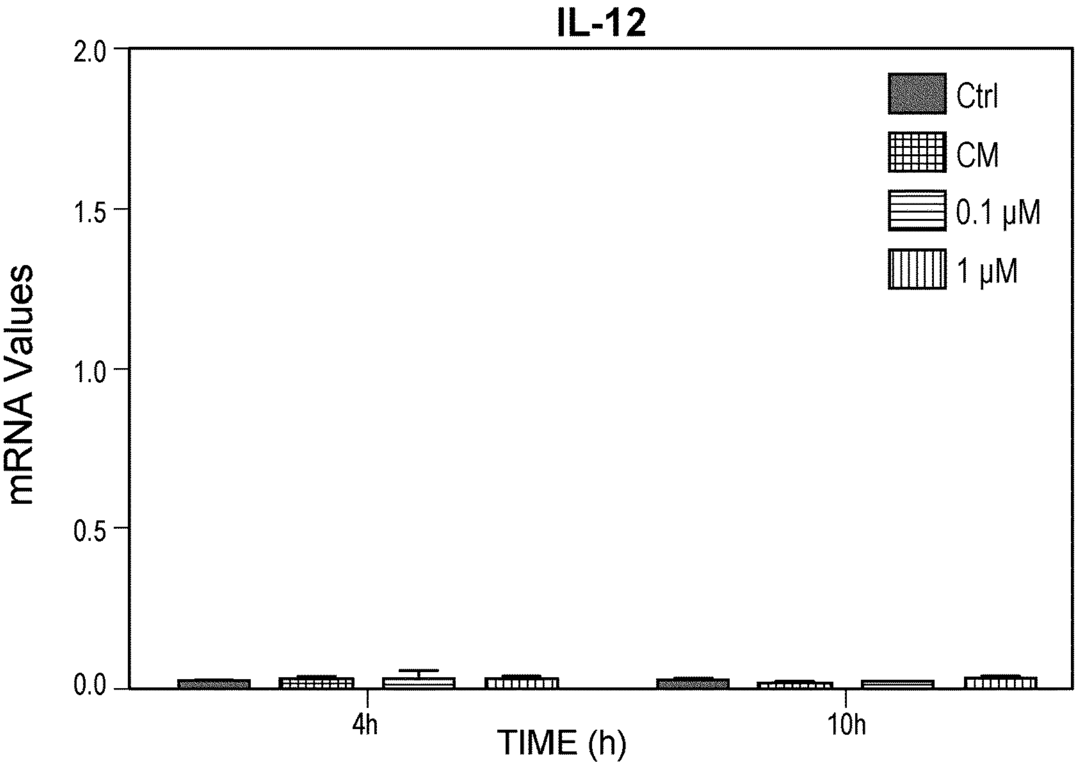
Figure 18D:
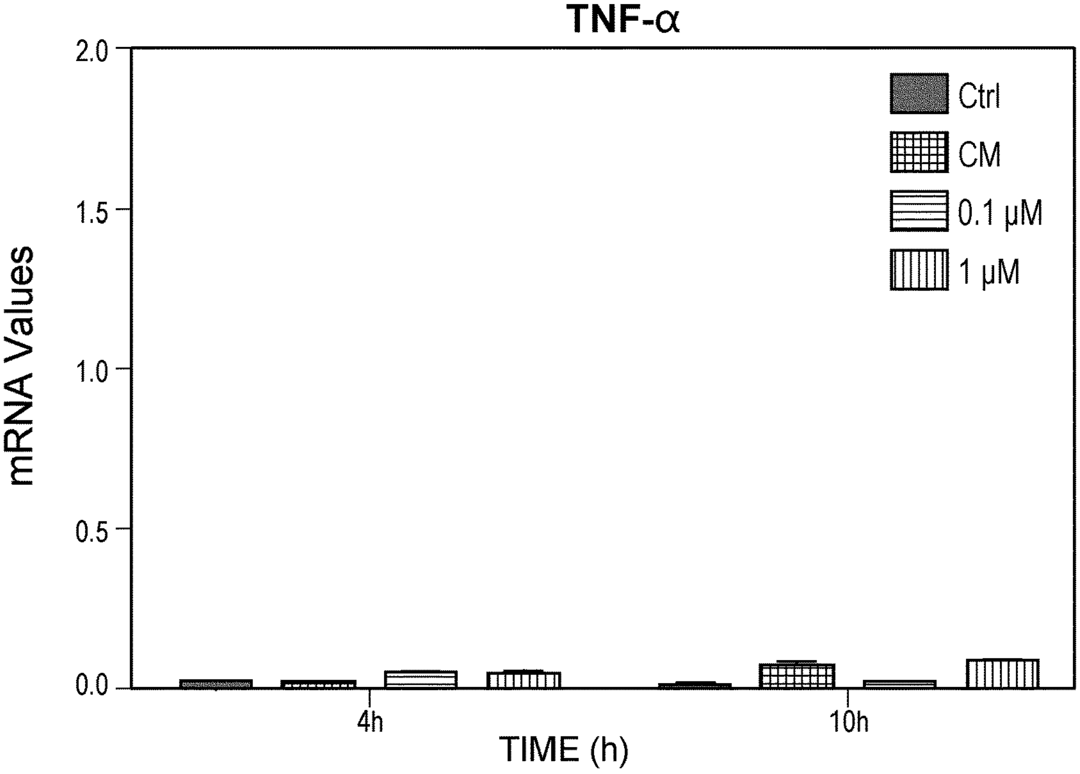
Figure 19A:
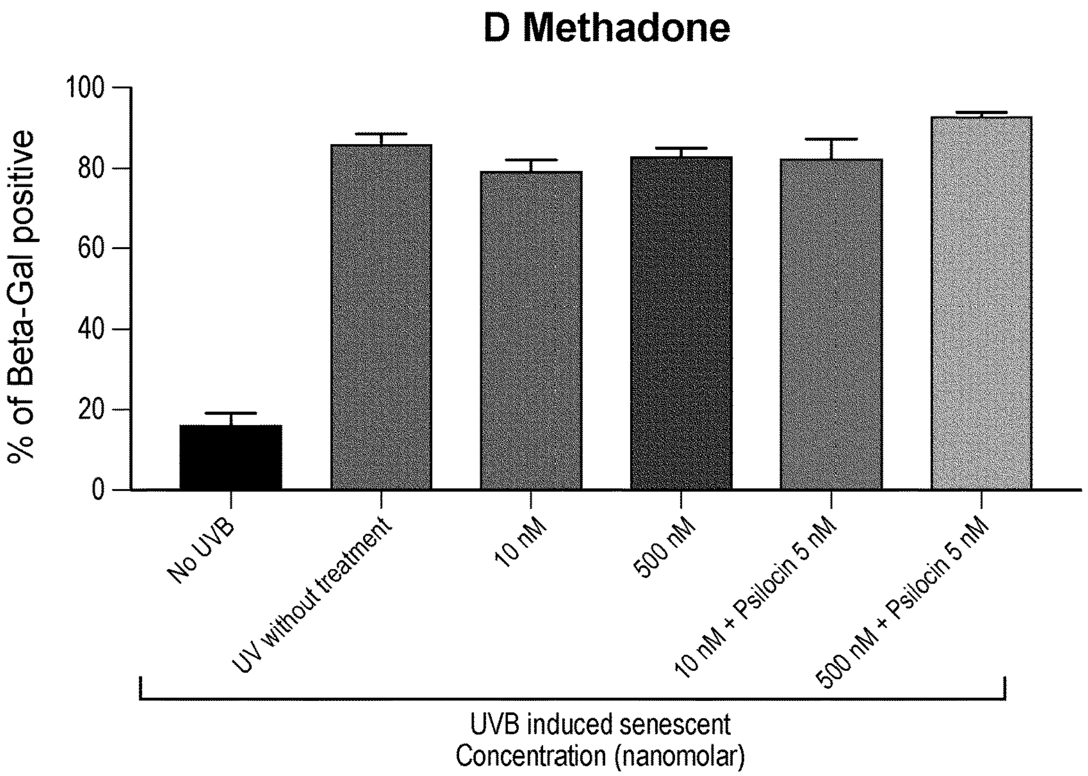
FIG. 19A is a graph showing beta-gal assay results in cells treated with d-methadone.
Figure 19B:
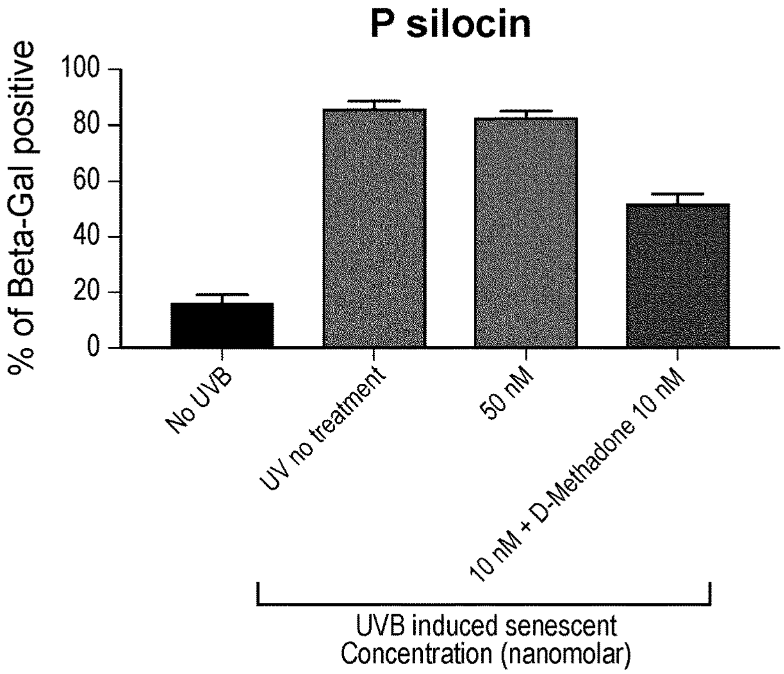
FIG. 19B is a graph showing an antisenescence effect observed with 10 nm psilocin in combination with 10 nm d-methadone with a 34% reduction in beta-gal positive cells.
Figure 20A:
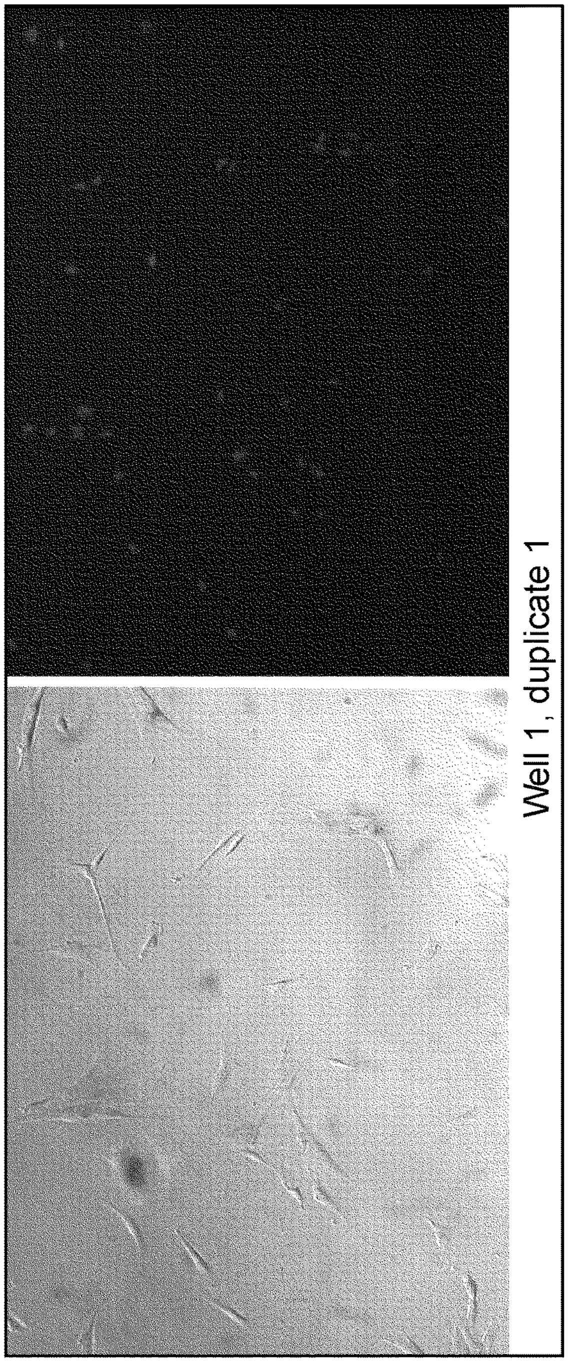
FIGS. 20A-20D are photographs of cells with no UVB induction.
Figure 20B:
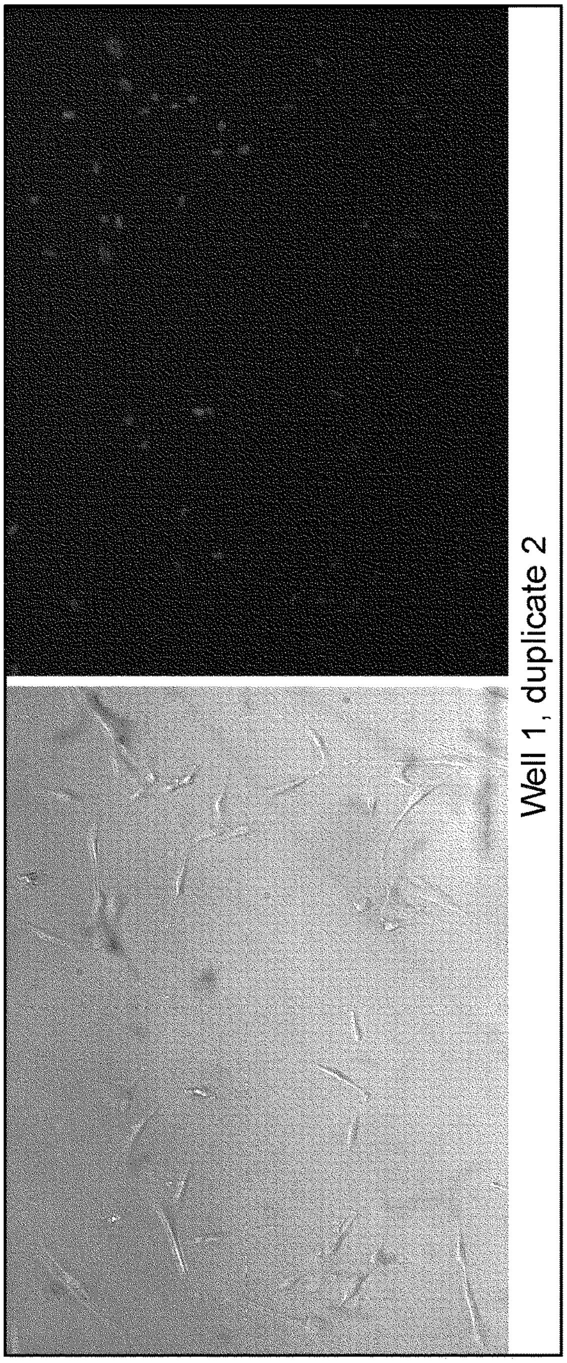
Figure 20C:
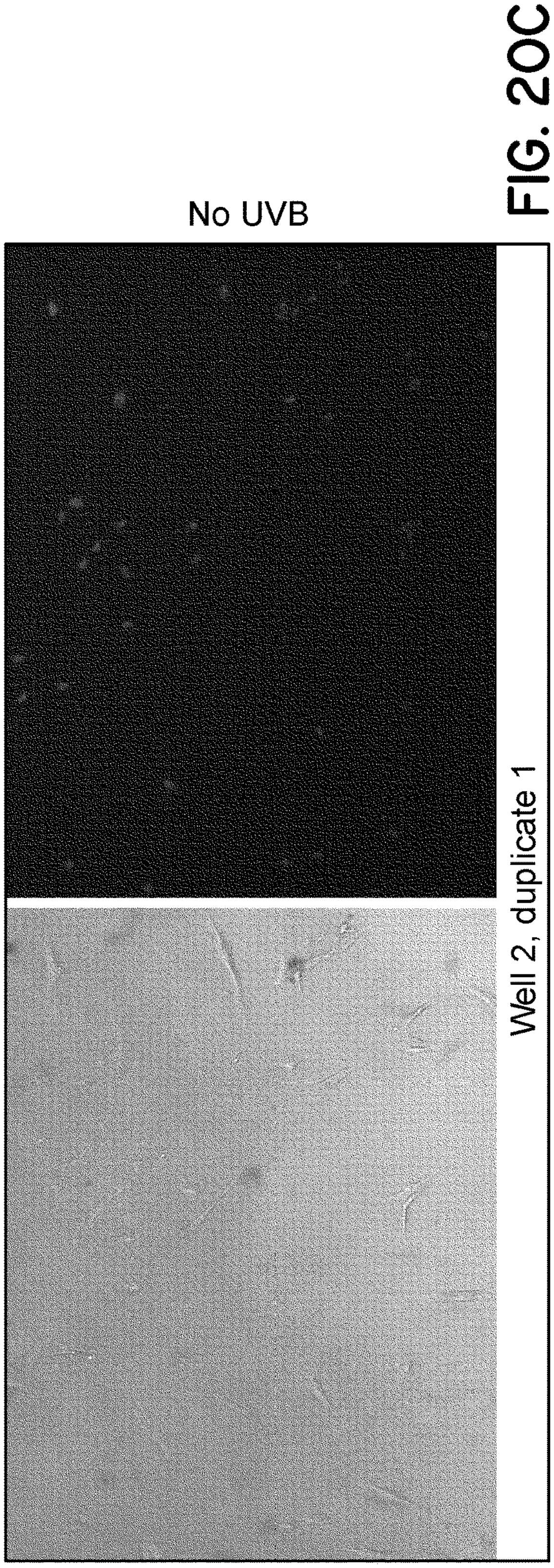
Figure 20D:
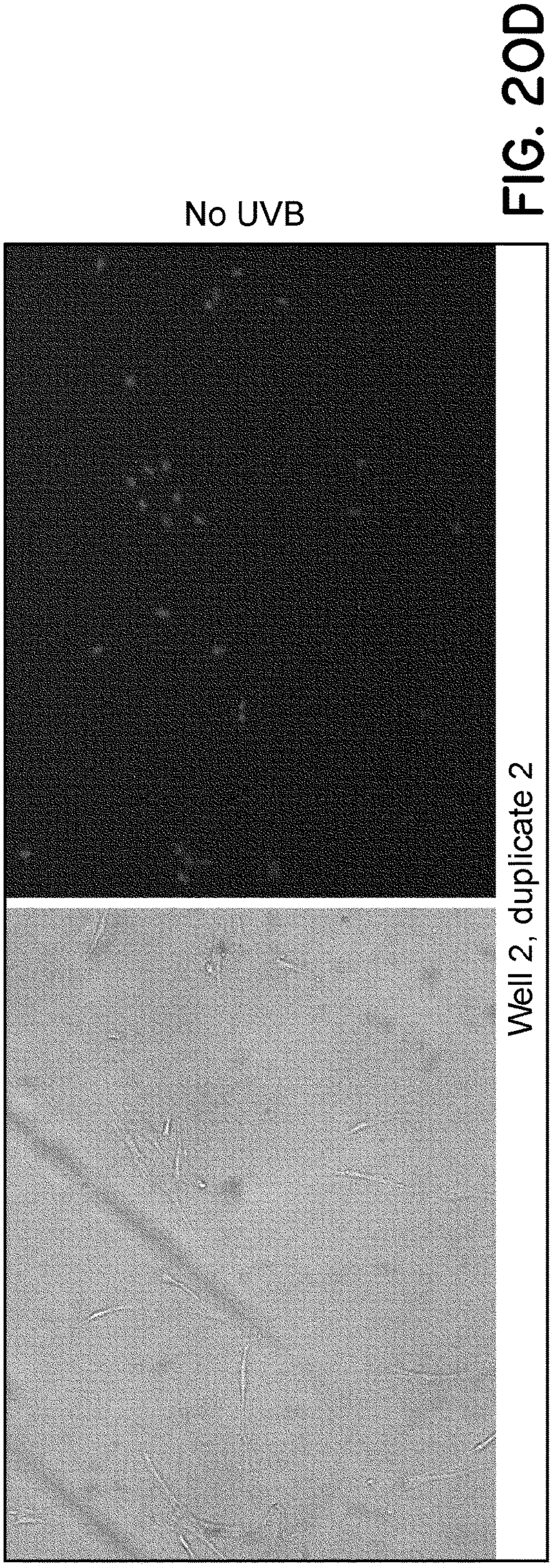
Figure 21A:
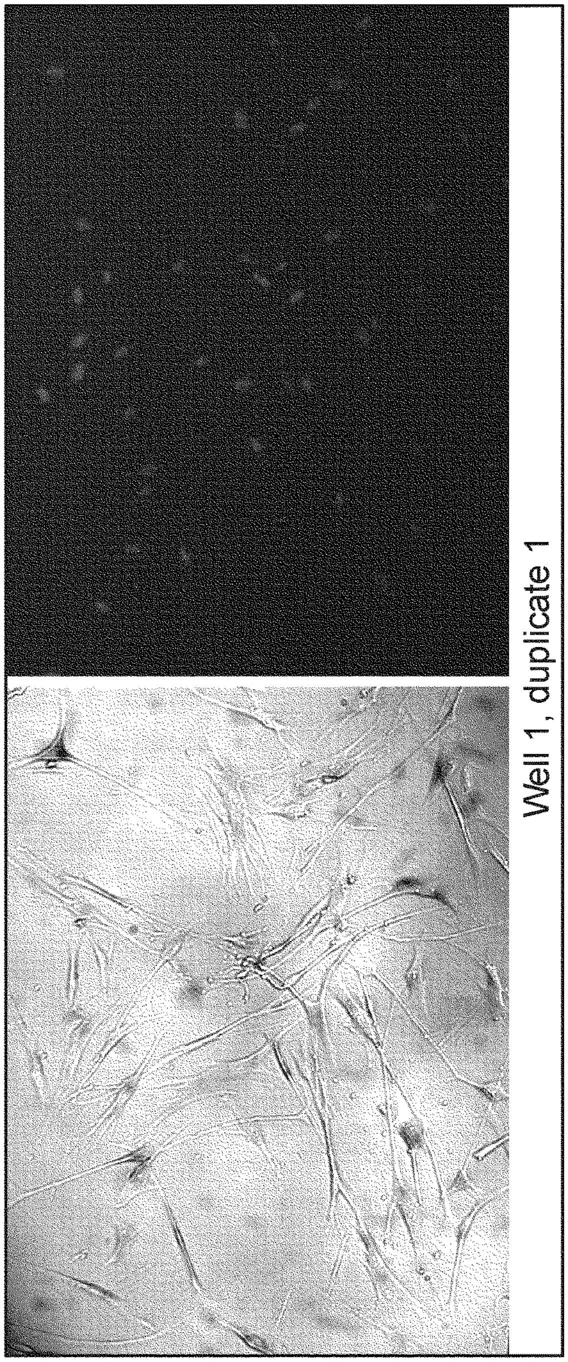
FIGS. 21A-21D are photographs of cells with UVB induction but without treatment.
Figure 21B:
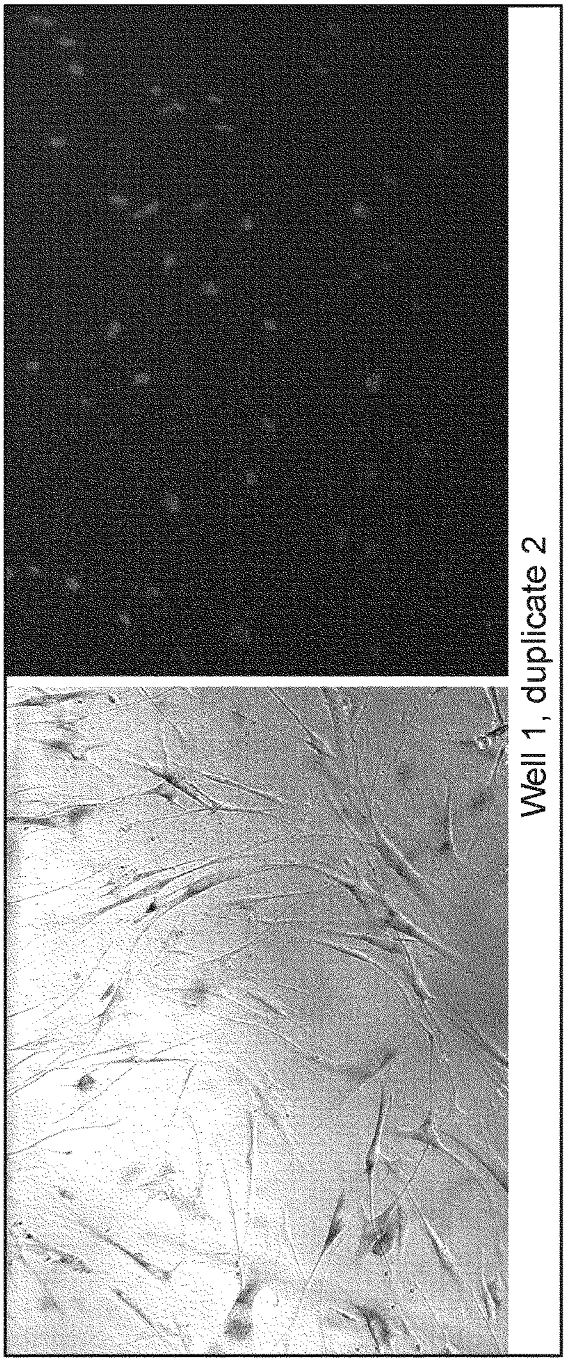
Figure 21C:
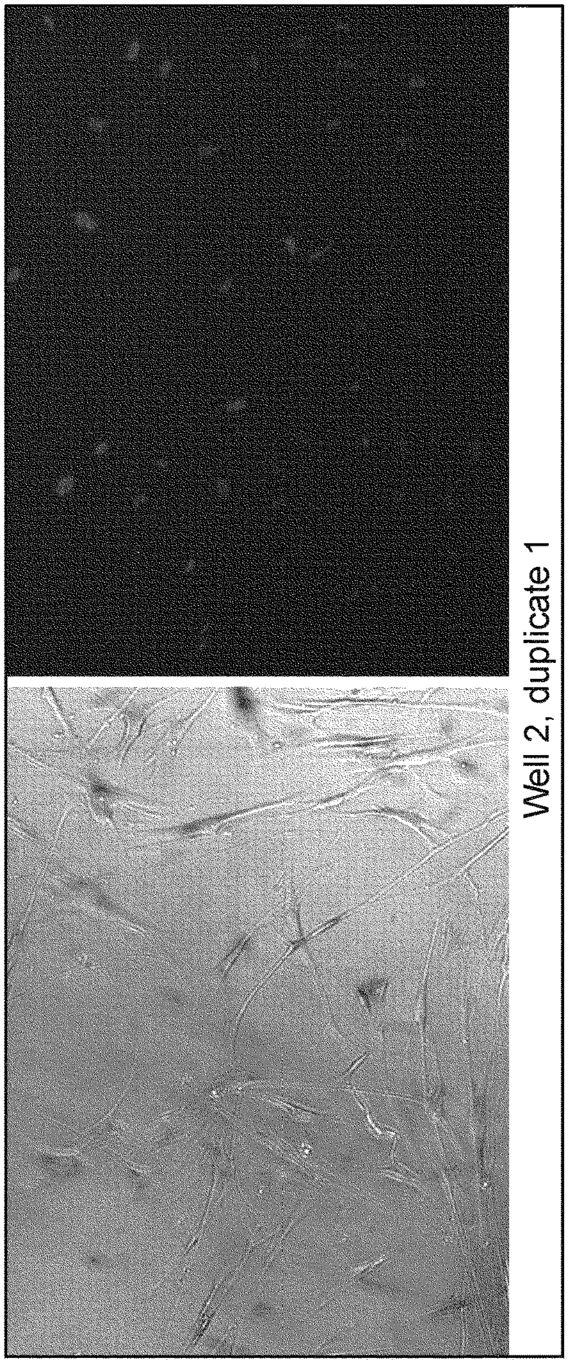
Figure 21D:
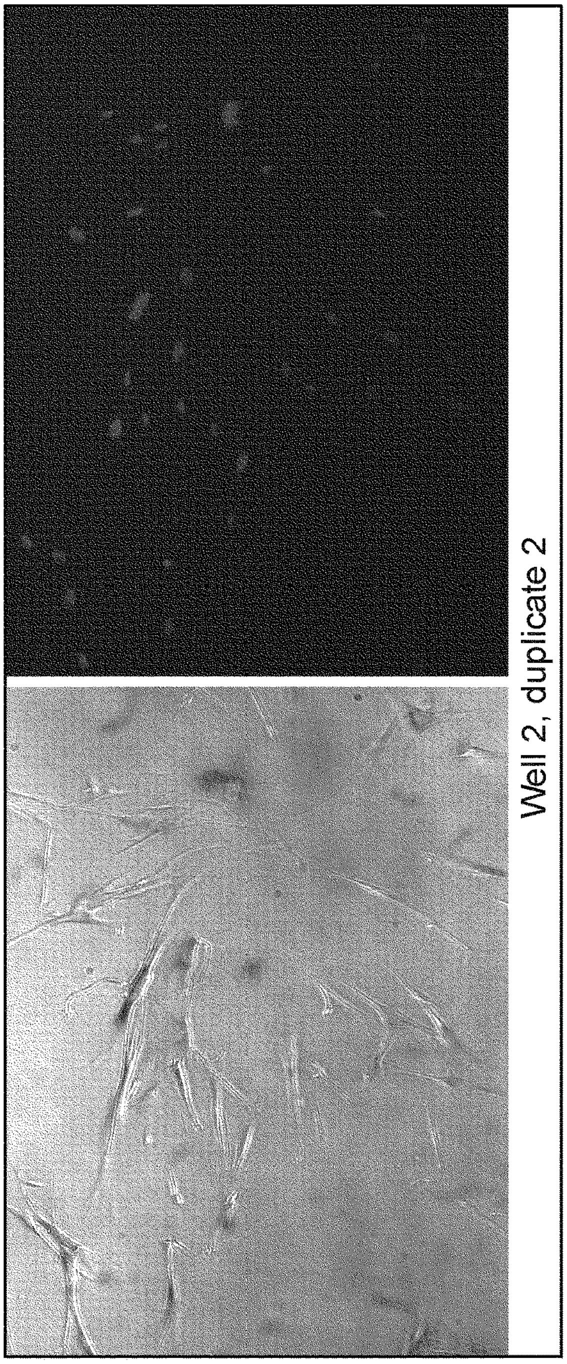
Figure 22A:
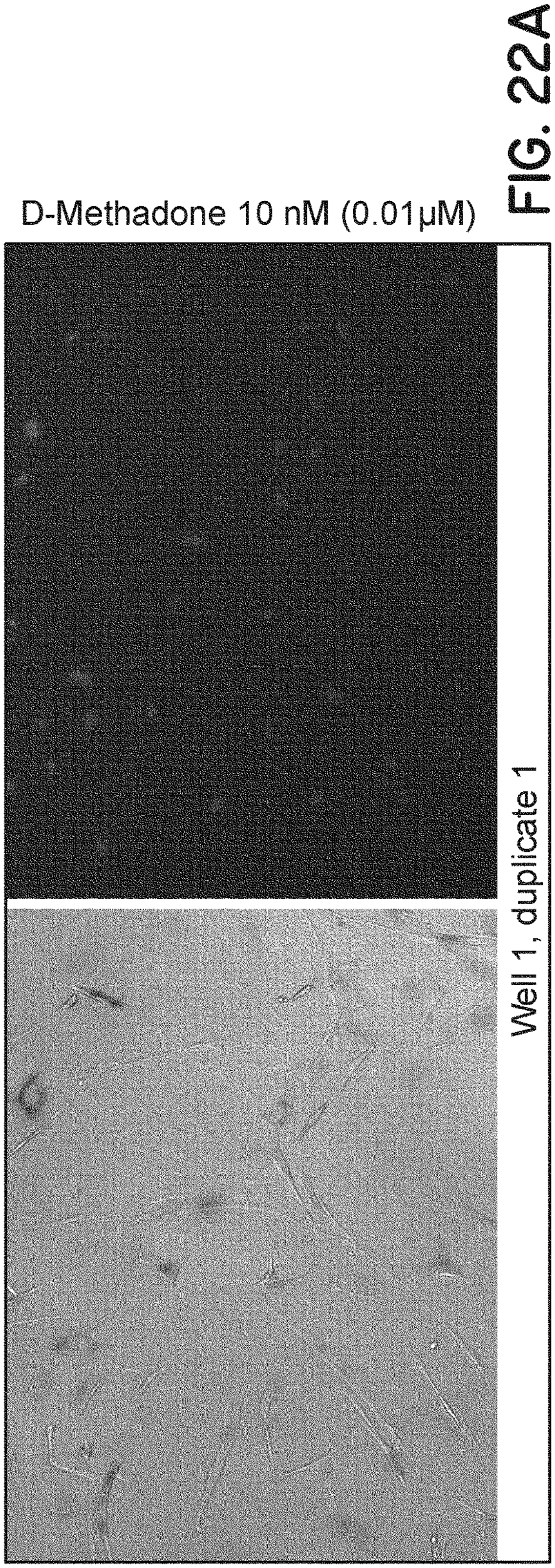
FIGS. 22A-22D are photographs of cells treated with d-methadone 10 nm (0.01 μM).
Figure 22B:
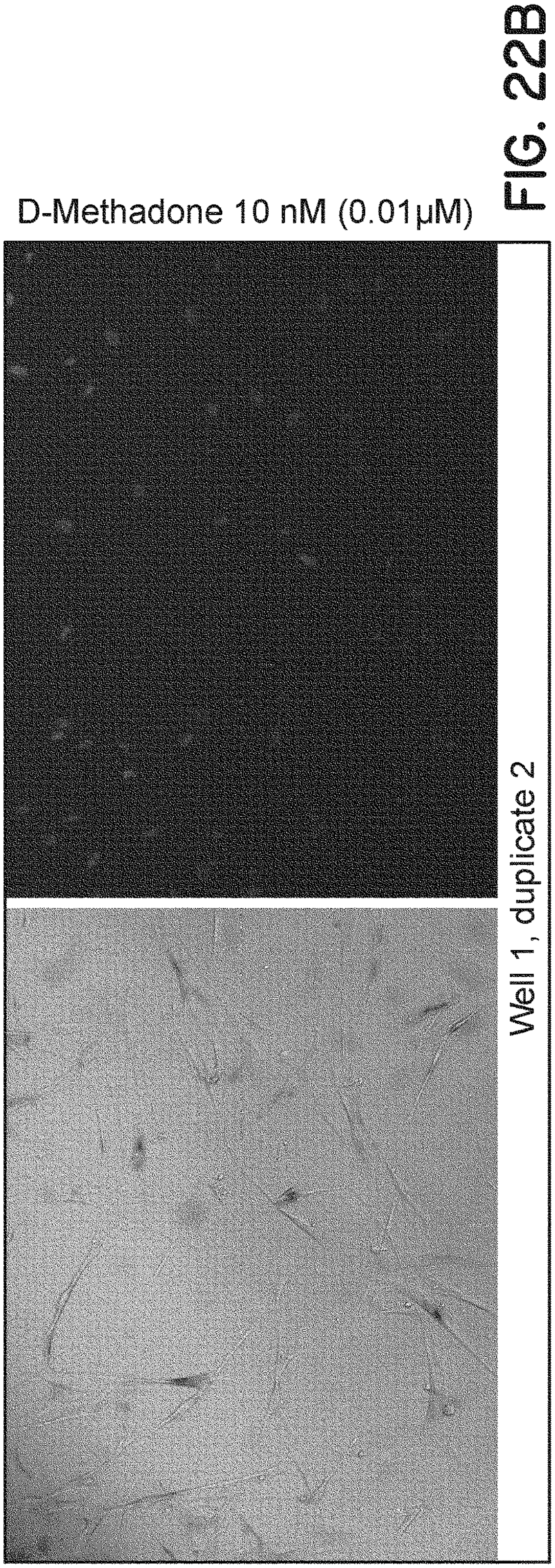
Figure 22C:
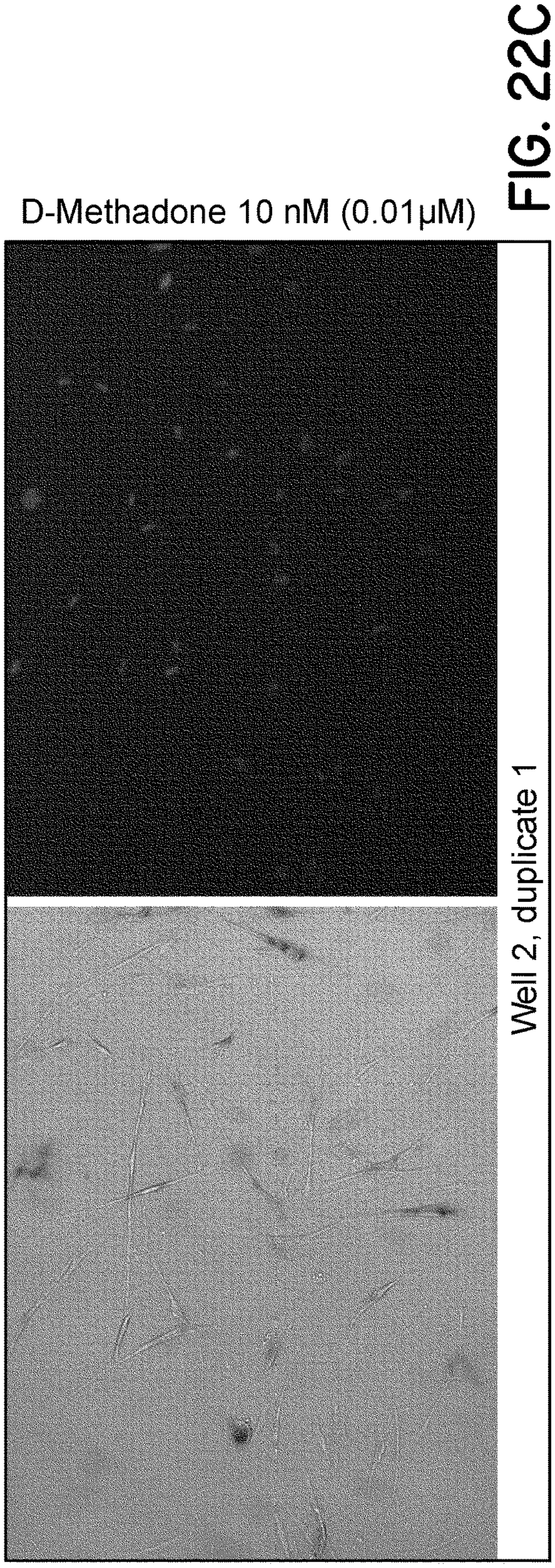
Figure 22D:
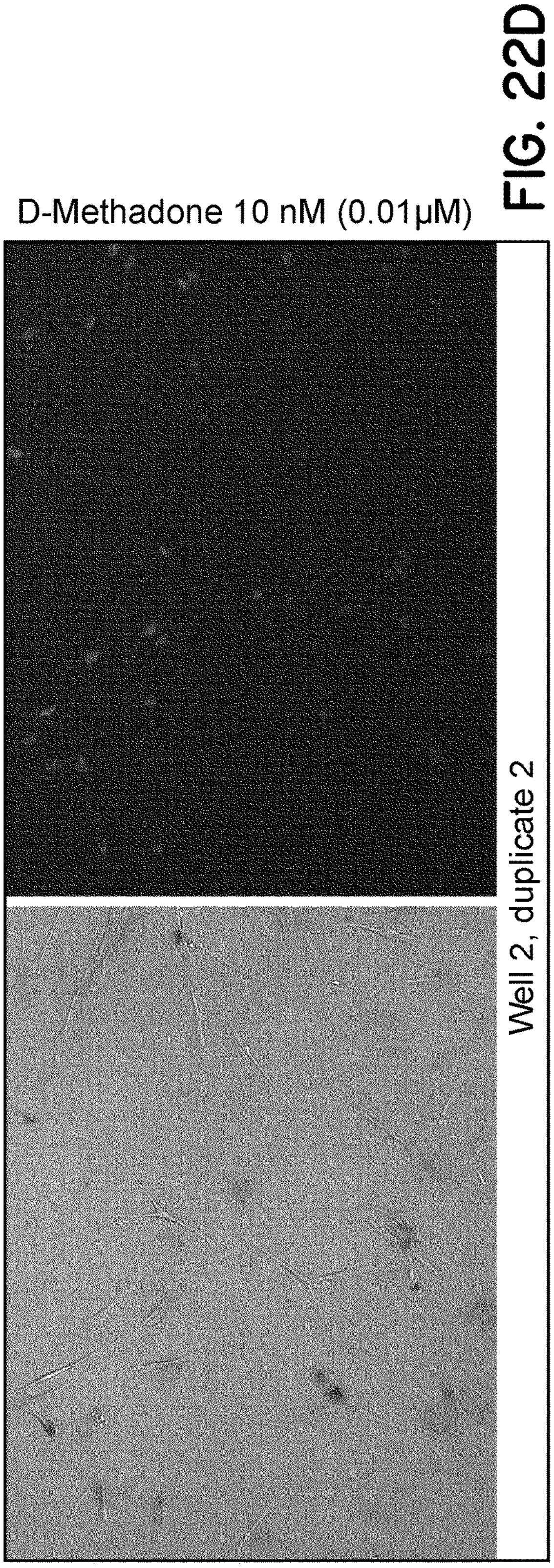
Figure 23A:
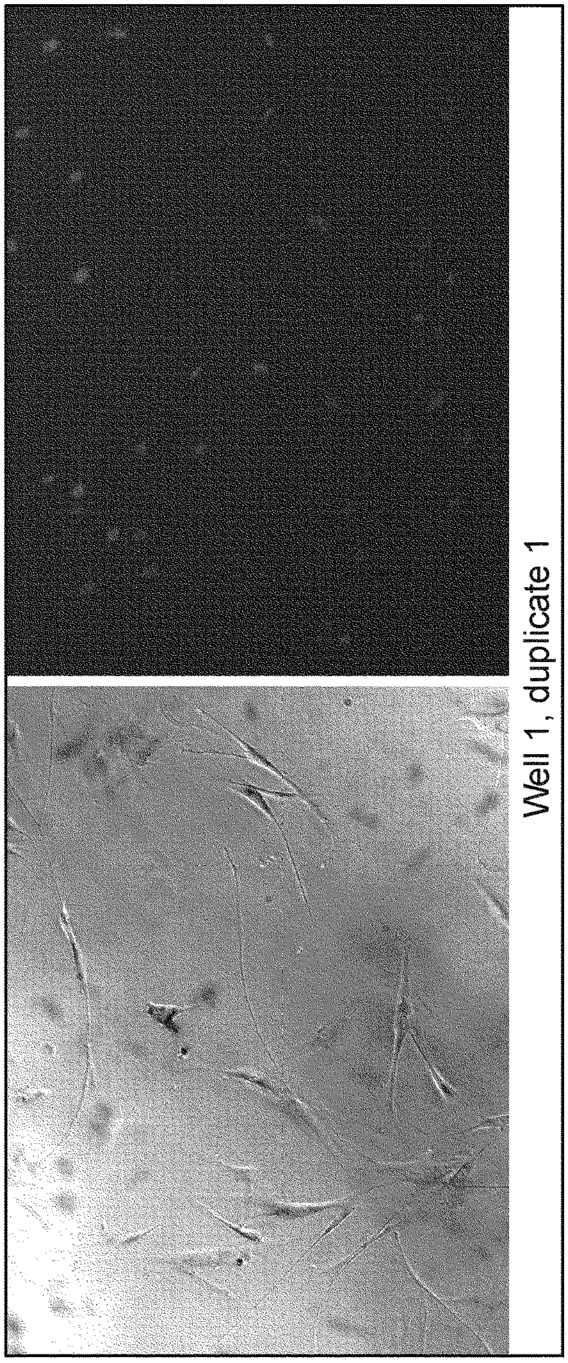
FIGS. 23A-23D are photographs of cells treated with d-methadone 500 nm.
Figure 23B:
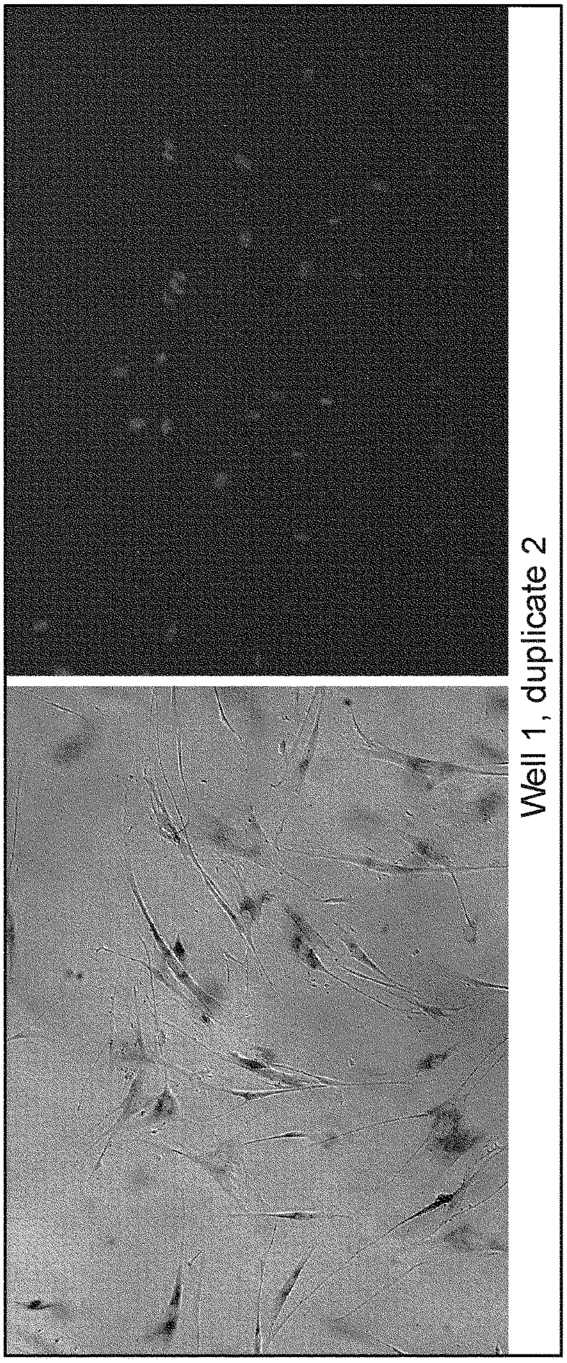
Figure 23C:
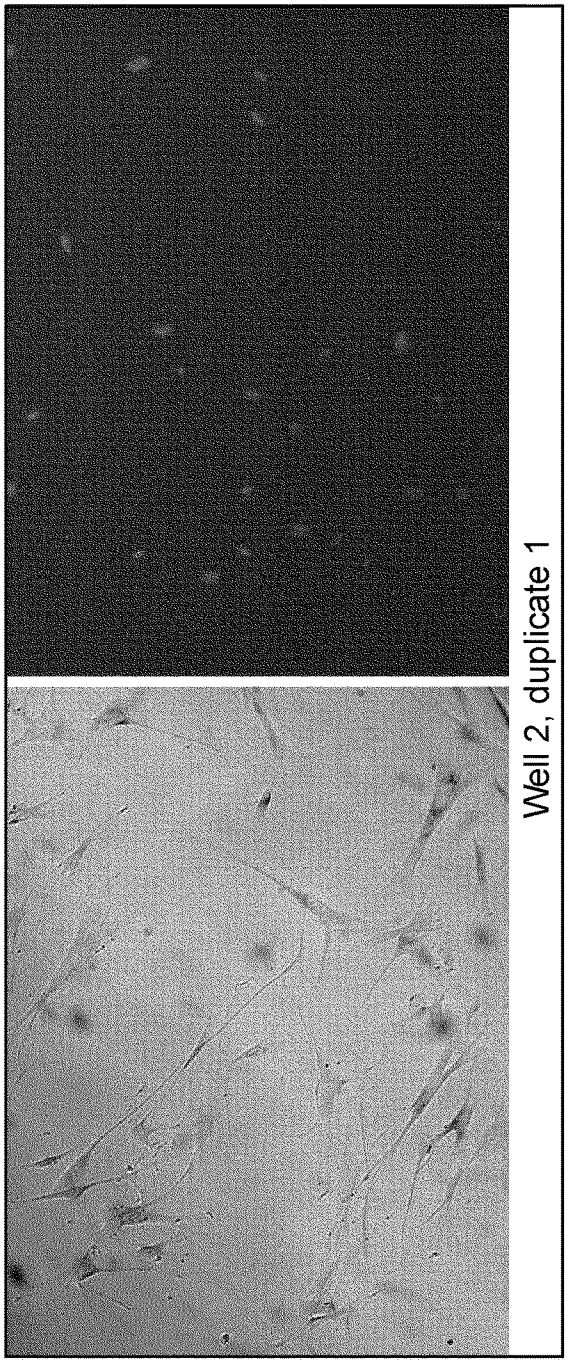
Figure 23D:
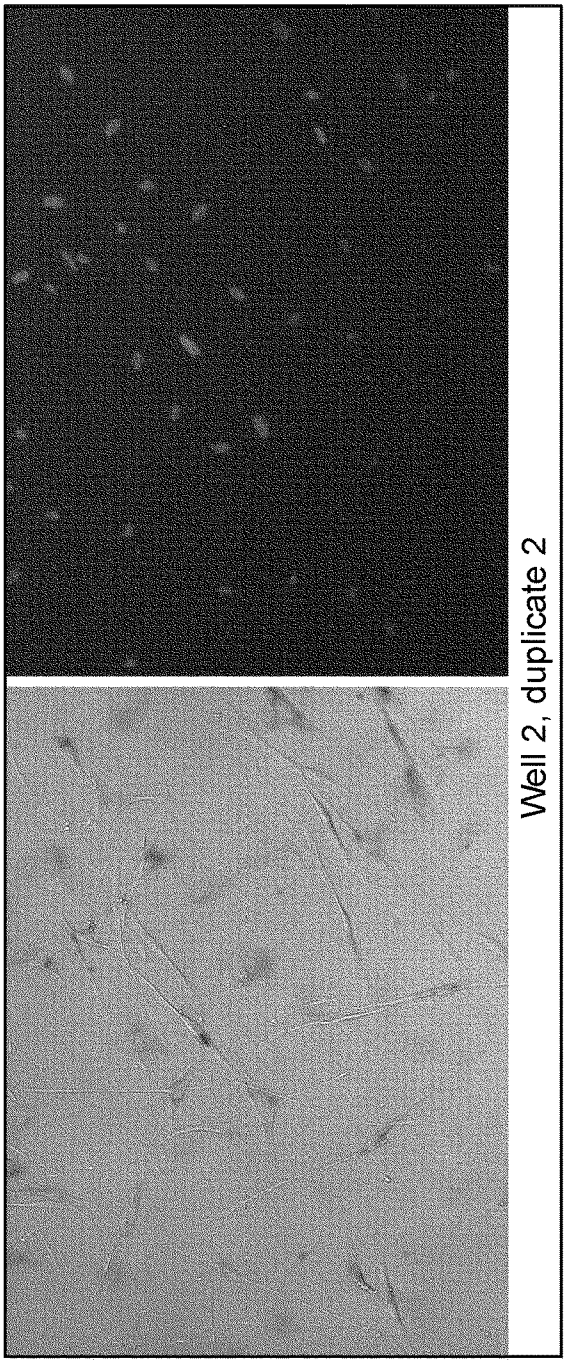
Figure 24A:
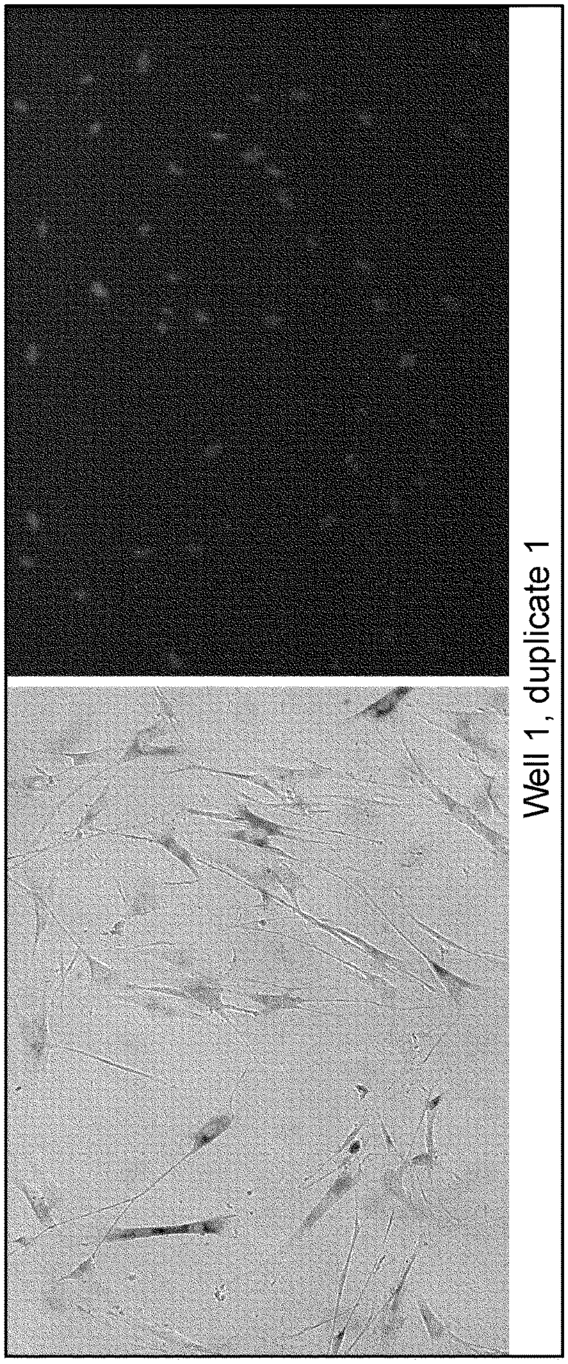
FIGS. 24A-24D are photographs of cells treated with d-methadone 10 nm+psilocin 5 nm.
Figure 24B:
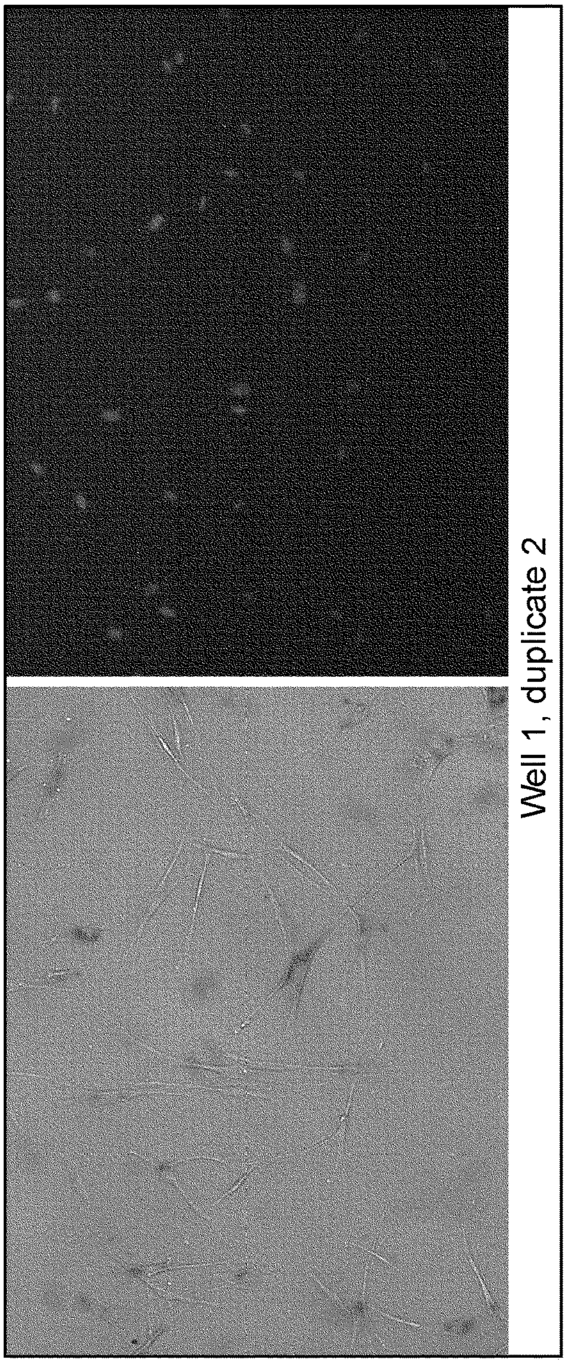
Figure 24C:
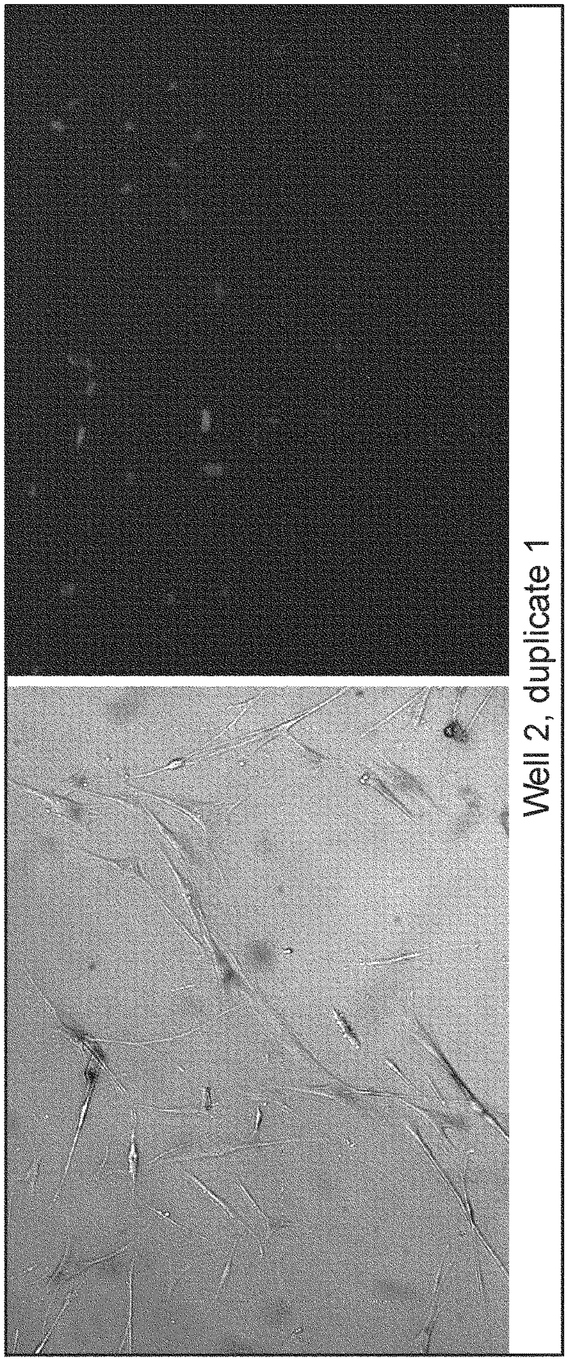
Figure 24D:
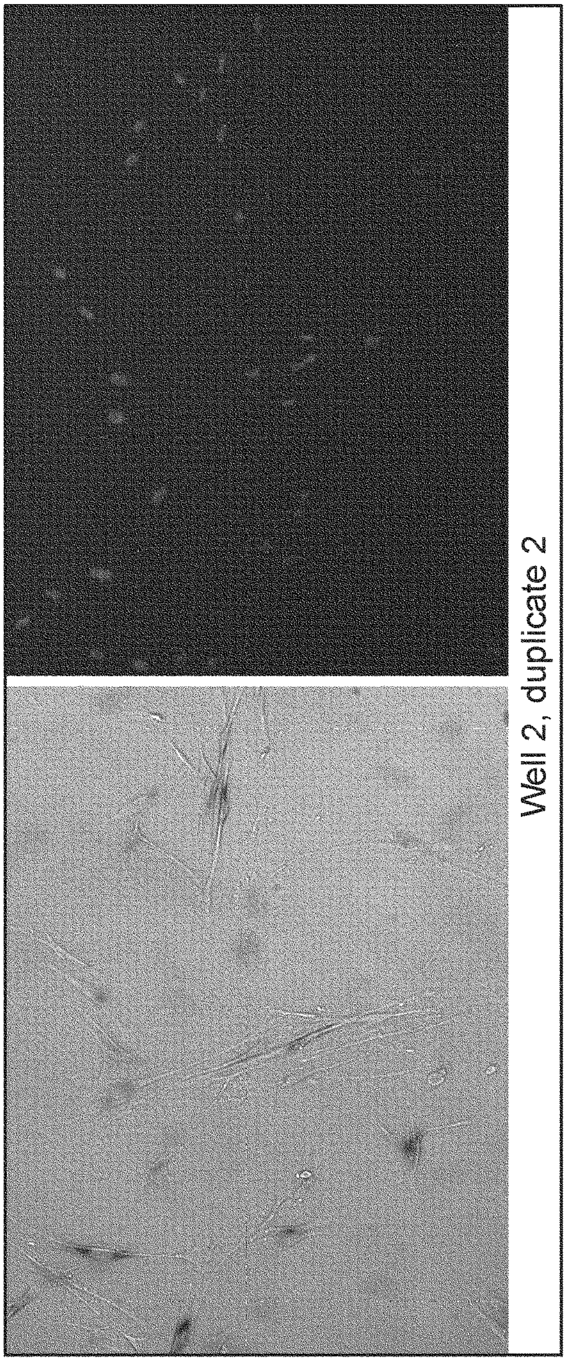
Figure 25A:
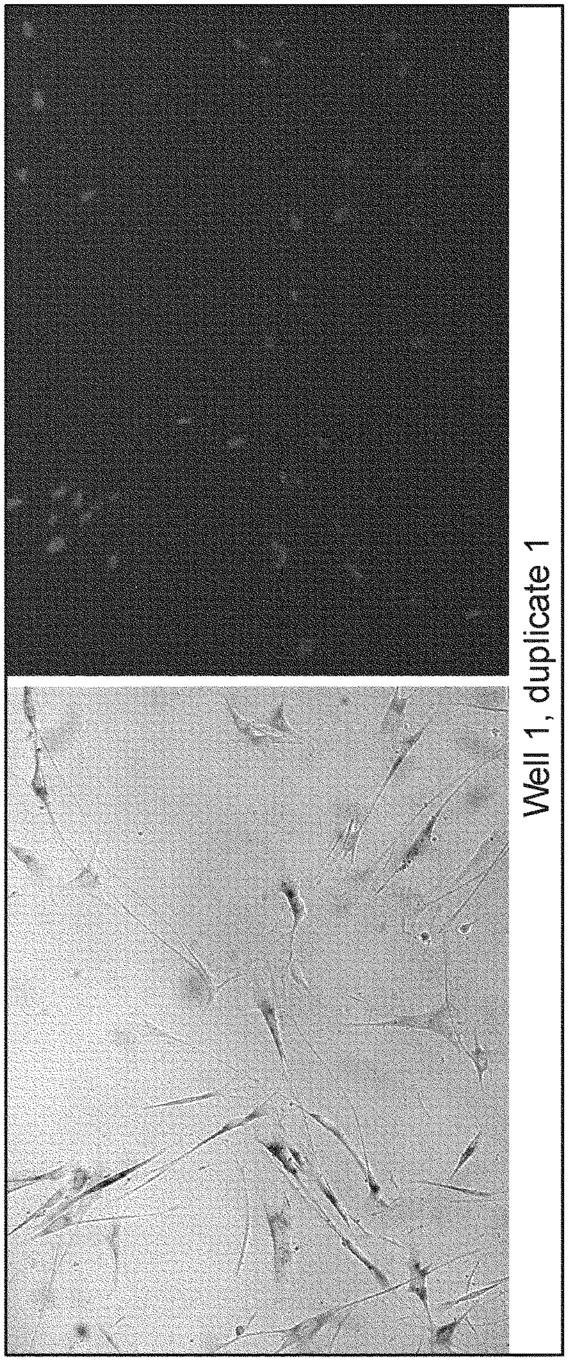
FIGS. 25A-25D are photographs of cells treated with d-methadone 500 nm+psilocin 5 nm.
Figure 25B:
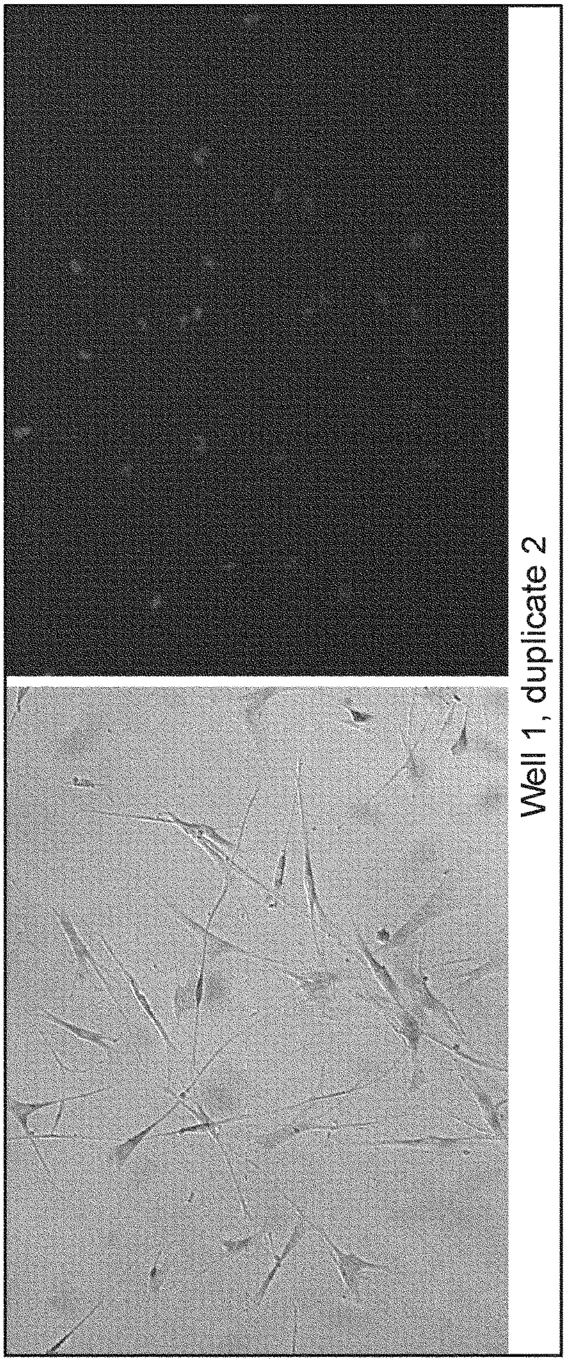
Figure 25C:
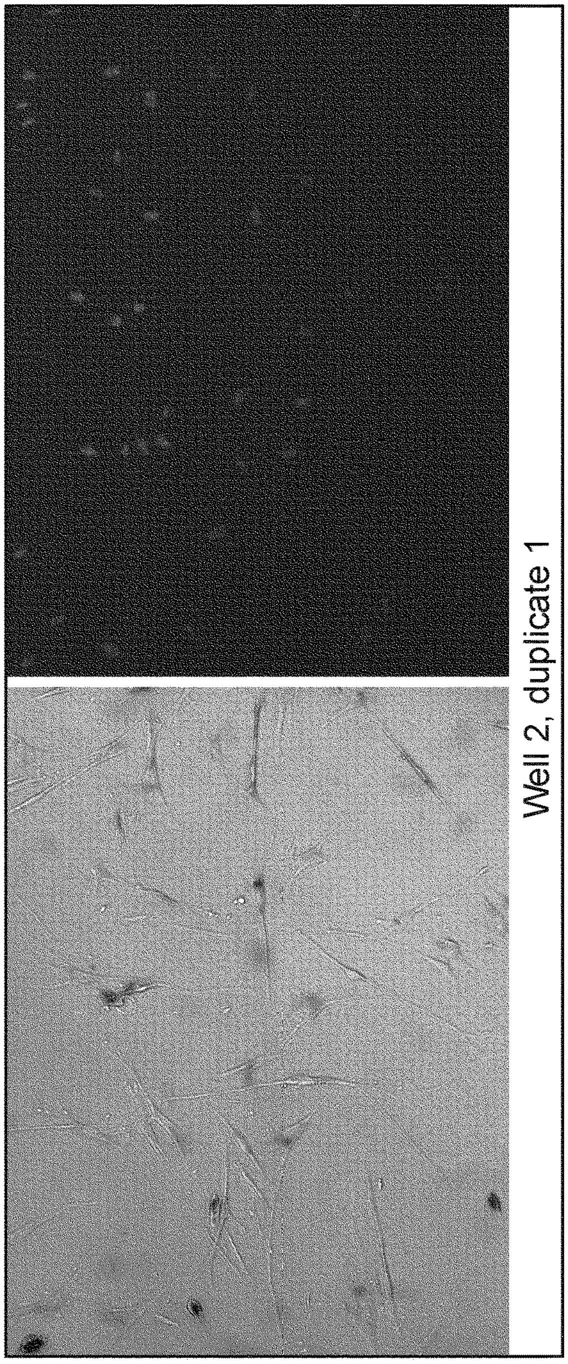
Figure 25D:
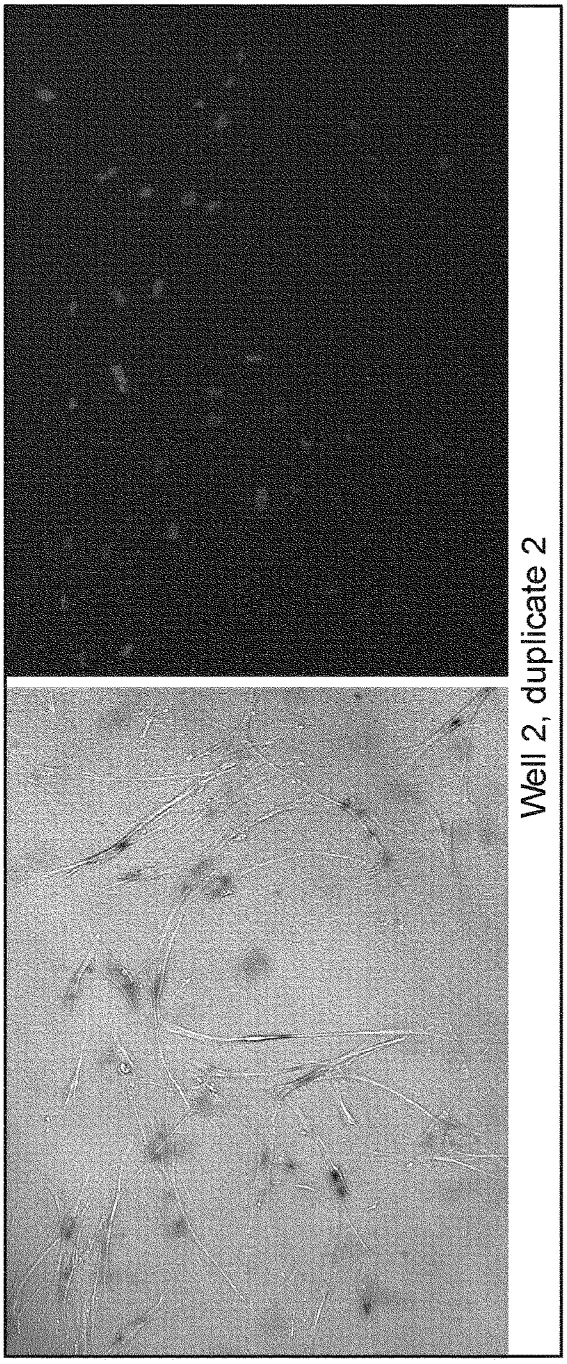
Figure 26A:
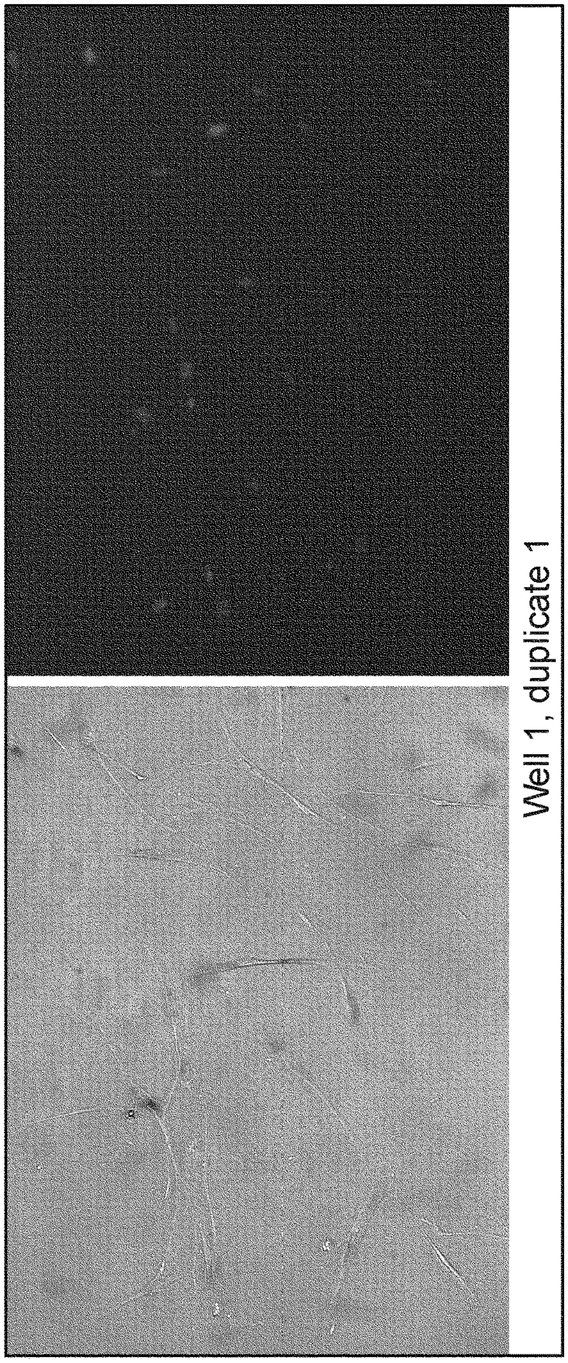
FIGS. 26A-26D are photographs of cells treated with psilocin 5 nm.
Figure 26B:
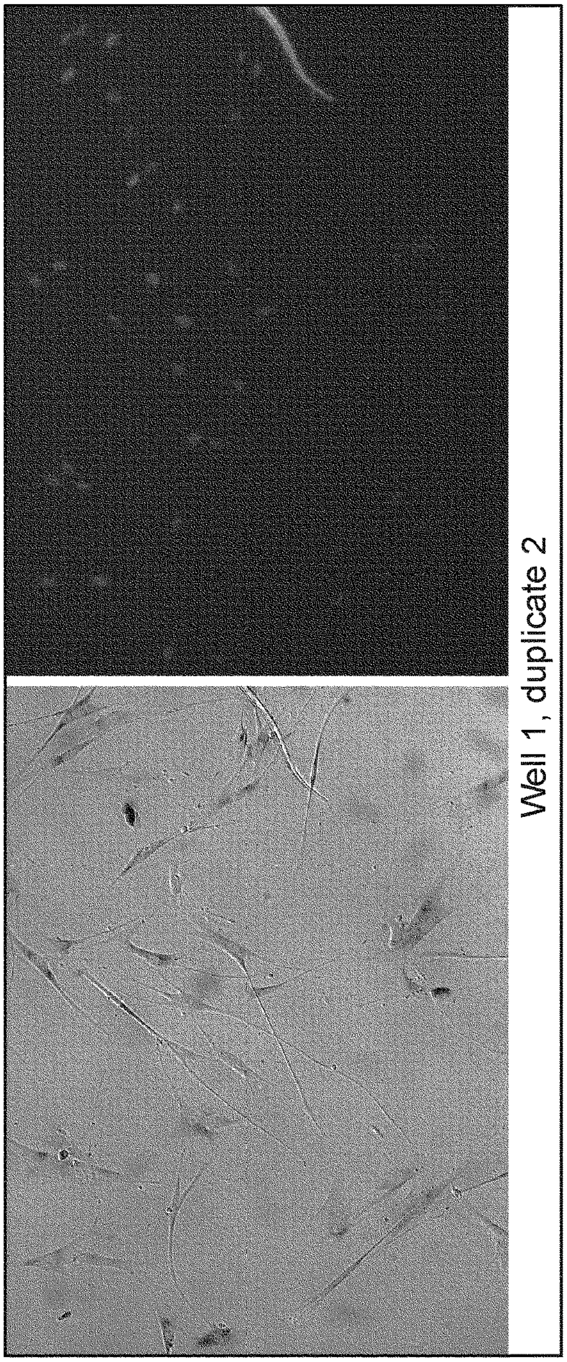
Figure 26C:
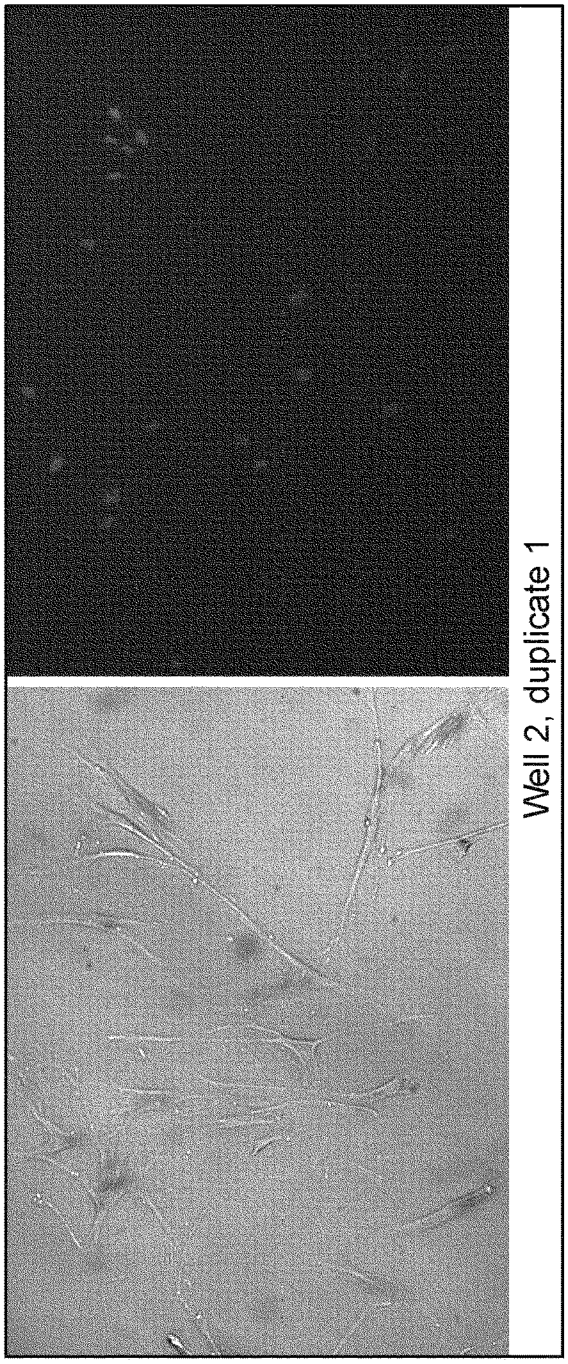
Figure 26D:
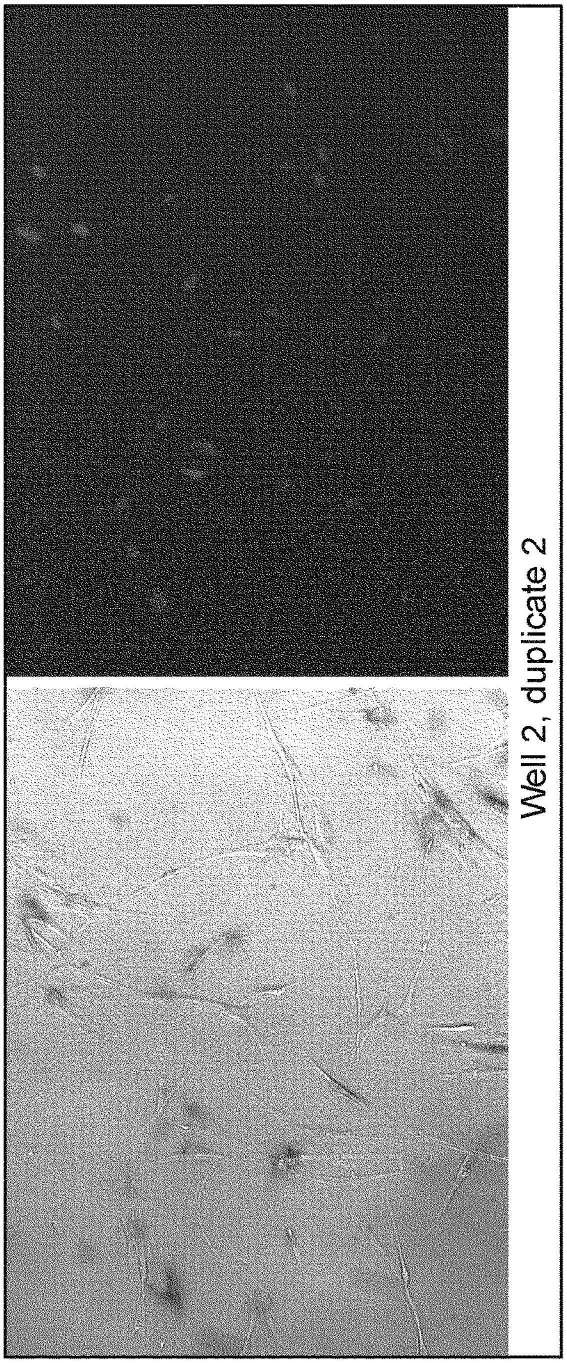
Figure 27A:
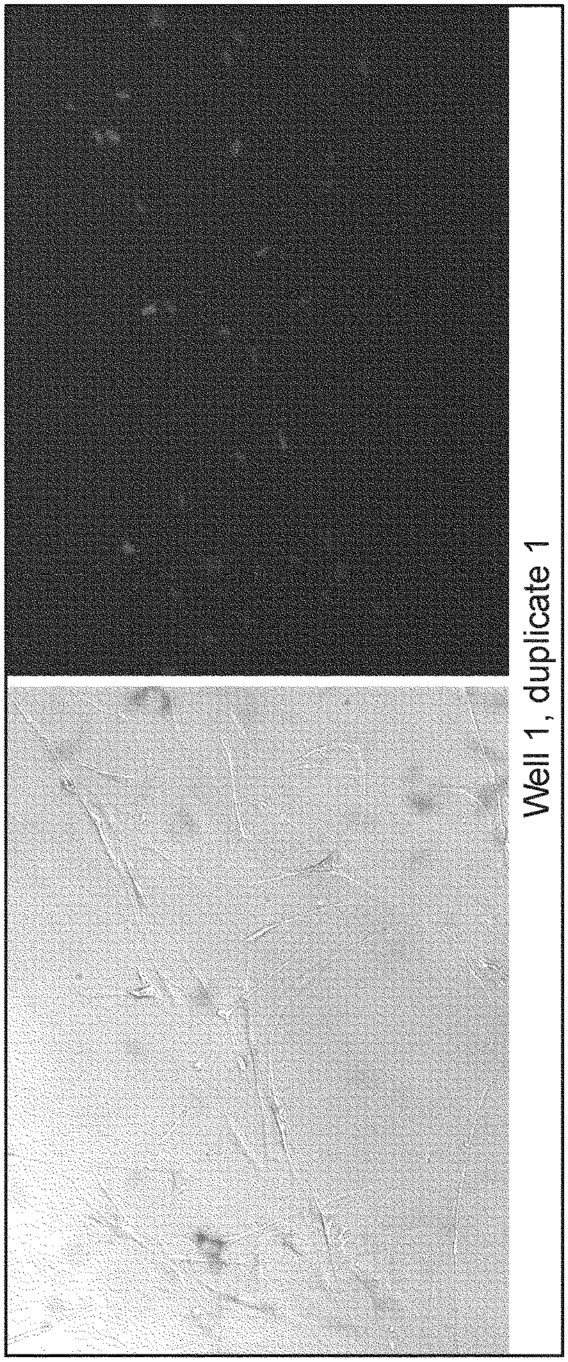
FIGS. 27A-27D are photographs of cells treated with psilocin 10 nm+d-methadone 10 nm.
Figure 27B:
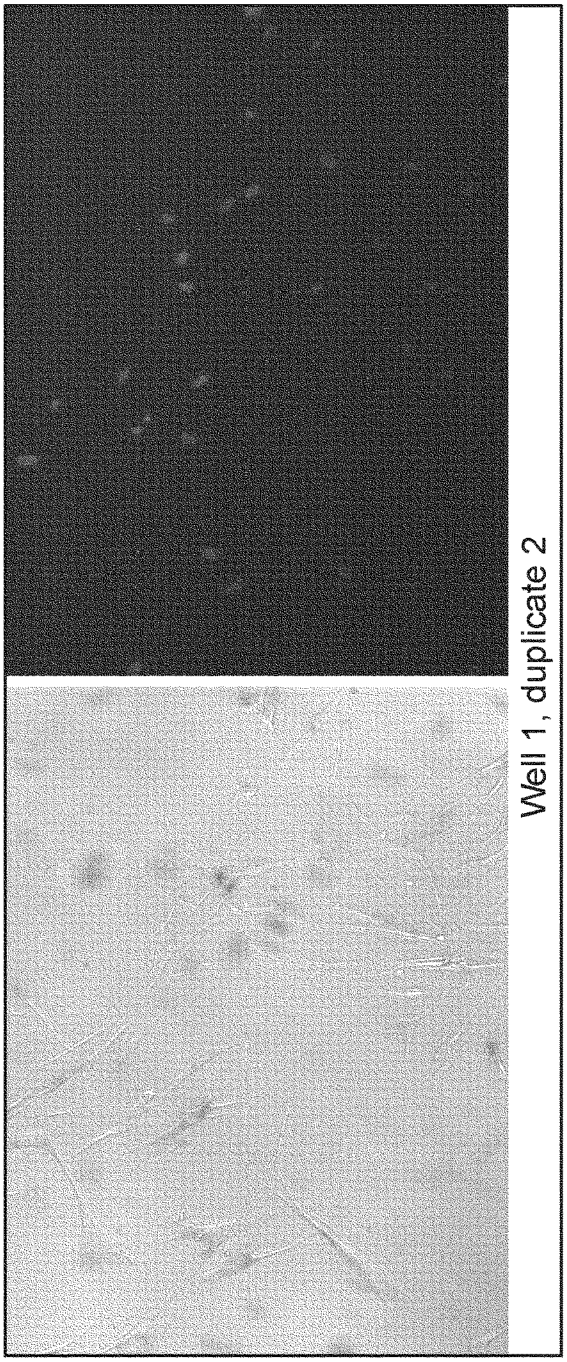
Figure 27C:
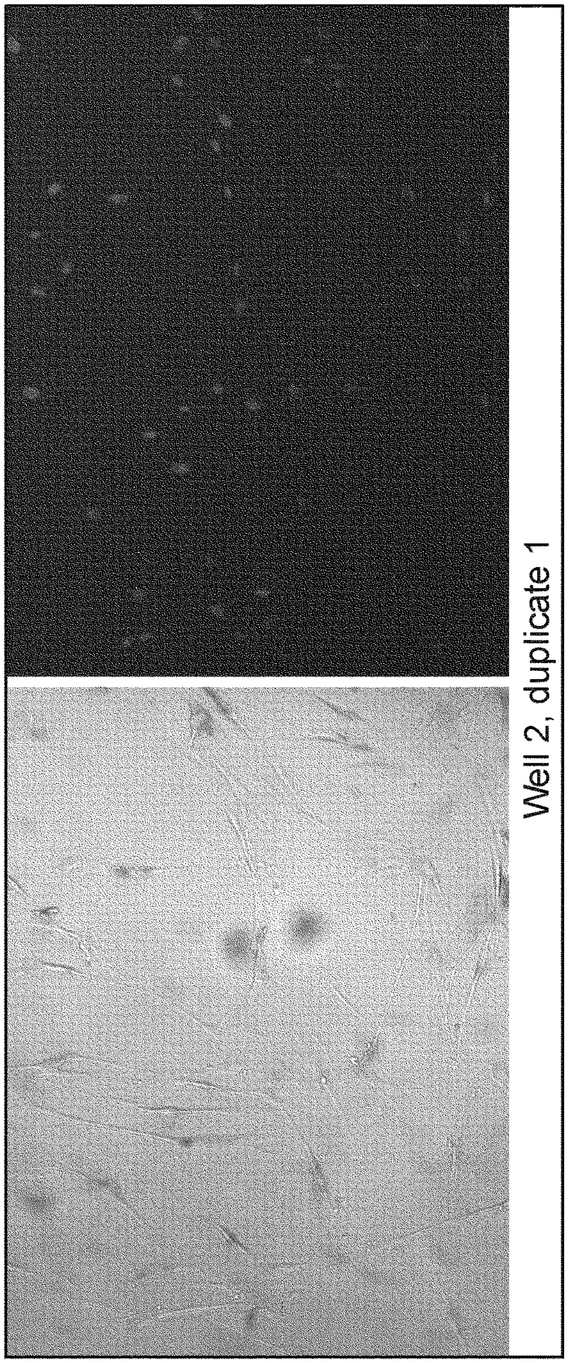
Figure 27D:
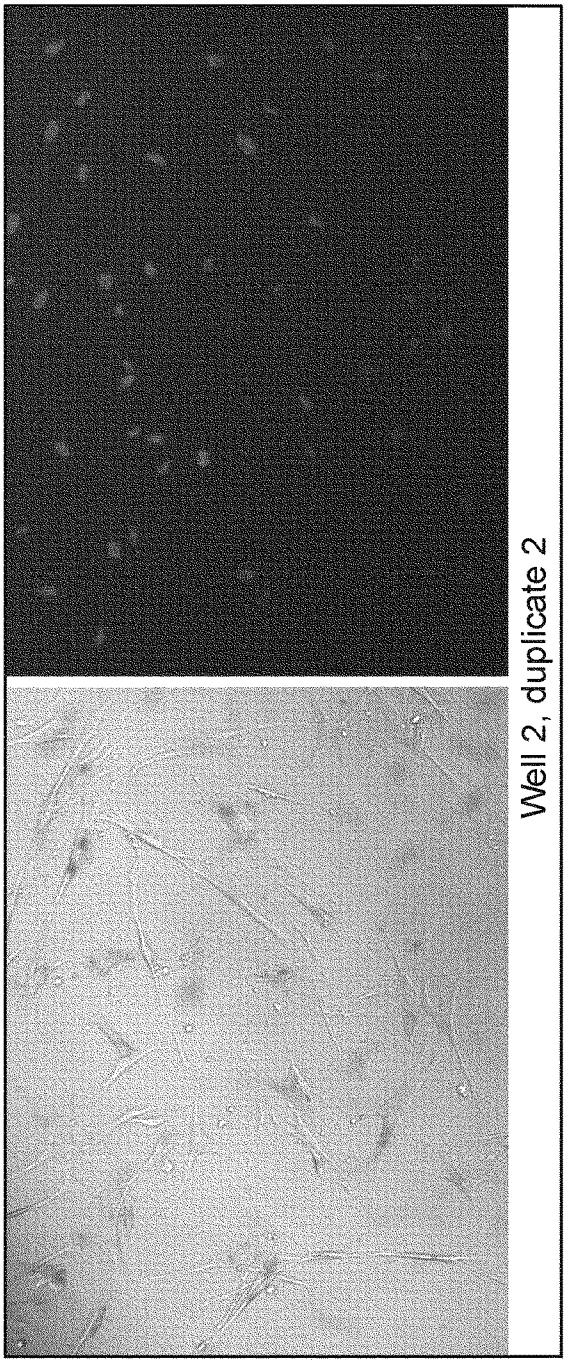

VEGF I (FIG. 17) and collagen type I gene expression did not change significantly in the keratocyte cultures treated with U937 activated CM and subsequently cultivated in the presence of 0.1 and 1 μM psilocin for 4, 10 and 24 h.

Gene expression of pro-inflammatory cytokines IL-113, IL-8, IL-12 and TNF-α was much less evident in HCE cells treated with the same CM of U937 activated monocytes (FIGS. 18A-18D). Furthermore, a significant down-regulation of gene expression was observed only for IL-8, after 10 h of treatment, in the presence of 0.1 and 1 μM psilocin.

Conclusions

This study demonstrated that psilocin, does not have a cytotoxic effect in vitro from 0.001 to 10 μM concentration. Additionally, psilocin induced a significant increase in corneal cell viability in vitro at 3 and 6 days after treatment at 0.01, 0.1 and 1 μM concentration. Moreover, at 0.1 μM and 1 μM concentration, psilocin exerts anti-inflammatory effects on keratocytes and HCE cells that could be therapeutic for anti-inflammatory treatment of ocular disorders (0.01 μM was not tested in this experiment). VEGF I (FIG. 17) and collagen type I gene expression did not change significantly in the keratocyte cultures treated with U937 activated CM and therefore no anti fibrotic effect of the molecule could be demonstrated in this model. Alternative studies should be considered to better evaluate the anti-fibrotic effects of psilocin on corneal cells using other models of inflammation or different inflammatory stimuli. The signaling pathways controlled by psilocin should also be analyzed.

Additionally, based on the study of this Example, the present inventors concluded:

a) HCE cells express NMDAR and 5-HT2A receptors; keratocytes express 5-HT2A receptors (qPCR and immunofluorescence analysis);
b) 5-HT2A agonists are not cytotoxic;
c) 5-HT2A agonists potentially increase cellular viability at neuroplastogen doses (0.01 and 0.1 microM);
d) 5-HT2A agonists are potentially effective for the treatment of inflammatory states; and
e) 5-HT2A agonists are potentially effective for the treatment of dry eye disease and dry eye syndrome.

Of note, regulation of Ca2+ influx through NMDAR may be the mechanism by which cellular viability is increased (Liu Z Y, Zhong Q W, Tian C N, Ma H M, Yu J J, Hu S. NMDA receptor-driven calcium influx promotes ischemic human cardiomyocyte apoptosis through a p38 MAPK-mediated mechanism. J Cell Biochem. 2019; 120(4):4872-4882).

Example 5—Molecular Modeling

The NMDAR modulation by 5-HT2A agonists, including the induction of select NMDAR subunits and the prevention of excitotoxicity induced by L-glutamate (as disclosed in Example 3), potentially signals an allosteric interaction downregulating excessive Ca2+ influx via the pore of excessively open NMDAR channels. This allosteric interaction could also play a role in the actions of known NMDAR antagonists that also have an effect on serotonin pathways (e.g., racemetorphan and its isomers, levometorphan and dextromethorphan, methadone and its isomers, levomethadone and dextromethadone (Codd et al. 1995), ketamine (du Jardin K. G., Liebenberg N., Muller H. K. et al. Differential interaction with the serotonin system by S-ketamine, vortioxetine, and fluoxetine in a genetic rat model of depression. Psychopharmacology 2016; 233, 2813-2825), and memantine (Onogi H, Ishigaki S, Nakagawasai O, et al. Influence of memantine on brain monoaminergic neurotransmission parameters in mice: neurochemical and behavioral study. Biol Pharm Bull. 2009; 32(5):850-855).

Conversely, the NMDAR modulation by 5-HT2A agonists and Structurally Modified Serotonergic Neuroplastogens (SMSNs) could be due to the same mechanism postulated for the known pore channel blockers, and could therefore be due to an interaction at the intra-membrane portion of the NMDAR. The present inventors tested this second hypothesis, direct interaction of 5-HT2A agonists and SMSNs with the channel pore in silico by molecular modeling investigations of select 5-HT2A agonists and SMSNs binding to the trans-membrane site of the NMDA receptor GluN1-GluN2B tetramer subtype in its closed state. The computational NMDAR subtype built for in silico testing is the GluN1-GluN2B tetramer composed by 2 GluN1 subunits and 2 GluN2B subunits. Of note N2B subunits are essential for formation of super-complexes that include NMDARs. To improve the computational efficiency of calculations, only the trans-membrane region of the receptor, where the presumed PCP binding site is located, and where the tested FDA-approved and clinically tolerated NMDA antagonists also are likely to act (dextromethorphan, ketamine, memantine), and where the present inventors hypothesize 5-HT2A agonists and their derivatives (SMSNs) may also act.

The present inventors used the structure identified by the Protein Data Bank (PDB) code 4TLM as the starting point for the computational studies to investigated the drugs shown in Table 1A and positive controls (ketamine, memantine, dextromethorphan, amantadine, MK-801, PCP all known NMDA open channel blockers presumed to act at the PCP site at the trans-membrane domain with known affinities and known clinical effects. PCP is a schedule I drug and MK-801 is a high affinity antagonist with severe side effects that impede its clinical use. The other four drugs are in clinical use and FDA approved for various indications, as indicated throughout the application. As seen in Table 1 B, the docking scores for many of the SMSNs are in a similar range as those of established NMDAR channel blockers shown in Table 3 below.

TABLE 3

| Molecule | Predicted Affinity (Docking) (Delta G, kcal/mol) |
|---|---|
| MK-801 | −6.8 |
| PCP | −6 |
| Ketamine | −5.8 |
| Memantine | −5.8 |
| Amantadine | −5.23 |
| Dextromethorphan | −6.3 |

Most tested compounds show predicted affinity results (docking results, Table 1 B) in a range similar to compounds with known NMDAR blocking actions (−5-7 predicted affinity, Table 3). These in silico results signal potential NMDAR blocking effects at the pore channel for 5-HT2A compounds and select SMSNs. The present inventors are now planning in silico dynamic modeling and in vitro FLIPR calcium assays to better define and quantify the NMDAR blocking actions of Table 1A molecules.

These in silico results signal potential NMDAR blocking effects at the pore channel for 5-HT2A compounds and select SMSNs.

Example 6—Antisenescence Effects

The present inventors analyzed the antisenescence effects of psilocin and d-methadone on UVB induced senescence in IMR-90, passage 20. Seeding occurred on Day 1, with pretreatment on Day 2, and UVB-induction and retreatment on Day 3, SABG on Day 8, and microscopy (SABG) on Day 9. Antisenescence effect was observed with 10 nM psilocin in combination with 10 nM d-methadone with a 34% reduction in of Beta Gal positive cells. Higher doses of psilocin (up 24 microM, experiment not shown) and lower doses (5 nM, from this Example 6), showed no antisenescence effects. Results for Example 6 can be seen in FIGS. 19A-27D, and Tables 4, 5, and 6 below.

TABLE 4

| Beta Gal assay<br>Experiment 3: Analyzing antisenescence effect of D-Methadone and Psilocin on UVB induced senescence | | | | | |
|---|---|---|---|---|---|
| Cell Line | IMR-90, passage 20 | | | | |
| Drug Concentration | D-methadone | 10 nM | 500 nM | 10 nM + Psilocin 5 nM | 500 nM + Psilocin 5 nM |
| | Psilocin | 5 nM | 10 nM +10 nM D-methadone | | |

TABLE 5

| Beta Gal assay (raw data) | | | | | | | | | |
|---|---|---|---|---|---|---|---|---|---|
| Compounds | Concentration (nM) | Wall | Duplicate | Total number of cells | Bata Gal+ | % | Avg % | SEM | Total % |
| No UVB | — | 1 | 1 | 39 | 4 | 10.25641 | 15.98411 | 3.15094 | 61.32479 |
| | | | 2 | 34 | 7 | 20.58824 | | | |
| | | 2 | 1 | 46 | 5 | 10.86957 | | | |
| | | | 2 | 27 | 6 | 22.22222 | | | |
| UVB without treatment | — | 1 | 1 | 41 | 35 | 85.36585 | 85.63514 | 2.877047 | 72.81106 |
| | | | 2 | 41 | 32 | 78.09878 | | | |
| | | 2 | 1 | 47 | 41 | 87.23404 | | | |
| | | | 2 | 37 | 34 | 91.89189 | | | |
| D methadone | 10 | 1 | 1 | 32 | 23 | 71.875 | 79.00807 | 2.946393 | 81.29496 |
| | | | 2 | 35 | 30 | 85.71429 | | | |
| | | 2 | 1 | 57 | 44 | 77.19298 | | | |
| | | | 2 | 32 | 26 | 81.25 | | | |
| | 500 | 1 | 1 | 35 | 29 | 82.85714 | 83.33683 | 3.13222 | 83.93939 |
| | | | 2 | 17 | 14 | 82.35294 | | | |
| | | 2 | 1 | 34 | 26 | 76.47059 | | | |
| | | | 2 | 36 | 33 | 91.66667 | | | |
| | 10 + Psilocin 5 nm | 1 | 1 | 45 | 39 | 86.66667 | 82.08539 | 5.23897 | 87.41007 |
| | | | 2 | 35 | 24 | 68.57143 | | | |
| | | 2 | 1 | 30 | 24 | 80 | | | |
| | | | 2 | 29 | 27 | 93.10345 | | | |
| | 500 + Psilocin 5 nm | 1 | 1 | 37 | 35 | 94.59459 | 92.5917 | 1.272872 | 73.86831 |
| | | | 2 | 37 | 35 | 94.59459 | | | |
| | | 2 | 1 | 28 | 25 | 89.28571 | | | |
| | | | 2 | 37 | 34 | 91.89189 | | | |

TABLE 6

| Beta Gal assay (raw data) | | | | | | | | | |
|---|---|---|---|---|---|---|---|---|---|
| Compounds | Concentration (nM) | Wall | Duplicate | Total number of cells | Bata Gal+ | % | Avg % | SEM | Total % |
| Psilocin | 5 | 1 | 1 | 20 | 15 | 75 | 82.29978 | 2.649643 | 64.45313 |
| | | | 2 | 21 | 18 | 85.71429 | | | |
| | | 2 | 1 | 33 | 27 | 81.81818 | | | |
| | | | 2 | 30 | 26 | 86.66667 | | | |
| | 10 + D Methadone 10 nm | 1 | 1 | 34 | 14 | 41.17647 | 51.77845 | 3.695966 | 51.97368 |
| | | | 2 | 46 | 26 | 56.52174 | | | |
| | | 2 | 1 | 44 | 23 | 52.27273 | | | |
| | | | 2 | 28 | 16 | 57.14286 | | | |
| | | | 2 | 37 | 35 | 94.59459 | | | |
| | | 2 | 1 | 28 | 25 | 89.28571 | | | |
| | | | 2 | 37 | 34 | 91.89189 | | | |

Example 7—Psilocin-Carbamate

1. Effects of Isoleucinyl Carbamate on Young, Adult and Old Mice Fed with High Fructose Hypothesis: Low dose chronic treatment with psilocin-carbamate (isoleucinyl carbamate) is well tolerated and ameliorates cognitive and metabolic performances of high fructose-treated mice of different ages.

Background:

Psilocybin is believed to act as a prodrug for psilocin (Jacob III, P.; Shulgin, A. T. in NIDA Research Monograph 146 (Hallucinogens, an Update), 2000, Eds. Lin, G. C.; Glennon, R. A., pp. 74), since it is dephosphorylated in vivo by alkaline phosphatase to the active compound psilocin. Furthermore, psilocin chemically degrades quickly in the presence of air, heat, and/or light, due to the presence of the free 4-hydroxy group on the tryptamine scaffold, which is susceptible to oxidation. On the other hand, psilocybin is far more stable than psilocin due to the presence of a phosphate ester, which protects the 4-OH group from both chemical and metabolic degradation. Thus, the prodrug approach might be considered a "smart" strategy to overcome psilocin limitations and obtain sustained plasma levels of psilocin after administration of the more stable psilocybin molecule.

The present inventors here evaluated the efficacy and safety of a new psilocin carbamate prodrug (isoleucinyl carbamate) in which the 4-hydroxyl moiety is reversibly protected as a carbamate ester linked to the N-terminus of an isoleucine. It has been shown that lipophilic amino acid carbamate ester prodrugs of phenolic compounds strongly improve their bioavailability, by increasing absorption after oral administration, reducing metabolism and leading to a sustained release, up to 24 hours, of low concentrations of the active compound particularly to brain tissue (See, e.g., Azzolini et al. (2017) Eur J Pharm Biopharm volume 115, pages 149-158). A sustained release formulation of the active compound psilocin with lower Cmax and Tmax concentrations could represent an advantage for psilocin pharmacological safe uses by potentially avoiding the psychedelic/psychotomimetic effects of psilocin and psilocybin administration (which are dependent on reaching certain plasma concentrations as disclosed in the present application) while potentially maintaining the ability to promote both structural and functional plasticity in brain tissue. Therefore, the present inventors designed, synthesized, and administered this novel drug, isoleucinyl carbamate, designed to young, adult and old mice fed with a standard diet enriched with 30% fructose in drinking water to obtain information about i) the preliminary toxicological profile of this psilocin prodrug in mice of different ages; ii) preliminary signals about its potential efficacy for the treatment of diseases and conditions. In particular, the effect of the administration of psilocin-carbamate on cognitive behavior and some synaptic markers was evaluated, since recent studies reported that obesity and the consumption of fat and sugar-enriched diets accelerate the aging process and potentially leads to neuro-psychiatric effects. (Ogrodnik M, Zhu Y, Langhi L G P, Tchkonia T, Kruger P, Fielder E, Victorelli S, Ruswhandi R A, Giorgadze N, Pirtskhalava T, Podgorni O, Enikolopov G, Johnson K O, Xu M, Inman C, Palmer A K, Schafer M, Weigl M, Ikeno Y, Burns T C, Passos J F, von Zglinicki T, Kirkland J L, Jurk D. Obesity-Induced Cellular Senescence Drives Anxiety and Impairs Neurogenesis. Cell Metab 2019; 29: 1233, 2019).

Methods:

12 c57BL/6 male mice of different ages (young: 2 months old, adult: 5 months old, old: 18 months old) were housed 4 per cage at a temperature of 21° C., alternating 12 hours of light and 12 hours of dark. Mice were fed with standard diet and fructose (30% w/v in drinking water) was added to their diet 4 days before randomization. Then, mice were randomly divided into 2 subgroups per age (N=2 animals per group) treated daily for 15 days by gastric gavage respectively with aqueous vehicle or psilocin-carbamate (0.05 mg/kg body weight).

All procedures involving animals were performed in compliance with institutional guidelines in compliance with national and international laws and policies (Council Directive of the European Economic Community 86/609, OJ L 358, 1, Dec. 12, 1987; NIH Guide for the Care and Use of Laboratory Animals, NIH Publication No. 85-23, 1985). The study design was approved by the Ethics Committee of the University of Padua for the care and use of laboratory animals and by the Italian Ministry of Health.

Results:

During the experiment, the animals were carefully monitored every day for a period not exceeding the maximum experimental endpoints. Access to water (30% w/v fructose) and food ad libitum was allowed. No obvious clinical symptoms were observed during the experimental period. No signs of toxicity and no mortality was observed during the 14 days of psilocin-carbamate or vehicle administration via gastric gavage.

Body and Liver Weight

Figure 28A:
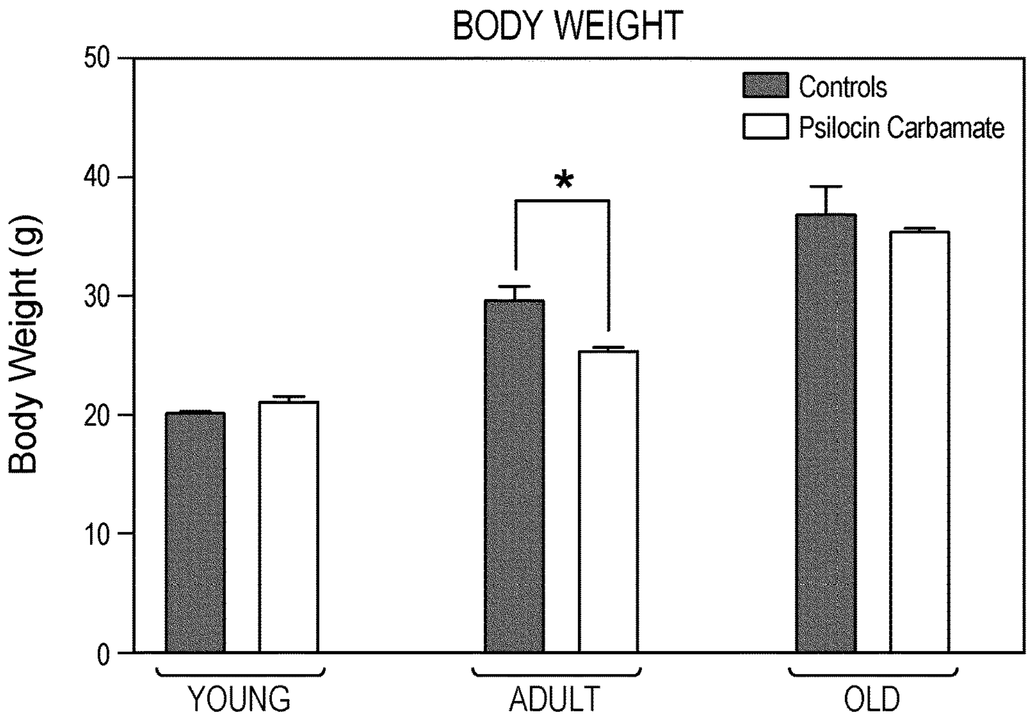
FIG. 28A is a graph showing the effect of psilocin-carbamate on body (pre-treatment and after treatment) at sacrifice. *$P<0.05$, Student's t test for unpaired data.
Figure 28B:
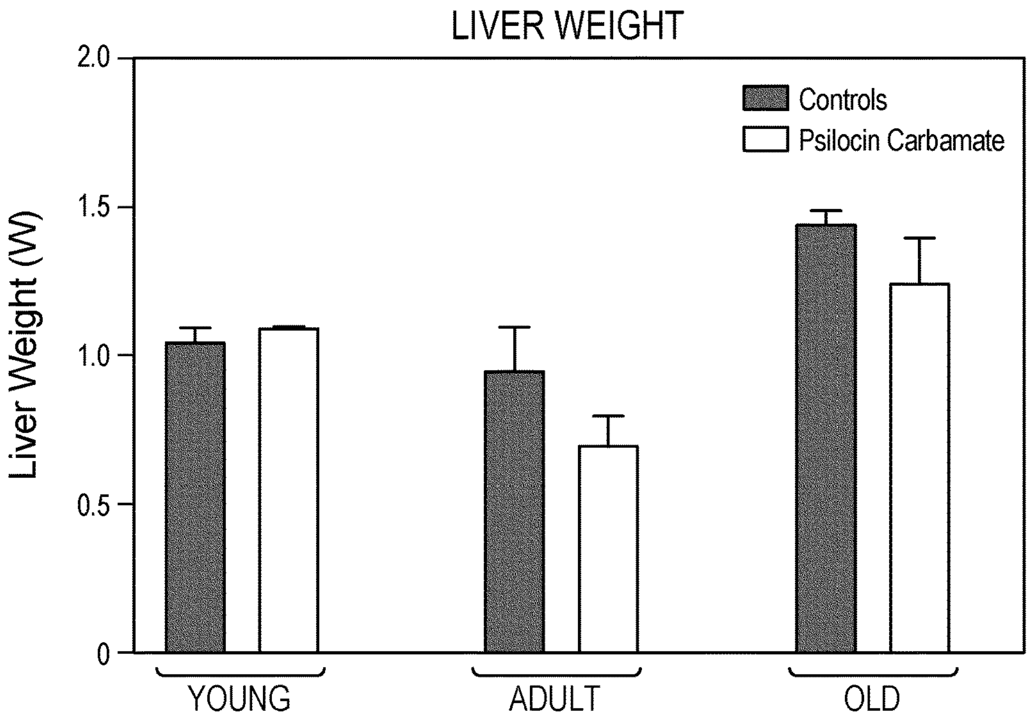
FIG. 28B is a graph showing the effect of psilocin-carbamate on liver weight (pre-treatment and after treatment) at sacrifice. *$P<0.05$, Student's t test for unpaired data.

Referring to FIGS. 28A and 28B, at sacrifice, the present inventors observed a decrease in body ($p<0.05$) and liver weight in adult mice treated with psilocin-carbamate. Notably, the same tendency could be observed in old mice, while the treatment with psilocin-carbamate has no effect on body and liver weight of young mice.

Blood Glucose

Figure 29:
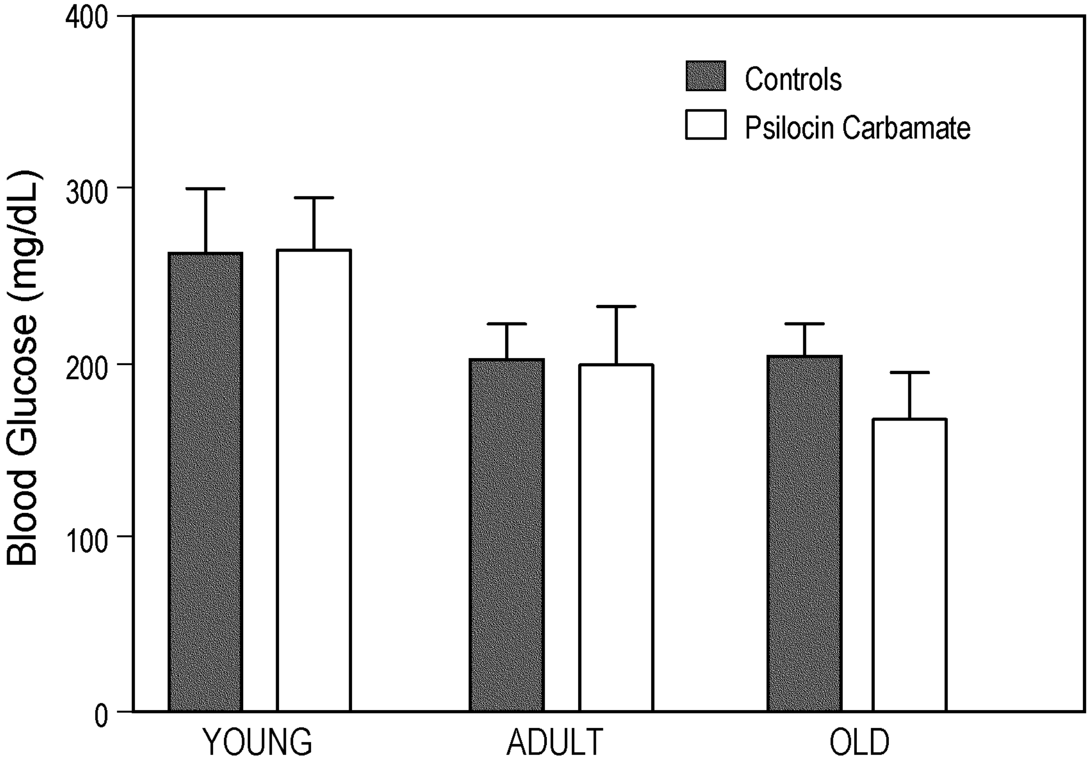
FIG. 29 is a graph showing the effect of psilocin-carbamate on blood glucose.

Before sacrifice, the present inventors measured the blood glucose concentration of the mice after a 2-hours fasting. The present inventors did not observe statistically significant differences between groups, although FIG. 29 shows that young mice have higher blood glucose levels than adult and old mice, and psilocin-carbamate has no effect on blood glucose control. A tendency towards a lower blood glucose concentration was observed in the old mice treated with psilocin-carbamate.

Behavioral Testing

In order to ascertain whether the chronic administration of low dose psilocin-carbamate alters behavior in tested mice, the present inventors performed the Locomotion Activity Test (LMA), the Novelty Suppressed Feeding (NSF) test and the olfactory habitation/dishabituation test before and after the psilocin-carbamate treatment.

LMA has the aim of assessing spontaneous locomotor activity in laboratory animals. This test is performed in a gray arena (open field) exposed to light of regulated intensity (24 and 30 lux), avoiding light-shadow zones within the perimeter in which the experiment takes place. Along the base of the open field, 4 standard sized squares have been drawn, clearly visible even in the dark and large enough to allow the animal to remain inside them in all its length. The LMA test has been preceded by one hour of habituation, at the end of which the rat was inserted inside the open field, in one of the previously designed squares. The movements and behaviors in reaction to the environment were then recorded for 10 minutes.

Three fundamental aspects were assessed: 1. the number of crossings, i.e., the number of crossings made by the animal from one square to another, passing the line defining it with both legs. This value gives an indication of the distance traveled by the animal during the test and of its locomotor activity; 2. the number of rearings, i.e, the number of times the animal lifts up on the two posterior legs. This value is proportional to the state of anxiety experienced; and 3. the time of grooming, i.e., the interval of time spent by the animal in washing itself, another indicative value of the state of anxiety experienced during the test.

Figure 30A:
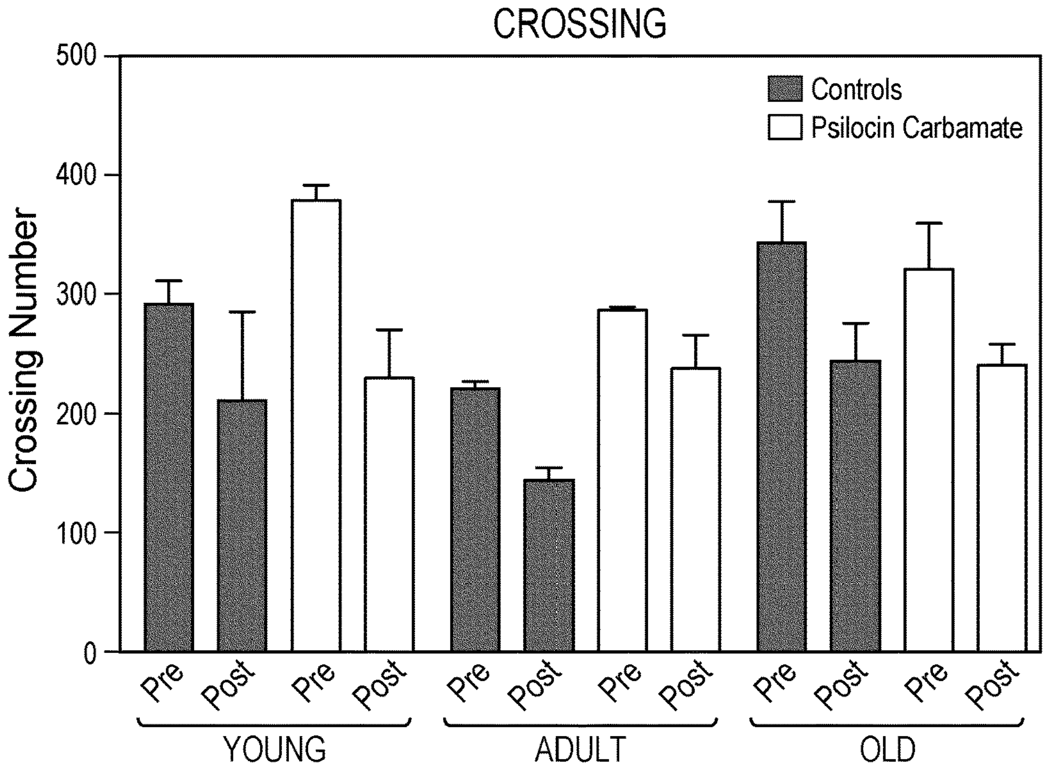
FIGS. 30A-30C are graphs showing the results for a Locomotion Activity Test for crossings (FIG. 30A), rearing (FIG. 30B), and grooming (FIG. 30C).
Figure 30B:
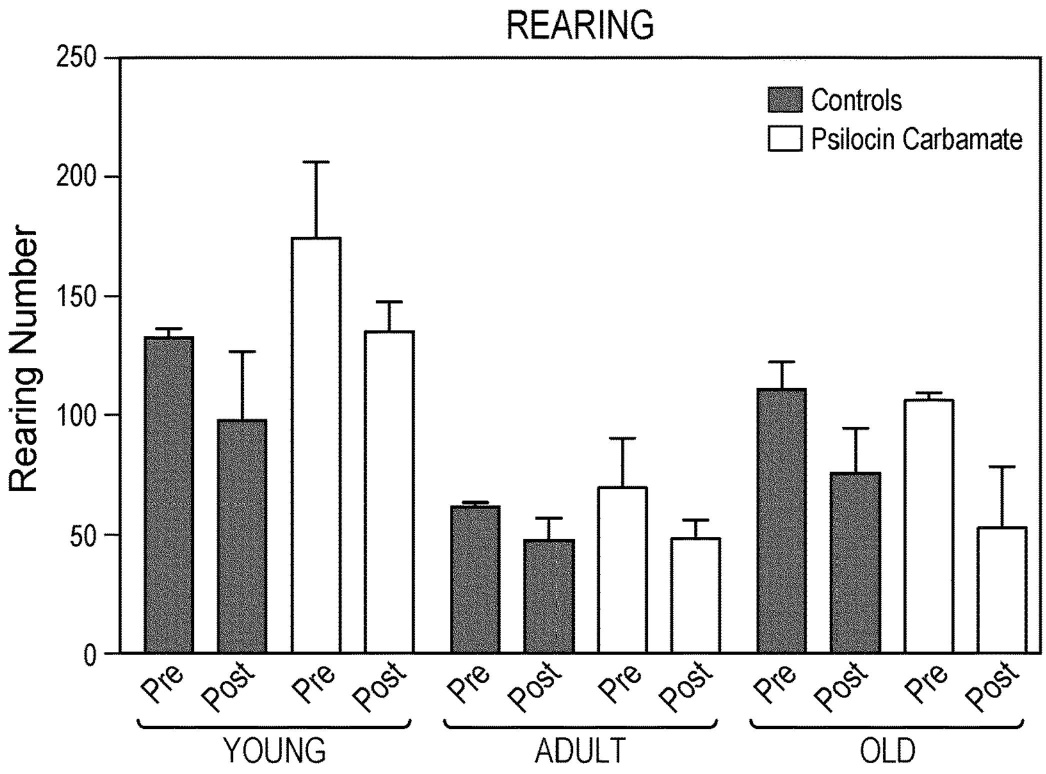
Figure 30C:
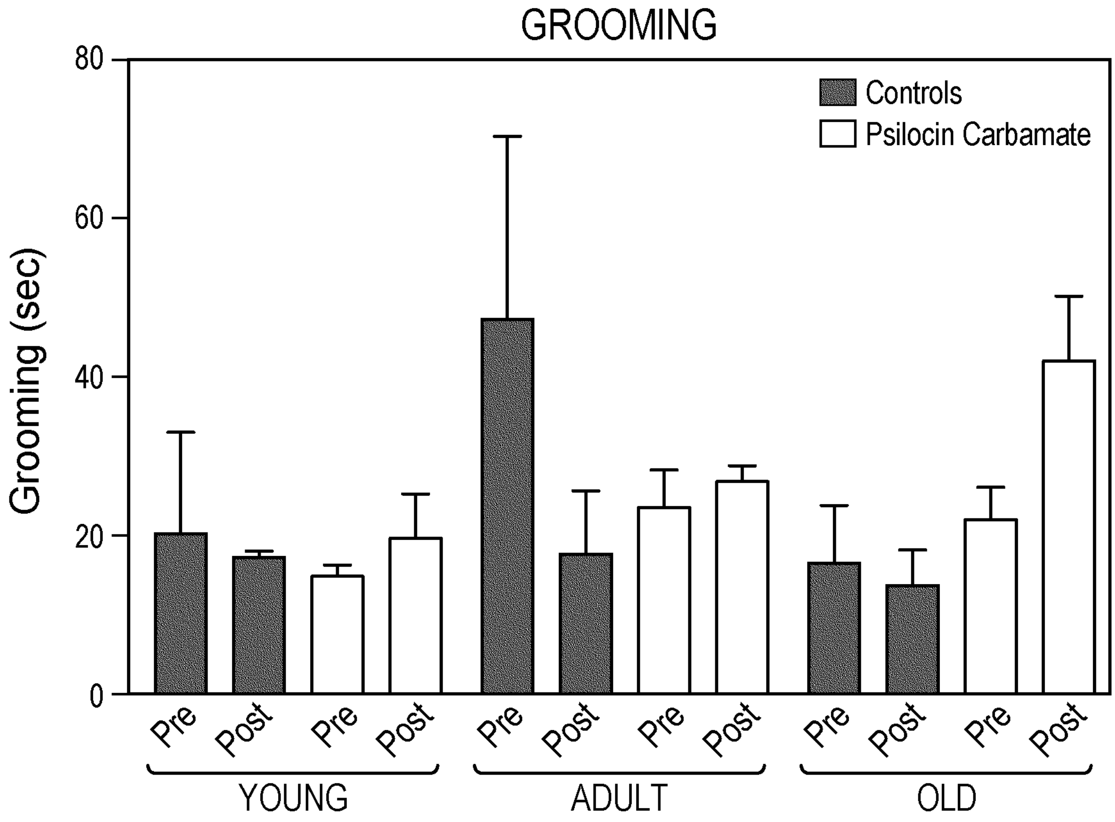

Referring to FIGS. 30A-30C, as far as the number of crossings is concerned, the present inventors observed a decreasing tendency in the post-treatment test of both treated and untreated mice. This is probably due to the habituation of animals to the test. The same observation could be made for rearing, whereas grooming was generally unaffected by habituation. Only in old mice an increasing tendency ($p=0.089$) of the time spent for grooming could be observed in psilocin-carbamate-treated mice. Of note, there was no evidence of psychedelic behavioral effects from chronic (14 day) low dose 0.05 mg/Kg psilocin-carbamate (isoleucinyl carbamate) administration.

The Novelty Suppressed Feeding (NSF) test was performed to evaluate stress and the degree of hunger of mice after an overnight fast according to an already described protocol (Blasco-Serra et al., 2017). The arena in which the test was performed was illuminated with a greater light intensity in the center and less in the periphery. In the center of the arena a platform was placed, consisting of a Petri dish with a paper disc and one feeding pellet. After fasting for at least 12 hours, animals were subjected to habituation for 60 min before starting the experiment, in order to get used to the new environment and minimize stress. Then, each mouse was placed in the arena and his behavior was monitored for maximum 10 minutes. When the mouse finally reached and started to eat the pellet, it was moved to another standard cage for 5 minutes, with an easily available feeding pellet.

Figure 31A:
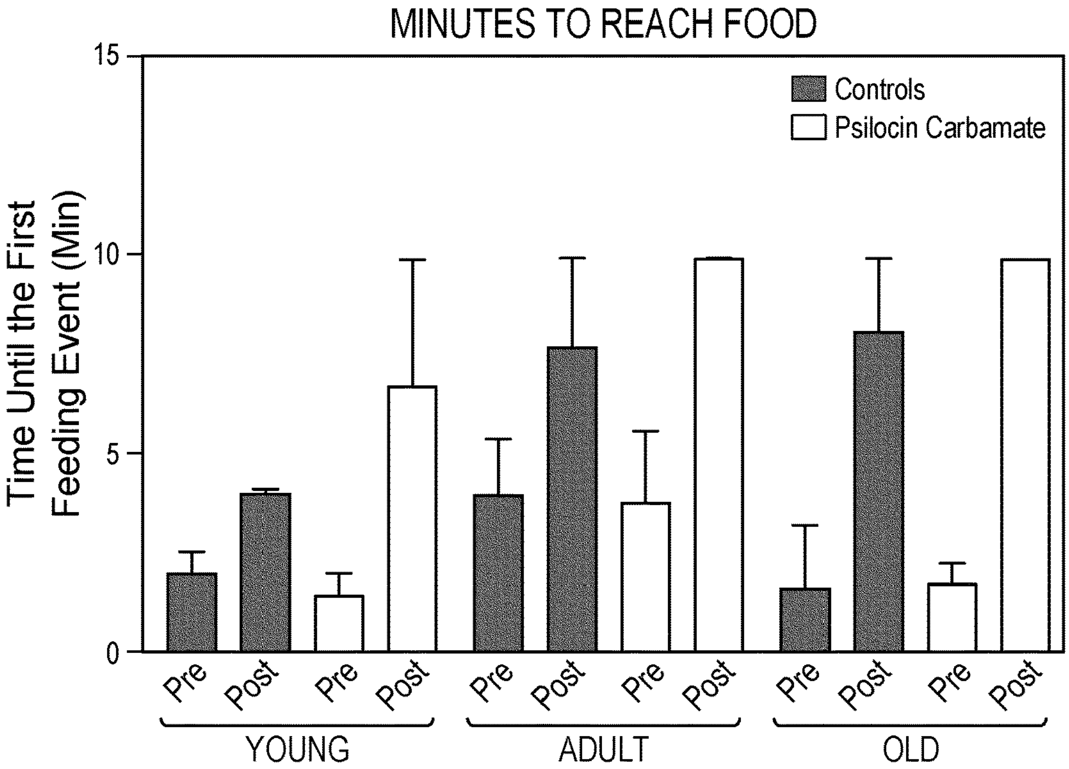
FIGS. 31A-31C are graphs showing the results for a Novelty Suppressed Feeding Test for minutes to reach food (FIG. 31A), times approaching food (FIG. 31B), and food eaten within five minutes (FIG. 31C).
Figure 31B:
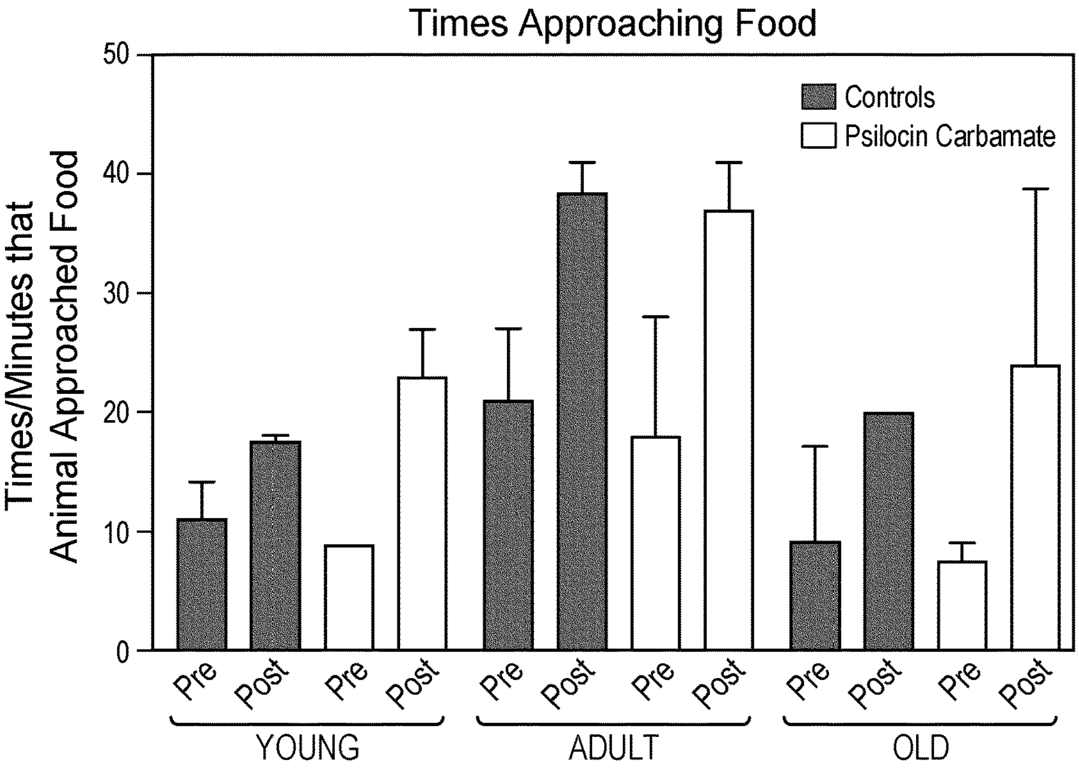
Figure 31C:
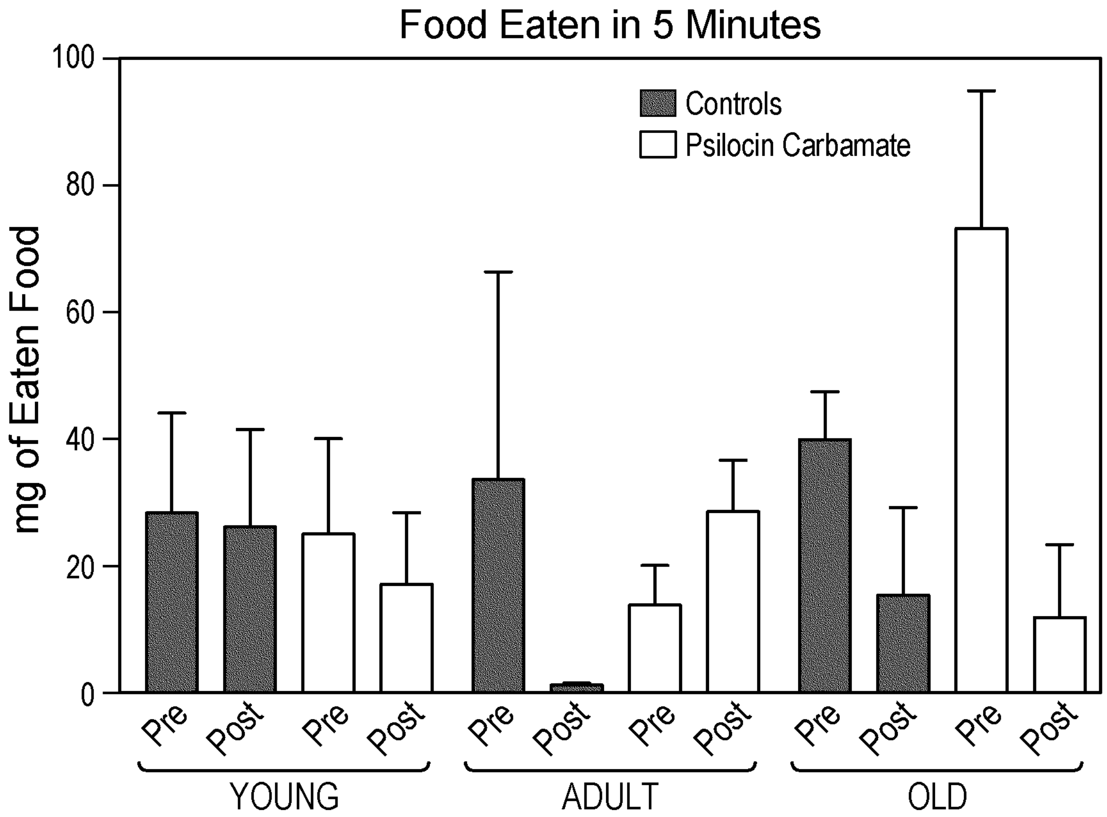
Figure 32A:
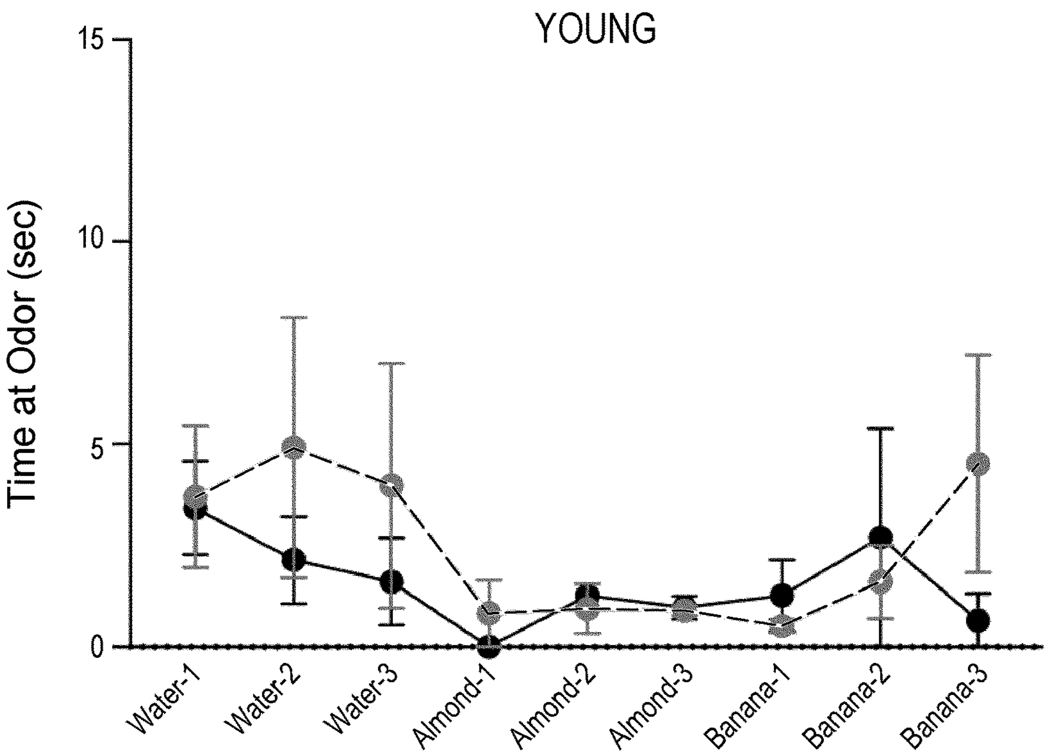
FIGS. 32A-32F are graphs showing the results of an olfactory habituation/dishabituation test with non-social stimuli. Control (black line) and psilocin-carbamate treated (dashed line) mice.
Figure 32B:
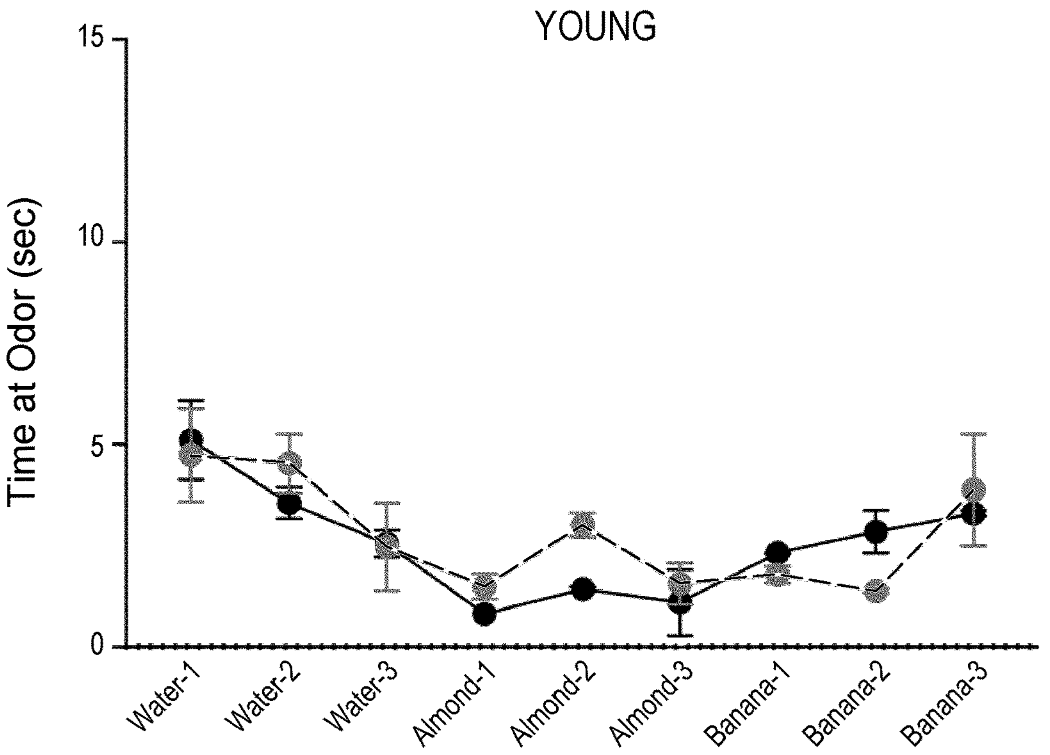
Figure 32C:
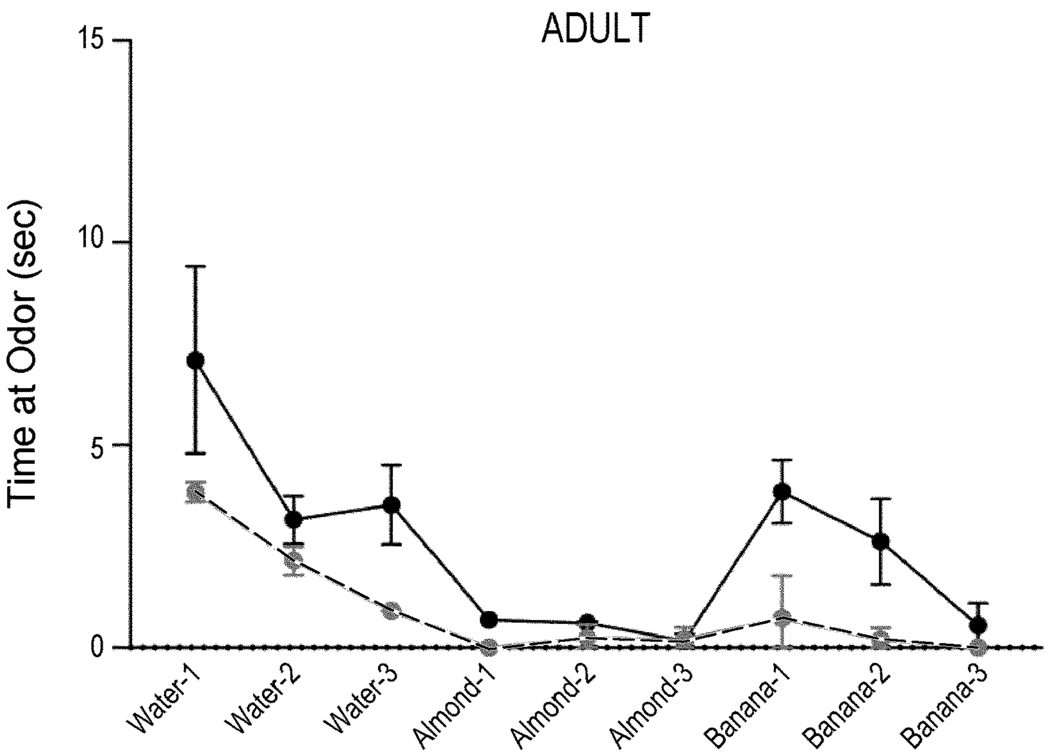
Figure 32D:
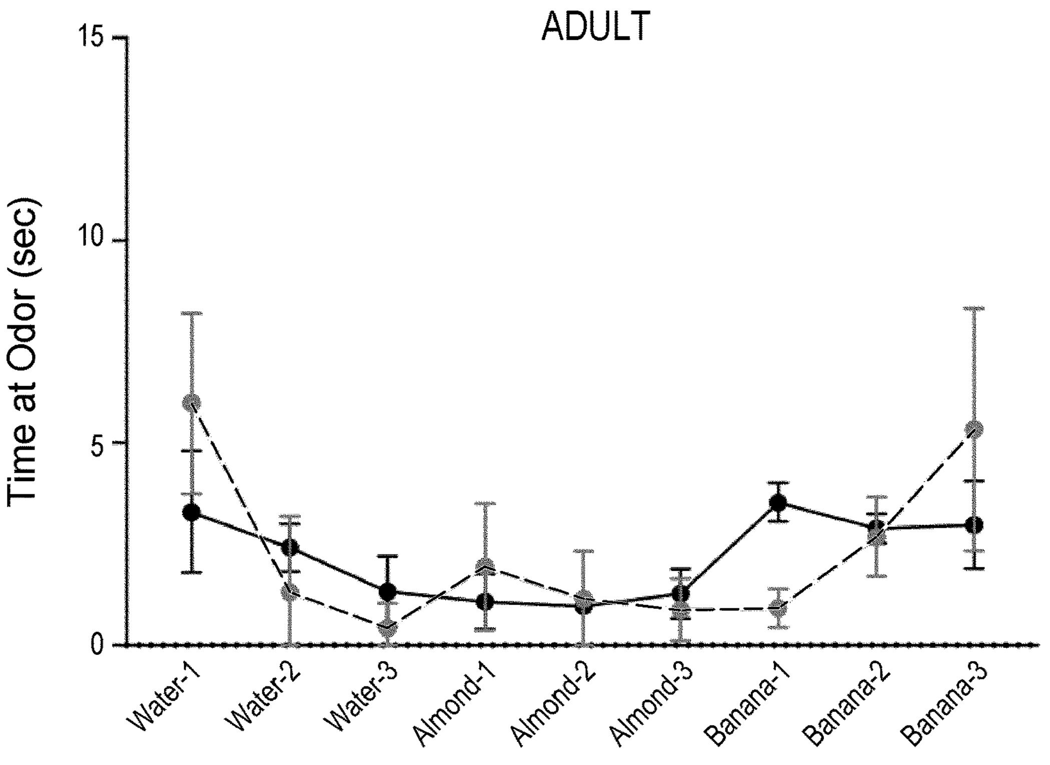
Figure 32E:
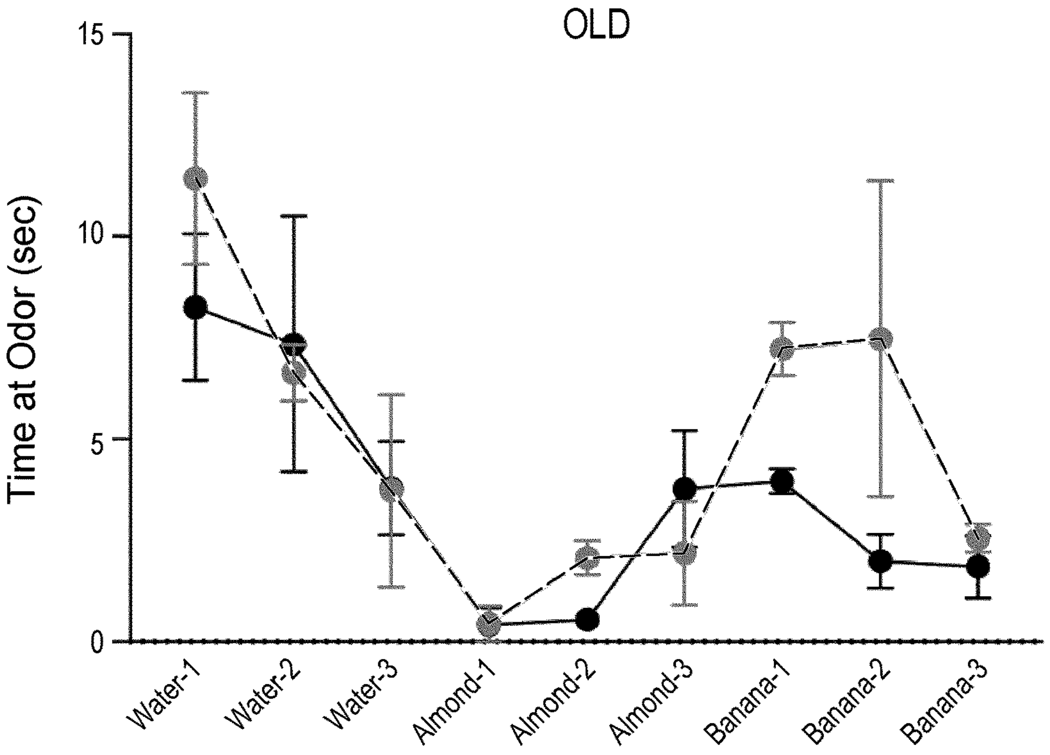
Figure 32F:
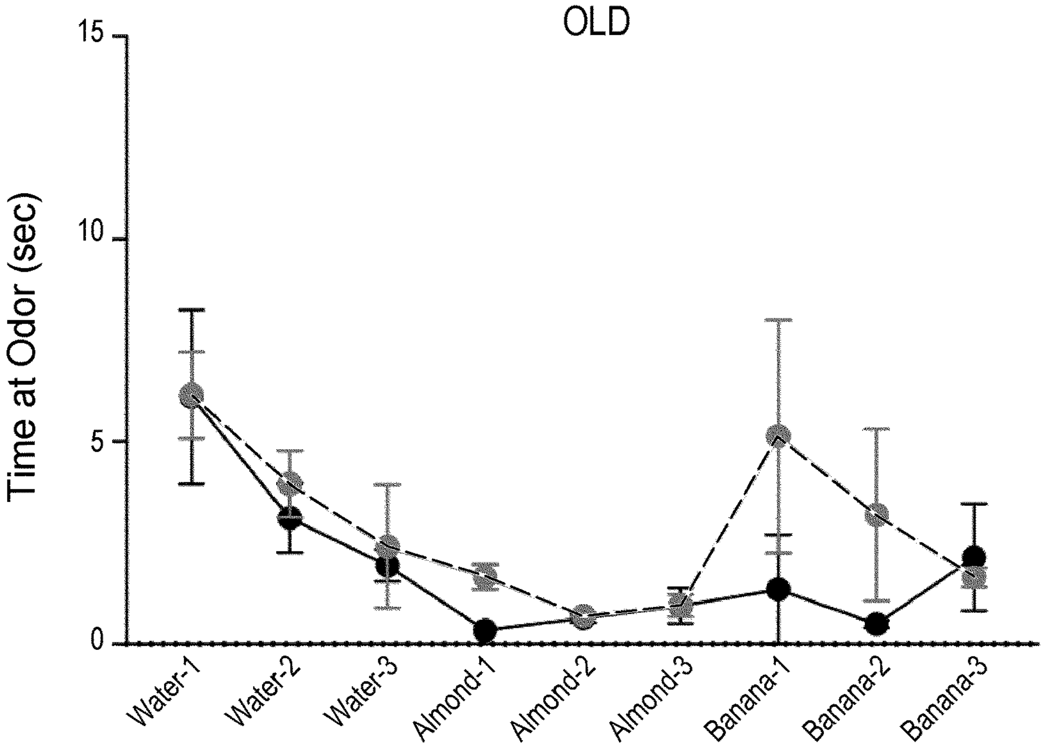
Figure 33A:
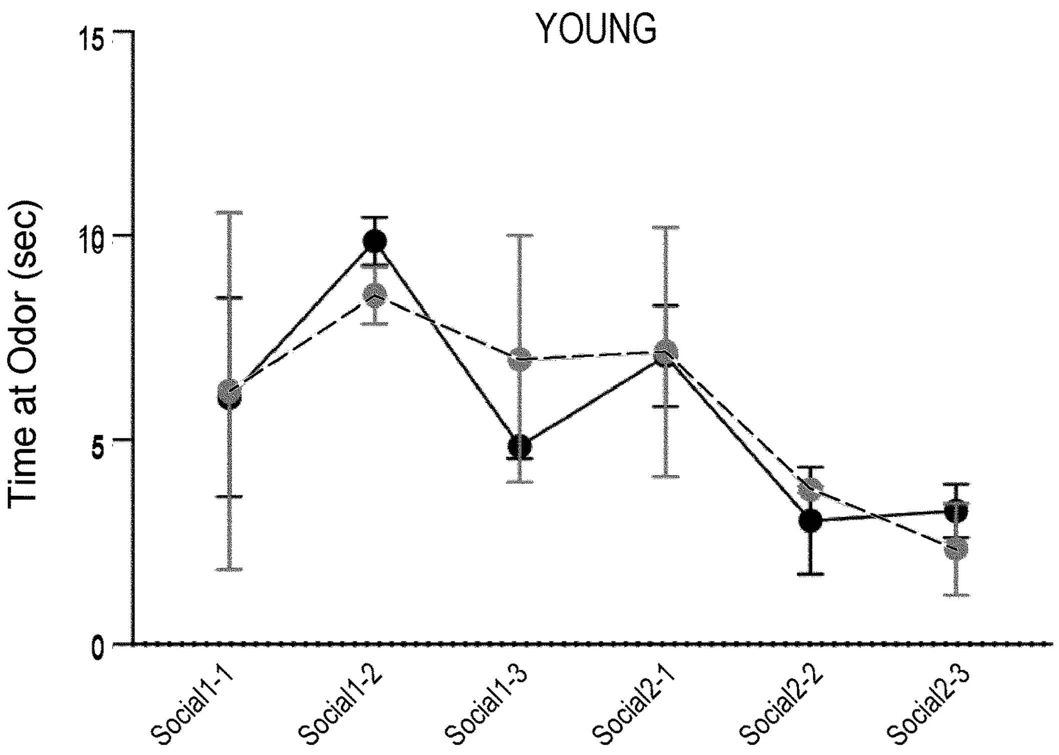
FIGS. 33A-33F are graphs showing the results of an olfactory habituation/dishabituation test with social stimuli. Control (black line) and psilocin-carbamate treated (dashed line) mice.
Figure 33B:
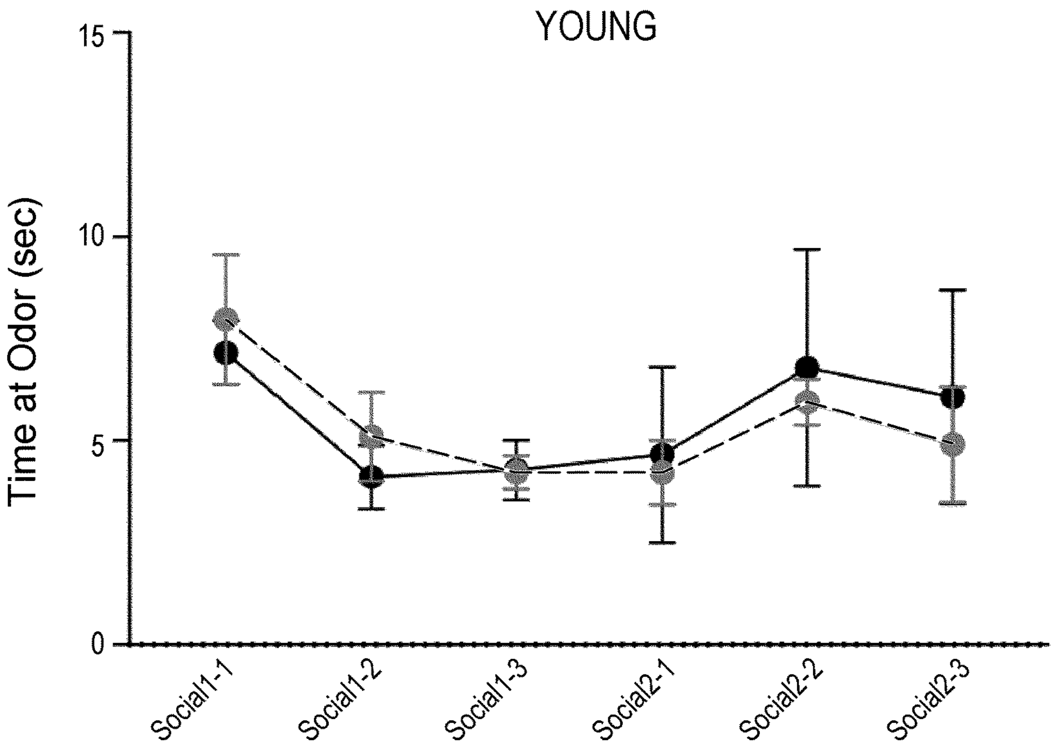
Figure 33C:
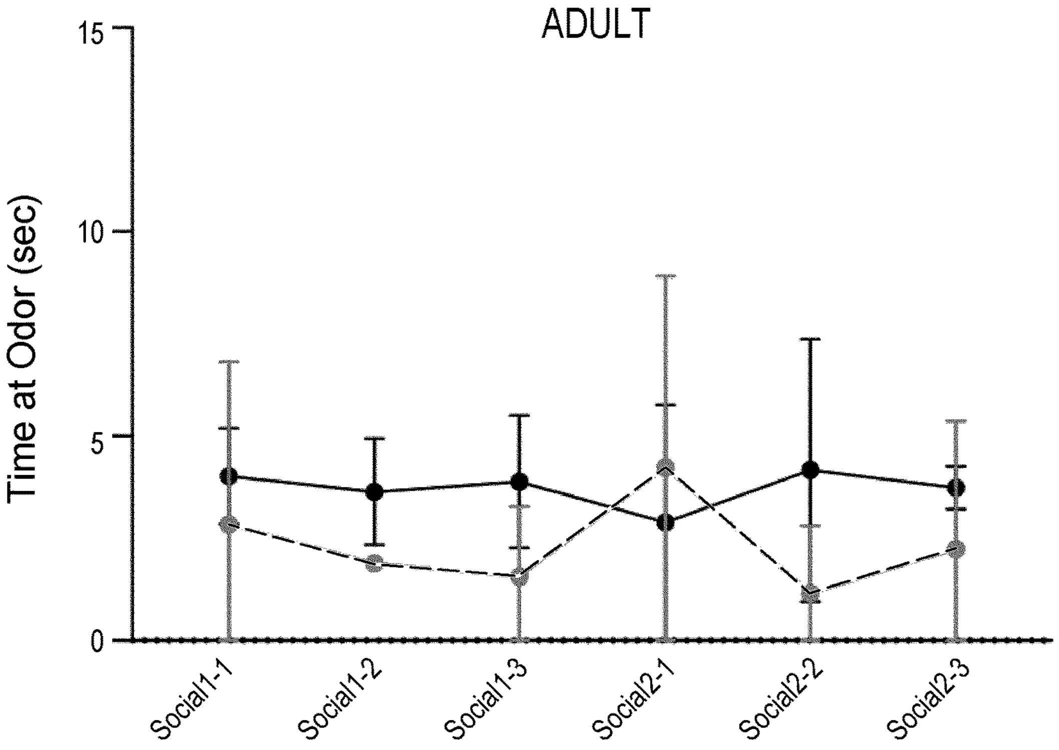
Figure 33D:
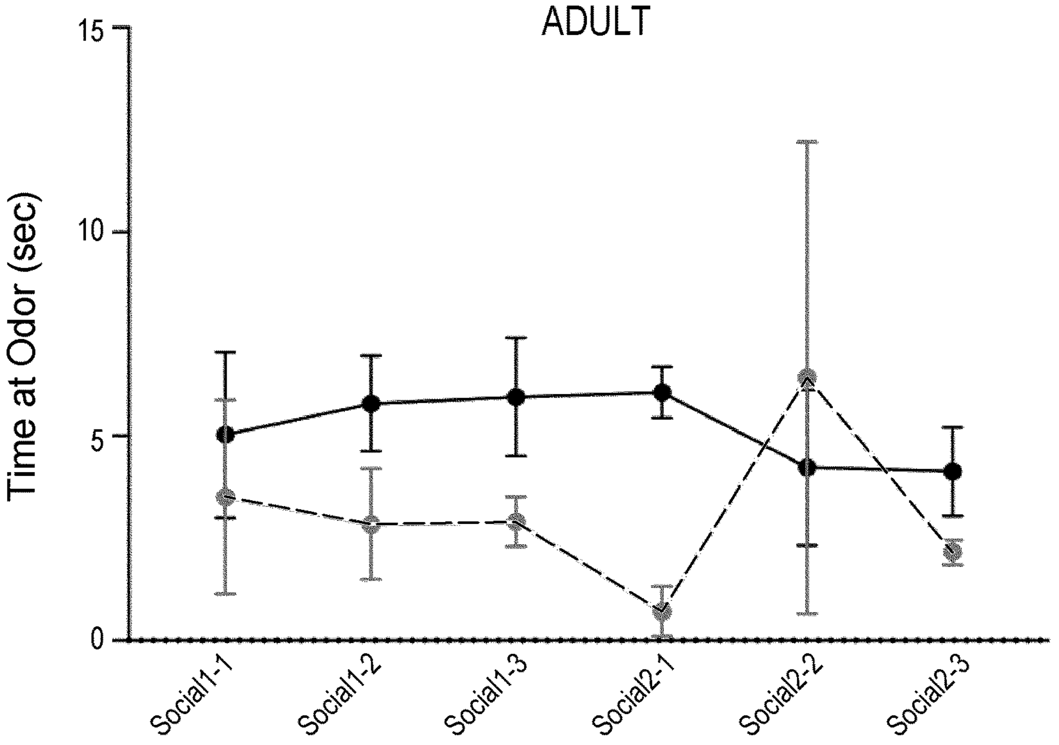
Figure 33E:
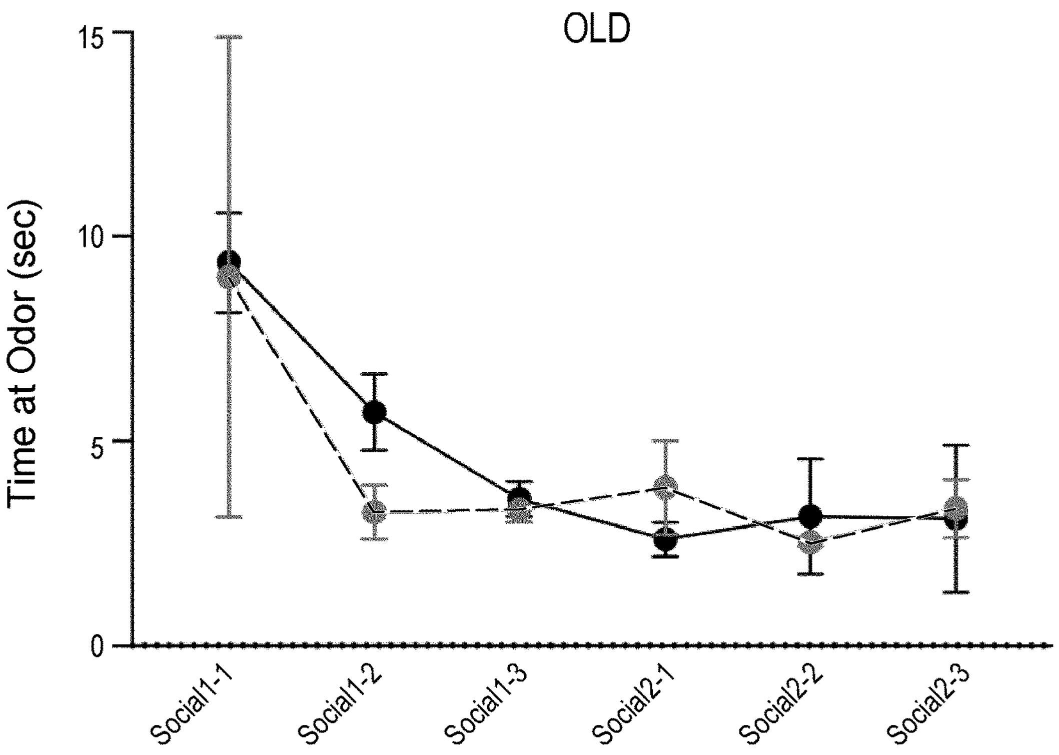
Figure 33F:
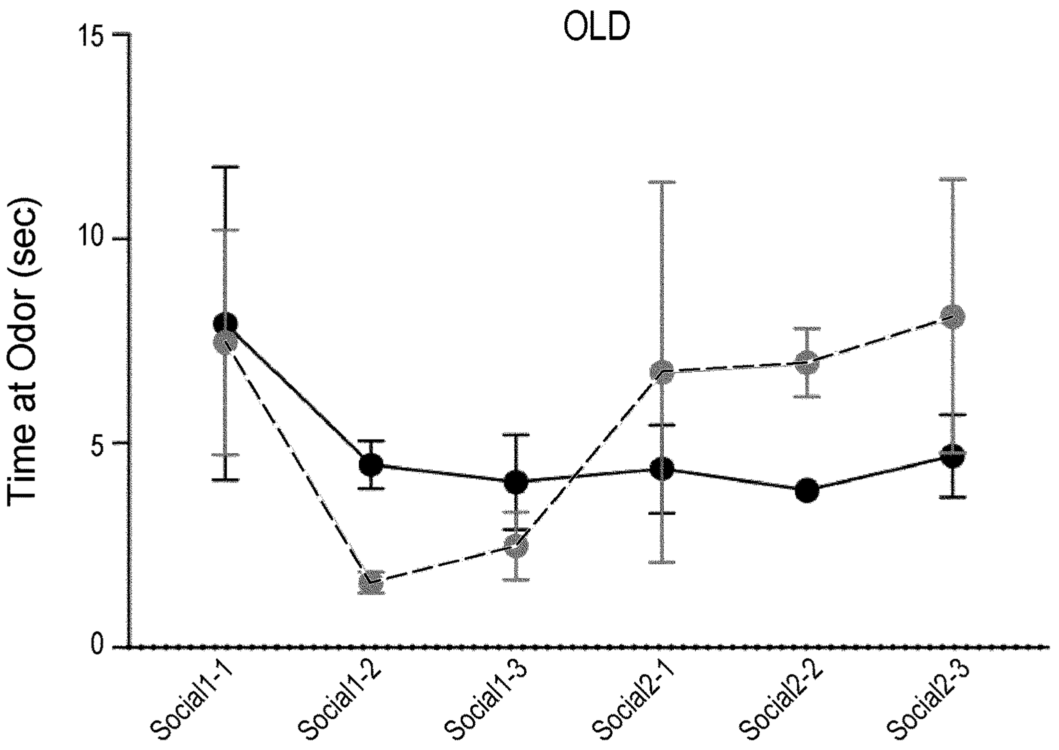

In this test, three parameters are usually measured: 1. The time needed by the animal to start eating the feeding pellet in the first cage (maximum time=10 minutes); 2. The number of times the mice is sniffing and approaching the pellet in the first cage; and 3. The amount of pellet eaten by the animal in the second cage in 5 minutes. Results can be seen in FIGS. 31A-31C.

In the olfactory habitation/dishabituation test, the mouse is repeatedly presented with several odors, which are presented three times for two minutes each. The investigator carefully records the sniffing time directed towards the odor as the measurement of olfactory responsiveness. A typical mouse shows a decrease in response to the odor over repeated presentations (the so-called habituation). The experimenter then presents a novel odor that elicits increased sniffing (dishabituation). After repeated presentation of the novel odor the animal again shows habituation. The protocol used in this study involves the presentation of water, two non-social odors (almond and banana), and two social odors.

Referring to FIGS. 32A-32F and FIGS. 33A-33F in general, the responses to this test were characterized by a wide variability. Globally, no significant effects could be observed following psilocin-carbamate treatment.

2. Effects of Psilocin-Carbamate Treatment on NMDAR and Synaptic Markers

Hypothesis: Low dose chronic treatment with psilocin-carbamate (isoleucinyl carbamate) modulates neuroplasticity.

Background:

It has been demonstrated that certain serotonergic psychedelics are capable of significantly increasing neuritogenesis and/or spinogenesis both in vitro and in vivo (Ly C, Greb A C, Cameron L P, et al. Psychedelics Promote Structural and Functional Neural Plasticity. Cell Rep. 2018; 23(11):3170-3182). These changes in neuronal structure are accompanied by increased synapse number and function.

Methods:

Mice were euthanized by cervical dislocation. Immediately after the sample, fresh tissues were cut isolating 4 brain regions (cerebellum, lateral cortex, olfactory bulb, and the remaining brain), quickly collected and put in cryovials in liquid nitrogen and then kept at −80° C.

Brain tissues were lysed in RIPA lysis buffer (Invitrogen) and 1% (v/v) protease and phosphatase inhibitor cocktail (Sigma). Proteins were extracted by centrifugation at 14000 rpm at 4° C. for 30 minutes. Bicinchoninic Acid Assay (BCA) kit (1113 catalog #23225 Thermo-Scientific) was used to determine the protein concentration following the manufacturer's instructions. Western blot analyses to determine NMDAR 1 (primary antibody: Abcam, ab68144), PSD95 (Bioss, bs-0179R-TR), p70 (Bioss, bs-3498R-TR) and synapsin 1 (Bioss, bs-3501 R-TR) protein expression were performed using 30 μg per lane of nuclear or lateral cortex lysates. SDS-PAGE was performed on 8% polyacrylamide gels in reducing-denaturing condition and proteins were transferred to a 0.45 μm nitrocellulose membrane (BioRad Laboratories). Signal intensity of immunoreactive bands was analyzed by the Quantity One software (Bio-Rad Laboratories S.r.l.) and was normalized to that of the loading control GAPDH.

Figure 34:
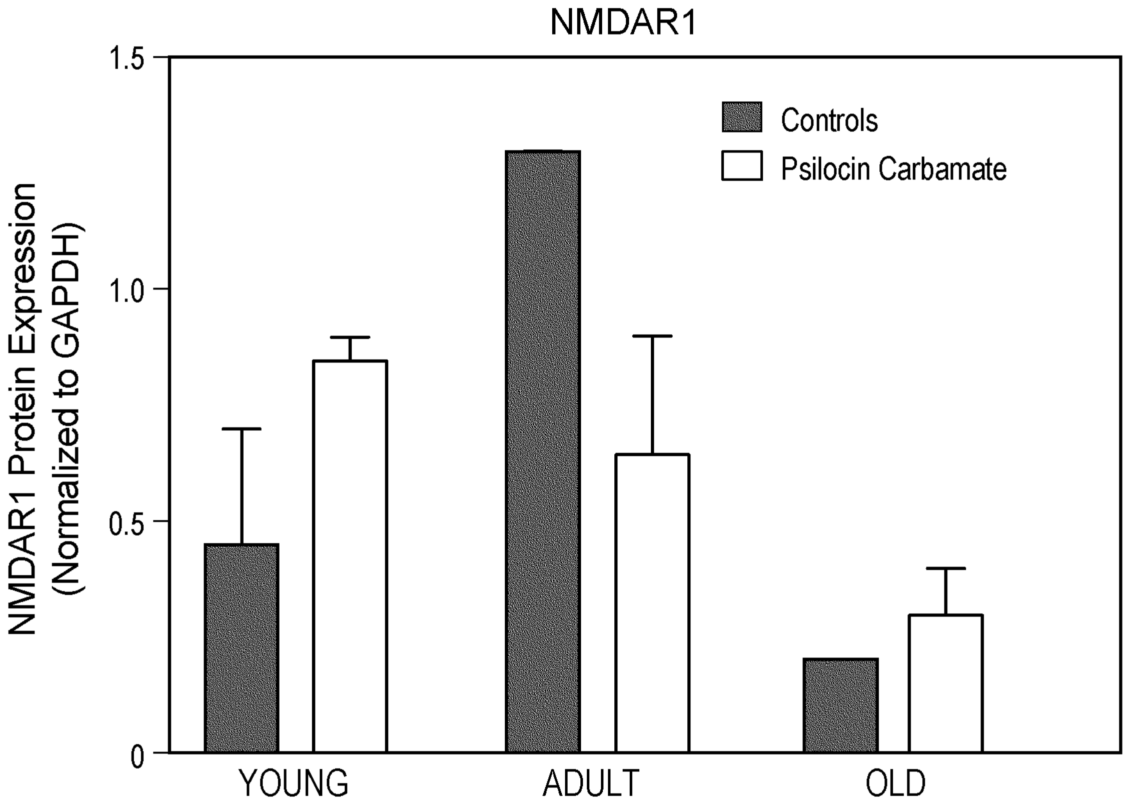
FIG. 34 is a graph showing protein expression of NMDAR1 after psilocin carbamate treatment.

Results:

The present inventors analyzed the protein expression of NMDAR1, PSD95, p70 and synapsin1 in the lateral cortex of young, adult and old mice. Referring to FIG. 34, NMDAR1 expression tended to increase in young and old mice after psilocin-carbamate (isoleucinyl carbamate) treatment, whereas it tended to decrease in adult mice. It has to be noticed that a high inter-group variability could be observed.

Figure 35A:
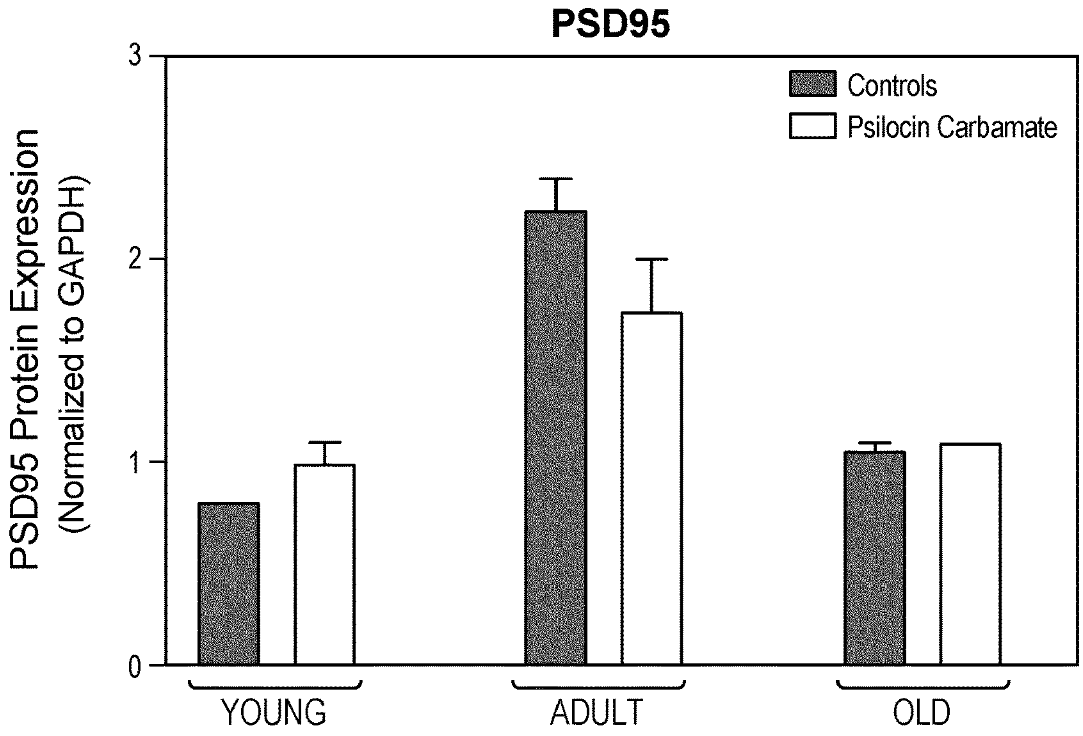
FIGS. 35A-35C are graphs showing the protein expression of the three synaptic proteins PSD95, p70 and synapsin 1 following psilocin carbamate treatment.
Figure 35B:
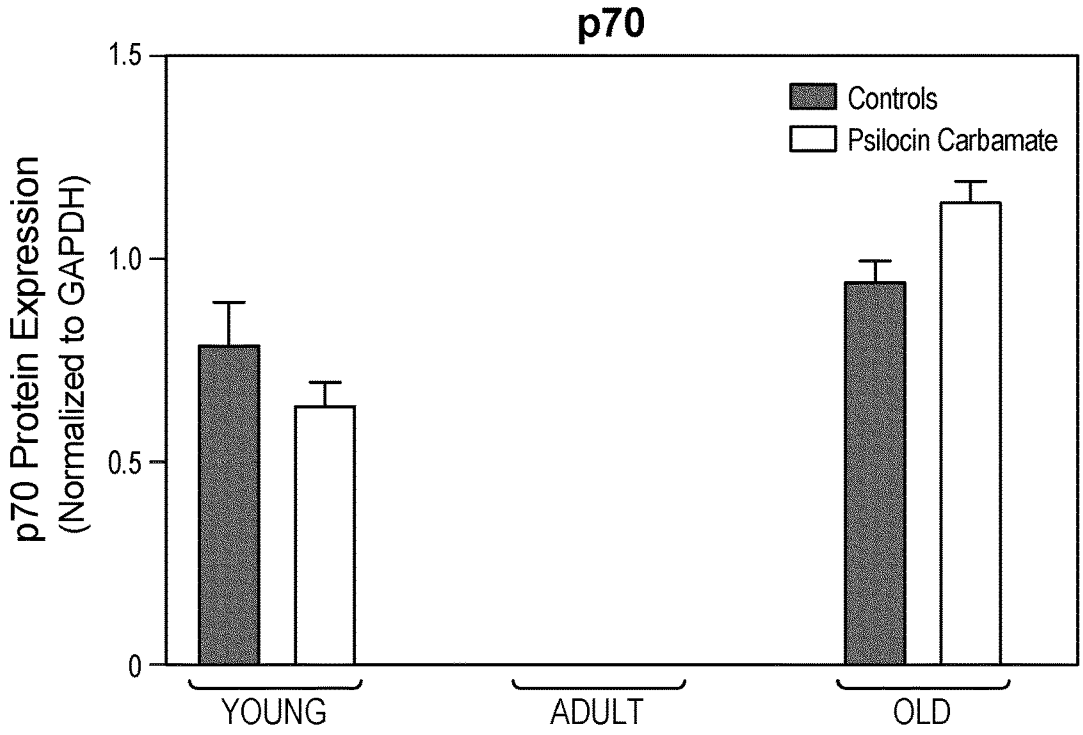
Figure 35C:
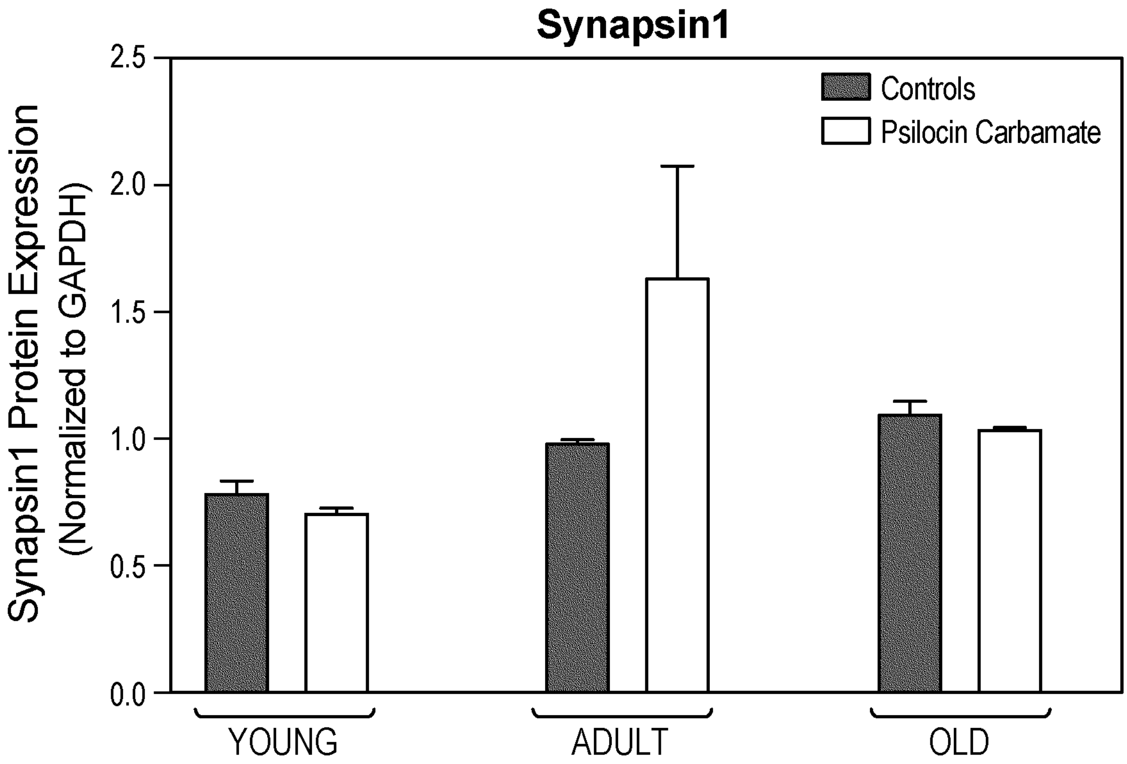

The present inventors also measured the protein expression of the three synaptic proteins PSD95, p70 and synapsin 1. Referring to FIGS. 35A-35C, no significant differences could be observed in the expression of these proteins. However, PSD95 displayed a different tendency in young and adult mice, since it tended to increase in young and decrease in adult mice after treatment, similarly to the NMDAR1 subunit. Conversely, sinapsyn1 expression tended to increase only in adult mice after treatment. Unexpectedly, p70 could not be detected in adult mice.

Conclusions:

Psilocin-carbamate (isoleucinyl carbamate), a prodrug of psilocin, appears to be safe and well-tolerated when administered at a dose of 0.05 mg/kg daily for 14 days to you, adult, and old mice. Safety and tolerability were also confirmed by behavioral observation. Isoleucinyl carbamate potentially modulates synaptic proteins; these effects need to be better elucidated with larger experiments. Based on these preliminary results, the present inventors can now plan experimental studies aimed to better characterize psilocin-carbamate PK and PD parameters, and obtain additional data on potential safety and efficacy for the treatment and prevention of diseases and conditions.

The results are in line with those of LMA test, showing that the mice are probably subjected to a habituation after the first test. Apparently, there is no effect of psilocin-carbamate on their performances at NSF test. Some tendencies could be observed in the amount of food eaten in the second cage in 5 minutes by adult mice, since the decrease observed for the control group was counteracted by the psilocin-carbamate treatment.

In summary, the in vivo effects on neurogenesis, metabolic parameters and inflammation (as seen in Example 2, rat study), the in vitro actions on NMDAR subunits (as seen in Example 3, ARPE-19 study) and on cellular viability (as seen in Example 4, corneal cells), the clinical observations in human subjects (as seen in Example 1) and the in silico results (as seen in Example 5, molecular modeling) the in vitro anti-senescence results (as seen in Example 6) and this Example 7 mouse experiment with psilocin carbamate are complementary in signaling that the chronic administration, continuous or intermittent, of 5-HT2A agonists drugs and their derivatives listed in Table 1A at neuroplastogen dosages (non-psychedelic/psychotomimetic dosages) exert actions on NMDAR modulation, neural plasticity, inflammation, metabolic parameters, and cellular viability potentially therapeutic for the treatment and prevention diseases and conditions.

The present inventors therefore disclose the use of 5-HT2A agonists and their derivatives (SMSNs) listed in Table 1A, alone or in combination with NMDAR open channel blockers, administered at non-psychedelic/psychotomimetic doses, repeatedly over days or months or chronically, continuously or intermittently, for the treatment of diseases and conditions, especially for patients that could potentially benefit from well tolerated drugs with effects on modulation of neural plasticity over time and on modulation of NMDARs without clinically meaningful side effects, including, especially, without psychedelic/psychotomimetic side effects.

While the present invention has been disclosed by reference to the details of preferred embodiments of the invention, it is to be understood that the disclosure is intended as an illustrative rather than in a limiting sense, as it is contemplated that modifications will readily occur to those skilled in the art, within the spirit of the invention and the scope of the amended claims.

What is claimed is:

1. A method for treating diseases and conditions or improving functions in patients or subjects, the method comprising:

administering a compound to a subject;

wherein the compound is chosen from a structural analogue of psilocin, a structural analogue of norpsilocin, a structural analogue of psilocybin, a structural analogue of baeocystin, a structural analogue of norbaeocystin, and a structural analogue of N,N-dimethyltryptamine;

wherein the compound is of formula I:

(I)

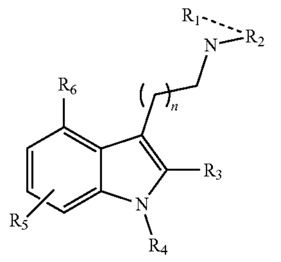

wherein $R_1$ and $R_2$ are, independently, hydrogen, deuterium, $C_1$-$C_8$ alkyl, $C_2$-$C_8$ alkenyl, $C_2$-$C_8$ alkynyl, $C_3$-$C_8$ cycloalkyl (independently or ring close with the nitrogen), $C_3$-$C_8$ cycloalkenyl (independently or ring close with the nitrogen), aryl or heterocyclyl, optionally substituted at one or more positions by deuterium, halogen, alkyl, alkyl ester, hydroxy, alkoxy, carboxy, formyl, aryl, aryloxy, heterocyclyl, amino, alkylamino, arylamido, alkylamido, thiol, thioalkyl, thioaryl, alkylsulfonyl, alkylcarbamoyl, arylcarbamoyl, nitro, cyano, or nitrate;

$R_3$ is hydrogen, deuterium, $C_1$-$C_8$ alkyl, $C_2$-$C_8$ alkenyl, $C_2$-$C_8$ alkynyl, $C_3$-$C_8$ cycloalkyl, $C_3$-$C_8$ cycloalkenyl, aryl or heterocyclyl, optionally substituted at one or more positions by deuterium, halogen, alkyl, alkyl ester, hydroxy, alkoxy, carboxy, formyl, aryl, aryloxy, heterocyclyl, amino, alkylamino, arylamido, alkylamido, thiol, thioalkyl, thioaryl, alkylsulfonyl, alkylcarbamoyl, arylcarbamoyl, nitro, cyano, or nitrate; or $R_3$ is selected from the group consisting of halogen, alkyl ester, hydroxy, alkoxy, carboxy, formyl, aryloxy, amino, alkylamino, arylamido, alkylamido, thiol, thioalkyl, thioaryl, alkylsulfonyl, alkylcarbamoyl, arylcarbamoyl, nitro, cyano, and nitrate;

$R_4$ is hydrogen, deuterium, $C_1$-$C_8$ alkyl, $C_2$-$C_8$ alkenyl, $C_2$-$C_8$ alkynyl, $C_3$-$C_8$ cycloalkyl, $C_3$-$C_8$ cycloalkenyl, aryl or heterocyclyl, any of which are optionally substituted at one or more positions by deuterium, halogen, alkyl, alkyl ester, hydroxy, alkoxy, carboxy, formyl, aryl, aryloxy, heterocyclyl, amino, alkylamino, arylamido, alkylamido, thiol, thioalkyl, thioaryl, alkylsulfonyl, alkylcarbamoyl, arylcarbamoyl, nitro, cyano, or nitrate; or $R_4$ is selected from the group consisting of alkyl ester, formyl, hydroxy, arylamido, alkylamido, alkylcarbamoyl, arylcarbamoyl, amino, alkylsulfonyl, and alkylamino;

$R_5$ represents 1-3 substituents selected from the group consisting of hydrogen, deuterium, halogen, $C_1$-$C_8$ alkyl, $C_2$-$C_8$ alkenyl, $C_2$-$C_8$ alkynyl, $C_3$-$C_8$ cycloalkyl, $C_3$-$C_8$ cycloalkenyl, aryl or heterocyclyl, optionally substituted at one or more positions by deuterium, halogen, alkyl, alkyl ester, hydroxy, alkoxy, carboxy, formyl, aryl, aryloxy, heterocyclyl, amino, alkylamino, arylamido, alkylamido, thiol, thioalkyl, thioaryl, alkylsulfonyl, alkylcarbamoyl, arylcarbamoyl, nitro, cyano, or nitrate;

$R_6$ is hydrogen, deuterium, $C_1$-$C_8$ alkyl, $C_2$-$C_8$ alkenyl, $C_2$-$C_8$ alkynyl, $C_3$-$C_8$ cycloalkyl, $C_3$-$C_8$ cycloalkenyl, aryl or heterocyclyl any of which are optionally substituted at one or more positions by deuterium, halogen, alkyl, alkyl ester, hydroxy, alkoxy, carboxy, formyl, aryl, aryloxy, heterocyclyl, amino, alkylamino, arylamido, alkylamido, thiol, thioalkyl, thioaryl, alkylsulfonyl, alkylcarbamoyl, arylcarbamoyl, nitro, cyano, or nitrate; or $R_6$ is selected from the group consisting of halogen, alkyl ester, hydroxy, alkoxy, carboxy, formyl, aryloxy, amino, alkylamino, arylamido, alkylamido, thiol, thioalkyl, thioaryl, alkylsulfonyl, alkylcarbamoyl, arylcarbamoyl, nitro, cyano, nitrate, $—OP(O)(OH)_2$, $—OC(O)R_7$, $—OSO_2OH$, $—OC(O)NHR_7$, $—OC(O)NR_7R_8$ and —SONH; and n is 1 to 5; and wherein the compound is administered at doses, dosages, posology, or formulations devoid of clinically meaningful psychedelic or psychotomimetic actions or effects.

2. The method of claim 1, wherein said clinical effects are of those exerted by human plasma psilocin Cmax of 2 ng/ml or less or 5-HT2A human CNS receptor occupancy of 40% or less.

3. The method of claim 1, wherein said clinical effects are of those exerted by human plasma psilocin Cmax of 1 ng/ml or less or 5-HT2A human CNS receptor occupancy of 30% or less.

4. The method of claim 1, wherein said PD effects are of those exerted by human plasma psilocin Tmax in excess of 120 minutes.

5. The method of claim 1, wherein said PD effects are of those exerted by human plasma psilocin Tmax in excess of 180 minutes.

6. The method of claim 1, wherein the administering of the compound occurs under conditions that may modulate NMDARs and their subunits in addition to modulate 5-HT2A receptors.

7. The method of claim 1, wherein the administering of the compound may provide excitotoxicity protection.

8. The method of claim 1, wherein the administering of the compound may modulate neurogenesis.

9. The method of claim 1, wherein the administering of the compound occurs under conditions effective for the substance to exert neuroplastogen effects, including modulation of neural plasticity.

10. The method of claim 1, wherein the administration of the compound is repeated over days or months or is chronic.

11. The method of claim 1, wherein the administration of the compound is intermittent and occurs every second day, every third day or every other week or every 2 weeks or every other month.

12. A method for treating diseases and conditions or improving functions in patients or subjects, the method comprising:

administering a 5-HT2A agonist substance to a subject;

wherein the 5-HT2A agonist substance is chosen from a structural analogue of psilocin, a structural analogue of norpsilocin, a structural analogue of psilocybin, a structural analogue of baeocystin, a structural analogue of norbaeocystin, and a structural analogue of N, N-dimethyltryptamine;

wherein the compound is of formula I:

(II)

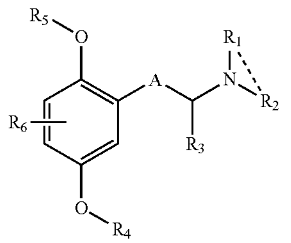

wherein $R_1$ and $R_2$ are, independently, hydrogen, deuterium, $C_1$-$C_8$ alkyl, $C_2$-$C_8$ alkenyl, $C_2$-$C_8$ alkynyl, $C_3$-$C_8$ cycloalkyl (independently or ring close with the nitrogen), $C_3$-$C_8$ cycloalkenyl (independently or ring close with the nitrogen), aryl or heterocyclyl, optionally substituted at one or more positions by deuterium, halogen, alkyl, alkyl ester, hydroxy, alkoxy, carboxy, formyl, aryl, aryloxy, heterocyclyl, amino, alkylamino, arylamido, alkylamido, thiol, thioalkyl, thioaryl, alkylsulfonyl, alkylcarbamoyl, arylcarbamoyl, nitro, cyano, or nitrate;

$R_3$ is hydrogen, deuterium, $C_1$-$C_8$ alkyl, $C_2$-$C_8$ alkenyl, $C_2$-$C_8$ alkynyl, $C_3$-$C_8$ cycloalkyl, $C_3$-$C_8$ cycloalkenyl, aryl or heterocyclyl, optionally substituted at one or more positions by deuterium, halogen, alkyl, alkyl ester, hydroxy, alkoxy, carboxy, formyl, aryl, aryloxy, heterocyclyl, amino, alkylamino, arylamido, alkylamido, thiol, thioalkyl, thioaryl, alkylsulfonyl, alkylcarbamoyl, arylcarbamoyl, nitro, cyano, or nitrate; or $R_3$ is selected from the group consisting of halogen, alkyl ester, hydroxy, alkoxy, carboxy, formyl, aryloxy, amino, alkylamino, arylamido, alkylamido, thiol, thioalkyl, thioaryl, alkylsulfonyl, alkylcarbamoyl, arylcarbamoyl, nitro, cyano, and nitrate;

$R_4$ is hydrogen, deuterium, $C_1$-$C_8$ alkyl, $C_2$-$C_8$ alkenyl, $C_2$-$C_8$ alkynyl, $C_3$-$C_8$ cycloalkyl, $C_3$-$C_8$ cycloalkenyl, aryl or heterocyclyl, any of which are optionally substituted at one or more positions by deuterium, halogen, alkyl, alkyl ester, hydroxy, alkoxy, carboxy, formyl, aryl, aryloxy, heterocyclyl, amino, alkylamino, arylamido, alkylamido, thiol, thioalkyl, thioaryl, alkylsulfonyl, alkylcarbamoyl, arylcarbamoyl, nitro, cyano, or nitrate; or $R_4$ is selected from the group consisting of alkyl ester, formyl, hydroxy, arylamido, alkylamido, alkylcarbamoyl, arylcarbamoyl, amino, alkylsulfonyl, and alkylamino;

$R_5$ represents 1-3 substituents selected from the group consisting of hydrogen, deuterium, halogen, $C_1$-$C_8$ alkyl, $C_2$-$C_8$ alkenyl, $C_2$-$C_8$ alkynyl, $C_3$-$C_8$ cycloalkyl, $C_3$-$C_8$ cycloalkenyl, aryl or heterocyclyl, optionally substituted at one or more positions by deuterium, halogen, alkyl, alkyl ester, hydroxy, alkoxy, carboxy, formyl, aryl, aryloxy, heterocyclyl, amino, alkylamino, arylamido, alkylamido, thiol, thioalkyl, thioaryl, alkylsulfonyl, alkylcarbamoyl, arylcarbamoyl, nitro, cyano, or nitrate;

$R_6$ is hydrogen, deuterium, $C_1$-$C_8$ alkyl, $C_2$-$C_5$ alkenyl, $C_2$-$C_8$ alkynyl, $C_3$-$C_8$ cycloalkyl, $C_3$-$C_8$ cycloalkenyl, aryl or heterocyclyl any of which are optionally substituted at one or more positions by deuterium, halogen, alkyl, alkyl ester, hydroxy, alkoxy, carboxy, formyl, aryl, aryloxy, heterocyclyl, amino, alkylamino, arylamido, alkylamido, thiol, thioalkyl, thioaryl, alkylsulfonyl, alkylcarbamoyl, arylcarbamoyl, nitro, cyano, or nitrate; or $R_6$ is selected from the group consisting of halogen, alkyl ester, hydroxy, alkoxy, carboxy, formyl, aryloxy, amino, alkylamino, arylamido, alkylamido, thiol, thioalkyl, thioaryl, alkylsulfonyl, alkylcarbamoyl, arylcarbamoyl, nitro, cyano, nitrate, —$OP(O)(OH)_2$, —$OC(O)R_7$, —$OSO_2OH$, —$OC(O)NHR_7$, —$OC(O)NR_7R_8$ and —SONH; and n is 1 to 5; and wherein the compound is administered at doses, dosages, posology, or formulations devoid of clinically meaningful psychedelic or psychotomimetic actions or effects.

13. The method of claim 12, wherein said clinical effects are of those exerted by human plasma psilocin Cmax of 2 ng/ml or less or 5-HT2A human CNS receptor occupancy of 40% or less.

14. The method of claim 12, wherein said clinical effects are of those exerted by human plasma psilocin Cmax of 1 ng/ml or less or 5-HT2A human CNS receptor occupancy of 30% or less.

15. The method of claim 12, wherein said PD effects are of those exerted by human plasma psilocin Tmax in excess of 120 minutes.

16. The method of claim 12, wherein said PD effects are of those exerted by human plasma psilocin Tmax in excess of 180 minutes.

17. The method of claim 12, wherein the administering of the 5-HT2A agonist substance occurs under conditions that may modulate NMDARs and their subunits in addition to modulate 5-HT2A receptors.

18. The method of claim 12, wherein the administering of the 5-HT2A agonist substance may provide excitotoxicity protection.

19. The method of claim 12, wherein the administering of the 5-HT2A agonist substance may modulate neurogenesis.

20. The method of claim 12, wherein the administering of the 5-HT2A agonist substance occurs under conditions effective for the substance to exert neuroplastogen effects, including modulation of neural plasticity.

21. The method of claim 12, wherein the administration of the 5-HT2A agonist substance is repeated over days or months or is chronic.

22. The method of claim 12, wherein the administration of the 5-HT2A agonist substance is intermittent and occurs every second day, every third day or every other week or every 2 weeks or every other month.

23. The method of claim 12, wherein the method includes the treatment of the metabolic syndrome and its complications.

24. The method of claim 12, wherein the method includes the treatment of impaired glucose tolerance, diabetes and their complication.

25. The method of claim 12, wherein the method includes the treatment of NAFL, NAFLD, NASH and their complications.

26. The method of claim 12, wherein the method includes the treatment of obesity and its complications.

27. The method of claim 12, wherein the method includes the treatment of vision impairment, and visual loss, including macular degeneration, and retinopathies.

28. The method of claim 12, wherein the method includes the treatment of Alzheimer's disease; presenile dementia; senile dementia; vascular dementia; Lewy body dementia; cognitive impairment, mild cognitive impairment associated with aging and with chronic disease and its treatment, cognitive impairment associated with chemotherapy, cognitive impairment associated with immunotherapy, cognitive impairment associated with radiotherapy, Parkinson's disease, Parkinsonian related disorders, Parkinson dementia; disorders associated with accumulation of beta amyloid protein, cerebrovascular amyloid angiopathy, posterior cortical atrophy; disorders associated with accumulation or disruption of tau protein and its metabolites; frontotemporal dementia and its variants, frontal variant, primary progressive aphasias; semantic dementia; progressive non fluent aphasia, corticobasal degeneration, supranuclear palsy; epilepsy; NS trauma; NS infections; NS inflammation, inflammation from autoimmune disorders, NMDAR encephalitis, cytopathology from toxins, cytopathology from microbial toxins, cytopathology from heavy metals, cytopathology from pesticides; stroke; multiple sclerosis; Huntington's disease; mitochondrial disorders; Fragile X syndrome; Angelman syndrome; hereditary ataxias; neuro-otological and eye movement disorders; neurodegenerative diseases of the retina, glaucoma, diabetic retinopathy, age-related macular degeneration; amyotrophic lateral sclerosis; tardive dyskinesias; hyperkinetic disorders; attention deficit hyperactivity disorder, attention deficit disorders; restless leg syndrome; Tourette's syndrome; schizophrenia; autism spectrum disorders; tuberous sclerosis; Rett syndrome; cerebral palsy; disorders of the reward system, eating disorders, anorexia nervosa ("AN"), bulimia nervosa ("BN"); binge eating disorder ("BED"), trichotillomania, dermotillomania, nail biting; migraine; fibromyalgia; and peripheral neuropathy of any etiology; a decline, impairment, or abnormality in cognitive abilities, a decline, impairment, or abnormality in executive function, a decline, impairment, or abnormality in attention, a decline, impairment, or abnormality in cognitive speed, a decline, impairment, or abnormality in memory, a decline, impairment, or abnormality in language functions, a decline, impairment, or abnormality in orientation in space and time, praxis, a decline, impairment, or abnormality in ability to perform actions, a decline, impairment, or abnormality in ability to recognize faces or objects, a decline, impairment, or abnormality in concentration, a decline, impairment, or abnormality in alertness; abnormal movements including akathisia, bradykinesia, tics, myoclonus, dyskinesias, dyskinesias relate to Huntington's disease, levodopa induced dyskinesias, neuroleptic induced dyskinesias, dystonias, tremors, essential tremor, restless leg syndrome; parasomnias, insomnia, disturbed sleep pattern; psychosis; delirium; agitation; headache; motor weakness, spasticity, impaired physical endurance; sensory impairment, impairment of vision and visual field defects, smell, taste, hearing and balance, dysesthesias; dysautonomia; ataxia, impairment of balance or coordination, tinnitus, neuro-otological and eye movement impairments, neurological symptoms of alcohol withdrawal, including delirium, headache, tremors, hallucinations, and hypertension.

29. The method of claim 12, wherein the method includes the treatment of psychiatric diseases selected form the group consisting of Schizophrenia spectrum and other psychotic disorders, Bipolar and related disorders, Depressive disorders, Anxiety disorders, Obsessive-compulsive and related disorders, Trauma-and stressor-related disorders, Dissociative disorders, Somatic symptom and related disorders, Feeding and eating disorders, Elimination disorders, Sleep-wake disorders, Sexual dysfunctions, Gender dysphoria, Disruptive disorders, impulse-control disorders, conduct disorders, Substance-related and addictive disorders, Neurocognitive disorders, Personality disorders, and Paraphilic disorders.

30. The method of claim 12, wherein the method includes the treatment of systemic inflammatory states and autoimmune disorders.

31. The method of claim 12, wherein the method includes the treatment of aging, senescence and associated deficits, or osteoporosis.

32. The method of claim 12, wherein the method includes the treatment of dry eye syndrome.

33. The method of claim 12, wherein the method includes the treatment of restless leg syndrome.

34. The method of claim 12, wherein the function is chosen from visual, auditory, sense of balance, olfactory, gustatory.

35. The method of claim 12, where the compound is a first compound and is in combination with at least a second compound, the first compound being administered at doses of 0.01-24 mg, and the second compound being an open-channel low-affinity uncompetitive NMDAR antagonist selected from the group comprising dextromethorphan, dextromethadone, ketamine and its isomers, memantine, amantadine, and noribogaine, and wherein the second compound is administered at doses of 0.01-50 mg.

36. The method of claim 12, further comprising administration of the 5-HT2A agonist substance in combination with magnesium and or zinc and or lithium and salts thereof.

37. The method of claim 1, wherein the substance is coated with an emetic drug to lower the abuse potential of the substance.

38. The method of claim 1, wherein the administering of substance is performed orally, buccally, sublingually, rectally, vaginally, nasally, via aerosol, trans-dermally, trans-mucosal, parenterally, epidurally, intrathecally, intra-auricularly, intraocularly, via implanted depot formulations, or topically.

39. The method of claim 1, wherein the method includes the treatment of the metabolic syndrome and its complications.

40. The method of claim 1, wherein the method includes the treatment of impaired glucose tolerance, diabetes and their complication.

41. The method of claim 1, wherein the method includes the treatment of NAFL, NAFLD, NASH and their complications.

42. The method of claim 1, wherein the method includes the treatment of obesity and its complications.

43. The method of claim 1, wherein the method includes the treatment of vision impairment, visual loss, macular degeneration, or retinopathies.

44. The method of claim 1, wherein the method includes the treatment of Alzheimer's disease; presenile dementia; senile dementia; vascular dementia; Lewy body dementia; cognitive impairment, mild cognitive impairment associated with aging and with chronic disease and its treatment, cognitive impairment associated with chemotherapy, cognitive impairment associated with immunotherapy, cognitive impairment associated with radiotherapy, Parkinson's disease, Parkinsonian related disorders, Parkinson dementia; disorders associated with accumulation of beta amyloid protein, cerebrovascular amyloid angiopathy, posterior cortical atrophy; disorders associated with accumulation or disruption of tau protein and its metabolites; frontotemporal dementia and its variants, frontal variant, primary progressive aphasias; semantic dementia; progressive non fluent aphasia, corticobasal degeneration, supranuclear palsy; epilepsy; NS trauma; NS infections; NS inflammation, inflammation from autoimmune disorders, NMDAR encephalitis, cytopathology from toxins, cytopathology from microbial toxins, cytopathology from heavy metals, cytopathology from pesticides; stroke; multiple sclerosis; Huntington's disease; mitochondrial disorders; Fragile X syndrome; Angelman syndrome; hereditary ataxias; neuro-otological and eye movement disorders; neurodegenerative diseases of the retina, glaucoma, diabetic retinopathy, and age-related macular degeneration; amyotrophic lateral sclerosis; tardive dyskinesias; hyperkinetic disorders; attention deficit hyperactivity disorder, attention deficit disorders; restless leg syndrome; Tourette's syndrome; schizophrenia; autism spectrum disorders; tuberous sclerosis; Rett syndrome; cerebral palsy; disorders of the reward system, eating disorders, anorexia nervosa ("AN"), bulimia nervosa ("BN"); binge eating disorder ("BED"), trichotillomania, dermotillomania, nail biting; migraine; fibromyalgia; and peripheral neuropathy of any etiology; a decline, impairment, or abnormality in cognitive abilities, a decline, impairment, or abnormality in executive function, a decline, impairment, or abnormality in attention, a decline, impairment, or abnormality in cognitive speed, a decline, impairment, or abnormality in memory, a decline, impairment, or abnormality in language functions, a decline, impairment, or abnormality in orientation in space and time, praxis, a decline, impairment, or abnormality in ability to perform actions, a decline, impairment, or abnormality in ability to recognize faces or objects, a decline, impairment, or abnormality in concentration, a decline, impairment, or abnormality in alertness; abnormal movements including akathisia, bradykinesia, tics, myoclonus, dyskinesias, dyskinesias relate to Huntington's disease, levodopa induced dyskinesias, neuroleptic induced dyskinesias, dystonias, tremors, essential tremor, restless leg syndrome; parasomnias, insomnia, disturbed sleep pattern; psychosis; delirium; agitation; headache; motor weakness, spasticity, impaired physical endurance; sensory impairment, impairment of vision and visual field defects, smell, taste, hearing and balance, dysesthesias; dysautonomia; ataxia, impairment of balance or coordination, tinnitus, neuro-otological and eye movement impairments, neurological symptoms of alcohol withdrawal, delirium, headache, tremors, hallucinations, and hypertension.

45. The method of claim 1, wherein the method includes the treatment of systemic inflammatory states and autoimmune disorders.

46. The method of claim 1, wherein the method includes the treatment of aging, senescence and associated deficits, or osteoporosis.

47. The method of claim 1, wherein the method includes the treatment of dry eye syndrome.

48. The method of claim 1, wherein the method includes the treatment of restless leg syndrome.

49. The method of claim 1, wherein the function is chosen from visual, auditory, sense of balance, olfactory, gustatory.

50. The method of claim 1, where the compound is a first compound and is in combination with at least a second compound, the first compound being administered at doses of 0.01-24 mg; and the second compound being an open-channel low-affinity uncompetitive NMDAR antagonist selected from the group consisting of dextromethorphan, dextromethadone, ketamine, an isomer of ketamine, memantine, amantadine, and noribogaine, wherein the second compound is administered at doses of 0.01-50 mg.

51. The method of claim 1, further comprising administration of the compound in combination with magnesium and or zinc and or lithium and salts thereof.

52. The method of claim 1, wherein the compound has clinical effects of those exerted by human plasma psilocin Cmax of 4 ng/ml or less, or human 5-HT2A CNS receptor occupancy of 50% or less, or PD effects of those exerted by human plasma psilocin Tmax in excess of 60 minutes.

53. The method of claim 12, wherein the 5-HT2A agonist has clinical effects of those exerted by human plasma psilocin Cmax of 4 ng/ml or less, or human 5-HT2A CNS receptor occupancy of 50% or less, or PD effects of those exerted by human plasma psilocin Tmax in excess of 60 minutes.

* * * * *